(12) United States Patent
Marfat et al.

(10) Patent No.: US 7,183,293 B2
(45) Date of Patent: *Feb. 27, 2007

(54) ETHER DERIVATIVES USEFUL AS INHIBITORS OF PDE4 ISOZYMES

(75) Inventors: Anthony Marfat, Mystic, CT (US); Robert J. Chambers, Msytic, CT (US); Thomas V. Magee, Mystic, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 97 days.

This patent is subject to a terminal disclaimer.

(21) Appl. No.: 10/918,820

(22) Filed: Aug. 13, 2004

(65) Prior Publication Data

US 2005/0049258 A1  Mar. 3, 2005

Related U.S. Application Data

(62) Division of application No. 10/066,503, filed on Jan. 31, 2002, now Pat. No. 6,828,333.

(60) Provisional application No. 60/265,304, filed on Jan. 31, 2001.

(51) Int. Cl.
C07D 405/12 (2006.01)
A61K 31/44 (2006.01)
(52) U.S. Cl. ............... 514/338; 546/284.1; 546/270.1; 546/281.1
(58) Field of Classification Search ............ 546/284.1, 546/270.1, 281.1; 514/338
See application file for complete search history.

(56) References Cited

U.S. PATENT DOCUMENTS

| | | | |
|---|---|---|---|
| 4,270,946 A | 6/1981 | Gutman ........................ | 71/94 |
| 4,692,185 A | 9/1987 | Michaely ...................... | 71/94 |
| 4,861,891 A | 8/1989 | Saccomano et al. ........ | 546/194 |
| 5,552,438 A | 9/1996 | Christensen, IV .......... | 514/520 |
| 5,602,157 A | 2/1997 | Christensen, IV .......... | 514/362 |
| 5,614,540 A | 3/1997 | Christensen, IV .......... | 514/362 |
| 5,863,926 A | 1/1999 | Christensen, IV et al. .. | 514/277 |
| 5,922,557 A | 7/1999 | Pon .............................. | 435/21 |
| 6,380,218 B1 | 4/2002 | Marfat et al. ................ | 514/326 |
| 6,828,333 B2 * | 12/2004 | Marfat et al. ................ | 514/338 |

FOREIGN PATENT DOCUMENTS

| | | |
|---|---|---|
| EP | 0550900 | 12/1992 |
| EP | 0773024 | 5/1997 |
| EP | 0500989 | 12/1998 |
| FR | 2140772 | 1/1973 |
| GB | 2327675 | 2/1999 |
| JP | 7304775 | 11/1995 |
| WO | WO 9500139 | 1/1995 |
| WO | WO 9818796 | 5/1998 |
| WO | WO 9845268 | 10/1998 |
| WO | WO 9845628 | 10/1998 |
| WO | WO 9918793 | 4/1999 |
| WO | WO 9920280 | 4/1999 |
| WO | WO 9920625 | 4/1999 |
| WO | WO 0157025 | 8/2001 |
| WO | WO 0157036 | 8/2001 |

OTHER PUBLICATIONS

Trophy, Theodore J. et al, "Phosphodiesterase IV Inhibitors as Therapy for Eosinophil-induced Lung Injury in Asthma," Environmental Health Perspectives, vol. 102 Suppl. 10, Dec. 1994, pp. 79-84.

(Continued)

*Primary Examiner*—Rita Desai
(74) *Attorney, Agent, or Firm*—Robert T. Ronau; Rosanne Goodman; Charles W. Ashbrook

(57) ABSTRACT

This application is directed to compounds of the formula

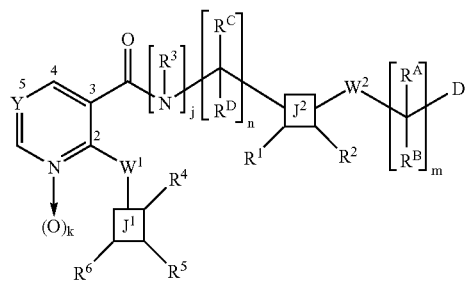

wherein j is 1; k is 0 or 1; m is 1, 2 or 3; n is 1 or 2; $W^1$ and $W^2$ are independently —O— or —S(=O)$_t$—, where t is 0, 1, or 2; Y is =C($R^1_a$)—, where $R^1_a$ is a member selected from the group consisting of H; F; Cl; CN; $NO_2$; —($C_1$–$C_4$) alkyl; —($C_2$–$C_4$)alkynyl; fluorinated-($C_1$–$C_3$)alkyl; fluorinated-($C_1$–$C_3$)alkoxy; —$OR^{16}$; and —C(=O)$NR^{22}_aR^{22}_b$; $R^{22}_a$ and $R^{22}_b$ are defined as set forth in the specification; —$R^A$ and $R^B$ are each a member independently selected from the group consisting of H; F; $CF_3$; —($C_1$–$C_4$)alkyl; —($C_3$–$C_7$)cycloalkyl; phenyl; and benzyl; wherein said cycloalkyl, phenyl, and benzyl moieties are each independently substituted with 0 to 3 substituents $R^{10}$, which is defined as set forth in the specification; $R^{16}$ and $R^{17}$ are defined as set forth in the specification; —$R^C$ and $R^D$ have the same meaning as defined above for $R^A$ and $R^B$ except that one of them must be —H, and they are selected independently of each other and of $R^A$ and $R^B$; $R^1$ and $R^2$ are each a member independently selected from the group consisting of H; F; Cl; CN; $NO_2$; —($C_1$–$C_4$)alkyl; —($C_2$–$C_4$)alkynyl; fluorinated-($C_1$–$C_3$)alkyl; $OR^{16}$; and —C(=O)$NR^{22}_aR^{22}_b$; —$R^3$ is H; —($C_1$–$C_3$)alkyl; phenyl; benzyl; or $OR^{16}$; $R^4$, $R^5$, and $R^6$ are defined as set forth in the specification; $J^1$ and $J^2$ are each independently a moiety comprising a saturated or unsaturated six-membered monocyclic carbon ring; and D is a member independently selected from the group consisting of partial Formulas (1.1.1) through (1.1.5) as set forth in the specification; a pharmaceutically acceptable salt thereof; which are useful as inhibitors of PDE4 in the treatment of diseases regulated by the activation and degranulation of eosinophils, especially asthma, chronic bronchitis, and chronic obstructuive pulmonary disease.

3 Claims, No Drawings

OTHER PUBLICATIONS

Duplantier, Allen J., et al., "Biarylcarboxylic Acids and -amides: Inhibition of Phosphodiesterase Type IV versus [³H]Rolipram Binding Activity and Their Relationship to Emetic Behavior in the Ferret, Journal of Medicinal Chemistry," 1996, vol. 39, No. 1, pp. 120-125.

Schneider, Herbert H, et al, "Discriminative Stimulus Properties of the Stereoisomers of the Phosphodiesterase Inhibitor Rolipram," Pharmacology Biochemistry and Behavior, vol. 50, No. 2, 1995, pp. 211-217.

Banner, Katherine H., et. al., "Acute versus chronic administration of phosphodiesterase inhibitors on allergen-induced pulmonary cell influx in sensitized guinea-pigs," British Journal of Pharmacology, 114, 1995, pp. 93-98.

Barnette, Mary S., et. al., "The Ability of Phosphodiesterase IV Inhibitors to Suppress Superoxide Production in Guinea Pig Eosinophils Is Correlated with Inhibition of Phosphodiesterase IV Catalytic Activity," The Journal of Pharmacology and Experimental Therapeutics, 273, 1995 pp. 674-679.

Wright, Kathryn, F., et al., "Differential in vivo and in vitro bronchorelaxant activities of CP-80,633, a selective phosphodiesterase 4 inhibitor,"Can. J. Physiol. Pharmacol. 75, 1997, pp. 1001-1008.

Manabe, Haruhiko, "Anti-Inflammatory and Bronchodilator Properties of KF19514, a Phosphodiesterase 4 and 1 Inhibitor," European Journal of Pharmacology, 332, 1997, pp. 97-107.

Ukita, Tatsuzo, et. al., Novel, Potent, and Selective Phosphodiesterase-4 Inhibitors as Antiasthmatic Agents: Synthesis and Biological Activities of a Series of 1-Pyridylnaphthalene Derivatives, J. Med. Chem, 48, 1999, pp. 1088-1099.

Compton, CH, et. al., The Efficacy of Ariflo™ (SB 207499, A Second Generation, Oral PDE4 Inhibitor, In Patients with COPD, Am. J. Respir. Crit. Care Med., 159, 1999.

Leeman, Marc M.D., et. al., "Reduction in Pulmonary Hypertension and in Airway Resistances by Enoximone (MDL 17,043) in Decompensated COPD*," Chest, 91, 1987, pp. 662-666.

Rabe, K.F., et. al., "Identification of PDE Isozymes in Human Pulmonary Artery and Effect of Selective PDE Inhibitors," Am. J. Physiol, 266 (LCMP 10), 1994, pp. L536-L543.

Hughes, Bernadette, et. al., PDE 4 inhibitors: the use of molecular cloning in the design and development of novel drugs, Drug Discovery Today, Science Direct, 2(3), 1997, pp. 89-101.

Banner, K.H., et. al., "The Effect of Selective Phosphodiesterase Inhibitors in Comparison with other Anti-asthma Drugs on Allergen-induced Eosinophilia in Guinea-pig Airways," Pulmonary Pharmacology, 8, 1995, pp. 37-42.

Raebum, David, et.al., "Anti-inflammatory and bronchodilator properties of RP 73401, a novel and selective phosphodiesterase typed IV inhibitor," Br, J. Pharmacol., 113, 1994, pp. 1423-1431.

Karlsson, J.A., et. al., "Anti-Inflammatory Effects of the Novel Phosphodiesterase IV Inhibitor RP 73401," Int. Arch Allergy Immunol, 107, 1995, pp. 425-426.

Escott, K.J., et. al., Pharmacological Profiling of Phosphodiesterase, 4 (PDE4) Inhibitors and Analysis of the Therapeutic Ratio in Rats and Dogs, Br, J. Pharmacol, 123 (Proc suppl.) 1998 40P.

Landells, L.J., et. al., "Oral Administration of the Phosphodiesterase (PDE) 4 Inhibitor, V11294A Inhibits Ex-Vivo Agonist-induced Cell Activation," Eur. Resp. J., 12 (Suppl. 28), 362s, 1998, P2393.

Gale, D.D., et. al., "Pharmacodynamic-Pharmacokinetic (PD/PK) Profile of the Phosphodiesterase (PDE)4 Inhibitor, V11294A, in Human Volunteers," Am. J. Respir. Crit Care Med., 159, A611, 1999, pp. A108.

Montana, J., et. al., "Activity of D4418, A Novel Phosphodiesterase 4 (PDE4) Inhibitor, Effects in Cellular and Animal Models of Asthma and Early Clinical Studies,"Am. J. Respir. Crit., Care Med., 159, A108, 1999, pp. A624.

Cavalla, D., et. al., "Activity of V11294A, A Novel Phosphodiesterase 4 (PDE4) Inhibitor, In Cellular and Animal Models of Asthma," Am. J. Respir. Crit. Care Med. 155, 1997, pp. A660.

Pascal, Y., et. al., "Synthesis and Structure,-activity Relationships of 4-oxo-1 pheyl-3,4,5,7-Tetrahydro-[1,4]Diazepino[6,7,1-HI]Indolines: Novel PDE4 Inhibitors," 215th ACS, MEDI, 50, 1998.

Burnouf, C., et. al., "Pharmacology of the Novel Phosphodiesterase Type 4 Inhibitor, CI-1018," 215th ACS, MEDL 008, 1998.

Mueller, George W., et. al., N-Phthaloyl-β- Aryl- β- Amino Derivatives Potent TNF-α And PDE4 Inhibitors, MEDI, 299, 1999.

Mueller, George W., et. al., "Thalidomide Analogs and PDE4 Inhibition," Bioorganic & Medicinal Chemistry Letters, 8, 1998, pp. 2669-2674.

Takayama, K., "Synthetic Studies on Selective Type IV Phosphodiesterase (PDE IV) Inhibitors," MEDI 245, 1997.

Gordon, T., et. al., "Anti-Inflammatory Effects of a PDE4 Inhibitor in a Rat Model of Chronic Bronchitis," Am. J. Respir. Crit. Care Med., 159, A33, 1999.

Perrier, Helene, et. al., "Substituted Furans as Inhibitors of the PDE4 Enzyme," Bioorganic & Medicinal Chemistry Letters 9, 1999, pp. 323-326.

Groneberg, Robert D., et. al., "Dual Inhibition of Phosphodiesterase 4 and Matrix Metalloproteinases by an (Arylsulfonyl)hydroxamic Acid Template," Journal of Medicinal Chemistry, 1999, vol. 42, No. 4, pp. 541-544.

Fujimura, Masaki, et. al. Bronchoprotective Effects of KF-19514 and Cilostazol in Guinea Pigs In Vivo, European Journal of Pharmacology, 327, 1997, pp. 57-63.

Manabe, Haruhiko, et. al., "KF19514, a Phosphodiesterase 4 and 1 Inhibitor, Inhibits PAF-Induced Lung Inflammatory Responses by Inhaled Administration in Guinea Pigs," International Archives of Allergy-Immunology, 1997, 114, pp. 389-399.

Suzuki, Fumio, et. al., "New Bronchodilators, 3. Imidazo[4,5-c][1,8]naphthyridin-4(5H)-ones," Journal of Medicinal Chemistry, 1992, vol. 35, No. 26, pp. 4866-4874.

Matsuura, Akihiro, et. al., "Substituted 1,8-Naphthyridin-2(1H)-ones as Selective Phosphodiesterase IV Inhibitors," Biol. Pharm. Bull. vol. 17(4), 1994, pp. 498-503.

Manabe, Haruhiko, et. al., "Pharmacological properties of a New Bronchodilator, KF17625," Jpn. J. Pharmacol., 58 (Suppl 1)., 1992 pp. 238.

Montana, John G., et. al., "PDE4 Inhibitors: New Xanthine Analogues," Bioorganic & Medicinal Chemistry Letters 8, 1998, pp. 2925-2930.

Merz, Karl-Heinz, et. al., "Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth," Journal of Medicinal Chemistry, vol. 41, No. 24, 1998, pp. 4733-4743.

Danhaive, P., et. al., "UCB29936, A Selective Phosphodiesterase Type IV Inhibitor; Therapeutic Potential In Endotoxic Shock," Am. J. Respir, Crit. Care Med., 159, A611, 1999.

Tian, Gaochao, et. al., "Dual Inhibition of Human Type 4 Phosphodiesterase Isostates by (R*,R*)-(±)-Methyl 3-Acetyl-4-[3-(cyclopentyloxy)-4-methoxyphenyl]-3-methyl-1-pyr-rolindinecarboxylate," Biochemistry, 37(19), 1998 pp. 6894-6904.

Norman, Peter, "PDE4 Inhibitors 1999," Exp. Opin. Ther. Patents 9(8) 1999, pp. 1101-1118.

Dyke, Hazel J. & Montana, John G., "The Therapeutic Potential of PDE4 Inhibitors," Expert Opinion on Investigational Drugs, 8(9), 1999, pp. 1301-1325.

XP-002066969, Vinivk, Fredric J., et. al., "Nicotinamide Ethers: Novel Inhibitors of Calcium-Independent Phosphodiesterase and [3H]Rolipram Binding," Journal of Medicinal Chemistry, vol. 34, No. 1., 1991, pp. 86-89.

Pruniaux, M.P., et. al., "The novel phosphodiesterase 4 inhibitor CI-1018 inhibits antigen-induced lung eosinophilia in sensitized brown-norway rats—comparison with rolipram," Mediators of Inflammation, vol. 8, Supplement 1, 1999, S-04-6, pp. S10.

* cited by examiner

ETHER DERIVATIVES USEFUL AS INHIBITORS OF PDE4 ISOZYMES

CROSS REFERENCE TO RELATED APPLICATIONS

This application is a division of U.S. application Ser. No. 10/066,503, filed Jan. 31, 2002, now U.S. Pat. No. 6,828,333 which claims the benefit of U.S. Provisional Application No. 60/265,304, filed Jan. 31, 2001.

1.0 REFERENCE TO RELATED APPLICATIONS

Reference is made to International application and US application based thereon, Ser. No. PCT/IB98/00315, both filed Mar. 10, 1998, and published as WO 98/45268 on Oct. 15, 1998; claiming priority from application Ser. No. 60/043,403 filed Apr. 4, 1997, now abandoned; which discloses nicotinamide derivatives having biological activity as inhibitors of PDE4 isozymes, and thus being useful in the treatment of inflammatory, respiratory and allergic diseases and conditions. Nothing that is disclosed in the above-mentioned applications would teach the person of ordinary skill in the pertinent art the novel compounds of the present invention or their unexpectedly high level of inhibitory selectivity for PDE 4 isozymes.

Reference is also made to copending application Ser. No. 09/345,185 filed Jun. 30, 1999; claiming priority from application Ser. No. 60/105,120 filed Oct. 21, 1998, which discloses compounds and processes for preparing N-substituted nicotinamide derivatives. However, the disclosed compounds and processes are not the same as those of the present invention.

Reference is further made to copending applications filed of even date with the instant application, Ser. Nos. 60/265,531; 60/265,250; 60/265,491; 60/265,486; 60/265,240; and 60/265,492, which involve other classes of nicotinamide derivatives useful as inhibitors of PDE4 isozymes. The disclosures of all of said copending applications are incorporated herein by reference in their entireties.

2.0 BACKGROUND OF THE INVENTION

The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. A total of more than fifteen gene products is included within this class, and further diversity results from differential splicing and post-translational processing of those gene products. The present invention relates to the four gene products of the fourth family of PDEs, i.e., PDE4A, PDE4B, PDE4C, and PDE4D, and their inhibition, including selective inhibition of PDE4D. These enzymes are collectively referred to as being isoforms or subtypes of the PDE4 isozyme family. Further below will be found a more detailed discussion of the genomic organization, molecular structure and enzymatic activity, differential splicing, transcriptional regulation and phosphorylation, distribution and expression, and selective inhibition of the PDE4 isozyme subtypes.

The PDE4s are characterized by selective, high affinity hydrolytic degradation of the second messenger cyclic nucleotide, adenosine 3',5'-cyclic monophosphate (cAMP), and by sensitivity to inhibition by rolipram. A number of selective inhibitors of the PDE4s have been discovered in recent years, and beneficial pharmacological effects resulting from that inhibition have been shown in a variety of disease models. See, e.g., Torphy et al., *Environ. Health Perspect.* 102 Suppl. 10, 79–84, 1994; Duplantier et al., *J. Med. Chem.* 39 120–125, 1996; Schneider et al., *Pharmacol. Biochem. Behav.* 50 211–217, 1995; Banner and Page, *Br. J. Pharmacol.* 114 93–98, 1995; Barnette et al., *J. Pharmacol. Exp. Ther.* 273 674–679, 1995; Wright et al., "Differential in vivo and in vitro bronchorelaxant activities of CP-80633, a selective phosphodiesterase 4 inhibitor," *Can. J. Physiol. Pharmacol.* 75 1001–1008, 1997; Manabe et al., "Anti-inflammatory and bronchodilator properties of KF19514, a phosphodiesterase 4 and 1 inhibitor," *Eur. J. Pharmacol.* 332 97–107, 1997; and Ukita et al. "Novel, potent, and selective phosphodiesterase-4 inhibitors as antiasthmatic agents: synthesis and biological activities of a series of 1-pyridylnaphthalene derivatives," *J. Med. Chem.* 42 1088–1099, 1999. Accordingly, there continues to be considerable interest in the art with regard to the discovery of further selective inhibitors of PDE4s.

The present invention is also concerned with the use of selective PDE4 inhibitors for the improved therapeutic treatment of a number of inflammatory, respiratory and allergic diseases and conditions, but especially for the treatment of asthma; chronic obstructive pulmonary disease (COPD) including chronic bronchitis, emphysema, and bronchiectasis; chronic rhinitis; and chronic sinusitis. Heretofore in the art, however, the first-line therapy for treatment of asthma and other obstructive airway diseases has been the nonselective PDE inhibitor theophylline, as well as pentoxifylline and IBMX, which may be represented by Formulas (0.0.1), (0.0.2), and (0.0.3), respectively:

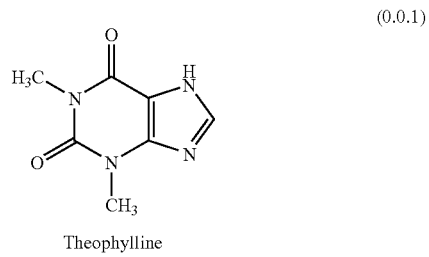

Theophylline (0.0.1)

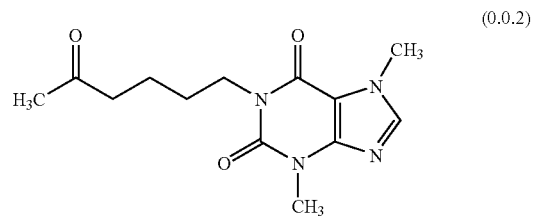

Pentoxifylline (0.0.2)

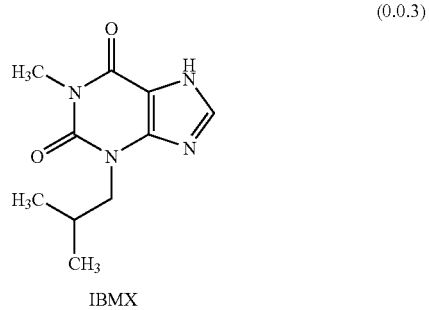

IBMX (0.0.3)

Theophylline, which has the PDEs as one of its biochemical targets, in addition to its well characterized bronchodilatory activity, affects the vasculature of patients with increased pulmonary artery pressure, suppresses inflammatory cell responses, and induces apoptosis of eosinophils. Theophylline's adverse events, most commonly cardiac dysrhythmias and nausea, are also mediated by PDE inhibition, however, leading to the search for more selective inhibitors of PDEs that are able to suppress both immune cell functions in vitro and allergic pulmonary inflammation in vivo, while at the same time having improved side-effect profiles. Within the airways of patients suffering from asthma and other obstructive airway diseases, PDE4 is the most important of the PDE isozymes as a target for drug discovery because of its distribution in airway smooth muscle and inflammatory cells. Several PDE4 inhibitors introduced to the art thus far have been designed to have an improved therapeutic index concerning the cardiovascular, gastrointestinal, and central nervous system side effects of the above-mentioned nonselective xanthines.

Airflow obstruction and airway inflammation are features of asthma as well as COPD. While bronchial asthma is predominantly characterized by an eosinophilic inflammation, neutrophils appear to play a major role in the pathogenesis of COPD. Thus, PDEs that are involved in smooth muscle relaxation and are also found in eosinophils as well as neutrophils probably constitute an essential element of the progress of both diseases. The PDEs involved include PDE3s as well as PDE4s, and bronchodilating inhibitors have been discovered which are selective PDE3 inhibitors and dual PDE3/4 selective inhibitors. Examples of these are milrinone, a selective PDE3 inhibitor, as well as zardaverine and benafentrine, both dual PDE3/4 selective inhibitors, which may be represented by Formulas (0.0.4), (0.0.5), and (0.0.6), respectively:

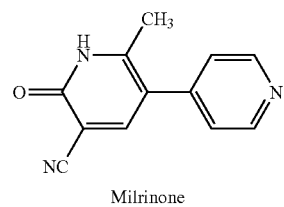

Milrinone (0.0.4)

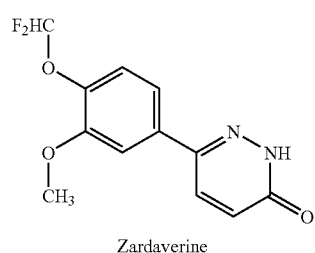

Zardaverine (0.0.5)

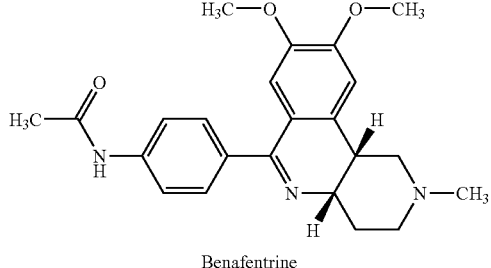

Benafentrine (0.0.6)

However, benafentrine results in bronchodilation only when administered by inhalation, and zardaverine produces only a modest and short-lived bronchodilation. Milrinone, a cardiotonic agent, induces short-lived bronchodilation and a slight degree of protection against induced bronchoconstriction, but has marked adverse events, e.g., tachycardia and hypotension. Unsatisfactory results have also been obtained with a weakly selective PDE4 inhibitor, tibenelast, and a selective PDE5 inhibitor, zaprinast, which may be represented by Formulas (0.0.7) and (0.0.8):

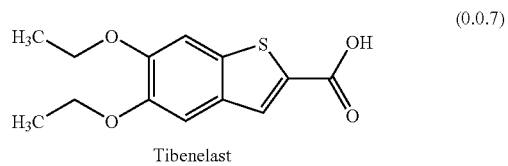

Tibenelast (0.0.7)

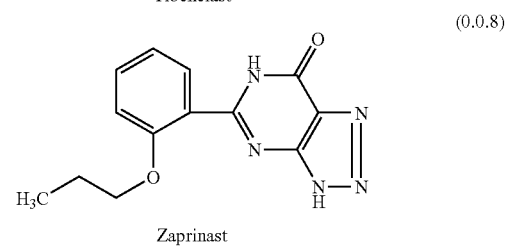

Zaprinast (0.0.8)

More relative success has been obtained in the art with the discovery and development of selective PDE4 inhibitors.

In vivo, PDE4 inhibitors reduce the influx of eosinophils to the lungs of allergen-challenged animals while also reducing the bronchoconstriction and elevated bronchial responsiveness occurring after allergen challenge. PDE4 inhibitors also suppress the activity of immune cells, including CD4[+] T-lymphocytes, monocytes, mast cells, and basophils; reduce pulmonary edema; inhibit excitatory nonadrenergic noncholinergic neurotransmission (eNANC); potentiate inhibitory nonadrenergic noncholinergic neurotransmission (iNANC); reduce airway smooth muscle mitogenesis; and induce bronchodilation. PDE4 inhibitors also suppress the activity of a number of inflammatory cells associated with the pathophysiology of COPD, including monocytes/macrophages, CD8[+] T-lymphocytes, and neutrophils. PDE4 inhibitors also reduce vascular smooth muscle mitogenesis and, and potentially interfere with the ability of airway epithelial cells to generate pro-inflammatory mediators. Through the release of neutral proteases and acid hydrolases from their granules, and the generation of reactive oxygen species, neutrophils contribute to the tissue destruction associated with chronic inflammation, and are further implicated in the pathology of conditions such as emphysema.

Selective PDE4 inhibitors which have been discovered thus far that provide therapeutic advantages include SB-207,499, identified as ARIFLO®, which may be represented by Formula (0.1.9):

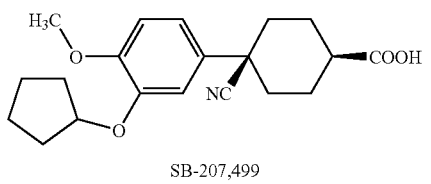

SB-207,499

SB-207,499, administered orally at dosages of 5, 10, and 15 mg b.i.d., has produced significant increases in trough $FEV_1$ (forced expiratory volume in 1 second) from placebo at week 2 of a study involving a large number of patients. Another potent, selective PDE4 inhibitor, CDP840, has shown suppression of late reactions to inhaled allergen after 9.5 days of oral administration at doses of 15 and 30 mg in a group of patients with bronchial asthma. CDP840 may be represented by Formula (0.0.9):

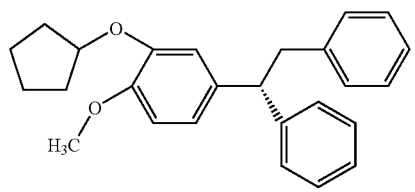

CDP840

PDEs have also been investigated as potential therapy for obstructive lung disease, including COPD. In a large study of SB-207,499 in patients with COPD, the group of patients receiving 15 mg b.i.d. has experienced a progressive improvement in trough $FEV_1$, reaching a maximum mean difference compared with placebo of 160 mL at week 6, which represents an 11% improvement. See Compton et al., "The efficacy of Ariflo (SB207499), a second generation, oral PDE4 inhibitor, in patients with COPD," *Am. J. Respir. Crit. Care Med.* 159, 1999. Patients with severe COPD have been observed to have pulmonary hypertension, and decreases in mean pulmonary artery pressure under clinical conditions have been achieved by oral administration of the selective PDE3 inhibitors milrinone and enoximone. Enoximone has also been shown to reduce airway resistance in patients hospitalized with decompensated COPD. See Leeman et al., *Chest* 91 662–6, 1987. Using selective PDE3 inhibition by motapizone and selective PDE5 inhibition by zaprinast, it has been shown that combined inhibition of PDE 3 and 5 exerts a relaxation of pulmonary artery rings which corresponds broadly to the pattern of PDE isozymes found in the pulmonary artery smooth muscle. See Rabe et al., *Am. J. Physiol.* 266 (LCMP 10): L536–L543, 1994. The structures of milrinone and zaprinast are shown above as Formulas (0.0.4) and (0.0.8), respectively. The structures of enoximone and motapizone may be represented by Formulas (0.0.10) and (0.0.11), respectively:

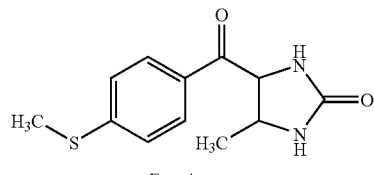

Enoximone

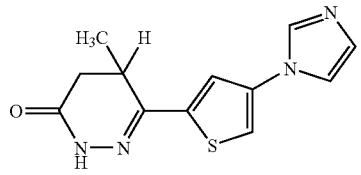

Motapizone

The effects of PDE4 inhibitors on various inflammatory cell responses can be used as a basis for profiling and selecting inhibitors for further study. These effects include elevation of cAMP and inhibition of superoxide production, degranulation, chemotaxis, and tumor necrosis factor alpha (TNFα) release in eosinophils, neutrophils and monocytes. PDE4 inhibitors may induce emesis, i.e., nausea and vomiting, which, as expected, is an adverse effect. The emesis adverse effect became apparent when PDE4 inhibitors were first investigated for CNS indications such as depression, when rolipram and denbufylline were used in clinical trials. Rolipram and denbufylline may be represented by Formulas (0.0.12) and (0.0.13), respectively:

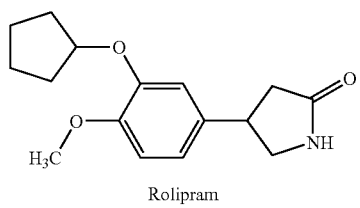

Rolipram

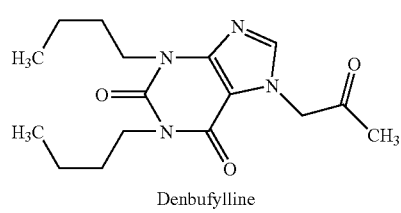

Denbufylline

The mechanism(s) by which PDE4 inhibitors may potentially induce emesis is/are uncertain, but a study of the PDE4 inhibitor Ro-20-1724 suggests that nausea and vomiting are at least partially mediated by the emesis centers in the brain. Gastrointestinal adverse events may be caused by local effects, e.g., rolipram is a very potent stimulator of acid secretion from gastric parietal cells, and the resulting excess acid, by producing local irritation, may exacerbate gastrointestinal disturbances. Ro-20-1724 may be represented by Formula (0.0.14):

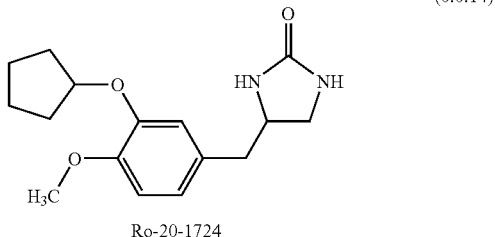

Ro-20-1724 (0.0.14)

Efforts to minimize or eliminate the above-mentioned adverse events sometimes associated with PDE4 inhibitors have included creating inhibitors which do not penetrate the central nervous system, and administering PDE4 inhibitors by inhalation rather than orally.

With regard to the PDE4 subtypes, A, B, C, and D, it has been found that PDE4C is usually less sensitive to all inhibitors; whereas, with respect to the subtypes A, B, and D, there is as yet no clear evidence of inhibitor specificity, which is defined as a 10-fold difference in $IC_{50}$ values. While most inhibitors, especially RS-25,344, are more potent against PDE4D, this does not amount to selectivity. RS-25,344 may be represented by Formula (0.0.15):

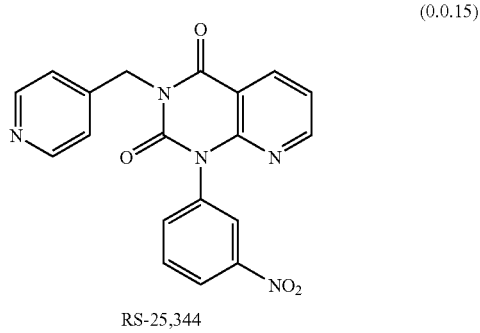

RS-25,344 (0.0.15)

On the other hand, there is a stereoselective effect on the elevation of cAMP in a range of cell types, which has been demonstrated with the results of an investigation of CDP840, shown above as Formula (0.0.9), and its less active enantiomer CT-1731, which is represented by Formula (0.0.16):

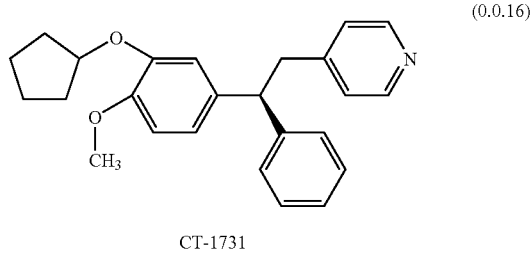

CT-1731 (0.0.16)

It has been known for some time that rolipram had the ability to interact with a high-affinity binding site on brain membranes, and it was later established in the art that this high-affinity rolipram binding site ($S_r$), which is distinct from the catalytic site ($S_c$), exists in a truncated recombinant PDE4A and a full-length recombinant PDE4B. More recently, $S_r$ has been identified on all four PDE4 subtypes. See Hughes et al., *Drug Discovery Today* 2(3) 89–101, 1997. The presence of $S_r$ appears to have a profound effect on the ability of certain inhibitors such as rolipram and RS-25,344 to inhibit the catalytic activity of PDE4 isozymes.

The impact of residues on inhibitor binding is also significant. A single amino acid substitution (alanine for aspartate) in the catalytic region of PDE4B has been shown to be critical for inhibition by rolipram, and this appears to be a class effect because related inhibitors RP-73,401 and Ro-20-1724 also lose potency on the mutant enzyme. However, the role of binding of inhibitors to the $S_c$ or to the $S_r$, in terms of elevation of cAMP and inhibition of cell responses, is not fully understood at the present time.

RP-73,401, in guinea-pig studies, has been found to be active in (1) the inhibition of antigen-induced lung eosinophilia and eosinophil peroxidase (EPO), Banner, K. H., "The effect of selective phosphodiesterase inhibitors in comparison with other anti-asthma drugs on allergen-induced eosinophilia in guinea-pig airways," *Pulm. Pharmacol.* 8 37–42, 1995; (2) antigen-induced bronchoalveolar lavage (BAL) eosinophilia, Raeburn et al., "Anti-inflammatory and bronchodilator properties of RP73401, a novel and selective phosphodiesterase Type IV inhibitor," *Br. J. Pharmacol.* 113 1423–1431, 1994; (3) antigen-induced airway eosinophilia and platelet activating factor-(PAF)- and ozone-induced airway hyper-responsiveness (AHR), Karlsson et al., "Anti-inflammatory effects of the novel phosphodiesterase IV inhibitor RP73401," *Int. Arch. Allergy Immunol.* 107 425–426, 1995; and (4) IL-5 induced pleural eosinophila. Development of RP-73,401, piclamilast, has been discontinued. Piclamilast may be represented by Formula (0.0.17):

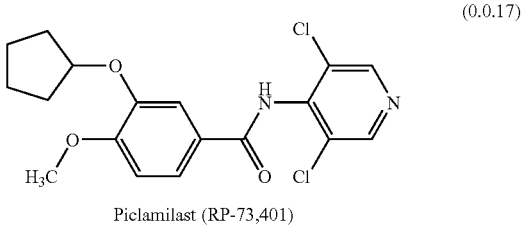

Piclamilast (RP-73,401) (0.0.17)

A related series of compounds is represented by RPR-132294 and RPR-132703, which have been demonstrated in rat studies to have activity in the inhibition of antigen-induced bronchospasm; Escott et al., "Pharmacological profiling of phosphodiesterase 4 (PDE4) inhibitors and analysis of the therapeutic ratio in rats and dogs," *Br. J. Pharmacol.* 123(Proc. Suppl.) 40P, 1998; and Thurairatnam et al., "Biological activity and side effect profile of RPR-132294 and RPR-132703—novel PDE4 inhibitors," $XV^{th}$ *EFMC Int. Symp. Med. Chem.*, 1998. The structure of RPR-132294 may be represented by Formula (0.0.18):

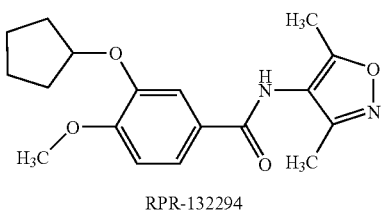

RPR-132294 (0.0.18)

Another compound whose development has been discontinued is WAY-PDA-641, filaminast, which in studies in the dog, has been found to be active in the inhibition of seratonin-induced bronchoconstriction. Filaminast may be represented by Formula (0.0.19):

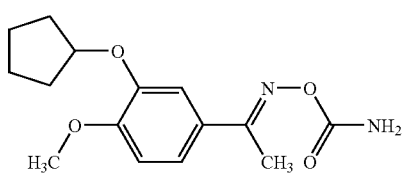

Filaminast (WAY-PDA-641) (0.0.19)

It has been suggested in the art that PDE4 inhibitors that have a high affinity at the $S_r$ can be correlated with emesis and increased gastric acid secretion. RS-23,544, RP-73,401, and CP-80,633 elicit emesis and have a high affinity at the $S_r$. CDP840 and SB-207,499 have a comparatively low affinity at the $S_r$, but CDP840 has a significantly higher potency at the $S_c$ than does SB-207,499. CDP840 has been demonstrated to provide significant inhibition of late-phase response in the treatment of asthma without any adverse events of nausea or headache. Another PDE4 inhibitor that has been shown to have adverse events of nausea and vomiting is BRL-61,063, also referred to as cipamfylline, which is described further below. The development of CDP840 has been discontinued, while CP-80,633, atizoram, has been advanced into clinical studies. CP-80,633 and BRL-61,063 may be represented by Formulas (0.0.20) and (0.1.12), respectively:

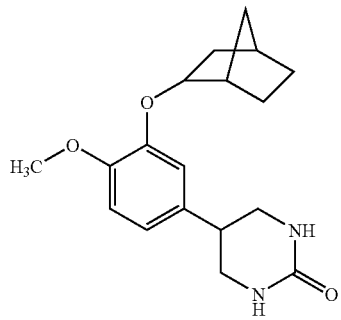

Atizoram (CP-80,633) (0.0.20)

-continued

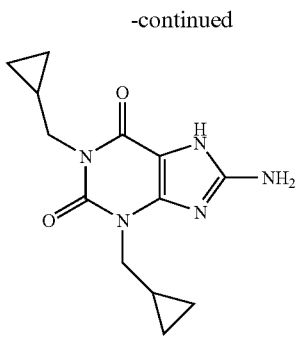

Cipamfylline (BRL-61,063) (0.1.12)

Another compound which is in development is LAS-31025, arofylline, which in guinea-pig studies, has been found to be active in the inhibition of antigen-induced bronchoconstriction; Beleta, B. J., "Characterization of LAS31025: a new selective PDE IV inhibitor for bronchial asthma," *Third Int. Conf. On Cyclic Nucleotide Phosphodiesterase: From Genes to Therapies*, Glasgow, UK, 1996, Abstract 73. LAS-31025, arofylline, may be represented by Formula (0.0.21):

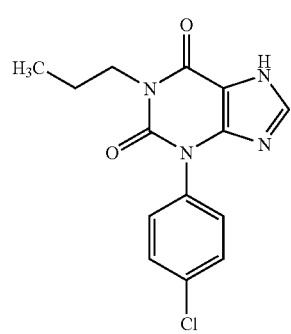

Arofylline (LAS-31025) (0.0.21)

A number of PDE4 inhibitors have been advanced in development. For example, the effects of V-11294A on LPS-stimulated ex vivo TNF release and PHA induced lymphocyte proliferation have been determined in a randomized, double-blind placebo-controlled study which has found that an oral dose of 300 mg is effective in reducing TNF levels and lymphocyte proliferation; Landells et al., "Oral administration of the phosphodiesterase (PDE) 4 inhibitor, V11294A inhibits ex-vivo agonist-induced cell activation," *Eur. Resp. J.* 12(Suppl. 28) 362s, 1998; and Gale et al., "Pharmacodynamic-pharmacokinetic (PD/PK) profile of the phosphodiesterase (PDE) 4 inhibitor, V11294A, in human volunteers," *Am. J. Respir. Crit Care Med.* 159 A611, 1999.

The compound D4418 has been administered to healthy volunteers in a single escalating dose, randomized, placebo-controlled Phase I study; Montana et al., "Activity of D4418, a novel phosphodiesterase 4 (PDE4) inhibitor, effects in cellular and animal models of asthma and early clinical studies," *Am. J. Respir. Crit. Care Med.* 159 A108, 1999. D4418 is a moderately potent PDE4 inhibitor with an $IC_{50}$ of 200 nM. It has good oral absorption; a 200 mg dose provides a plasma $C_{max}$ of 1.4 µg/ml. D4418 has been discontinued from development due to its moderate potency, and has been replaced by the preclinical development candidate D4396.

V-11294A and D4418 may be represented by Formulas (0.0.22) and (0.0.23), respectively:

(0.0.22)

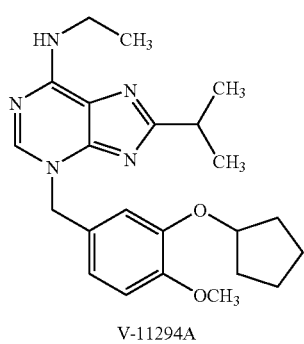

V-11294A (0.0.23)

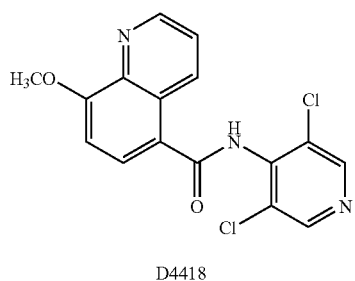

D4418

Another compound, Cl-1018, has been evaluated in 54 subjects and no adverse events were reported at doses up to 400 mg; Pruniaux et al., "The novel phosphodiesterase inhibitor Cl-1018 inhibits antigen-induced lung eosinophilia in sensitized brown-norway rats—comparison with rolipram," *Inflammation* S-04-6, 1999. Cl-1018 has been demonstrated to have good oral bioavailability (57% in the rat) and good oral potency of with an $ED_{50}$ of 5 mg/kg in that same species. Cl-1018 is a relatively weak PDE4 inhibitor with an $IC_{50}$ of 1.1 µM in U937 cells. Cl-1018 has also been identified as, or associated with as closely related in structure to, PD-168787, which in rat studies has been demonstrated to have activity in the inhibition of antigen-induced eosinophilia; Pascal et al., "Synthesis and structure-activity relationships of 4-oxo-1-phenyl-3,4,6,7-tetrahydro-[1,4]-diazepino[6,7,1-hi] indolines: novel PDE4 inhibitors," 215th *ACS*, Dallas, USA, MEDI 50, 1998. Inferred structures for Cl-1018 and PD-168787 belong to a diazepinone class whose nucleus may be represented by Formula (0.0.24):

(0.0.24)

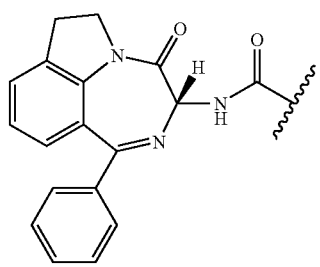

The above-mentioned compounds have also been evaluated in animal models which demonstrate their PDE4 inhibition activity. For example, V-11294A, in guinea-pig studies, has been found to be active in the inhibition of antigen-induced bronchoconstriction; Cavalla et al., "Activity of V11294A, a novel phosphodiesterase 4 (PDE4) inhibitor, in cellular and animal models of asthma," *Amer. J. Respir. Crit. Care Med,* 155 A660, 1997. D4418, in guinea-pig studies, has been found to be active in the inhibition of antigen-induced early and late phase bronchoconstriction and BAL eosinophilia; Montana, et al., Ibid. Cl-1018, in rat studies, has been found to be active in the inhibition of antigen-induced eosinophilia; Burnouf, et al., "Pharmacology of the novel phosphodiesterase Type 4 inhibitor, Cl-1018," 215th *ACS Nat. Meeting,* MEDI 008, 1998.

Other compounds which have been advanced in development include CDC-3052, D-22888, YM-58997, and roflumilast, which may be represented by Formulas (0.0.27), (0.0.28), (0.0.29), and (0.0.30), respectively:

(0.0.27)

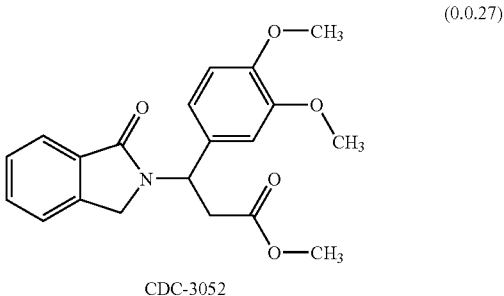

CDC-3052

(0.0.28)

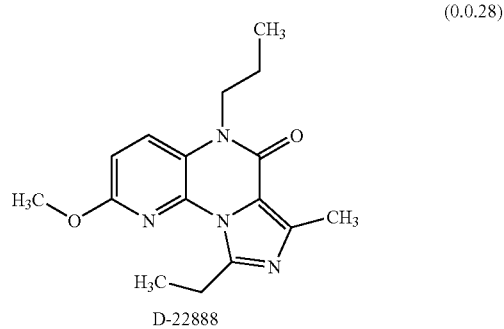

D-22888

(0.0.29)

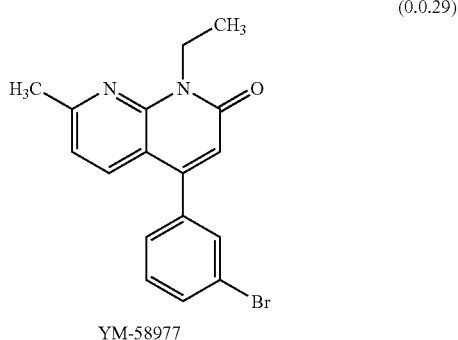

YM-58977

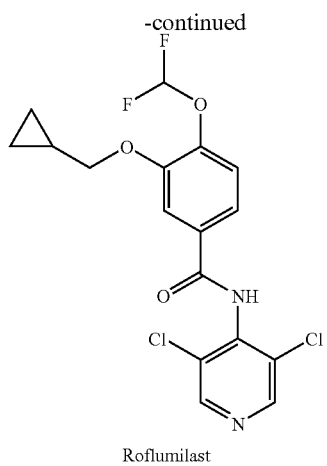

Roflumilast

CDC-3052 has been discontinued from development, but has been succeeded by very potent inhibitors of PDE4 such as the compound represented by Formula (0.0.31), and by the anti-inflammatory compound CDC-801 represented by Formula (0.0.32), respectively:

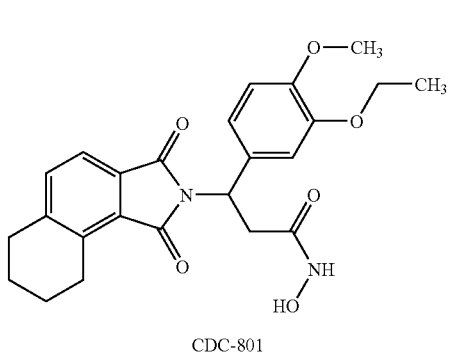

The compound of Formula (0.0.32) is reported to have $IC_{50}$ values of 42 pM and 130 nM as an inhibitor of PDE4 and TNF production, respectively; Muller et al., "N-Phthaloyl beta-aryl-beta-amino derivatives: Potent TNF-alpha and PDE4 inhibitors," 217th American Chemical Society, Annheim, Germany, MEDI 200, 1999; and Muller et al., "Thalidomide analogs and PDE4 inhibition," Bioorg. Med. Chem. Letts. 8 2669–2674, 1998.

CDC-801 is from a series of compounds based on thalidomide and has been developed primarily to improve the TNF-α inhibitory activity of thalidomide for the treatment of autoimmune diseases. Thalidomide may be represented by Formula (0.0.33):

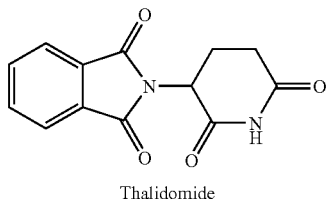

Thalidomide

CDC-801 has also been studied for the treatment of Crohn's disease, a chronic granulomatous inflammatory disease of unknown etiology commonly involving the terminal ileum, with scarring and thickening of the bowel wall which frequently leads to intestinal obstruction and fistula and abscess formation. Crohn's disease has a high rate of recurrence after treatment.

YM-58997 has an $IC_{50}$ value of 1.2 nM against PDE4; Takayama et al., "Synthetic studies on selective Type IV phosphodiesterase (PDE IV) inhibitors," 214th American Chemical Society, Las Vegas, USA, MEDI 245, 1997. YM-58997 has a 1,8-naphthyridin-2-one structure, as does YM-976.

Roflumilast has been studied for the treatment of both COPD and asthma, and has an $IC_{50}$ value of 3.5 nM in standard in vitro guinea-pig models of asthma. The use of roflumilast and a surfactant for the treatment of adult respiratory distress syndrome (ARDS) has also been described.

AWD-12,281, which is now designated as loteprednol, has been shown to be active in a rat model of allergic rhinitis, as described further below in a section which deals with allergic rhinitis and the use of PDE4 inhibitors to treat it. AWD-12,281 may be represented by Formula (0.0.34):

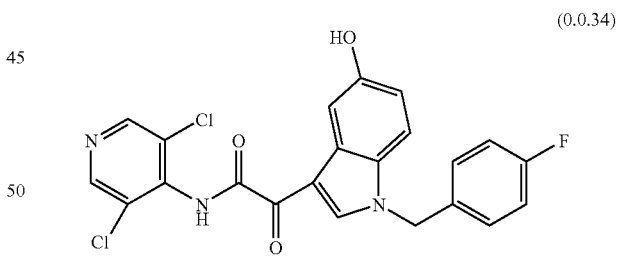

Loteprednol (AWD-12,281)

Compounds related in structure to CDP840, shown further above as Formula (0.0.9), include L-826,141, which has been reported to have activity in a rat model of bronchitis; Gordon et al., "Anti-inflammatory effects of a PDE4 inhibitor in a rat model of chronic bronchitis," Am. J. Respir. Crit. Care Med. 159 A33, 1999. Another such compound is related in structure to those reported in Perrier et al., "Substituted furans as inhibitors of the PDE4 enzyme," Bioorg. Med. Chem. Letts. 9 323–326, 1999, and is represented by Formula (0.0.35):

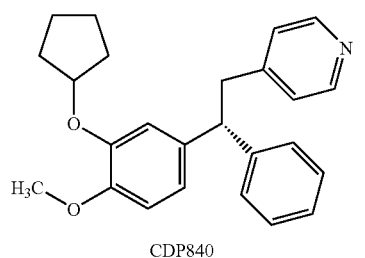

CDP840 (0.0.9)

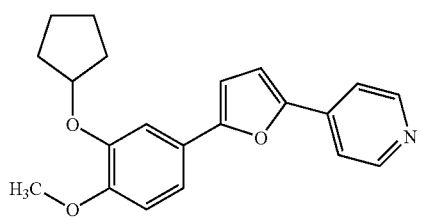

(0.0.35)

Other compounds which been found to be very potent PDE4 inhibitors are those represented by Formulas (0.0.36), (0.0.37), and (0.0.38):

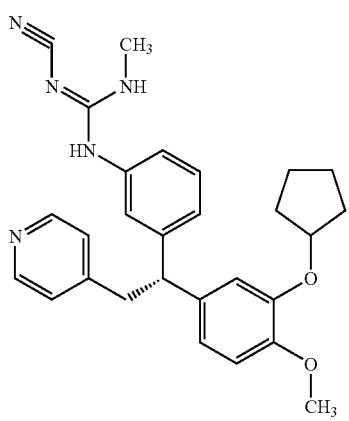

(0.0.36)

(0.0.37)

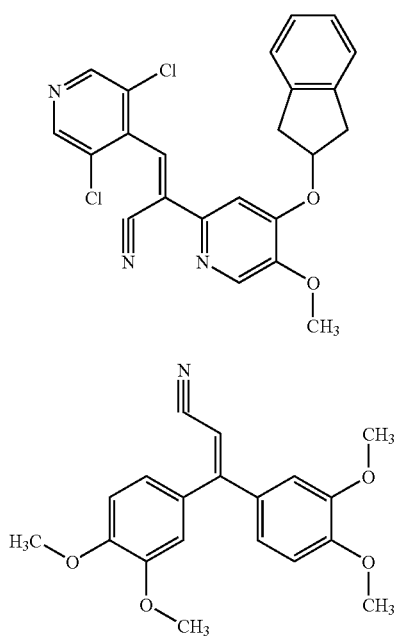

(0.0.38)

Compounds have been created which combine PDE4 and matrix metalloproteinase (MMP) inhibitory activity in a single molecule; Groneberg et al., "Dual inhibition of phosphodiesterase 4 and matrix metalloproteinases by an (arylsulfonyl)hydroxamic acid template," *J. Med. Chem.* 42(4) 541–544, 1999. Two examples of such compounds are represented by Formulas (0.0.39) and (0.0.40):

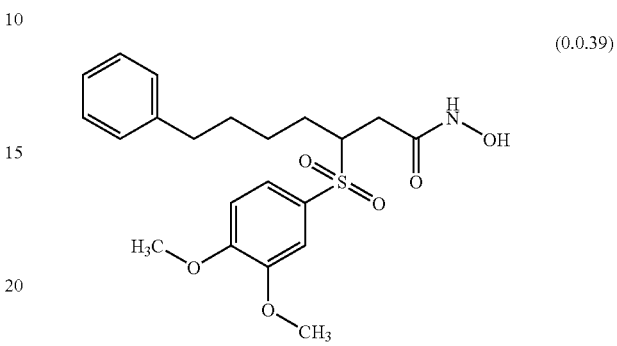

(0.0.39)

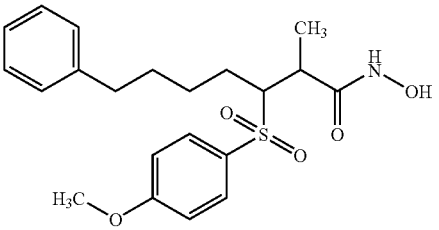

(0.0.40)

The respective $IC_{50}$ values for the compounds of Formulas (0.1.36) and (0.1.37) using a guinea-pig macrophage PDE4 assay were 1 nM and 30 nM.

The compounds identified as KF19514 and KF17625 have been shown in guinea-pig studies to have activity in the inhibition of the following: histamine-induced and antigen-induced bronchoconstriction; PAF-induced lung eosinophilia and antigen-induced BAL eosinophilia; acetylcholine (ACh)-induced AHR; PAF-induced BAL eosinophilia and neutrophilia, and AHR; antigen-induced bronchospasm; and anaphylactic bronchoconstriction; Fujimura et al., "Bronchoprotective effects of KF-19514 and cilostazol in guinea-pigs in vivo," *Eur. J. Pharmacol.* 327 57–63, 1997; Manabe et al., Ibid.; Manabe et al., "KF19514, a phosphodiesterase 4 and 1 inhibitor, inhibits PAF-induced lung inflammatory responses by inhaled administration in guinea-pigs," *Int. Arch. Allergy Immunol.* 114 389–399, 1997; Suzuki et al., "New bronchodilators. 3. Imidazo[4,5-c][1,8]naphthyridin-4(5H)-ones," *J. Med. Chem.* 35 4866–4874, 1992; Matsuura et al., "Substituted 1,8-naphthyridin-2(1H)-ones as selective phosphodiesterase IV inhibitors," *Biol. Pharm. Bull.* 17(4) 498–503, 1994; and Manabe et al., "Pharmacological properties of a new bronchodilator, KF17625," *Jpn. J. Pharmacol.* 58(Suppl. 1) 238P, 1992. KF19514 and KF17625 may be represented by Formulas (0.0.41) and (0.0.42):

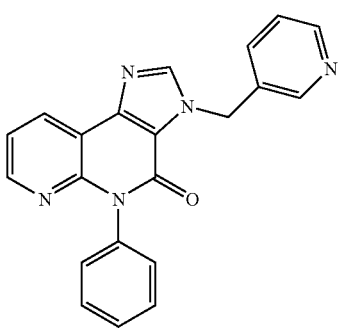

KF19514

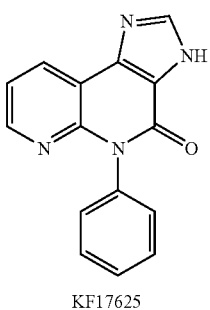

KF17625

The reported potency and lack of emesis in a series of indandiones suggests that the hypothesis that has related side-effects such as emesis to the ratio of affinity for the PDE4 enzyme relative to that for the high affinity rolipram binding site (HARBS) is erroneous. Such indandiones may be represented by Formulas (0.0.43) and (0.0.44):

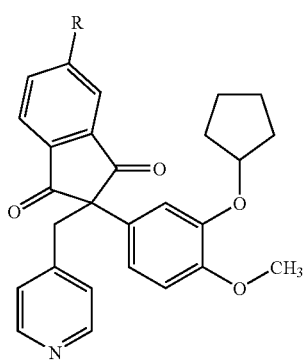

R = benzyloxy (0.0.43)
R = [1,4′]-piperidinyl-1′-carbonyloxy (0.0.44)

The PDE4 inhibitors that have been created heretofore fall into a significant number of different classes in terms of their chemical structures. Such classes have been as diverse as phenanthridines and naphthyridines. One class of PDE4 inhibitors are lignans such as T-440, which has been demonstrated to have activity in the inhibition of the following: early phase bronchoconstriction induced by antigen, histamine, LTD4, U-46619, Ach, neurokinin A, and endothelin-1; allergen-induced early phase and late phase bronchoconstriction and BAL eosinophilia; and ozone-induced AHR and airway epithelial injury. Optimization of the PDE4 inhibitory potency of such compounds has led to the discovery of T-2585, one of the most potent PDE4 inhibitors described to date with an $IC_{50}$ value of 0.13 nM against guinea-pig lung PDE4. T-440 and T-2585 may be represented by Formulas (0.0.45) and (0.0.46):

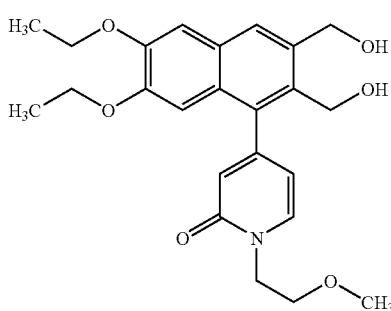

T-440

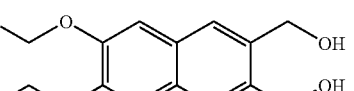
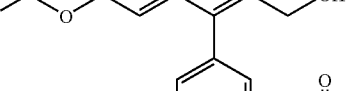
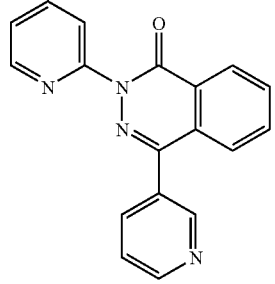

T-2585

Another class of PDE4 inhibitors consists of benzofurans and benzothiophenes. In particular, furan and chroman rings have been utilized as surrogates for the cyclopentylether of the rolipram pharmacophore. An example of such a compound is one that is apparently related in structure to BAY 19–8004, and which may be represented by Formula (0.0.47):

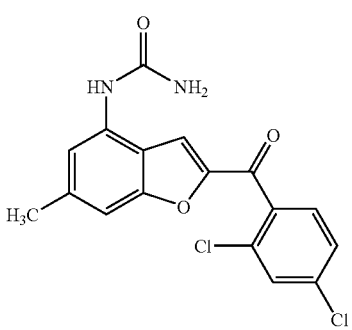

Another benzofuran-type compound has been reported to have an $IC_{50}$ value of 2.5 nM, and may be represented by Formula (0.0.48):

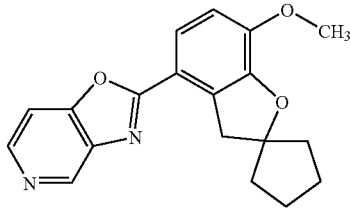

(0.0.48)

A compound with a related structure, which is not, however, a benzofuran, is characterized by a fused dioxicin ring and is reported to produce almost complete inhibition of canine tracheal PDE4 at 100 nM. This compound may be represented by Formula (0.0.49):

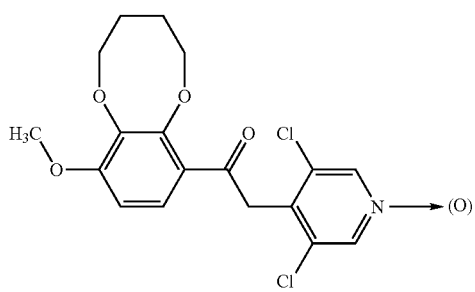

(0.0.49)

Quinolines and quinolones are a further class of PDE4 inhibitor structures, and they serve as surrogates for the catechol moiety of rolipram. This compound and two compounds of similar structure may be represented by Formulas (0.0.50), (0.0.51), and (0.0.52):

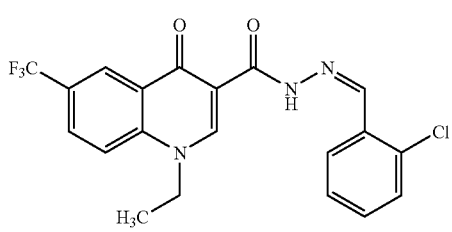

(0.0.50)

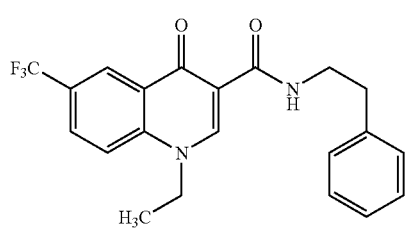

(0.0.51)

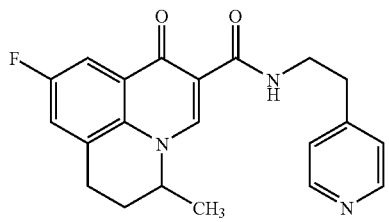

(0.0.52)

Purines, xanthines, and pteridines represent yet further classes of chemical compounds to which PDE4 inhibitors described heretofore in the art belong. The compound V-11294A described further above and represented by Formula (0.0.22), is a purine. A PDE4 inhibitor which is a xanthine compound, the class of compounds to which theophylline belongs, has been described in the art; Montana et al., "PDE4 inhibitors, new xanthine analogues," *Bioorg. Med. Chem. Letts.* 8 2925–2930, 1998. The xanthine compound may be represented by Formula (0.0.54):

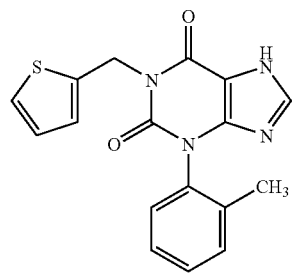

(0.0.54)

A potent PDE4 inhibitor belonging to the pteridine class of compounds has been demonstrated to have an $IC_{50}$ value of 16 nM against a PDE4 derived from tumor cells and to inhibit the growth of tumor cells at micromolar concentrations; Merz et al., "Synthesis of 7-Benzylamino-6-chloro-2-piperazino-4-pyrrolidinopteridine and novel derivatives free of positional isomers. Potent inhibitors of cAMP-specific phosphodiesterase and of malignant tumor cell growth," *J. Med. Chem.* 41(24) 4733–4743, 1998. The pteridine PDE4 inhibitor may be represented by Formula (0.0.55):

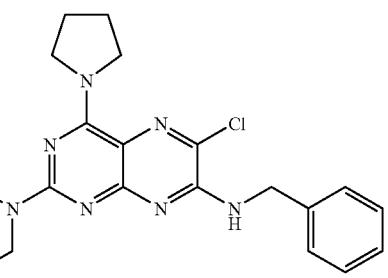

(0.0.55)

Triazines represent a still further class of chemical compounds to which PDE4 inhibitors belong that have been described in the art heretofore. Two such triazines have been described which display bronchodilator activity and are potent relaxant agents in a guinea-pig trachea model. These compounds, which may be represented by Formulas (0.0.56) and (0.0.57) below, are also moderately potent PDE4 inhibitors with $IC_{50}$ values of 150 and 140 nM, respectively:

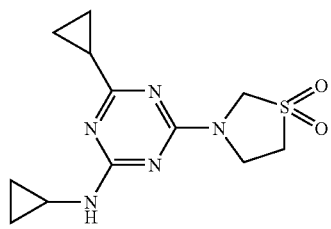

(0.0.56)

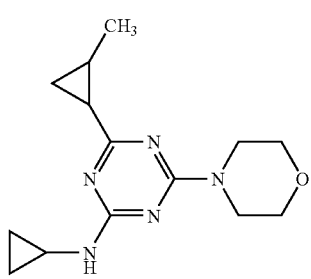

(0.0.57)

A triazine having a structure assumed to be closely related to that of the compounds of Formulas (0.0.56) and (0.0.57) is UCB-29936, which has been demonstrated to have activity in a murine model of septic shock; Danhaive et al., "UCB29936, a selective phosphodiesterase Type IV inhibitor: therapeutic potential in endotoxic shock," *Am. J. Respir. Crit. Care. Med.* 159 A611, 1999.

Efforts have also been made in the art to improve the selectivity of PDE4 inhibitors with respect to the A through D subtypes described further above. There are presently four known isoforms (subtypes) of the PDE4 isozyme, encompassing seven splice variants, also described further above. The PDE4D isoform mRNA is expressed in inflammatory cells such as neutrophils and eosinophils, and it has been suggested in the art that D-selective inhibitors of PDE4 will provide good clinical efficacy with reduced side-effects. A nicotinamide derivative displaying selectivity for inhibition of the PDE4D isoform has been described; WO 98/45268; as well as a naphthyridine derivative reported to be a PDE4D selective inhibitor; WO 98/18796. These compounds may be represented by Formulas (0.0.58) and (0.0.59), respectively:

(0.0.58)

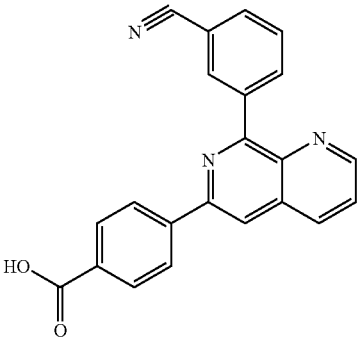

(0.0.59)

Another nicotinamide compound has been described in the art which may be useful in the treatment of CNS diseases such as multiple sclerosis; GB-2327675; and a rolipram derivative has been described in the art which is a PDE4 inhibitor which binds with equal affinity to both the catalytic and the HARB sites on human PDE4B2B; Tian et al., "Dual inhibition of human Type 4 phosphodiesterase isostates by (R,R)-(+/−)-methyl-3-acetyl-4-[3-(cyclopentyloxy)-4-methoxyphenyl]-3-methyl-1-pyrrolidine carboxylate," *Biochemistry* 37(19) 6894–6904, 1998. The nicotinamide derivative and the rolipram derivative may be represented by Formulas (0.0.60) and (0.0.61), respectively:

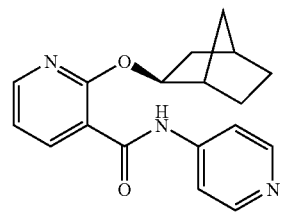

(0.0.60)

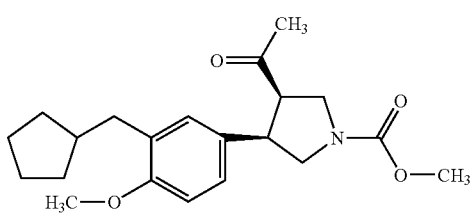

(0.0.61)

Further background information concerning selective PDE4 isozymes may be found in publications available in the art, e.g., Norman, "PDE4 inhibitors 1999," *Exp. Opin. Ther. Patents* 9(8) 1101–1118, 1999 (Ashley Publications Ltd.); and Dyke and Montana, "The therapeutic potential of PDE4 inhibitors," *Exp. Opin. Invest. Drugs* 8(9) 1301–1325, 1999 (Ashley Publications Ltd.).

3.0 DESCRIPTION OF THE STATE OF THE ART

WO 98/45268 (Marfat et al.), published Oct. 15, 1998, discloses nicotinamide derivatives having activity as selective inhibitors of PDE4D isozyme. These selective inhibitors are represented by Formula (0.1.1):

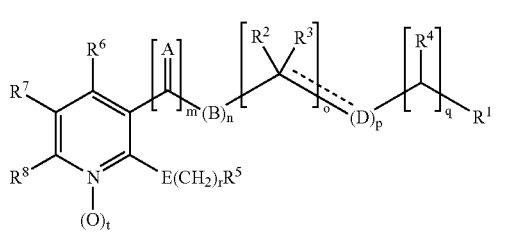

(0.1.1)

U.S. Pat. No. 4,861,891 (Saccomano et al.), issued Aug. 29, 1989, discloses nicotinamide compounds which function as calcium independent C-AMP phosphodiesterase inhibitors useful as antidepressants, of Formula (0.1.2):

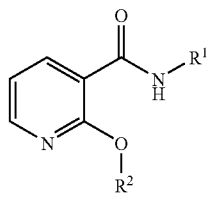

(0.1.2)

The nicotinamide nucleus of a typical compound disclosed in this patent is bonded directly to the $R^1$ group, which is defined as 1-piperidyl, 1-(3-indolyl)ethyl, $C_1$–$C_4$ alkyl, phenyl, 1-(1-phenylethyl), or benzyl optionally mono-substituted by methyl, methoxy, chloro or fluoro. The $R^2$ substituent is bicyclo[2.2.1]hept-2-yl or

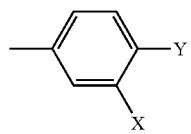

where Y is H, F or Cl; and X is H, F, Cl, $OCH_3$, $CF_3$, CN, COOH, —C(=O)($C_1$–$C_4$)alkoxy, $NH(CH_3)C$(=O)-(methylcarbamoyl) or $N(CH_3)_2C$(=O)-(dimethylcarbamoyl).

U.S. Pat. No. 4,692,185 (Michaely et al.) discloses herbicides such as those of Formula (0.1.3):

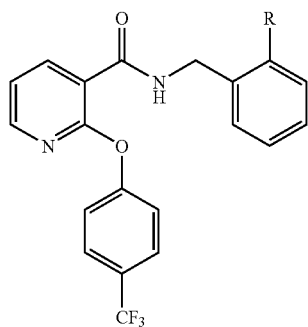

(0.1.3)

where R is ($C_1$–$C_4$)alkyl, ($C_1$–$C_4$)haloalkyl, or halo.

EP 550 900 (Jeschke et al.) discloses herbicides and plant nematicides of Formula (0.1.4):

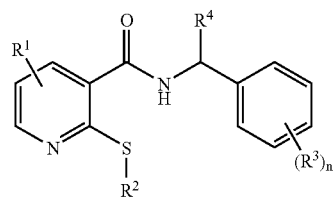

(0.1.4)

where n is 0–3; $R^1$ is selected from numerous groups, but is usually H, 6-$CH_3$, or 5-Cl; $R^2$ is alkyl, alkenyl, alkynyl, cycloalkyl, aryl or aralkyl; R1 and R2 is halo, CN, $NO_2$, alkyl, haloalkyl, alkoxy, haloalkoxy, alkylthio, haloalkylthio, alkylsulfonyl, haloalkylsulfonyl, aryl, aryloxy, or arylthio; and $R^4$ is alkyl.

EP 500 989 (Mollner et al.) discloses ACE inhibitors of Formula (0.1.5):

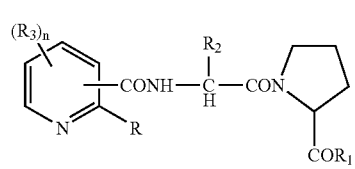

(0.1.5)

where n is 0–3; R is OH, SH, COOH, $NH_2$, halo, $OR_4$, $SR_4$, $COOR_4$, $NHR_4$ or $N(R_4)_2$, where $R_4$ is lower alkyl, optionally substituted aryl, or acyl; $R_1$ is OH, lower alkoxy, optionally substituted aryl lower alkoxy, aryloxy, or disubstituted amino; $R_2$ is lower alkyl or amino lower alkyl; and R1 and R2 is halo, $NO_2$, lower alkyl, halo lower alkyl, aryl lower alkyl, or aryl. Specific embodiments disclosed include compounds such as that of Formula (0.1.6):

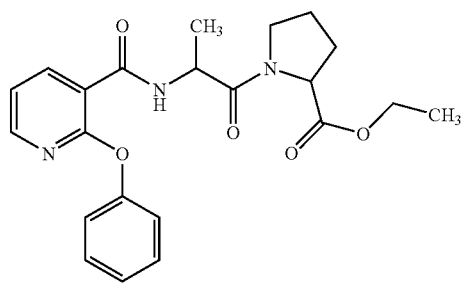

(0.1.6)

FR2.140.772 (Aries) discloses compounds asserted to have utility as analgesics, tranquilizers, antipyretics, antiinflammatories, and antirheumatics, of Formula (0.1.7):

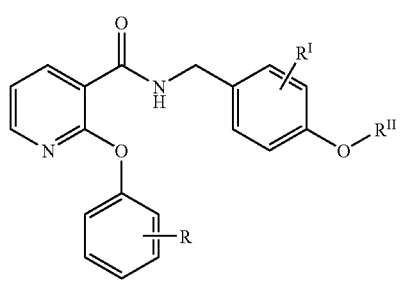

(0.1.7)

where R is 1 or 2 substituents chosen from lower alkyl, trihalomethyl, alkoxy, and halo; R' is H or alkyl; and R" is hydrogen or alkyl.

JP 07 304775 (Otsuka et al.) discloses naphthyridine and pyridopyrazine derivatives which have anti-inflammatory, immunomodulating, analgesic, antipyretic, antiallergic, and antidepressant action. Also disclosed are intermediates of Formula (0.1.8):

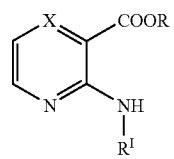
(0.1.8)

where X may be CH, and R and R' are each lower alkyl.

With regard to the disclosures of the above-identified patents and published patent applications, it will be appreciated that only the disclosure of WO 98/45268 (Marfat et al.) concerns the inhibition of PDE4 isozymes. The state of the art also contains information regarding compounds wholly dissimilar in chemical structure to those of Formula (1.0.0) of the present invention, but which, on the other hand, possess biological activity similar to that of the compounds of Formula (1.0.0). Representative patents and published patent applications disclosing said information are illustrated further below.

U.S. Pat. Nos. 5,552,438; 5,602,157; and 5,614,540 (all to Christensen), which all share the same Apr. 2, 1992 priority date, relate to a therapeutic agent identified as ARIFLO®, which is a compound of Formula (0.1.9) and named as indicated below:

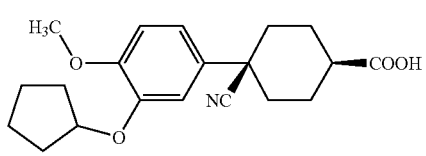
(0.1.9)

ARIFLO®
cis-[4-cyano-4-(3-cyclopentyl-oxy-4-methoxyphenyl)cyclo-hexane-1-carboxylic acid The compound of Formula (0.1.9) falls within the scope of U.S. Pat. No. 5,552,438 which discloses a genus of compounds of Formula (0.1.10):

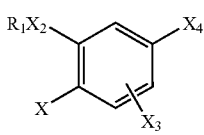
(0.1.10)

where $R_1=-(CR_4R_5)_rR_6$ where $r=0$ and $R_6=C_{3-6}$ cycloalkyl; $X=YR_2$ where $Y=O$ and $R_2=-CH_3$; $X_2=O$; $X_3=H$; and $X_4=$a moiety of partial Formula (0.1.10.1)

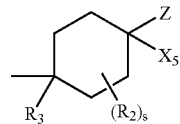
(0.1.10.1)

where $X_5=H$; $s=0$; $R_1$ and $R_2=CN$; and $Z=C(O)OR_{14}$ where $R_{14}=H$. The disclosures of U.S. Pat. Nos. 5,602,157 and 5,614,540 differ from that of U.S. Pat. No. 5,552,438 and each other as to the definition of the $R_3$ group, which in the case of the ARIFLO® compound, is CN. A preferred salt form of the ARIFLO® compound is disclosed to be the tris(hydroxymethyl)ammonium methane salt.

U.S. Pat. No. 5,863,926 (Christensen et al.,) discloses analogs of the ARIFLO® compound, e.g., that of Formula (0.1.11):

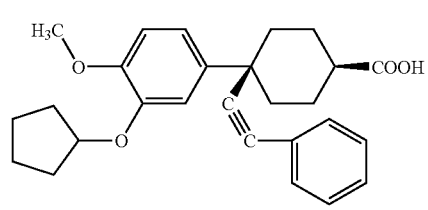
(0.1.11)

WO 99/18793 (Webb et al.) discloses a process of making the ARIFLO® and related compounds. WO 95/00139 (Barnette et al., claims a compound which has an $IC_{50}$ ratio of about 0.1 or greater as regards the $IC_{50}$ for the PDE IV catalytic form which binds rolipram with a high affinity, divided by the $IC_{50}$ for the form which binds rolipram with a low affinity; but in a dependent claim restricts the scope thereof to a compound which was not known to be a PDE4 inhibitor prior to Jun. 21, 1993.

WO 99/20625 (Eggleston) discloses crystalline polymorphic forms of cipamfylline for treatment of $PDE_4$ and TNF mediated diseases, of Formula (0.1.12):

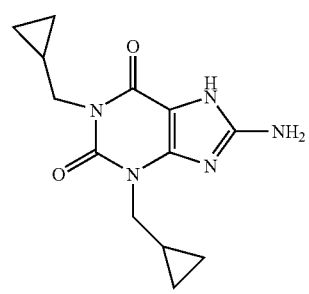
(0.1.12)

Cipamfylline

WO 99/20280 (Griswold et al.) discloses a method of treating pruritis by administering an effective amount of a PDE4 inhibitor, e.g., a compound of Formula (0.1.13):

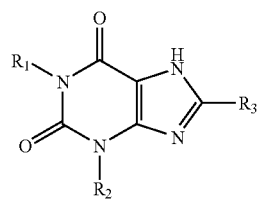
(0.1.13)

U.S. Pat. No. 5,922,557 (Pon) discloses a CHO-K1 cell line which stably expresses high levels of a full length low-Km cAMP specific PDE4A enzyme, which has, in turn, been used to examine potent PDE4 enzyme inhibitors and compare the rank order of their potencies in elevating cAMP in a whole-cell preparation with their ability to inhibit phosphodiesterase activity in a broken-cell preparation. It is further said to be found that the soluble enzyme inhibition assay described in the prior art does not reflect behavior of the inhibitors acting in vivo. An improved soluble enzyme whole-cell assay is then disclosed which is said to reflect the behavior of inhibitors acting in vivo. It is further disclosed that there exist at least four distinct PDE4 isoforms or subtypes, and that each subtype has been shown to give rise to a number of splice variants, which in themselves can exhibit different cellular localization and affinities for inhibitors.

With regard to the disclosures of the above-identified patents and published patent applications, it will be appreciated that the compounds involved possess the same biological activity as the compounds of Formula (1.0.0). At the same time, however, the artisan will observe that the chemical structures of said compounds disclosed in the prior art are not only diverse from each other but dissimilar to that of the novel compounds of the present invention as well. The state of the art contains still further information regarding compounds which are dissimilar in chemical structure to those of Formula (1.0.0), and which, moreover, do not possess PDE4 inhibitory activity similar to that of the compounds of Formula (1.0.0). Such compounds disclosed in the prior art do, nevertheless, often have therapeutic utility similar to that possessed by the compounds of Formula (1.0.0), i.e., in the treatment of inflammatory, respiratory and allergic diseases and conditions. In particular this is applicable to certain inhibitors of enzymes and antagonists of receptors in the so-called leukotriene pathway. This is especially the case with regard to the leukotrienes $LTB_4$ and $LTD_4$. Accordingly, representative patents and published patent applications disclosing further information of this type are described below.

Arachidonic acid is metabolized by cyclooxygenase-1 and by 5-lipoxygenase. The 5-lipoxygenase pathway leads to the production of leukotrienes (LTs) which contribute to the inflammatory response through their effect on neutrophil aggregation, degranulation and chemotaxis; vascular permeability; smooth muscle contractility; and on lymphocytes. The cysteinyl leukotrienes, $LTC_4$, $LTD_4$, and $LTE_4$, play an important role in the pathogenesis of asthma. The components of the leukotriene pathway which afford targets for therapeutic intervention are illustrated in the following diagram:

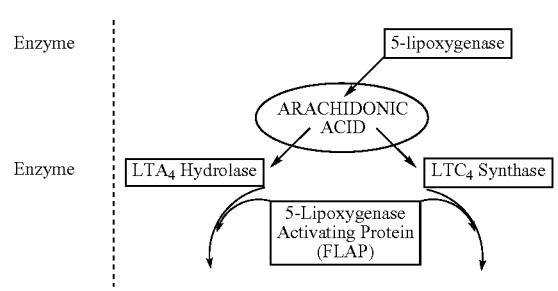

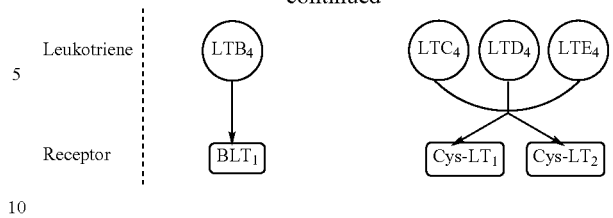

Accordingly, agents which are able to intervene in any of the steps of the 5-lipoxygenase pathway afford an opportunity for therapeutic treatment. An example of one such agent is the 5-lipoxygenase inhibitor, zileuton, a therapeutic agent identified as ZYFLO® which may be represented by Formula (0.1.14):

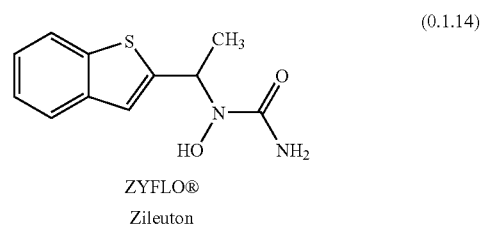

Another such agent is the $LTD_4$ receptor antagonist zafirlukast, a therapeutic agent identified as ACCOLATE® which may be represented by Formula (0.1.15):

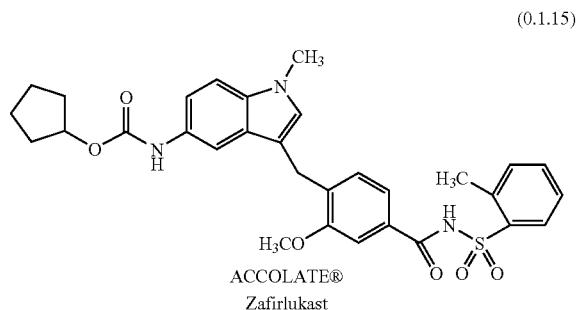

A further such $LTD_4$ receptor antagonist is montelukast, a therapeutic agent identified as SINGULAIR® which may be represented by Formula (0.1.16):

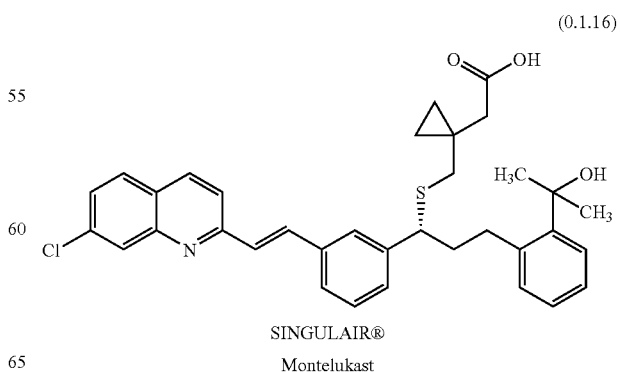

Another type of the above-mentioned therapeutic targets is the LTB$_4$ receptor, and an example of an antagonist for said receptor is BIIL-260, a therapeutic agent which may be represented by Formula (0.1.17):

(0.1.17)

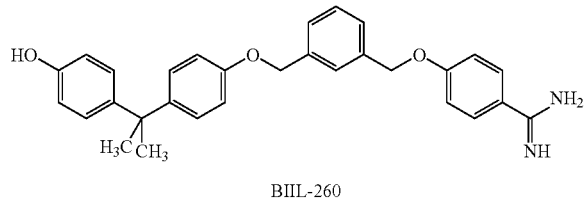

BIIL-260

Another example of a therapeutic agent which is an LTB$_4$ receptor antagonist is CGS-25019c which may be represented by Formula (0.1.18):

(0.1.18)

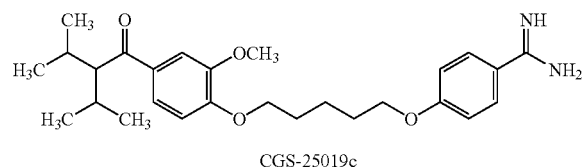

CGS-25019c

Nothing in the above-described state of the art discloses or would suggest to the artisan the novel compounds of the present invention or their PDE4 inhibitory activity and the resulting significant improvement in therapeutic utility and therapeutic index in the treatment of inflammatory, respiratory and allergic diseases and conditions.

4.0 SUMMARY OF THE INVENTION

The present invention is concerned with novel compounds which have biological activity as inhibitors of the phosphodiesterase so-called "Type IV" isoenzyme ("PDE4 isozyme"). Embodiments of the novel compounds of the present invention are active as non-selective inhibitors of the PDE4 isozyme. Other embodiments of said novel compounds have PDE4 isozyme substrate specificity, especially for the D subtype. Said novel compounds having non-selective or D-selective PDE4 inhibitor activity are generally useful in the therapeutic treatment of various inflammatory, allergic, and respiratory diseases and conditions, and they afford in particular a significant improvement in the therapeutic treatment of obstructive respiratory diseases, especially asthma and chronic obstructive pulmonary disease (COPD).

The present invention relates to a compound of Formula (1.0.0):

(1.0.0)

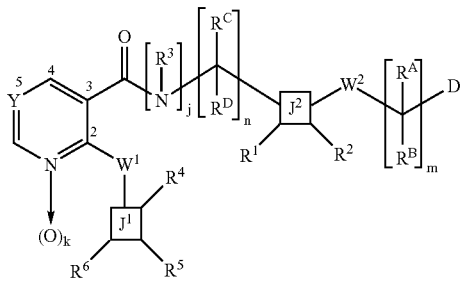

wherein j is 0 or 1; provided that when j is 0, n must be 2;

k is 0 or 1 m is 1, 2, or 3;

n is 1 or 2;

$W^1$ and $W^2$ are independently —O—; —S(═O)$_t$—, where t is 0, 1, or 2; or —N(R$^3$)— where R$^3$ has the same meaning as defined below;

Y is ═C(R$^1_a$)—, where R$^1_a$ has the same meaning as defined below; or —[N⇒(O)$_k$]— where k is 0 or 1;

where

R$^1_a$ is a member selected from the group consisting of —H; —F; —Cl; —CN; —NO$_2$; —(C$_1$–C$_4$)alkyl; —(C$_2$–C$_4$) alkynyl; fluorinated-(C$_1$–C$_3$)alkyl; fluorinated-(C$_1$–C$_3$) alkoxy; —OR$^{16}$; and —C(═O)NR$^{22}_a$R$^{22}_b$;

where

R$^{22}_a$ and R$^{22}_b$ are each independently —H; —CH$_3$; —CH$_2$CH$_3$; —CH$_2$CH$_2$CH$_3$; —CH$_2$(CH$_3$)$_2$; —CH$_2$CH$_2$CH$_2$CH$_3$; —CH(CH$_3$)CH$_2$CH$_3$; —CH$_2$CH (CH$_3$)$_2$; —C(CH$_3$)$_3$; cyclopropyl; cyclobutyl; or cyclopentyl;

R$^A$ and R$^B$ are each a member independently selected from the group consisting of —H; —F; —CF$_3$; —(C$_1$–C$_4$) alkyl; —(C$_3$–C$_7$)cycloalkyl; phenyl; and benzyl; wherein said cycloalkyl, phenyl, and benzyl moieties are each independently substituted with 0 to 3 substituents R$^{10}$;

where

R$^{10}$ is a member selected from the group consisting of phenyl; pyridyl; —F; —Cl; —CF$_3$; oxo (═O); —OR$^{16}$; —NO$_2$; —CN; —C(═O)OR$^{16}$; —O—C(═O)R$^{16}$; —C(═O)NR$^{16}$R$^{17}$; —O—C(═O)NR$^{16}$R$^{17}$; —NR$^{16}$R$^{17}$; —NR$^{16}$C(═O)R$^{17}$; —NR$^{16}$C(═O)OR$^{17}$; —NR$^{16}$S (═O)$_2$R$^{17}$; and —S(═O)$_2$NR$^{16}$R$^{17}$; where said phenyl or pyridyl is substituted by 0 to 3 R$^{11}$;

where

R$^{11}$ is —F; —Cl; —CF$_3$; —CN; —NO$_2$; —OH; —(C$_1$–C$_3$) alkoxy; —(C$_1$–C$_3$) alkyl; or —NR$^{16}$R$^{17}$;

and

R$^{16}$ and R$^{17}$ are each a member independently selected from the group consisting of —H; —(C$_1$–C$_4$) alkyl; —(C$_2$–C$_4$) alkenyl; —(C$_3$–C$_6$)cycloalkyl; phenyl; benzyl; and pyridyl; wherein said alkyl, alkenyl, cycloalkyl, phenyl, benzyl, or pyridyl is substituted by 0 to 3 substituents selected from the group consisting of —F, —Cl, —CF$_3$, —CN, and —(C$_1$–C$_3$)alkyl;

or

R$^A$ and R$^B$ are taken together, but only in the case where m is 1, to form a Spiro moiety of Formula (1.2.0):

(1.2.0)

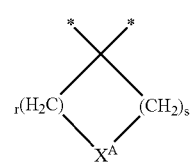

where r and s are independently 0 to 4 provided that the sum of r+s is at least 1 but not greater than 5;
and $X^A$ is selected from —$CH_2$—, —$CH(R^{11})$—, or $C(R^{11})_2$—, where each $R^{11}$ is selected independently of the other and each has the same meaning as defined above; —$NR^{15}$—, where $R^{15}$ has the same meaning as defined below; —O—; and —$S(=O)_t$—, where t is 0, 1, or 2;
and said spiro moiety of partial Formula (1.2.0) is substituted as to any one or more carbon atoms thereof, other than that defining $X^A$, by 0 to 3 substituents $R^{14}$, where $R^{14}$ has the same meaning as defined below; as to a nitrogen atom thereof by 0 or 1 substituent $R^{15}$, where $R^{15}$ has the same meaning as defined below; and as to a sulfur atom thereof by 0 or 2 oxygen atoms;

$R^C$ and $R^D$ have the same meaning as defined above for $R^A$ and $R^B$ except that one of them must be —H, and they are selected independently of each other and of $R^A$ and $R^B$;

$R^1$ and $R^2$ may individually or together appear on any ring or rings comprising a meaning of the moiety $*^2$ as defined below; and $R^1$ and $R^2$ are each a member independently selected from the group consisting of —H; —F; —Cl; —CN; —$NO_2$; —($C_1$–$C_4$)alkyl; —($C_2$–$C_4$)alkynyl; fluorinated-($C_1$–$C_3$)alkyl; —$OR^{16}$; and —$C(=O)NR^{22}_aR^{22}_b$; where $R^{16}$, $R^{22}_a$, and $R^{22}_b$ have the same meanings as defined above;

—$R^3$ is —H; —($C_1$–$C_3$)alkyl; phenyl; benzyl; or —$OR^{16}$, where $R^{16}$ has the same meaning as defined above;

$R^4$, $R^5$ and $R^6$ may individually or together appear on any ring or rings comprising a meaning of the moiety $*^1$ as defined below; and $R^4$, $R^5$ and $R^6$ are each a member independently selected from the group consisting of the following:

(a) —H; —F; —Cl; —($C_2$–$C_4$) alkynyl; —$R^{16}$; —$OR^{16}$; —$S(=O)_pR^{16}$; —$C(=O)R^{16}$; —$C(=O)OR^{16}$; —$OC(=O)R^{16}$; —CN; —$NO_2$; —$C(=O)NR^{16}R^{17}$; —$OC(=O)NR^{16}R^{17}$; —$NR^{22}_aC(=O)NR^{16}R^{17}$; —$NR^{22}_aC(=NR^{12})NR^{16}R^{17}$; —$NR^{22}_aC(=NCN)NR^{16}R^{17}$; —$NR^{22}_aC(=N—NO_2)NR^{16}R^{17}$; —$C(=NR^{22}_a)NR^{16}R^{17}$; —$CH_2C(=NR^{22}_a)NR^{16}R^{17}$; —$OC(=NR^{22}_a)NR^{16}R^{17}$; —$OC(=N—NO_2)NR^{16}R^{17}$; —$NR^{16}R^{17}$; —$CH_2NR^{16}R^{17}$; —$NR^{22}_aC(=O)R^{16}$; —$NR^{22}_aC(=O)OR^{16}$; =$NOR^{16}$; —$NR^{22}_aS(=O)_pR^{17}$—$S(=O)_pNR^{16}R^{17}$; and —$CH_2C(=NR^{22}_a)NR^{16}R^{17}$;
where p is 0, 1, or 2; and $R^{22}_a$, $R^{16}$, and $R^{17}$ have the same meanings as defined above;

(b) —($C_1$–$C_4$) alkyl; and —($C_1$–$C_4$) alkoxy in the case where one or more of $R^4$, $R^5$, or $R^6$ has the meaning of —$OR^{16}$ under (a) above and $R^{16}$ is defined as —($C_1$–$C_4$) alkyl; wherein said alkyl and alkoxy are each independently substituted with 0 to 3 substituents —F or —Cl; or 0 or 1 substituent ($C_1$–$C_2$) alkoxycarbonyl-; ($C_1$–$C_2$) alkylcarbonyl-; or ($C_1$–$C_2$) alkylcarbonyloxy-;
and (c) an aryl or heterocyclyl moiety selected from the group consisting of phenyl; benzyl; furanyl; tetrahydrofuranyl; oxetanyl; thienyl; tetrahydrothienyl; pyrrolyl; pyrrolidinyl; oxazolyl; oxazolidinyl; isoxazolyl; isoxazolidinyl; thiazolyl; thiazolidinyl; isothiazolyl; isothiazolidinyl; pyrazolyl; pyrazolidinyl; oxadiazolyl; thiadiazolyl; imidazolyl; imidazolidinyl; pyridinyl; pyrazinyl; pyrimidinyl; pyridazinyl; piperidinyl; piperazinyl; triazolyl; triazinyl; tetrazolyl; pyranyl; azetidinyl; morpholinyl; parathiazinyl; indolyl; indolinyl; benzo[b]furanyl; 2,3-dihydrobenzofuranyl; 2-H-chromenyl; chromanyl; benzothienyl; 1-H-indazolyl; benzimidazolyl; benzoxazolyl; benzisoxazolyl; benzthiazolyl; quinolinyl; isoquinolinyl; phthalazinyl; quinazolinyl; quinoxalinyl; and purinyl; wherein said aryl and heterocyclyl moieties are each independently substituted with 0 to 2 substituents $R^{14}$
where $R^{14}$ is a member selected from the group consisting of —($C_1$–$C_4$) alkyl; —($C_3$–$C_7$) cycloalkyl; phenyl; benzyl; pyridyl; and quinolinyl; where said alkyl, cycloalkyl, phenyl, benzyl, pyridyl, or quinolinyl is substituted by 0, 1, or 2 substituents —F, —Cl, —$CH_3$, —$OR^{16}$—$NO_2$, —CN, or —$NR^{16}R^{17}$; and said $R^{14}$ group further consists of —F; —Cl; —$CF_3$; oxo (=O); —$OR^{16}$; —$NO_2$; —CN; —$C(=O)OR^{16}$; —O—$C(=O)R^{16}$; —$C(=O)NR^{16}R^{17}$; —O—$C(=O)NR^{16}R^{17}$; —$NR^{16}R^{17}$; —$NR^{16}C(=O)R^{17}$; —$NR^{16}C(=O)OR^{17}$; —$NR^{16}S(=O)_2R^{17}$; or —$S(=O)_2NR^{16}R^{17}$; where $R^{16}$ and $R^{17}$ have the same meanings as defined above;

and further where $R^{15}$ is a member independently selected from the group consisting of —H; —$NR^{16}R^{17}$; —$C(=O)R^{16}$; —$OR^{16}$; —($C_1$–$C_4$) alkyl-$OR^{16}$; —$C(=O)OR^{16}$; —($C_1$–$C_2$) alkyl-$C(=O)OR^{16}$; —$C(=O)NR^{16}R^{17}$; —($C_1$–$C_4$) alkyl; —($C_2$–$C_4$) alkenyl; —$(CH_2)_u$—($C_3$–$C_7$) cycloalkyl where u is 0, 1 or 2; phenyl; benzyl; pyridyl; and quinolinyl; wherein said alkyl, alkenyl, alkoxy, cycloalkyl, phenyl, benzyl, pyridyl or quinolinyl is substituted with 0 to 3 substituents $R^{12}$; where $R^{16}$ and $R^{17}$ have the same meanings as defined above; and
where $R^{12}$ is a member independently selected from the group consisting of —F; —Cl; —$CO_2R^{18}$; —$OR^{16}$; —CN; —$C(=O)NR^{18}R^{19}$; —$NR^{18}R^{19}$; —$NR^{18}C(=O)R^{19}$; —$NR^{18}C(=O)OR^{19}$; —$NR^{18}S(=O)_pR^{19}$; —$S(=O)_pNR^{18}R^{19}$, where p is 1 or 2; —($C_1$–$C_4$) alkyl; and —($C_1$–$C_4$) alkoxy in the case where $R^{12}$ has the meaning of —$OR^{16}$ above and $R^{16}$ is defined as —($C_1$–$C_4$) alkyl; wherein said alkyl and alkoxy are each independently substituted with 0 to 3 substituents independently selected from —F; —Cl; —($C_1$–$C_2$) alkoxycarbonyl; —($C_1$–$C_2$) alkylcarbonyl; and —($C_1$–$C_2$) alkylcarbonyloxy; where $R^{16}$ has the same meaning as defined above; and
where $R^{18}$ and $R^{19}$ are independently selected from the group consisting of —H; —($C_1$–$C_4$) alkyl; and phenyl; where said alkyl or phenyl is substituted by 0–3 of —F; or —Cl;

or in the case where) $*^1$ is phenyl (d) $R^5$ and $R^6$ are taken together to form a moiety which is a member selected from the group consisting of partial Formulas (1.3.1) through (1.3.15):

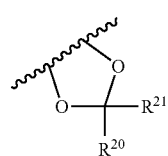

(1.3.1)

-continued (1.3.2) 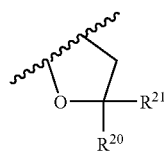

(1.3.3) 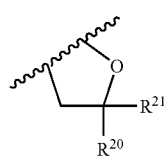

(1.3.4) 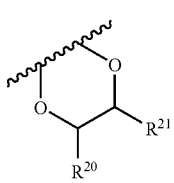

(1.3.5) 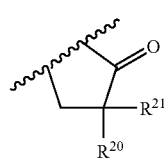

(1.3.6) 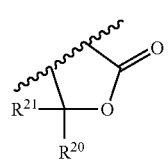

(1.3.7) 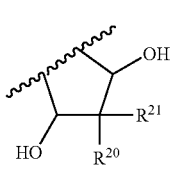

(1.3.8) 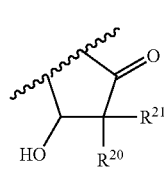

(1.3.9) 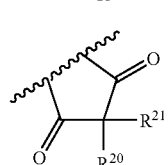

(1.3.10) 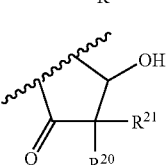

(1.3.11) 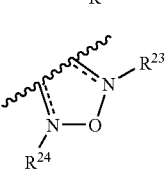

-continued (1.3.12) 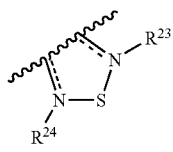

(1.3.13) 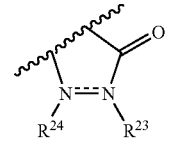

(1.3.14) 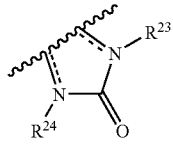

(1.3.15) 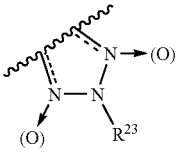

wherein $R^{20}$ and $R^{21}$ are each a member independently selected from the group consisting of —H; —F; —Cl; —CH$_3$; —CH$_2$F; —CHF$_2$; —CF$_3$; —OCH$_3$; and —OCF$_3$;

$R^{23}$ and $R^{24}$ are each independently —H; —CH$_3$; —OCH$_3$; —CH$_2$CH$_3$; —OCH$_2$CH$_3$; —CH$_2$CH$_2$CH$_3$; —CH$_2$(CH$_3$)$_2$; —CH$_2$CH$_2$CH$_2$CH$_3$; —CH(CH$_3$)CH$_2$CH$_3$: —CH$_2$CH(CH$_3$)$_2$; —C(CH$_3$)$_3$; or absent, in which case the dashed line - - - - represents a double bond;

$*^1$ is a moiety comprising a saturated or unsaturated carbon ring system that is a 3- to 7-membered monocyclic, or that is a 7- to 12-membered, fused polycyclic; provided that $*^1$ is not a discontinuous or restricted biaryl moiety; and wherein optionally one carbon atom of said carbon ring system may be replaced by a heteroatom selected from N, O, and S; where optionally a second carbon atom thereof, and further optionally a third carbon atom thereof may be replaced by N;

wherein said moiety defining $*^1$ is substituted on any ring or rings thereof by $R^4$, $R^5$ and $R^6$, which have the same meaning as defined above;

$*^2$ is a moiety comprising a saturated or unsaturated carbon ring system that is a 3- to 7-membered monocyclic, or that is a 7- to 12-membered, fused polycyclic; provided that $*^2$ is not a discontinuous or restricted biaryl moiety; and wherein optionally one carbon atom of said carbon ring system may be replaced by a heteroatom selected from N, O, and S; where optionally a second carbon atom thereof, and further optionally a third carbon atom thereof may be replaced by N;

wherein said moiety defining $*^2$ is substituted on any ring or rings thereof by $R^1$ and $R^2$, which have the same meaning as defined above;

D is a member independently selected from the group consisting of
the following
(a) the group consisting of partial Formulas (1.1.1) through (1.1.9):

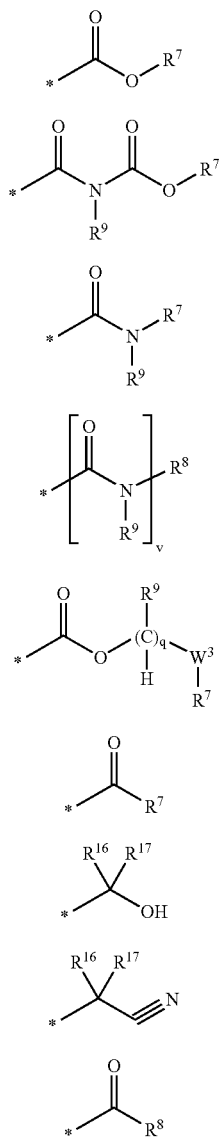

wherein
"*" indicates the point of attachment of each partial Formula (1.1.1) through (1.1.9) to the remaining portion of Formula (1.0.0);
q is 1, 2, or 3, provided that where q is 2 or 3, $R^9$ has the meaning of —H in at least one instance, or two instances, respectively;
v 0 or 1;
$W^3$ is —O—; —N($R^9$)—, where $R^9$ has the same meaning as defined below; or —OC(=O)—;
$R^7$ is a member independently selected from the group consisting of
the following:

(1) —H;
(2) —($C_1$–$C_6$) alkyl; —($C_2$–$C_6$) alkenyl; or —($C_2$–$C_6$) alkynyl; where said alkyl, alkenyl or alkynyl is substituted by 0 to 3 substituents $R^{10}$, where $R^{10}$ has the same meaning as defined above;
(3) —$(CH_2)_u$—($C_3$–$C_7$) cycloalkyl where u is 0, 1 or 2; and further where said ($C_3$–$C_7$) cycloalkyl is substituted by 0 to 3 substituents $R^{10}$ where $R^{10}$ has the same meaning as defined above;
and
(4) phenyl or benzyl, where said phenyl or benzyl is independently substituted by 0 to 3 substituents $R^{10}$ where $R^{10}$ has the same meaning as defined above; —
$R^8$ is a member independently selected from the group consisting of
the following:
(1) phenyl; tetrazol-5-yl; 1,2,4-triazol-3-yl; 1,2,4-triazol-3-on-5-yl; 1,2,3-triazol-5-yl; imidazol-2-yl; imidazol-4-yl; imidazolidin-2-on-4-yl; 1,3,4-oxadiazolyl; 1,3,4-oxadiazol-2-on-5-yl; 1,2,4-oxadiazol-3-yl; 1,2,4-oxadiazol-5-on-3-yl; 1,2,4-oxadiazol-5-yl; 1,2,4-oxadiazol-3-on-5-yl; 1,2,5-thiadiazolyl; 1,3,4-thiadiazolyl; morpholinyl; parathiazinyl; oxazolyl; isoxazolyl; thiazolyl; isothiazolyl; pyrrolyl; pyrazolyl; succinimidyl; glutarimidyl; pyrrolidonyl; 2-piperidonyl; 2-pyridonyl; 4-pyridonyl; pyridazin-3-onyl; pyridyl; pyrimidinyl; pyrazinyl; pyridazinyl;
and
(2) indolyl; indolinyl; isoindolinyl; benzo[b]furanyl; 2,3-dihydrobenzofuranyl; 1,3-dihydroisobenzofuranyl; 2H-1-benzopyranyl; 2-H-chromenyl; chromanyl; benzothienyl; 1H-indazolyl; benzimidazolyl; benzoxazolyl; benzisoxazolyl; benzothiazolyl; benzotriazolyl; benzotriazinyl; phthalazinyl; 1,8-naphthyridinyl; quinolinyl; isoquinolinyl; quinazolinyl; quinoxalinyl; pyrazolo[3,4-d]pyrimidinyl; pyrimido[4,5-d]pyrimidinyl; imidazo[1,2-a]pyridinyl; pyridopyridinyl; pteridinyl; and 1H-purinyl;
where
any moiety recited in (1) or (2) above is optionally substituted with respect to (i) any one or more carbon atoms thereof optionally by a substituent $R^{14}$ where $R^{14}$ has the same meaning as defined above; (ii) any one or more nitrogen atoms thereof that is not a point of attachment of said moiety, optionally by a substituent $R^{15}$ where $R^{15}$ has the same meaning as defined above, and all tautomer forms thereof; and (iii) any sulfur atom thereof that is not a point of attachment of said moiety, by 0, 1, or 2 oxygen atoms;
$R^9$ is a member selected from the group consisting of —H; —($C_1$–$C_4$) alkyl; —($C_3$–$C_7$) cycloalkyl; phenyl; benzyl; pyridyl; —C(=O)$OR^{16}$; —C(=O)$R^{16}$; —$OR^{16}$; —($C_1$–$C_2$) alkyl-$OR^{16}$; and —($C_1$–$C_2$) alkyl-C(=O)$OR^{16}$; where $R^{16}$ has the same meaning as defined above;
and D is further selected from
(b) a moiety comprising a member selected from the group consisting of —O—P(=O)(OH)$_2$ (phosphoric); —PH(=O)OH (phosphinic); —P(=O)(OH)$_2$ (phosphonic); —[P(=O)(OH)—O($C_1$–$C_4$) alkyl] (alkylphosphono); —P(=O)(OH)—O($C_1$–$C_4$) alkyl) (alkylphosphinyl); —P(=O)(OH)$NH_2$ (phosphoramido); —P(=O)(OH)NH($C_1$–$C_4$) alkyl and —P(=O)(OH)$NHR^{25}$ (substituted phosphoramido); —O—S(=O)$_2$OH (sulfuric); —S(=O)$_2$OH (sulfonic); —S(=O)$_2NHR_{26}$ or —NHS(=O)$_2R^{26}$ (sulfonamido) where $R^{26}$ is —$CH_3$, —$CF_3$, or o-toluyl; and acylsulfonamido selected from the group consisting of —C(=O)NHS(=O)$_2R^{25}$; —C(=O)NHS(=O)$_2NH_2$; —C(=O)NHS(=O)$_2$($C_1$–$C_4$) alkyl; —C(=O)NHS(=O)$_2$NH($C_1$–$C_4$) alkyl; —C(=O)NHS (=O)₂N[(C₁–C₄) alkyl]₂; —S(=O)₂NHC(=O)(C₁–C₄) alkyl; —S(=O)₂NHC(=O)NH₂; —S(=O)₂NHC(=O)NH(C₁–C₄) alkyl; —S(=O)₂NHC(=O)N[(C₁–C₄) alkyl]₂; —S(=O)₂NHC(=O)R²⁵; —S(=O)₂NHCN; —S(=O)₂NHC(=S)NH₂; —S(=O)₂NHC(=S)NH(C₁–C₄) alkyl; —S(=O)₂NHC(=S)N[(C₁–C₄) alkyl]₂; and —S(=O)₂ NHS(=O)₂R²⁵;

where

R²⁵ is —H; —(C₁–C₄) alkyl; phenyl; or —OR¹⁸ where R¹⁸ has the same meaning as defined above;

or a pharmaceutically acceptable salt thereof.

The present invention is concerned in particular with a compound of Formula (1.0.0) as above-recited wherein the moiety D comprises as a preferred meaning of R⁷, phenyl, benzyl, or cyclohexyl illustrated in partial Formulas (1.1.45) through (1.1.47) below; or the moiety D comprises R⁸ of partial Formula (1.1.4) where v is 0 or 1, comprising a member selected from the group consisting of partial Formulas (1.1.11) through (1.1.44) illustrated below:

(1.1.11) tetrazol-5-yl (1.1.12) 1,2,4-triazol-3-yl (1.1.13) 1,2,4-triazol-3-on-5-yl (1.1.14) 1,2,3-triazol-5-yl (1.1.15) imidazol-2-yl (1.1.16) imidazol-4-yl -continued (1.1.17) imidazolidin-2-on-4-yl (1.1.18) 1,3,4-oxadiazolyl (1.1.19) 1,3,4-oxadiazol-2-on-5-yl (1.1.20) 1,2,4-oxadiazol-3-yl (1.1.21) 1,2,4-oxadiazol-5-on-3-yl (1.1.22) 1,2,4-oxadiazol-5-yl (1.1.23) 1,2,4-oxadiazol-3-on-5-yl (1.1.24) 1,2,5-thiadiazol-2-yl (1.1.25) 1,3,4-thiadiazolyl (1.1.26) morpholin-3-yl -continued
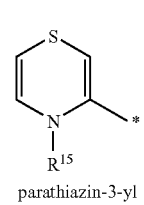
parathiazin-3-yl (1.1.27)
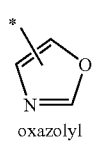
oxazolyl (1.1.28)
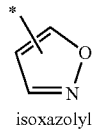
isoxazolyl (1.1.29)
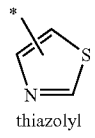
thiazolyl (1.1.30)
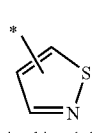
isothiazolyl (1.1.31)
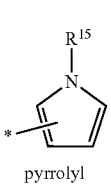
pyrrolyl (1.1.32)
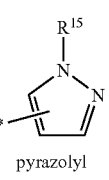
pyrazolyl (1.1.33)
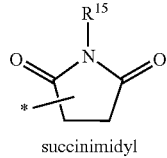
succinimidyl (1.1.34)
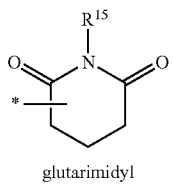
glutarimidyl (1.1.35)
-continued
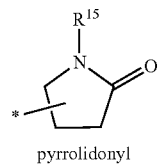
pyrrolidonyl (1.1.36)
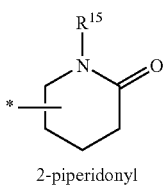
2-piperidonyl (1.1.37)
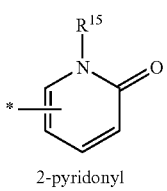
2-pyridonyl (1.1.38)
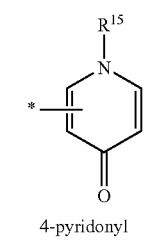
4-pyridonyl (1.1.39)
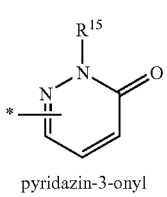
pyridazin-3-onyl (1.1.40)
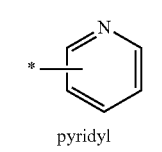
pyridyl (1.1.41)
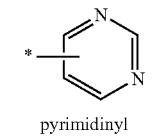
pyrimidinyl (1.1.42)
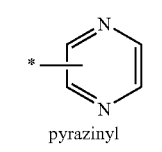
pyrazinyl (1.1.43)
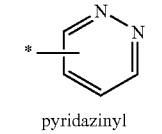
pyridazinyl (1.1.44)

-continued (1.1.45)

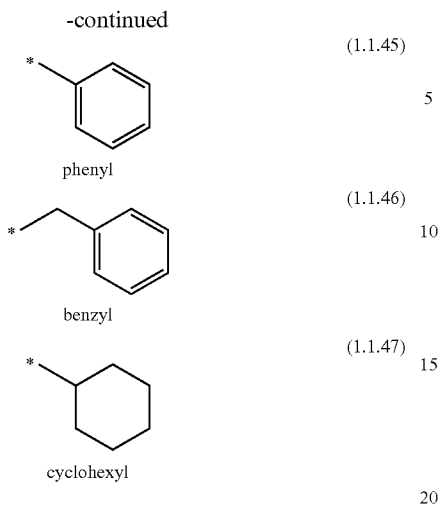

phenyl (1.1.46)

benzyl (1.1.47)

cyclohexyl wherein "*" indicates the point of attachment of each partial Formula (1.1.11) through (1.1.47) to the remaining portion of Formula (1.0.0); and wherein each carbon atom of partial Formulas (1.1.11) through (1.1.44) is optionally substituted by a substituent $R^{14}$; where $R^{14}$ and $R^{15}$ have the same meaning as defined above; and all tautomer forms, and optionally N-oxide forms, thereof; and further wherein each carbon atom of partial Formulas (1.1.45) through (1.1.47) is optionally substituted by a substituent $R^{10}$; where $R^{10}$ has the same meaning as defined above.

The present invention is further concerned more particularly with a compound of Formula (1.0.0) as above-recited wherein the moiety D is especially the below-indicated member selected from the above-recited group consisting of partial Formulas (1.1.11) through (1.1.47):

(1.1.11)

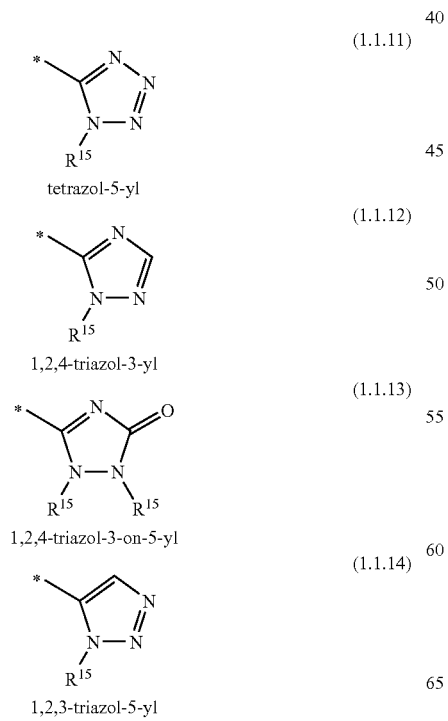

tetrazol-5-yl (1.1.12)

1,2,4-triazol-3-yl (1.1.13)

1,2,4-triazol-3-on-5-yl (1.1.14)

1,2,3-triazol-5-yl

-continued

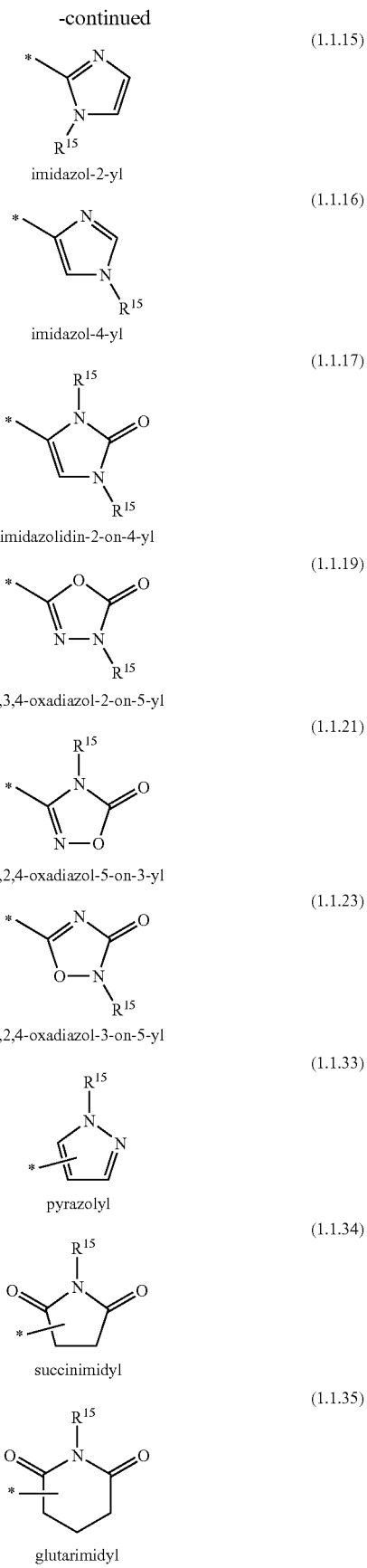

(1.1.15)

imidazol-2-yl (1.1.16)

imidazol-4-yl (1.1.17)

imidazolidin-2-on-4-yl (1.1.19)

1,3,4-oxadiazol-2-on-5-yl (1.1.21)

1,2,4-oxadiazol-5-on-3-yl (1.1.23)

1,2,4-oxadiazol-3-on-5-yl (1.1.33)

pyrazolyl (1.1.34)

succinimidyl (1.1.35)

glutarimidyl

-continued
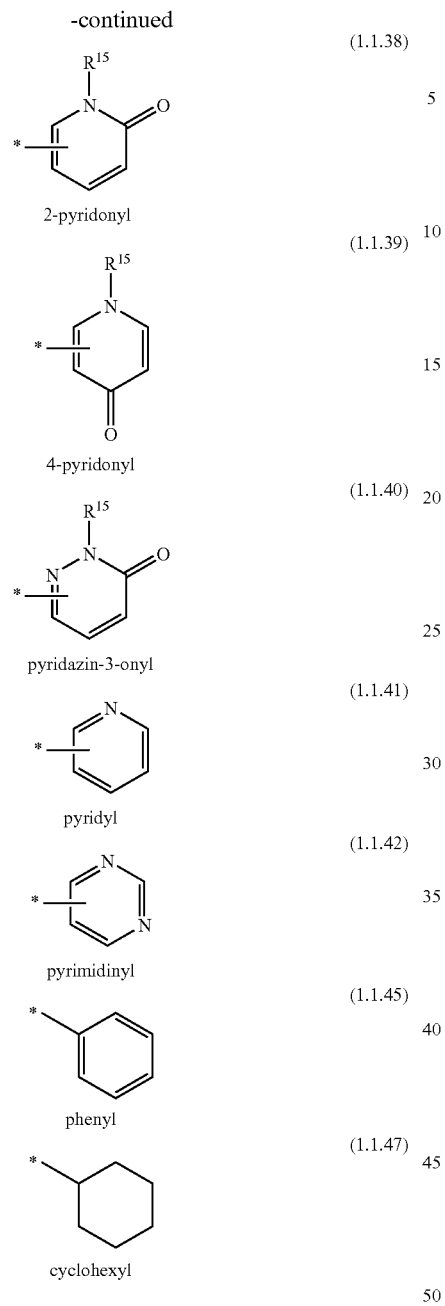
The present invention is further concerned in particular with a compound of Formula (1.0.0) as above-recited wherein the moiety D comprises $R^8$ of partial Formula (1.1.4) where v is 0 or 1, and $R^8$ of said partial Formula (1.1.4) is a member selected from the group consisting of partial Formulas (1.4.1) through (1.4.28):
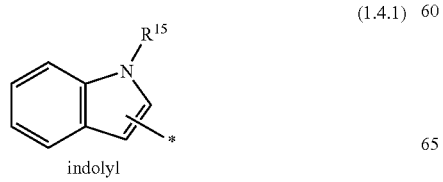
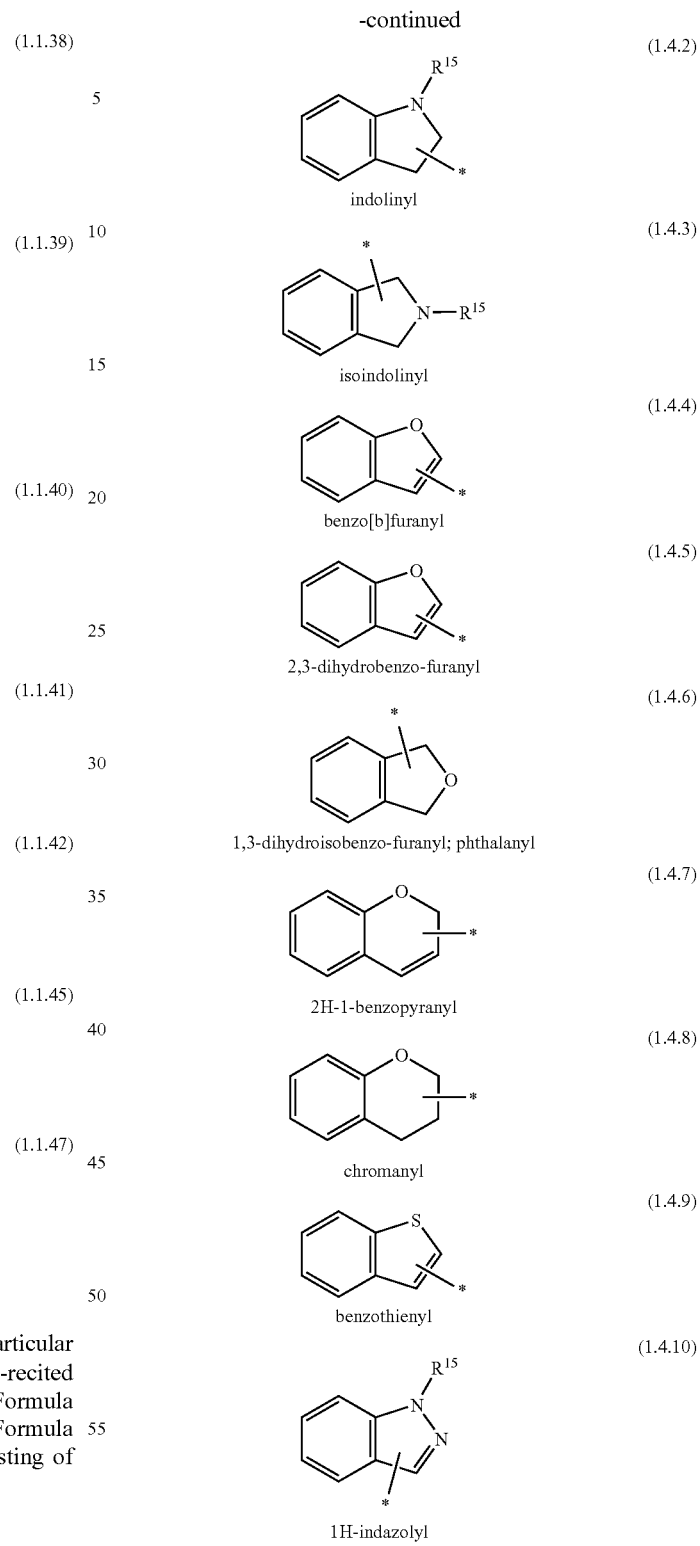
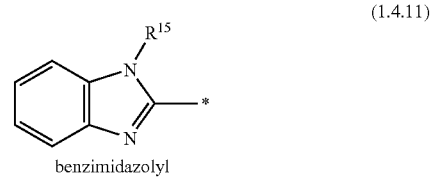

-continued (1.4.12) 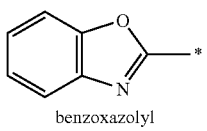
benzoxazolyl (1.4.13) 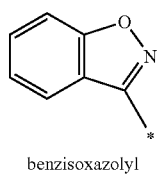
benzisoxazolyl (1.4.14) 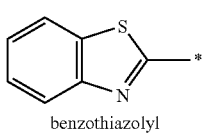
benzothiazolyl (1.4.15) 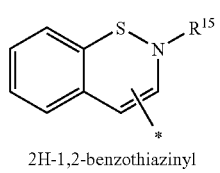
2H-1,2-benzothiazinyl (1.4.16) 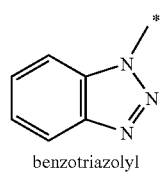
benzotriazolyl (1.4.17) 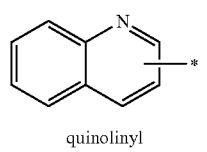
quinolinyl (1.4.18) 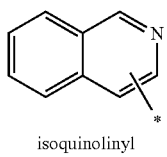
isoquinolinyl (1.4.19) 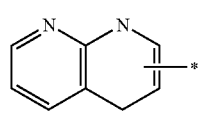
1,8-naphthyridinyl (1.4.20) 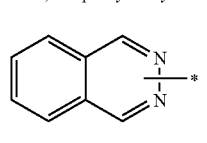
phthalazinyl (1.4.21) 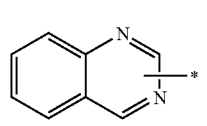
quinazolinyl -continued (1.4.22) 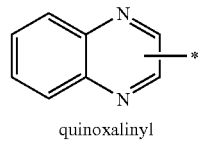
quinoxalinyl (1.4.23) 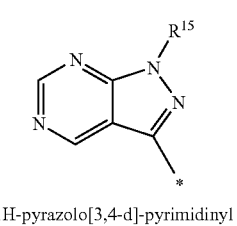
1H-pyrazolo[3,4-d]-pyrimidinyl (1.4.24) 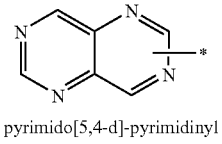
pyrimido[5,4-d]-pyrimidinyl (1.4.25) 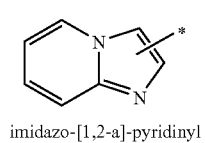
imidazo-[1,2-a]-pyridinyl (1.4.26) 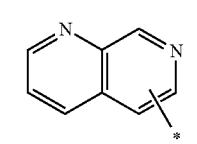
pyridopyridinyl (1.4.27) 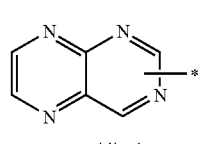
pteridinyl (1.4.28) 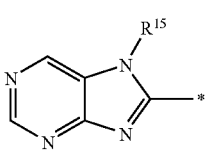
1H-purinyl where "*" indicates the point of attachment to the remaining portion of Formula (1.0.0); and where each carbon atom is optionally substituted by a substituent $R^{14}$; and where $R^{14}$ and $R^{15}$ have the same meaning as defined above; and all tautomer forms, and optionally N-oxide forms, thereof.

The present invention is further concerned with a compound of Formula (1.0.0) wherein $*^1$ comprises especially a member selected from the group consisting of phenyl; pyrrolyl; pyrrolidinyl; furanyl; thienyl; pyridyl; pyrimidinyl; piperidinyl; piperazinyl; imidazolyl; imidazolidinyl; oxazolyl; isoxazolyl; morpholinyl; thiazolyl; indolyl; quinolinyl; isoquinolinyl; benzimidazolyl; benzoxazolyl; quinuclidinyl; and azabicyclo[3.3.0]octanyl; a monocyclic $—(C_3—C_7)$ cycloalkyl moiety; a monocyclic $—(C_5—C_7)$ cycloalkenyl moiety that is a member selected from the group consisting of cyclopentenyl, cyclohexenyl, and cycloheptenyl; and a bicyclic —(C7–C10) cycloalkyl or —(C7–C10) cycloalkenyl moiety that is a member selected from the group consisting of norbornanyl, norbornenyl, bicyclo[2.2.2]octanyl, bicyclo[3.2.1]octanyl, bicyclo[3.3.0]octanyl, bicyclo[2.2.2]oct-5-enyl, bicyclo[2.2.2]oct-7-enyl, bicyclo[3.3.1]nonanyl, cyclodecanyl, and adamantanyl.

The present invention is still further concerned especially with a compound of Formula (1.0.0) wherein particularly *[1] and the substituents $R^4$, $R^5$, and $R^6$ are selected in such a way that the left-hand terminus of said compound of Formula (1.0.0) is represented by the following partial Formulas (2.0.1) through (2.0.72):

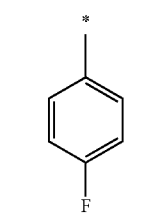
(2.0.1)

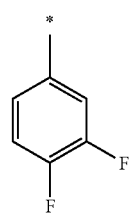
(2.0.2)

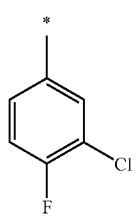
(2.0.3)

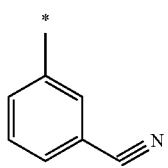
(2.0.4)

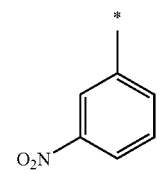
(2.0.5)

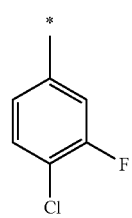
(2.0.6)

-continued

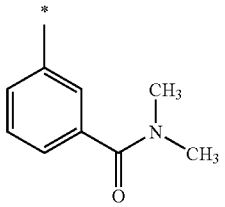
(2.0.7)

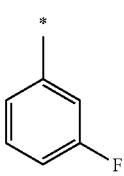
(2.0.8)

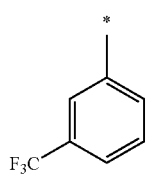
(2.0.9)

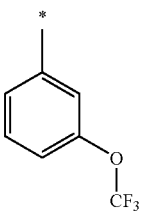
(2.0.10)

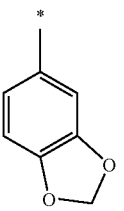
(2.0.11)

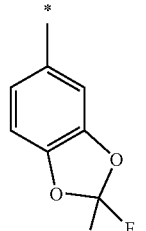
(2.0.12)

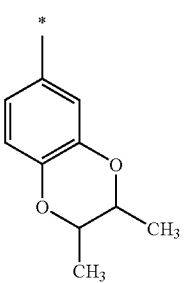
(2.0.13)

-continued
(2.0.14)
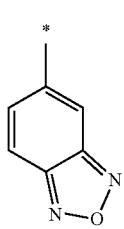
(2.0.15)
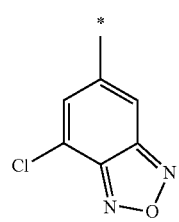
(2.0.16)
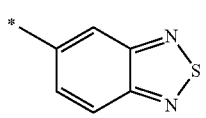
(2.0.17)
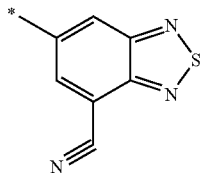
(2.0.18)
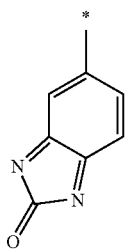
(2.0.19)
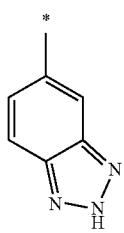
(2.0.20)
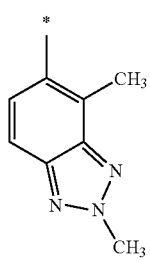
-continued
(2.0.21)
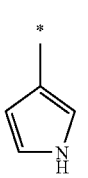
(2.0.22)
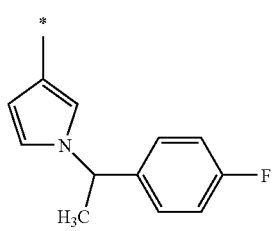
(2.0.23)
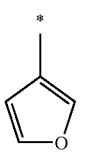
(2.0.24)
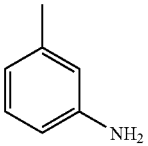
(2.0.25)
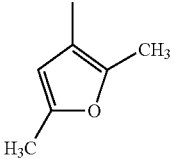
(2.0.26)
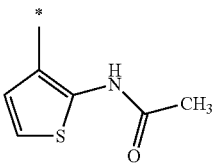
(2.0.27)
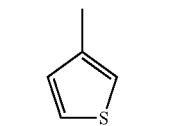
(2.0.28)
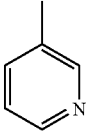
(2.0.29)
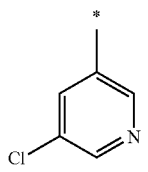

-continued
(2.0.30)
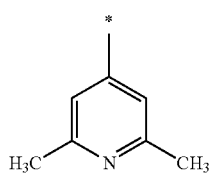
(2.0.31)
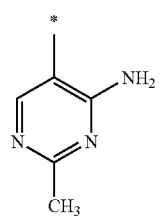
(2.0.32)
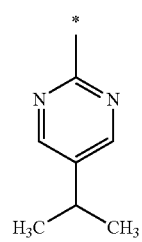
(2.0.33)
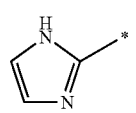
(2.0.34)
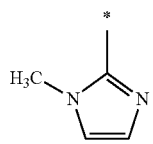
(2.0.35)
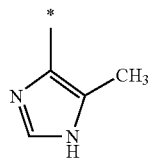
(2.0.36)
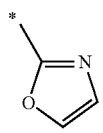
(2.0.37)
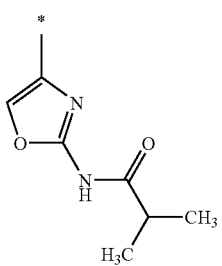
-continued
(2.0.38)
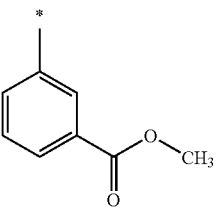
(2.0.39)
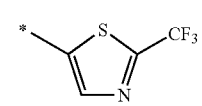
(2.0.40)
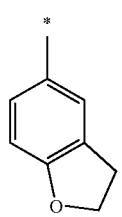
(2.0.41)
(2.0.42)
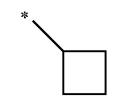
(2.0.43)
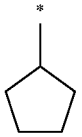
(2.0.44)
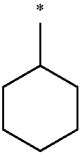
(2.0.45)
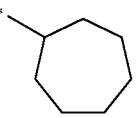
(2.0.46)
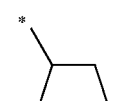
(2.0.47)
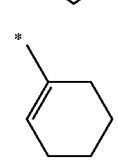
(2.0.48)
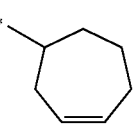

-continued
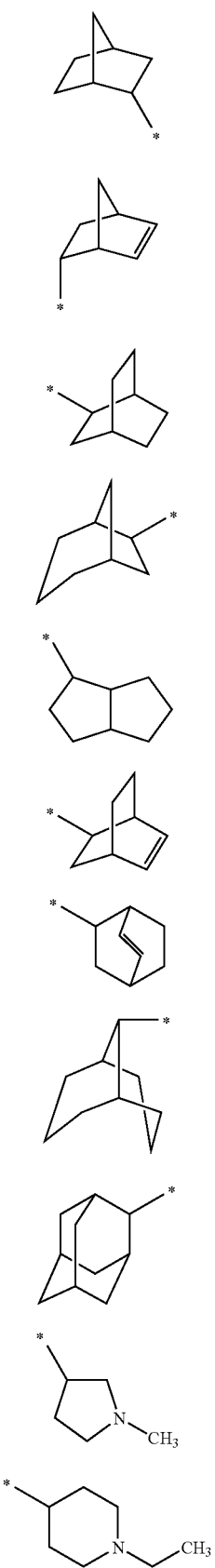
(2.0.49)
(2.0.50)
(2.0.51)
(2.0.52)
(2.0.53)
(2.0.54)
(2.0.55)
(2.0.56)
(2.0.57)
(2.0.58)
(2.0.59)
-continued
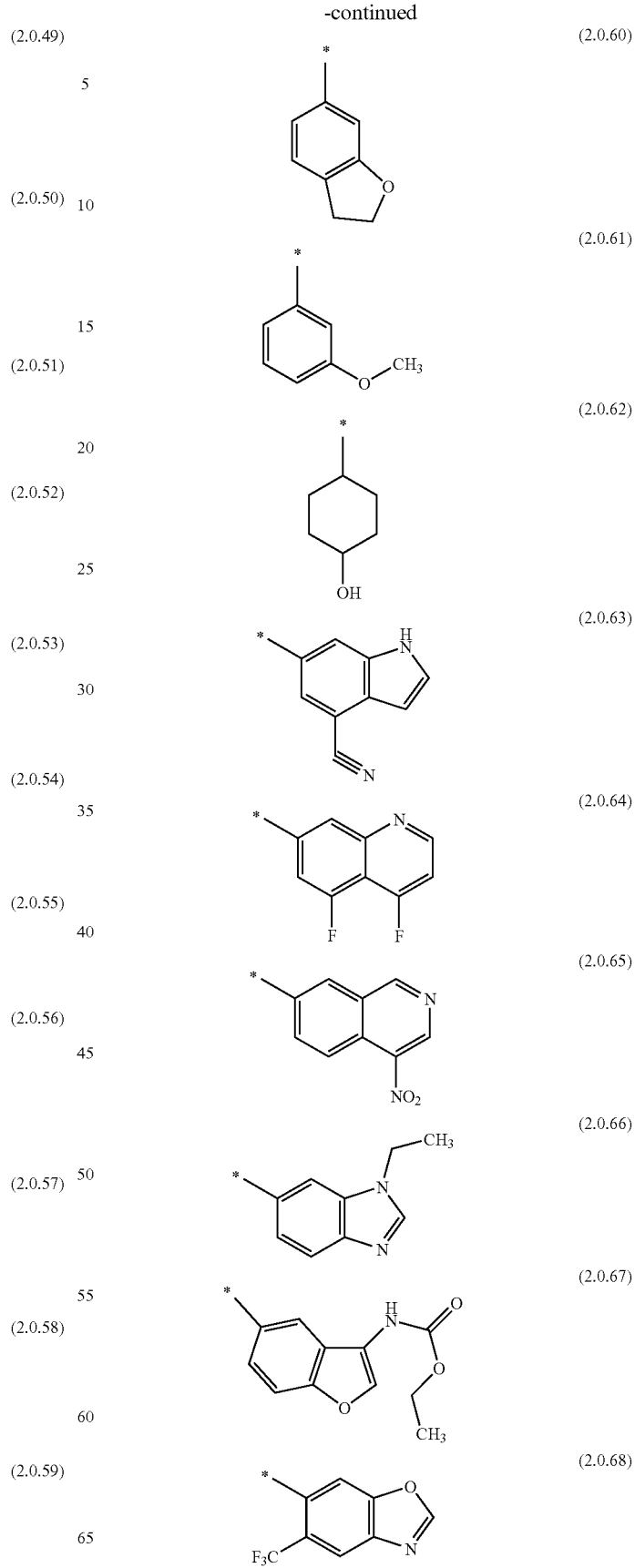
(2.0.60)
(2.0.61)
(2.0.62)
(2.0.63)
(2.0.64)
(2.0.65)
(2.0.66)
(2.0.67)
(2.0.68)

-continued

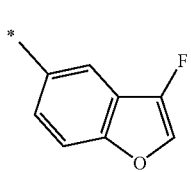
(2.0.69)

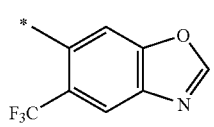
(2.0.70)

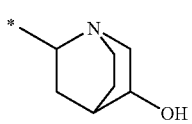
(2.0.71)

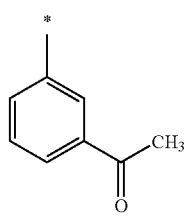
(2.0.72)

The present invention is further concerned with a compound of Formula (1.0.0) wherein *² comprises especially a member selected from the group consisting of phenyl; pyrrolyl; pyrrolidinyl; furanyl; thienyl; pyridyl; pyrimidinyl; piperidinyl; piperazinyl; imidazolyl; imidazolidinyl; oxazolyl; isoxazolyl; thiazolyl; indolyl; quinolinyl; isoquinolinyl; benzimidazolyl; benzoxazolyl; morpholinyl; quinuclidinyl; and azabicyclo[3.3.0]octanyl; a monocyclic —($C_3$–$C_7$) cycloalkyl moiety; a monocyclic —($C_5$–$C_7$) cycloalkenyl moiety that is a member selected from the group consisting of cyclopentenyl, cyclohexenyl, and cycloheptenyl; and a bicyclic —($C_7$–$C_{10}$) cycloalkyl or —($C_7$–$C_{10}$) cycloalkenyl moiety that is a member selected from the group consisting of norbornanyl, norbornenyl, bicyclo[2.2.2]octanyl, bicyclo[3.2.1]octanyl, bicyclo[3.3.0]octanyl, bicyclo[2.2.2]oct-5-enyl, bicyclo[2.2.2]oct-7-enyl, bicyclo[3.3.1]nonanyl, cyclodecanyl, and adamantanyl.

The present invention is also further concerned especially with a compound of Formula (1.0.0) wherein particularly *² and the substituents $R^1$ and $R^2$ are selected in such a way that this portion of the right-hand terminus of said compound of Formula (1.0.0) is represented by the following partial Formulas (2.5.1) through (2.5.50) set out below.

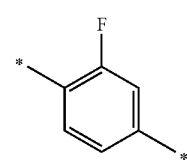
(2.5.1)

-continued

(2.5.2)

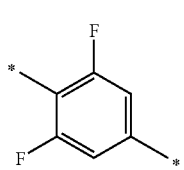
(2.5.3)

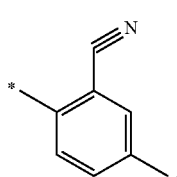
(2.5.4)

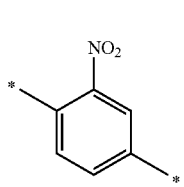
(2.5.5)

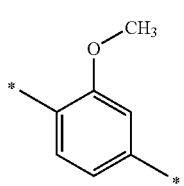
(2.5.6)

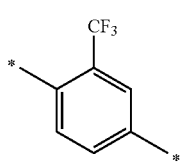
(2.5.7)

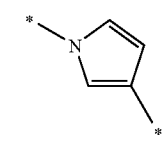
(2.5.8)

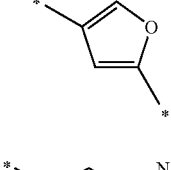
(2.5.9)

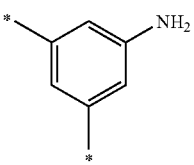
(2.5.10)

-continued
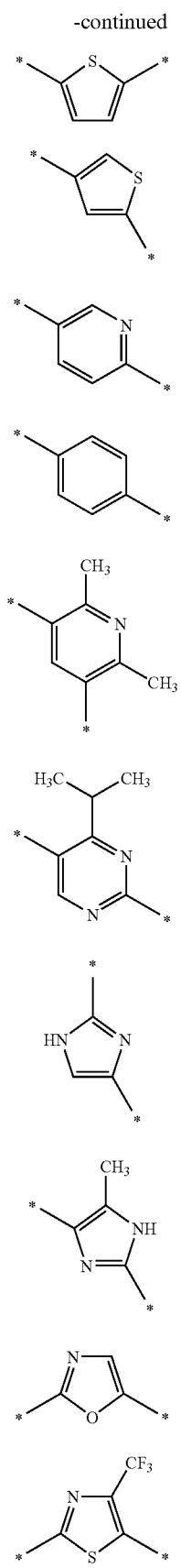
(2.5.11)
(2.5.12)
(2.5.13)
(2.5.14)
(2.5.15)
(2.5.16)
(2.5.17)
(2.5.18)
(2.5.19)
(2.5.20)
-continued
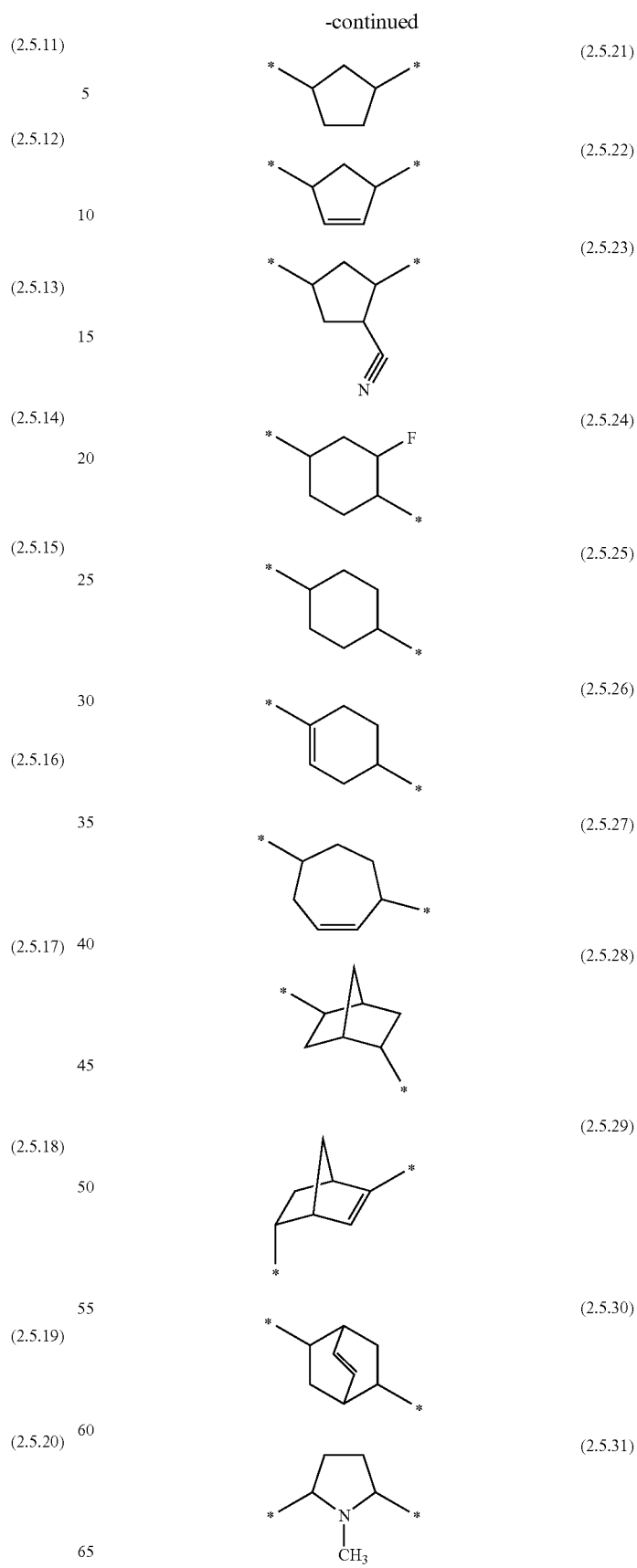
(2.5.21)
(2.5.22)
(2.5.23)
(2.5.24)
(2.5.25)
(2.5.26)
(2.5.27)
(2.5.28)
(2.5.29)
(2.5.30)
(2.5.31)

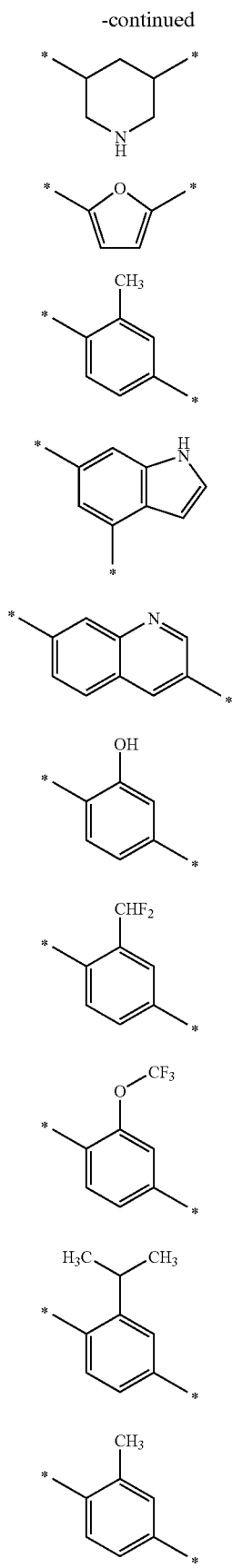
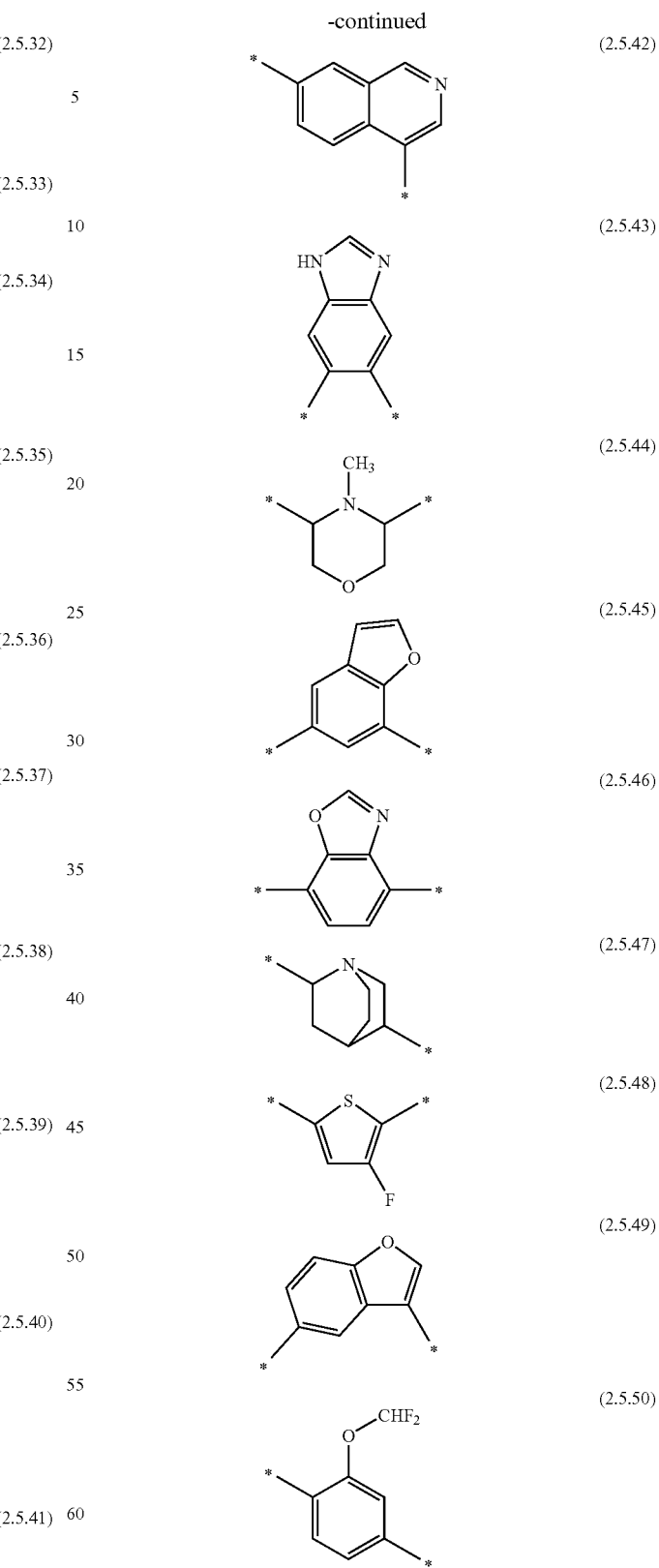
The present invention is still further concerned with a compound of Formula (1.0.0) characterized as to the right-hand side thereof, where m is 1, by partial Formula (1.0.5):

(1.0.5)

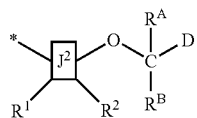

where "*" is a symbol representing the point of attachment of the group of partial Formula (1.0.5) to the remaining portion of a compound of Formula (1.0.0) where $R^A$ and $R^B$ are both —H, or one is —H and the other is —$CH_3$, or both are —$CH_3$, or both are taken together to form spiro-cyclopropyl or spiro-cyclobutyl; $R^1$ is —H, —$OCH_3$, or 2'-F; $R^2$ is —H; and the moieties $*^2$ and D are selected such that, said group of partial Formula (1.0.5) is a member selected from the group consisting of partial Formulas (1.5.1) through (1.5.54), as set out below. Where the moiety $*^2$ is phenyl, the 2'-position thereof is located as indicated in partial Formula (1.5.1):

(1.5.1)

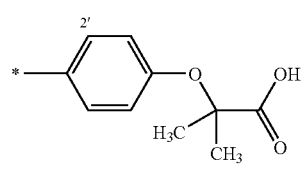

(1.5.2)

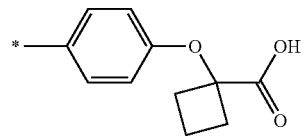

(1.5.3)

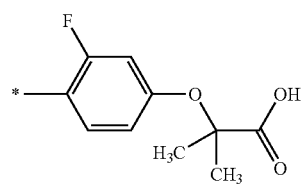

(1.5.4)

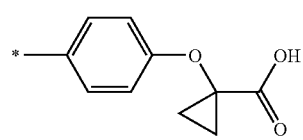

(1.5.5)

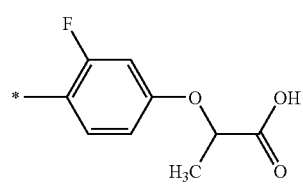

(1.5.6)

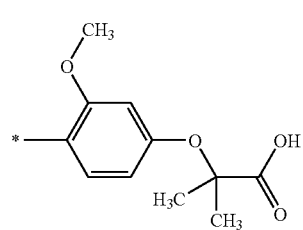

-continued (1.5.7)

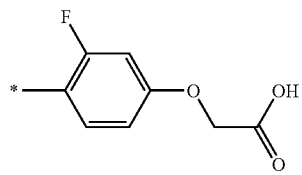

(1.5.8)

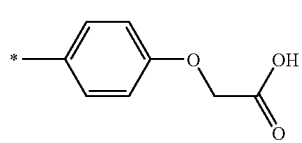

(1.5.9)

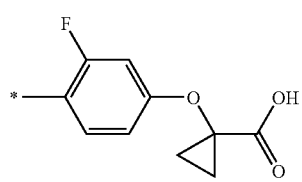

(1.5.10)

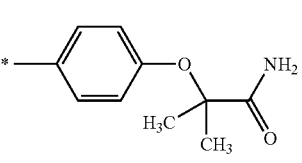

(1.5.11)

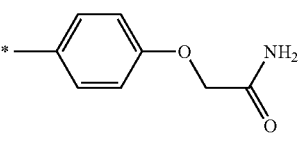

(1.5.12)

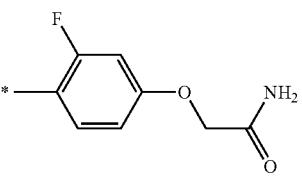

(1.5.13)

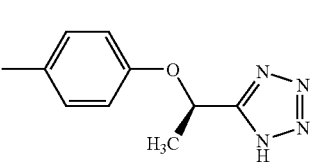

(1.5.14)

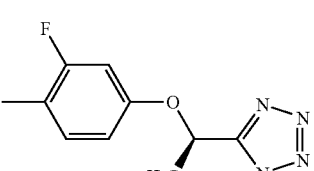

(1.5.15)

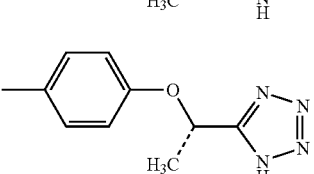

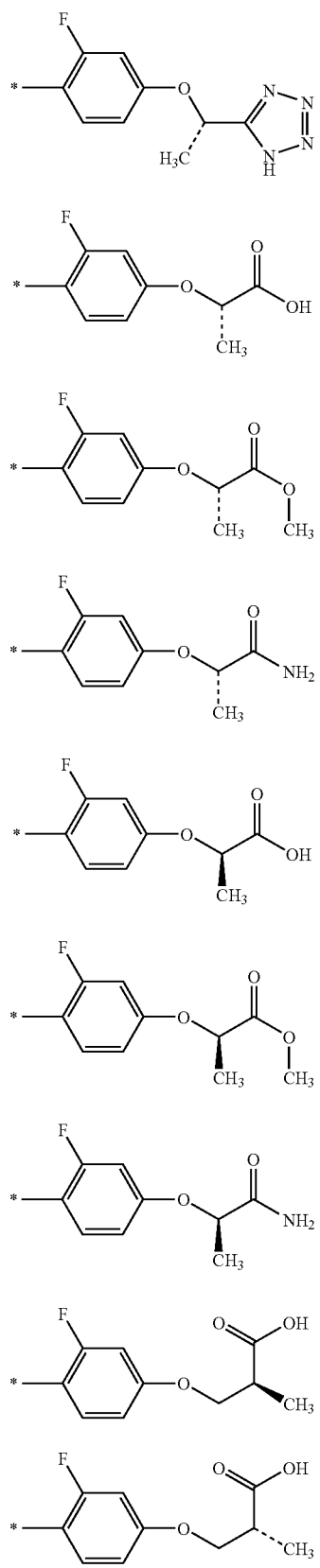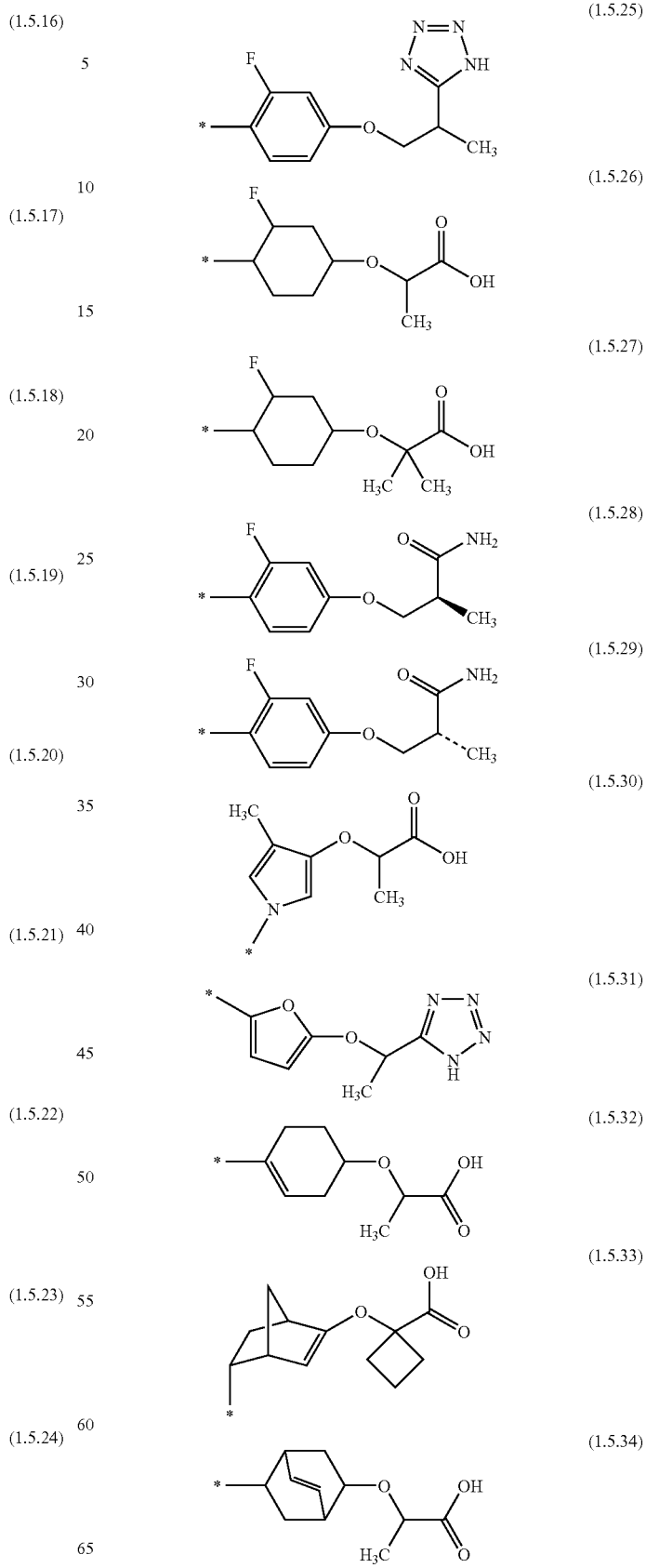

-continued
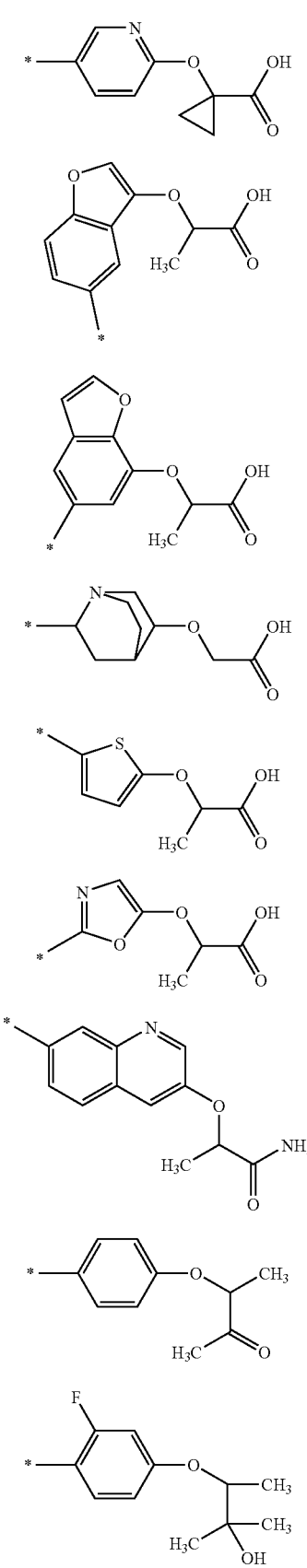
(1.5.35)
(1.5.36)
(1.5.37)
(1.5.38)
(1.5.39)
(1.5.40)
(1.5.41)
(1.5.42)
(1.5.43)
-continued
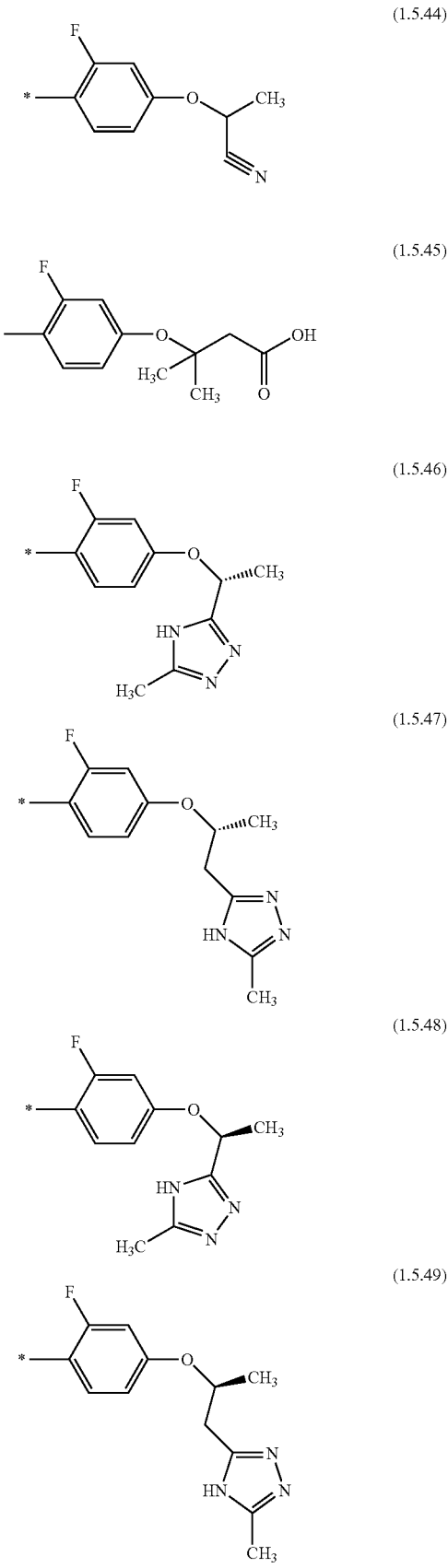
(1.5.44)
(1.5.45)
(1.5.46)
(1.5.47)
(1.5.48)
(1.5.49)

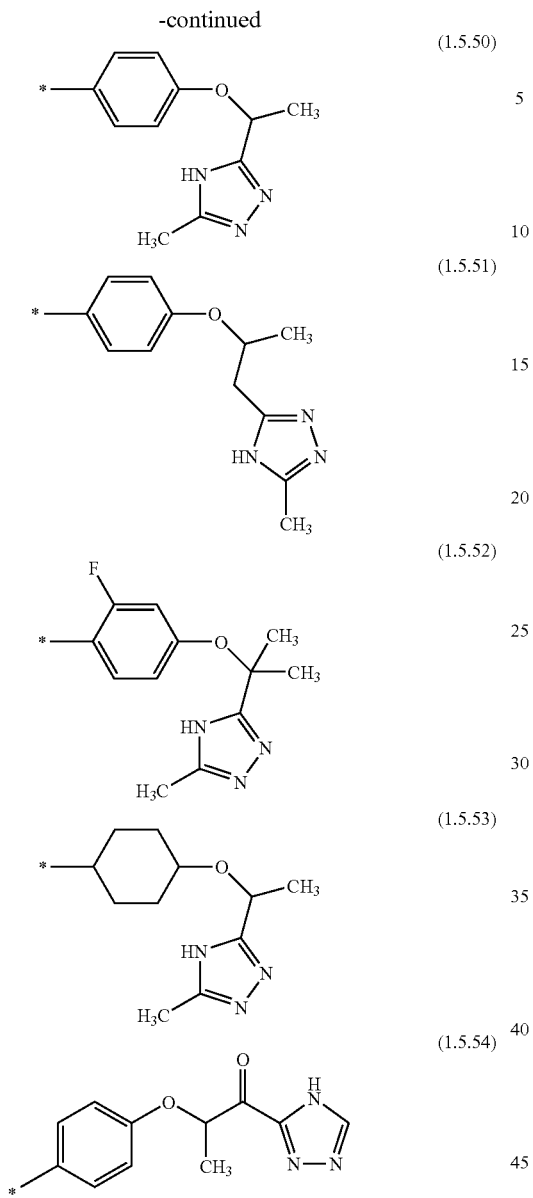

wherein

"*" indicates the point of attachment of each said group of partial Formula (1.0.5) represented by partial Formulas (1.5.1) through (1.5.54) to the remaining portion of Formula (1.0.0).

The present invention is further concerned with a method of treating a subject suffering from a disease or condition mediated by the PDE4 isozyme in its role of regulating the activation and degranulation of human eosinophils, comprising administering to said subject in need of said treatment a therapeutically effective amount of a compound of Formula (1.0.0) as described above. Similarly, the present invention is also concerned with a pharmaceutical composition for use in such a therapeutic treatment, comprising a compound of Formula (1.0.0) as described above together with a pharmaceutically acceptable carrier.

The present invention relates to PDE4 isozyme inhibitors comprising a compound of Formula (1.0.0) as described above which is useful in treating or preventing one or members selected from the groups of diseases, disorders, and conditions consisting of:

asthma of whatever type, etiology, or pathogenesis; or asthma that is a member selected from the group consisting of atopic asthma; non-atopic asthma; allergic asthma; atopic, bronchial, IgE-mediated asthma; bronchial asthma; essential asthma; true asthma; intrinsic asthma caused by pathophysiologic disturbances; extrinsic asthma caused by environmental factors; essential asthma of unknown or inapparent cause; non-atopic asthma; bronchitic asthma; emphysematous asthma; exercise-induced asthma; occupational asthma; infective asthma caused by bacterial, fungal, protozoal, or viral infection; non-allergic asthma; incipient asthma; wheezy infant syndrome;

chronic or acute bronchoconstriction; chronic bronchitis; small airways obstruction; and emphysema;

obstructive or inflammatory airways diseases of whatever type, etiology, or pathogenesis; or an obstructive or inflammatory airways disease that is a member selected from the group consisting of asthma; pneumoconiosis; chronic eosinophilic pneumonia; chronic obstructive pulmonary disease (COPD); COPD that includes chronic bronchitis, pulmonary emphysema or dyspnea associated therewith; COPD that is characterized by irreversible, progressive airways obstruction; adult respiratory distress syndrome (ARDS), and exacerbation of airways hyper-reactivity consequent to other drug therapy;

pneumoconiosis of whatever type, etiology, or pathogenesis; or pneumoconiosis that is a member selected from the group consisting of aluminosis or bauxite workers' disease; anthracosis or miners' asthma; asbestosis or steam-fitters' asthma; chalicosis or flint disease; ptilosis caused by inhaling the dust from ostrich feathers; siderosis caused by the inhalation of iron particles; silicosis or grinders' disease; byssinosis or cotton-dust asthma; and talc pneumoconiosis;

bronchitis of whatever type, etiology, or pathogenesis; or bronchitis that is a member selected from the group consisting of acute bronchitis; acute laryngotracheal bronchitis; arachidic bronchitis; catarrhal bronchitis; croupus bronchitis; dry bronchitis; infectious asthmatic bronchitis; productive bronchitis; *staphylococcus* or streptococcal bronchitis; and vesicular bronchitis;

bronchiectasis of whatever type, etiology, or pathogenesis; or bronchiectasis that is a member selected from the group consisting of cylindric bronchiectasis; sacculated bronchiectasis; fusiform bronchiectasis; capillary bronchiectasis; cystic bronchiectasis; dry bronchiectasis; and follicular bronchiectasis;

seasonal allergic rhinitis; or perennial allergic rhinitis; or sinusitis of whatever type, etiology, or pathogenesis; or sinusitis that is a member selected from the group consisting of purulent or nonpurulent sinusitis; acute or chronic sinusitis; and ethmoid, frontal, maxillary, or sphenoid sinusitis;

rheumatoid arthritis of whatever type, etiology, or pathogenesis; or rheumatoid arthritis that is a member selected from the group consisting of acute arthritis; acute gouty arthritis; chronic inflammatory arthritis; degenerative arthritis; infectious arthritis; Lyme arthritis; proliferative arthritis; psoriatic arthritis; and vertebral arthritis;

gout, and fever and pain associated with inflammation;
an eosinophil-related disorder of whatever type, etiology, or pathogenesis; or an eosinophil-related disorder that is a member selected from the group consisting of eosinophilia; pulmonary infiltration eosinophilia; Loffler's syndrome; chronic eosinophilic pneumonia; tropical pulmonary eosinophilia; bronchopneumonic aspergillosis; aspergilloma; granulomas containing eosinophils; allergic granulomatous angiitis or Churg-Strauss syndrome; polyarteritis nodosa (PAN); and systemic necrotizing vasculitis;
atopic dermatitis; or allergic dermatitis; or allergic or atopic eczema;
urticaria of whatever type, etiology, or pathogenesis; or urticaria that is a member selected from the group consisting of immune-mediated urticaria; complement-mediated urticaria; urticariogenic material-induced urticaria; physical agent-induced urticaria; stress-induced urticaria; idiopathic urticaria; acute urticaria; chronic urticaria; angioedema; cholinergic urticaria; cold urticaria in the autosomal dominant form or in the acquired form; contact urticaria; giant urticaria; and papular urticaria;
conjunctivitis of whatever type, etiology, or pathogenesis; or conjunctivitis that is a member selected from the group consisting of actinic conjunctivitis; acute catarrhal conjunctivitis; acute contagious conjunctivitis; allergic conjunctivitis; atopic conjunctivitis; chronic catarrhal conjunctivitis; purulent conjunctivitis; and vernal conjunctivitis
uveitis of whatever type, etiology, or pathogenesis; or uveitis that is a member selected from the group consisting of inflammation of all or part of the uvea; anterior uveitis; iritis; cyclitis; iridocyclitis; granulomatous uveitis; nongranulomatous uveitis; phacoantigenic uveitis; posterior uveitis; choroiditis; and chorioretinitis;
psoriasis;
multiple sclerosis of whatever type, etiology, or pathogenesis; or multiple sclerosis that is a member selected from the group consisting of primary progressive multiple sclerosis; and relapsing remitting multiple sclerosis;
autoimmune/inflammatory diseases of whatever type, etiology, or pathogenesis; or an autoimmune/inflammatory disease that is a member selected from the group consisting of autoimmune hematological disorders; hemolytic anemia; aplastic anemia; pure red cell anemia; idiopathic thrombocytopenic purpura; systemic lupus erythematosus; polychondritis; scleroderma; Wegner's granulomatosis; dermatomyositis; chronic active hepatitis; myasthenia gravis; Stevens-Johnson syndrome; idiopathic sprue; autoimmune inflammatory bowel diseases; ulcerative colitis; Crohn's disease; endocrin opthamopathy; Grave's disease; sarcoidosis; alveolitis; chronic hypersensitivity pneumonitis; primary biliary cirrhosis; juvenile diabetes or diabetes mellitus type I; anterior uveitis; granulomatous or posterior uveitis; keratoconjunctivitis sicca; epidemic keratoconjunctivitis; diffuse interstitial pulmonary fibrosis or interstitial lung fibrosis; idiopathic pulmonary fibrosis; cystic fibrosis; psoriatic arthritis; glomerulonephritis with and without nephrotic syndrome; acute glomerulonephritis; idiopathic nephrotic syndrome; minimal change nephropathy; inflammatory/hyperproliferative skin diseases; psoriasis; atopic dermatitis; contact dermatitis; allergic contact dermatitis; benign familial pemphigus; pemphigus erythematosus; pemphigus foliaceus; and pemphigus vulgaris;
prevention of allogeneic graft rejection following organ transplantation;
inflammatory bowel disease (IBD) of whatever type, etiology, or pathogenesis; or inflammatory bowel disease that is a member selected from the group consisting of ulcerative colitis (UC); collagenous colitis; colitis polyposa; transmural colitis; and Crohn's disease (CD);.
septic shock of whatever type, etiology, or pathogenesis; or septic shock that is a member selected from the group consisting of renal failure; acute renal failure; cachexia; malarial cachexia; hypophysial cachexia; uremic cachexia; cardiac cachexia; cachexia suprarenalis or Addison's disease; cancerous cachexia; and cachexia as a consequence of infection by the human immunodeficiency virus (HIV);
liver injury;
pulmonary hypertension; and hypoxia-induced pulmonary hypertension;
bone loss diseases; primary osteoporosis; and secondary osteoporosis;
central nervous system disorders of whatever type, etiology, or pathogenesis; or a central nervous system disorder that is a member selected from the group consisting of depression; Parkinson's disease; learning and memory impairment; tardive dyskinesia; drug dependence; arteriosclerotic dementia; and dementias that accompany Huntington's chorea, Wilson's disease, paralysis agitans, and thalamic atrophies;
infection, especially infection by viruses wherein such viruses increase the production of TNF-$\alpha$ in their host, or wherein such viruses are sensitive to upregulation of TNF-$\alpha$ in their host so that their replication or other vital activities are adversely impacted, including a virus which is a member selected from the group consisting of HIV-1, HIV-2, and HIV-3; cytomegalovirus, CMV; influenza; adenoviruses; and Herpes viruses, including Herpes zoster and Herpes simplex;
yeast and fungus infections wherein said yeast and fungi are sensitive to upregulation by TNF-$\alpha$ or elicit TNF-$\alpha$ production in their host, e.g., fungal meningitis; particularly when administered in conjunction with other drugs of choice for the treatment of systemic yeast and fungus infections, including but are not limited to, polymixins, e.g., Polymycin B; imidazoles, e.g., clotrimazole, econazole, miconazole, and ketoconazole; triazoles, e.g., fluconazole and itranazole; and amphotericins, e.g., Amphotericin B and liposomal Amphotericin B.
ischemia-reperfusion injury; autoimmune diabetes; retinal autoimmunity; chronic lymphocytic leukemia; HIV infections; lupus erythematosus; kidney and ureter disease; urogenital and gastrointestinal disorders; and prostate diseases.

In particular, the compounds of Formula (1.0.0) are useful in the treatment of (1) inflammatory diseases and conditions comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory diseases and conditions comprising: asthma, acute respiratory distress syndrome, chronic pulmonary inflammatory disease, bronchitis, chronic obstructive airway disease, and silicosis; (3) infectious diseases and conditions comprising: sepsis, septic shock, endotoxic shock, gram negative sepsis, toxic shock syndrome, fever and myalgias due to bacterial, viral or fungal infection, and influenza; (4) immune diseases and conditions comprising: autoimmune diabetes, systemic lupus erythematosis, graft vs. host reaction, allograft rejections, multiple sclerosis, psoriasis, and allergic rhinitis; and (5) other diseases and conditions comprising: bone resorption diseases; reperfusion injury; cachexia secondary to infection or malignancy; cachexia secondary to human acquired immune deficiency syndrome (AIDS), human immunodeficiency virus (HIV) infection, or AIDS related complex (ARC); keloid formation; scar tissue formation; type 1 diabetes mellitus; and leukemia.

The present invention still further relates to the combination of a compound of Formula (1.0.0) together with one or more members selected from the group consisting of the following: (a) leukotriene biosynthesis inhibitors: 5-lipoxygenase (5-LO) inhibitors and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2-alkylsulfonamides of Formula (5.2.8); 2,6-di-tert-butylphenol hydrazones of Formula (5.2.10); the class of methoxytetrahydropyrans which includes Zeneca ZD-2138 of Formula (5.2.11); the compound SB-210661 of Formula (5.2.12) and the class to which it belongs; the class of pyridinyl-substituted 2-cyanonaphthalene compounds to which L-739,010 belongs; the class of 2-cyanoquinoline compounds to which L-746,530 belongs; the classes of indole and quinoline compounds to which MK-591, MK-886, and BAY x 1005 belong; (b) receptor antagonists for leukotrienes $LTB_4$, $LTC_4$, $LTD_4$, and $LTE_4$ selected from the group consisting of the phenothiazin-3-one class of compounds to which L-651,392 belongs; the class of amidino compounds to which CGS-25019c belongs; the class of benzoxaolamines to which ontazolast belongs; the class of benzenecarboximidamides to which BIIL 284/260 belongs; and the classes of compounds to which zafirlukast, ablukast, montelukast, pranlukast, verlukast (MK-679), RG-12525, Ro-245913, iralukast (CGP 45715A), and BAY x 7195 belong; (c) PDE4 inhibitors including inhibitors of the isoform PDE4D; (d) 5-Lipoxygenase (5-LO) inhibitors; or 5-lipoxygenase activating protein (FLAP) antagonists; (e) dual inhibitors of 5-lipoxygenase (5-LO) and antagonists of platelet activating factor (PAF); (f) leukotriene antagonists (LTRAs) including antagonists of $LTB_4$, $LTC_4$, $LTD_4$, and $LTE_4$; (g) antihistaminic $H_1$ receptor antagonists including cetirizine, loratadine, desloratadine, fexofenadine, astemizole, azelastine, and chlorpheniramine; (h) gastroprotective $H_2$ receptor antagonists; (i) $\alpha_1$- and $\alpha_2$-adrenoceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (j) $\alpha_1$- and $\alpha_2$-adrenoceptor agonists in combination with inhibitors of 5-lipoxygenase (5-LO); (k) anticholinergic agents including ipratropium bromide; tiotropium bromide; oxitropium bromide; pirenzepine; and telenzepine; (l) $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol; (m) methylxanthanines including theophylline and aminophylline; (n) sodium cromoglycate; (o) muscarinic receptor (M1, M2, and M3) antagonists; (p) COX-1 inhibitors (NSAIDs); COX-2 selective inhibitors including rofecoxib; and nitric oxide NSAIDs; (q) insulin-like growth factor type I (IGF-1) mimetics; (r) ciclesonide; (s) inhaled glucocorticoids with reduced systemic side effects, including prednisone, prednisolone, flunisolide, triamcinolone acetonide, beclomethasone dipropionate, budesonide, fluticasone propionate, and mometasone furoate; (t) tryptase inhibitors; (u) platelet activating factor (PAF) antagonists; (v) monoclonal antibodies active against endogenous inflammatory entities; (w) IPL 576; (x) anti-tumor necrosis factor (TNFα) agents including Etanercept, Infliximab, and D2E7; (y) DMARDs including Leflunomide; (z) TCR peptides; (aa) interleukin converting enzyme (ICE) inhibitors; (bb) IMPDH inhibitors; (cc) adhesion molecule inhibitors including VLA-4 antagonists; (dd) cathepsins; (ee) MAP kinase inhibitors; (ff) glucose-6 phosphate dehydrogenase inhibitors; (gg) kinin-$B_1$- and $B_2$-receptor antagonists; (hh) gold in the form of an aurothio group together with various hydrophilic groups; (ii) immunosuppressive agents, e.g., cyclosporine, azathioprine, and methotrexate; (jj) anti-gout agents, e.g., colchicine; (kk) xanthine oxidase inhibitors, e.g., allopurinol; (ll) uricosuric agents, e.g., probenecid, sulfinpyrazone, and benzbromarone; (mm) antineoplastic agents, especially antimitotic drugs including the vinca alkaloids such as vinblastine and vincristine; (nn) growth hormone secretagogues; (oo) inhibitors of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11); (pp) transforming growth factor (TGFβ); (qq) platelet-derived growth factor (PDGF); (rr) fibroblast growth factor, e.g., basic fibroblast growth factor (bFGF); (ss) granulocyte macrophage colony stimulating factor (GM-CSF); (tt) capsaicin cream; (uu) Tachykinin $NK_1$ and $NK_3$ receptor antagonists selected from the group consisting of NKP-608C; SB-233412 (talnetant); and D-4418; and (vv) elastase inhibitors selected from the group consisting of UT-77 and ZD-0892.

DETAILED DESCRIPTION OF THE INVENTION 5.0 Compounds

The present invention is concerned with novel compounds which may be represented by Formula (1.0.0) as follows:

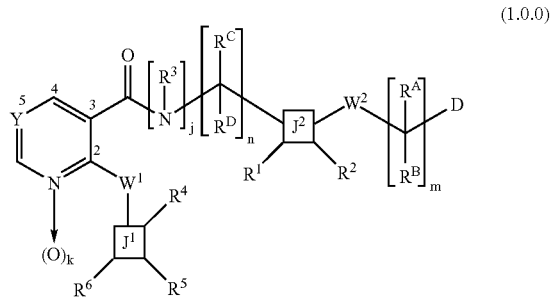

(1.0.0)

The broadest scope of the compounds of the present invention is circumscribed above under Section 4.0 relating to the Summary of the Invention. A further description of said compounds is provided hereafter in terms of a range of different types and groups of embodiments, as well as specific embodiments which characterize and exemplify the compounds of Formula (1.0.0). Preferred and more preferred embodiments of said compounds are also set forth, but it will be understood that the recital of such preferences is in no way intended to, and does not limit the scope of the present invention with regard to said compounds.

As used herein, the expressions "—$(C_1-C_3)$ alkyl", "—$(C_1-C_4)$ alkyl", and "—$(C_1-C_6)$ alkyl", as well as equivalent variations of the same, are intended to include branched as well as straight chain conformations of these aliphatic groups. Thus, the above-quoted expressions include, in addition to the straight chain entities methyl, ethyl, n-propyl, n-butyl, n-pentyl, and n-hexyl, the branched chain entities iso-propyl, iso-butyl, sec-butyl, tert-butyl, iso-pentane (2-methylbutane), 2-methylpentane, 3-methylpentane, 1-ethylpropane, and 1-ethylbutane. The meanings of the above-quoted expressions are also intended to apply to said expressions whether or not they are substituted. Thus, the expression "fluorinated-$(C_1-C_3)$ alkyl" is intended to encompass the various fluorinated species of the n-propyl and iso-propyl aliphatic groups.

As used herein, the expression "saturated or unsaturated carbon ring system that is 3- to 7-membered monocyclic" is intended to include such saturated monocyclic carbon ring systems as cyclopropane, cyclobutane, cyclopentane, cyclohexane, and cycloheptane. The above-quoted expression is also intended to include such mono-unsaturated monocyclic carbon ring systems as cyclopentene, cyclohexene, and cycloheptene; as well as such aromatic monocyclic carbon ring systems as phenylene.

As used herein, the expressions "fused or discontinuous, polycyclic" and "fused polycyclic" are intended to mean first, a carbon ring system having two or more rings, especially bicyclic and tricyclic, more especially bicyclic, in which the rings are fused, i.e., there is at least one pair of bridgehead carbon atoms present. These polycyclic ring systems may be saturated or unsaturated. Second, the above-quoted expression is intended to mean a carbon ring system having two or more rings in which said rings are discontinuous, i.e., they are attached to each other by a single or double covalent bond and there are no bridgehead carbon atoms present. These polycyclic ring systems may also be saturated or unsaturated.

The moiety $*^1$ may be discontinuous, while the moiety $*^2$ may not be discontinuous. It is also provided herein that $*^2$ may not have the meaning of a moiety which is biaryl or discontinuous. The expression "biaryl" as used herein is intended to mean a fused polycyclic ring system as defined immediately above in which (1) bridgehead carbon atoms are joined by a bond, i.e., there are no additional carbon atoms present between said bridgehead carbon atoms; and (2) heteroatoms, if present, are contained only in a tricyclic or higher polycyclic fused ring system. Further, as already mentioned, $*^2$ may not be discontinuous, as that expression is defined immediately above.

Consequently, the types of biaryl and discontinuous ring systems that may comprise a meaning of of $*^1$, but that may not comprise a meaning of $*^2$ include, inter alia, the following: biphenyl; biphenylene; fluorene; 9H-carbazole; phenanthridine; phenanthrene; 2,2'-bipyridine; iminodibenzyl; 2,2'-biquinoline; naphthalene; 2-phenylnaphthalene; 1-phenylnaphthalene; diphenylmethane; 1-phenylpiperadine; 1-phenylpiperazine; bibenzyl; azulene; 4,4'-diphenyl-2,2'-dipyridyl; 1-(diphenylmethyl) azetidine; 4,5-diphenyloxazole; 2,5-diphenyloxazole; diphenyl-2-pyridylmethane and diphenyl-4-pyridylmethane; 3,6-diphenyl-1,2,4,5-tetrazine; 1-benzylpiperazine; 1-benzylpiperidine; 2-benzylpyridine, 3-benzylpyridine and 4-benzylpyridine; 4,5-diphenylimidazole; phenothiazine; phenoxazine; phenazine; 1-phenyl-3,4-dihydronaphthalene; 2-phenylindene; 2-phenylindole; 4-phenylmorpholine; 2-phenylbenzothiazole; 2-phenylbenzoxazole; and 2-phenylbenzimidazole.

The above-recited types of biaryl and discontinuous ring systems may, on the other hand, comprise a meaning of $*^1$. As a further illustration, it will be understood that, e.g., a naphthyl moiety is biaryl as defined herein, since it is a fused bicyclic with a bond between the bridgehead carbon atoms, and there are no heteroatoms present. A quinolinyl moiety, on the other hand, while also a fused bicyclic with a bond between the bridgehead carbon atoms, is not biaryl as defined herein, since a nitrogen heteroatom is also present, and the definition of "biaryl" requires that in such a case the fused ring system be tricyclic or higher polycyclic. The biphenyl moiety is an example of a discontinuous ring system that, accordingly, may be a meaning of $*^1$, but may not be a meaning of $*^2$.

As used herein, the expression "saturated or unsaturated carbon ring system that is . . . 7- to 12-membered, fused or discontinuous, polycyclic" is intended to include such saturated fused bi- and tricyclic carbon ring systems as norbornane, bicyclo[2.2.2]octanyl, bicyclo[3.2.1]octanyl, bicyclo[3.3.0]octanyl, bicyclo[3.3.1]nonanyl, cyclodecanyl, and adamantanyl. The above-quoted expression is also intended to include such mono-unsaturated bi- and tricyclic carbon ring systems as norbornenyl, bicyclo[2.2.2]oct-5-enyl, and bicyclo[2.2.2]oct-7-enyl; as well as such aromatic bi- and tricyclic carbon ring systems as naphthylene and biphenylene. The above-quoted expression is further intended to include such aromatic disontinuous bicyclic carbon ring systems as biphenylene.

The carbon ring systems included within the scope of the above-quoted expression and described above also include moieties wherein optionally one carbon atom thereof may be replaced by a heteroatom selected from N, O, or S, and where N is selected, optionally a second carbon atom thereof may be replaced by a heteroatom selected from N, O, and S. The resulting moieties incude pyrrolyl; pyrrolidinyl; furanyl; thienyl; pyridyl; pyrimidinyl; piperidinyl; piperazinyl; imidazolyl; imidazolidinyl; oxazolyl; isoxazolyl; thiazolyl; indolyl; quinolinyl; isoquinolinyl; benzimidazolyl; benzoxazolyl; morpholinyl; quinuclidinyl; and azabicyclo[3.3.0]octanyl.

As used herein with respect to compounds of Formula (1.0.0), as well as other formulas and partial formulas relating thereto, where one or more nitrogen atom components thereof is or are represented as "[N⇒(O)$_u$]", it or they comprise(s) an optional nitrogen oxide form of said nitrogen atom(s). Where there is more than one such nitrogen oxide form, they are selected independently of each other. Further, it will be appreciated that said nitrogen oxide form(s) may also be represented as "[N⇒(O)$_u$]" where u is 0 or 1.

A portion of the core nucleus of the compounds of Formula (1.0.0) is that of a nicotinamide of Formula (1.0.1):

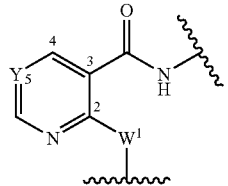
(1.0.1)

derived from nicotinic acid. This portion of the core nucleus is then elaborated by defining the Y moiety as being =C(R$^1$$_a$)—, or —[N⇒(O)$_k$]— where k is 0 or 1, and where the symbol ⇒(O) indicates a nitrogen heteroatom in the form of its N-oxide when k is 1. It should be noted that in the N-containing heterocyclyl moieties which define R$^8$, it is provided that optionally one or more of the N-heteroatoms comprising said heterocyclyl moieties may be in the form of the N-oxide of said N-heteroatoms. Accordingly, the considerations concerning N-oxides just described also apply to such N-oxide-containing moieties defining R$^8$.

Where Y has the meaning of —[N⇒(O)$_k$]— the compounds of the present invention are pyrimidines. The pyrimidine group of compounds of Formula (1.0.0) is a significant part of the scope of the present invention. It is preferred, nevertheless, that the compounds of Formula (1.0.0) have the Y moiety defined as =C(R$^1$$_a$)— where the substituent R$^1$$_a$ is selected independently from the other substituents that form the compounds of Formula (1.0.0).

In addition to —H, R$^1$$_a$ of the =C(R$^1$$_a$)— moiety is defined as a member selected from the group consisting of —F; —Cl; —CN; —NO$_2$; —(C$_1$–C$_4$) alkyl; —(C$_2$–C$_4$) alkynyl; fluorinated-(C$_1$–C$_3$) alkyl; fluorinated-(C$_1$–C$_3$) alkoxy; —OR$^{16}$; and —C(=O)NR$^{12}$$_a$R$^{12}$$_b$; where R$^{12}$$_b$ are each independently —H; —CH$_3$; —CH$_2$CH$_3$; —CH$_2$CH$_2$CH$_3$; —CH$_2$(CH$_3$)$_2$; —CH$_2$CH$_2$CH$_2$CH$_3$; —CH(CH$_3$)CH$_2$CH$_3$; —CH$_2$CH(CH$_3$)$_2$; —C(CH$_3$)$_3$; cyclopropyl; cyclobutyl; or cyclopentyl;

However, it is preferred that the R$^1$$_a$ substituent of the =C(R$^1$$_a$)— moiety have the meaning of —H; —F; —Cl; —CH$_3$; —OCH$_3$; or —(C$_2$–C$_4$) alkynyl; more preferably R$^1$$_a$ is —F or —H.

It will be noted that R$^1$$_a$ has several substituent definitions, especially —F, in common with those for the R$^1$ and R$^2$ substituents on the *$^2$ moiety. In the embodiments of the compounds of Formula (1.0.0) where Y is =C(R$^1$$_a$)—, and both the *$^1$ moiety and the *$^2$ moiety have the preferred meaning of phenyl, the substituents at the 5-position of the nicotinamide core nucleus and at the 2'-position, of the benzyl group attached to the amide portion thereof, are selected from the same group of definitions, although on an independent basis. The embodiments of the present invention wherein such substituents are involved, and where j is 1, k is 0, n is 1, both R$^C$ and R$^D$ are —H, and Y is =C(R$^1$$_a$)—, may be illustrated by generic Formula (1.0.2a) and sub-generic Formula (1.0.2b) as follows:

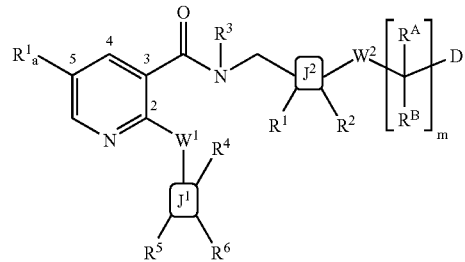
(1.0.2a)

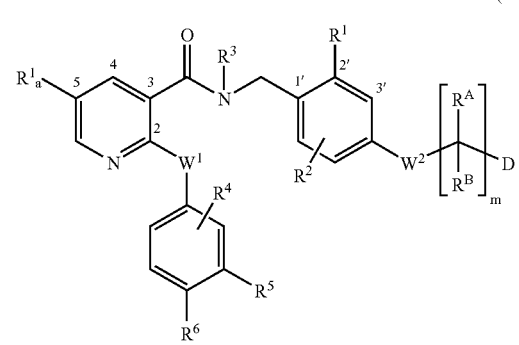
(1.0.2b)

In such embodiments of the present invention, the 5-position (R$^1$$_a$) and 2'-position (R$^1$) substituents serve the same function of modulating the properties of the overall compound of Formula (1.0.0) with respect to its pharmacological and pharmacokinetic properties such as potency, substrate specificity (selectivity), and physico-chemical properties. In preferred embodiments of the compounds of the present invention of this type, both the R$^1$ and R$^1$$_a$ substituents will have the same meaning, which will be —H or —F.

5.1.0 Terminal Moiety D Is a Moiety of Partial Formulas (1.1.1)–(1.1.9)

D is a member selected from the group of moieties defined by partial Formulas (1.1.1) through (1.1.9) illustrated further above. The moieties of partial Formulas (1.1.1) through (1.1.5) which define the D group are typically but not necessarily acids, amides, and heterocyclyl groups that act as acid and amide mimetics, but they are not limited to these types of functional groups. The moieties of partial Formulas (1.1.6) through (1.1.9) which define the D group are typically but not necessarily tertiary alcohols and their mimetics, especially analogous acyl and nitrile moieties, but they are not limited to these types of functional groups. Other moieties as described herein may be employed at the right-hand-side of the compounds of Formula (1.0.0). These moieties are bioisostereic in that they permit the compounds of Formula (1.0.0) containing them to achieve PDE4 inhibition essentially equivalent to that achieved by other moieties, especially acid, amide, and alcohol moieties.

5.1.1 D Is a Moiety of Partial Formulas (1.1.1). (1.1.2), or (1.1.3)

Embodiments of the present invention wherein the definition of the D group is illustrated by partial Formulas (1.1.1); (1.1.2); and (1.1.3), are as follows:

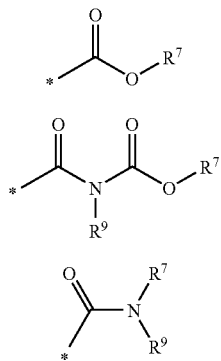

(1.1.1)

(1.1.2)

(1.1.3)

One of a number of preferred moieties for defining the D group is that of partial Formula (1.1.1) where $R^7$ has the meaning of —H, which is a preferred meaning of this substituent. Where $R^7$ is hydrogen and m is 1, 2, or 3 in Formula (1.0.0), a simple carboxylic acid —COOH results, and the group becomes a lower alkanoic acid. Benzoic acid as a meaning of the D group, however, is a less preferred embodiment of the present invention.

$R^{10}$ is an optional substituent of the moieties that define $R^7$, and there may be up to three such substituents when present. The meaning of the $R^{10}$ substituent includes phenyl or pyridyl where said phenyl or pyridyl is in turn optionally substituted by up to 3 substituents $R^{11}$ where $R^{11}$ is —F, —Cl, —CN, —NO$_2$, —OH, —(C$_1$–C$_3$) alkoxy, —(C$_1$–C$_3$) alkyl, or —NR$_R^{17}$. In preferred embodiments that include such $R^{11}$ substitution, there will be 1 or 2 substituents $R^{11}$ that have the meaning of —F, —Cl, —CH$_3$, —OCH$_3$, —OH, —CN, or —N(CH$_3$)$_2$. Preferably, there is 0 or 1 such $R^{11}$ substituent and when present it is —F or —Cl. The meaning of the $R^{10}$ substituent further includes —F, —Cl, —CF$_3$, oxo(=O), —OR$^{16}$, —NO$_2$, —CN, —C(=O)OR$^{16}$, —O—C(=O)R$^{16}$, —C(=O)NR$^{16}$R$^{17}$, —O—C(=O) NR$^{16}$R$^{17}$, —NR$^{16}$R$^{17}$, —NR$^{16}$C(=O)R$^{17}$, —NR$^{16}$C(=O) OR$^{17}$, —NR$^{16}$S(=O)$_2$R$^{17}$, or —S(=O)$_2$NR$^{16}$R$^{17}$.

The sub-substituents $R^{16}$ and $R^{17}$ comprise —H; —(C$_1$–C$_4$) alkyl, preferably —CH$_3$; —(C$_2$–C$_4$) alkenyl; —(C$_3$–C$_6$) cycloalkyl, preferably cyclopropyl; phenyl; benzyl; or pyridyl. Said alkyl, alkenyl, cycloalkyl, phenyl, benzyl, or pyridyl groups are in turn optionally substituted by up to 3 substituents —F, —Cl, or —CN. Among the above-recited additional meanings of $R^{10}$, it is preferred that the $R^{10}$ substituent when present be pyridyl optionally substituted by —F, —Cl, —OCH$_3$, —CN, —NO$_2$, or —NR$^{16}$R$^{17}$ where $R^{16}$ and $R^{17}$ are independently —H or —CH$_3$; or that the $R^{10}$ substituent when present be —F, —Cl, —CF$_3$, —CN, —NO$_2$, —C(=O)OR$^{16}$, or —NR$^{16}$R$^{17}$ where $R^{16}$ and $R^{17}$ are independently —H or —CH$_3$.

These and other preferred embodiments of the compounds of Formula (1.0.0) comprising the moieties of partial Formula (1.1.1) based on the preferred meanings of $R^7$ and $R^9$ as described above, include, inter alia, the following groups illustrated by partial Formulas (3.5.1) through (3.5.15):

(3.5.1)

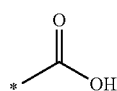

(3.5.2)

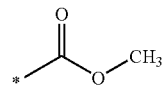

(3.5.3)

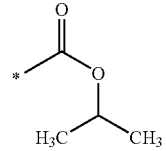

(3.5.4)

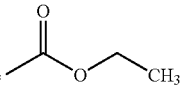

(3.5.5)

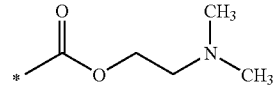

(3.5.6)

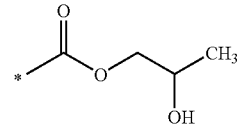

(3.5.7)

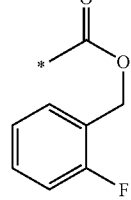

(3.5.8)

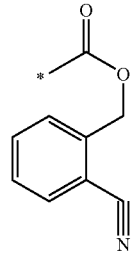

(3.5.9)

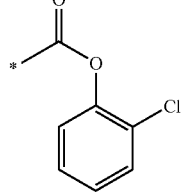

(3.5.10)

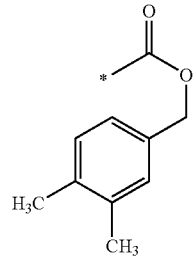

-continued

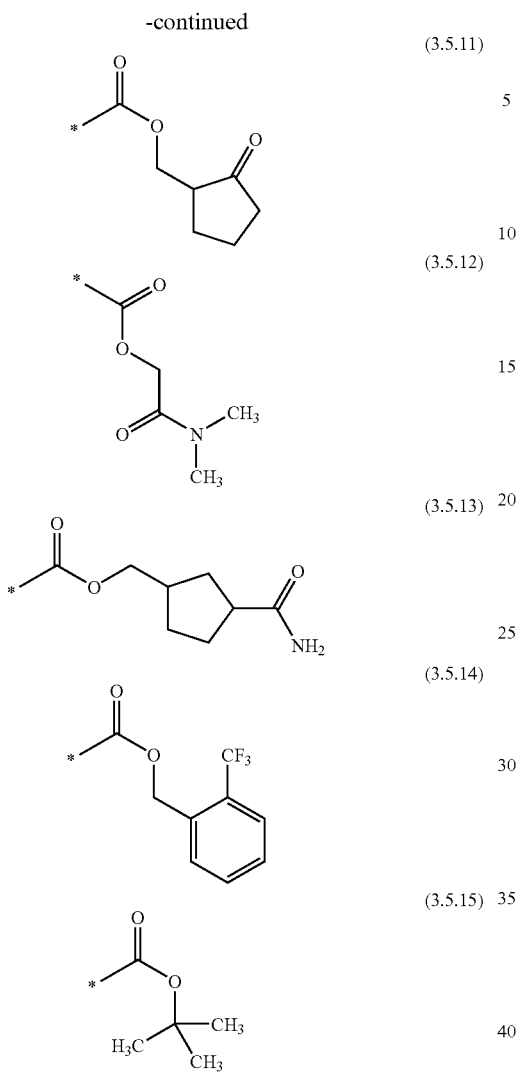

(3.5.11)

(3.5.12)

(3.5.13)

(3.5.14)

(3.5.15)

The D group is represented by partial Formula (1.1.2) in which the nitrogen atom is substituted by $R^9$ where $R^9$ has the meaning of —H; —($C_1$–$C_4$) alkyl; —($C_3$–$C_7$) cycloalkyl; phenyl; benzyl; —C(=O)O$R^{16}$; —C(=O)$R^{16}$; —O$R^{16}$; —($C_1$–$C_2$) alkyl-O$R^{16}$; or —($C_1$–$C_2$) alkyl-C(=O)O$R^{16}$; where $R^{16}$ is —H or —($C_1$–$C_4$) alkyl. $R^{16}$ is preferably —H or —$CH_3$.

Accordingly, embodiments of the present invention where the D group is represented by partial Formula (1.1.2) may be illustrated as follows by partial Formulas (4.1.1) through (4.1.5):

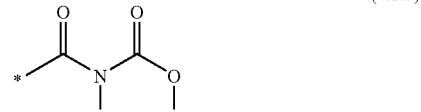

(4.1.1)

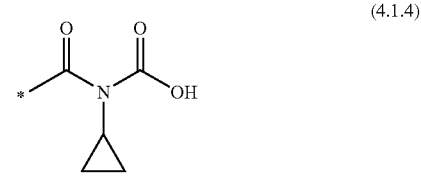

(4.1.2)

-continued (4.1.3)

(4.1.4)

(4.1.5)

Those embodiments wherein the definition of D is that of an amide group, are illustrated by partial Formula (1.1.3):

(1.1.3)

These and other preferred embodiments of the compounds of Formula (1.0.0) comprising moieties of partial Formula (1.1.3), based on the meanings of $R^7$ and $R^9$ described above, include, inter alia, the following groups illustrated by partial Formulas (4.5.1) through (4.5.20):

(4.5.1)

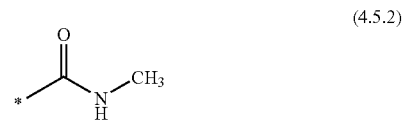

(4.5.2)

(4.5.3)

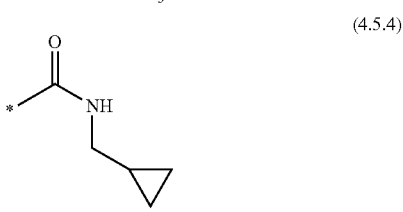

(4.5.4)

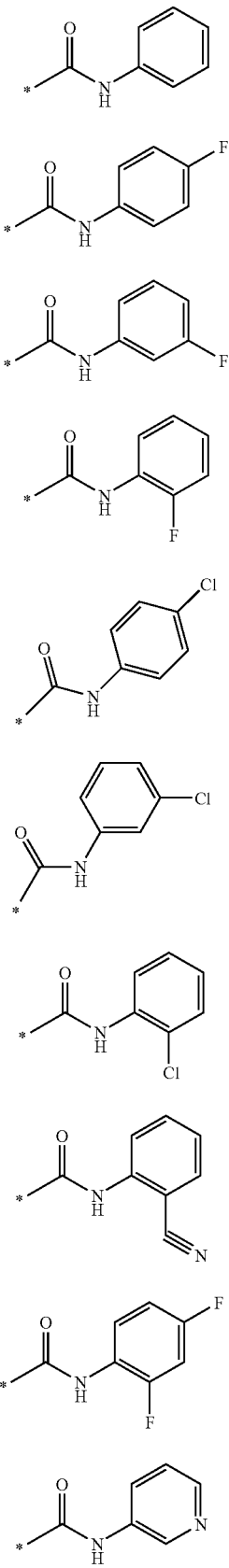

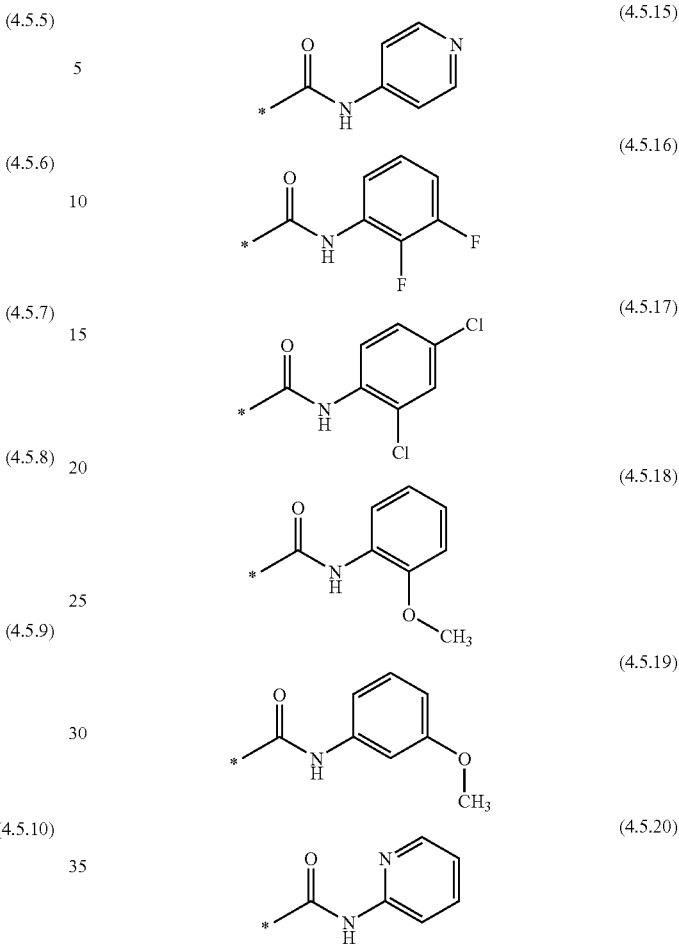

5.1.2 D Is a Moiety of Partial Formula (1.1.4)

Preferred embodiments of the present invention also comprise those compounds of Formula (1.0.0) wherein terminal moiety D falls within the scope of partial Formula (1.1.4), i.e., embodiments of this type are encompassed within the scope of the D moiety when it has the meaning of partial Formula (1.1.4):

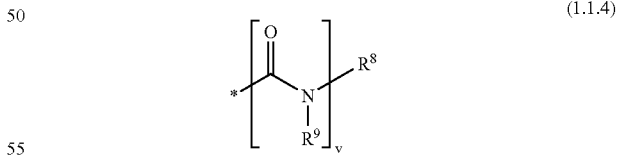

wherein $R^8$ is a monocyclic or bicyclic heterocyclyl which is a member selected from the group consisting of tetrazol-5-yl; 1,2,4-triazol-3-yl; 1,2,4-triazol-3-on-5-yl; 1,2,3-triazol-5-yl; imidazol-2-yl; imidazol-4-yl; imidazolidin-2-on-4-yl; 1,2,4-oxadiazol-3-yl; 1,2,4-oxadiazol-5-on-3-yl; 1,2,4-oxadiazol-5-yl; 1,2,4-oxadiazol-3-on-5-yl; 1,3,4-oxadiazolyl; 1,3,4-oxadiazol-2-on-5-yl; oxazolyl; isoxazolyl; pyrrolyl; pyrazolyl; succinimidyl; glutarimidyl; pyrrolidonyl; 2-piperidonyl; 2-pyridonyl; 4-pyridonyl; pyridazin-3-onyl; pyridazin-3-onyl; thiazolyl; isothiazolyl;

thiadiazolyl; morpholinyl; parathiazinyl; pyridyl; pyrimidinyl; pyrazinyl; pyridazinyl; indolyl; indolinyl; isoindolinyl; benzo[b]furanyl; 2,3-dihydrobenzofuranyl; 1,3-dihydroisobenzofuranyl; 2H-1-benzopyranyl; 2-H-chromenyl; chromanyl; benzothienyl; 1H-indazolyl; benzimidazolyl; benzoxazolyl; benzisoxazolyl; benzothiazolyl; benzotriazolyl; benzotriazinyl; phthalazinyl; 1,8-naphthyridinyl; quinolinyl; isoquinolinyl; quinazolinyl; quinoxalinyl; pyrazolo[3,4-d]pyrimidinyl; pyrimido[4,5-d]pyrimidinyl; imidazo[1,2-a]pyridinyl; pyridopyridinyl; pteridinyl; and 1H-purinyl.

Partial Formulas (1.1.3) and (1.1.4) are similar and the distinction between them should be noted. Partial Formulas (1.1.3) and (1.1.4) are as follows:

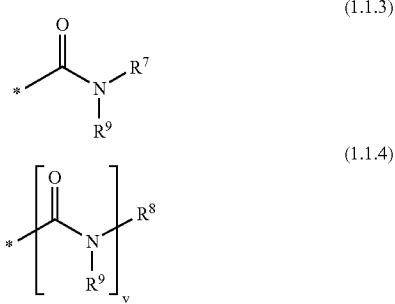

Where v is 0, $R^8$ is linked in a direct fashion to the remaining portion of a compound of Formula (1.0.0) and it is, accordingly, readily distinguishable from a moiety of partial Formula (1.1.3) in which $R^7$ is linked to the remaining portion of a compound of Formula (1.0.0) through the amide bridging moiety —C(=O)NR$^9$—. Where v is 1, on the other hand, both the $R^8$ and the $R^7$ moieties are linked to the remaining portion of a compound of Formula (1.0.0) through the amide bridging moiety —C(=O)NR$^9$—. In this instance, the distinction between the moieties of partial Formulas (1.1.3) and (1.1.4) comprises the difference between the meanings of the $R^8$ and the $R^7$ moieties. This difference has already been described above in detail.

In order to facilitate the following description, the monocyclic heterocyclyl moieties and the bicyclic heterocyclyl moieties are first treated together and thereafter are discussed as separate groups.

Any one or more of the carbon atoms of the phenyl, benzyl, or heterocyclyl moiety is substituted by 0 to 3 substituents $R^{14}$ where $R^{14}$ has the meanings and preferred meanings already described above with regard to partial Formulas (1.1.1), (1.1.2), and (1.1.3). Any one or more of the nitrogen atoms, which it will be appreciated occur only in the case of the heterocyclyl moieties, and which are not a point of attachment of said heterocyclyl moiety, are optionally substituted by up to 3 substituents $R^{15}$. Any sulfur atom which happens to occur in a heterocyclyl moiety, that is not a point of attachment of said heterocyclyl moiety, is substituted by 0, 1, or 2 oxygen atoms.

The optional nitrogen heterocyclyl substituent $R^{15}$ comprises —H; —NR$^{16}$R$^{17}$; —C(=O)R$^{16}$; —OR$^{16}$, preferably —OCH$_3$; —(C$_1$–C$_4$) alkyl-OR$^{16}$; —C(=O)OR$^{16}$; —(C$_1$–C$_2$) alkyl-C(=O)OR$^{16}$; —C(=O)NR$^{16}$R$^{17}$; —(C$_1$–C$_4$) alkyl, preferably —CH$_3$; —(C$_2$–C$_4$) alkenyl; —(CH$_2$)$_u$—(C$_3$–C$_7$) cycloalkyl where u is 0, 1 or 2, preferably cyclopropyl; phenyl; benzyl; pyridyl; or quinolinyl. The alkyl, alkenyl, alkoxy, cycloalkyl, phenyl, benzyl, pyridyl and quinolinyl groups thus included are optionally substituted with up to 2 substituents $R^{12}$.

The sub-substituent $R^{12}$ comprises —F; —Cl; —CO$_2$R$^{18}$; —OR$^{16}$; —CN; —C(=O)NR$^{18}$R$^{19}$; —NR$^{18}$R$^{19}$; —NR$^{18}$C(=O)R$^{19}$; —NR$^{18}$C(=O)OR$^{19}$; —NR$^{18}$S(=O)$_p$R$^{19}$; —S(=O)$_p$NR$^{18}$R$^{19}$, where p is 1 or 2, preferably 2; —(C$_1$–C$_4$) alkyl, preferably —CH$_3$; and —(C$_1$–C$_4$) alkoxy, where $R^{12}$ has the meaning of —OR$^{16}$ above and $R^{16}$ is defined as —(C$_1$–C$_4$) alkyl, and preferably $R^{12}$ is —OCH$_3$; where said alkyl and alkoxy are in turn optionally substituted with up to 3 substituents —F; —Cl; —(C$_1$–C$_2$) alkoxycarbonyl; —(C$_1$–C$_2$) alkylcarbonyl; and —(C$_1$–C$_2$) alkylcarbonyloxy. The $R^{18}$ and $R^{19}$ substituents are independently selected from —H; —(C$_1$–C$_2$) alkyl, preferably —CH$_3$; or phenyl; and are optionally substituted with up to 3—F; or —Cl.

No $R^9$ substituents are shown in partial Formulas (1.1.11) through (1.1.34) above, as well as further below, because the $R^9$ substituent is attached only to a nitrogen atom that does not form an integral, component part of an attached heterocyclic moiety. The $R^9$ substituent is optional in character in that "—H" is included as a definition of the $R^9$ substituent, and in many of the embodiments of the compounds of Formula (1.0.0) this is the preferred meaning of $R^9$. Another preferred meaning of $R^9$ is —CH$_3$.

There is also pointed out the distinction between the substituents $R^9$ and $R^{15}$, both of which are attached only to nitrogen atoms in any of the meanings of the moiety D. The substituent $R^{15}$ is attached only to a nitrogen atom that is an integral, component part of any heterocyclic moiety that may be defined via the $R^8$ substituent of partial Formula (1.1.4) and in particular with reference to the more specific heterocyclic moieties of partial Formulas (1.1.11) through (1.1.34), shown above as well as further below. The $R^9$ substituent, on the other hand, is attached only to a nitrogen atom that in turn is attached to, but is not an integral, component part of any of the heterocyclic moieties that is defined by partial Formulas (1.1.2), (1.1.3), and (1.1.5). The $R^{15}$ substituent may be attached to one or more nitrogen atoms and said nitrogen atoms may be present in any moieties falling within the scope of partial Formula (1.1.4) that can be characterized as containing or comprising a nitrogen-containing heterocyclic moiety.

As an illustration of preferred subgeneric embodiments of the present invention wherein the D group has the meaning of a moiety that falls within the scope of partial Formula (1.1.4), there is set out below the groups of partial Formulas (1.1.11) through (1.1.44):

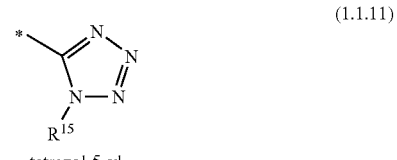

tetrazol-5-yl

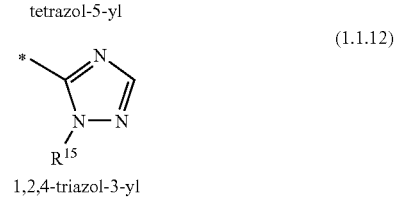

1,2,4-triazol-3-yl

-continued
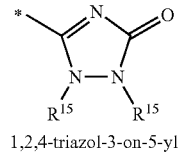 (1.1.13)
1,2,4-triazol-3-on-5-yl
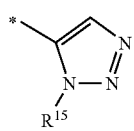 (1.1.14)
1,2,3-triazol-5-yl
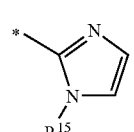 (1.1.15)
imidazol-2-yl
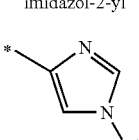 (1.1.16)
imidazol-4-yl
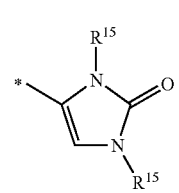 (1.1.17)
imidazolidin-2-on-4-yl
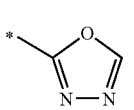 (1.1.18)
1,3,4-oxadiazolyl
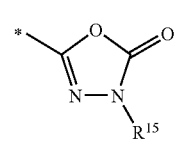 (1.1.19)
1,3,4-oxadiazol-2-on-5-yl
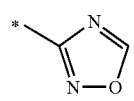 (1.1.20)
1,2,4-oxadiazol-3-yl
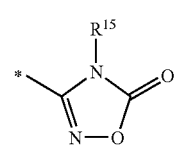 (1.1.21)
1,2,4-oxadiazol-5-on-3-yl
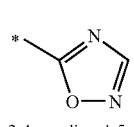 (1.1.22)
1,2,4-oxadiazol-5-yl
-continued
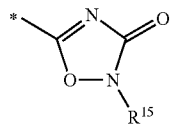 (1.1.23)
1,2,4-oxadiazol-3-on-5-yl
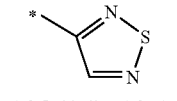 (1.1.24)
1,2,5-thiadiazol-2-yl
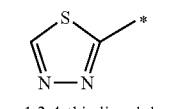 (1.1.25)
1,3,4-thiadiazolyl
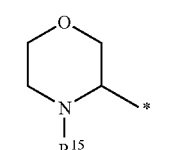 (1.1.26)
morpholin-3-yl
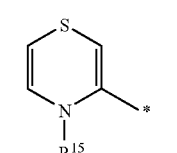 (1.1.27)
parathiazin-3-yl
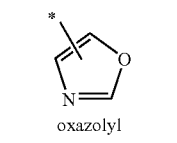 (1.1.28)
oxazolyl
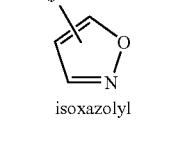 (1.1.29)
isoxazolyl
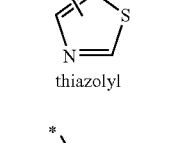 (1.1.30)
thiazolyl
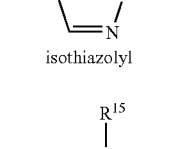 (1.1.31)
isothiazolyl
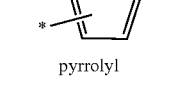 (1.1.32)
pyrrolyl -continued

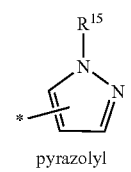
pyrazolyl (1.1.33)

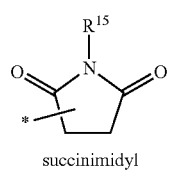
succinimidyl (1.1.34)

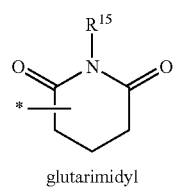
glutarimidyl (1.1.35)

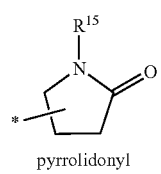
pyrrolidonyl (1.1.36)

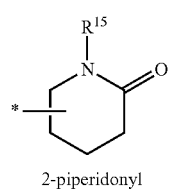
2-piperidonyl (1.1.37)

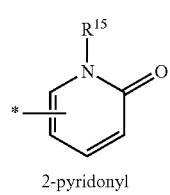
2-pyridonyl (1.1.38)

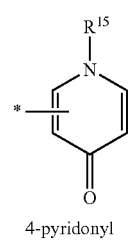
4-pyridonyl (1.1.39)

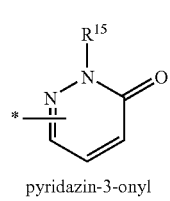
pyridazin-3-onyl (1.1.40)

-continued

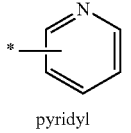
pyridyl (1.1.41)

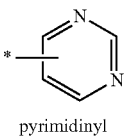
pyrimidinyl (1.1.42)

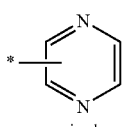
pyrazinyl (1.1.43)

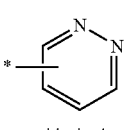
pyridazinyl (1.1.44)

In order to provide another demonstration of preferred embodiments of the compounds of Formula (1.0.0) with reference to the D group where it is a moiety of partial Formula (1.1.4) and v is 0 or 1, and $R^8$ is a monocyclic heterocyclic group, there is set out below the groups consisting of partial Formulas (4.8.1) through (4.8.80) from which the D moiety is selected in such preferred embodiments:

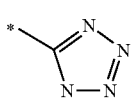
(4.8.1)

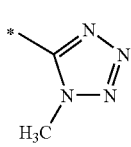
(4.8.2)

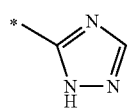
(4.8.3)

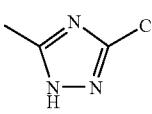
(4.8.4)

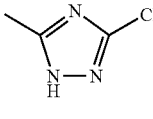
(4.8.5)

(4.8.6)

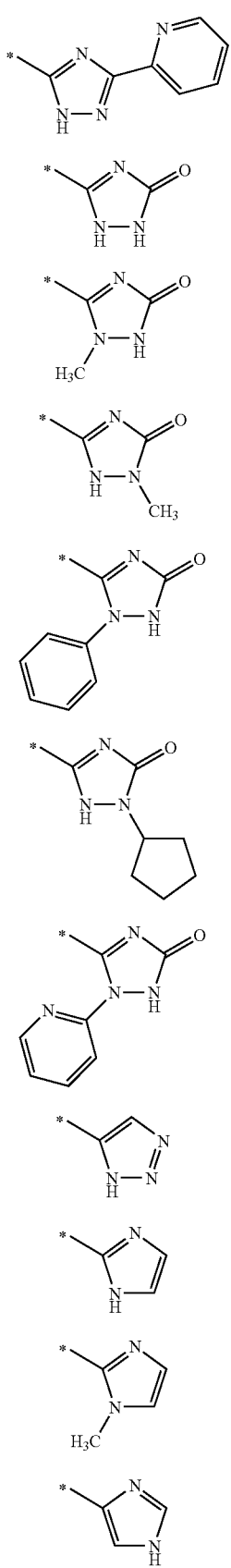
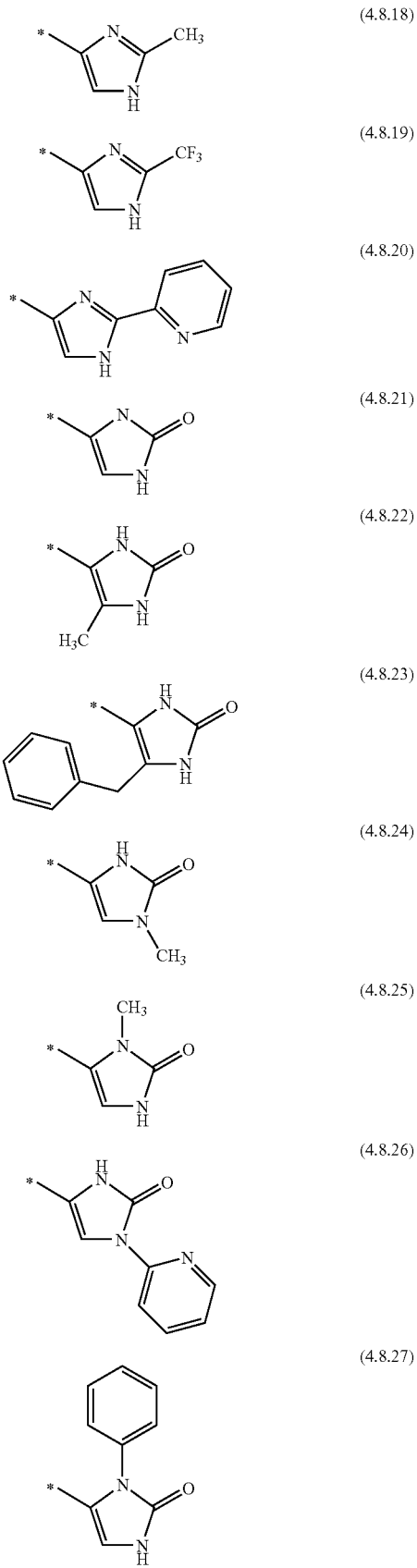

-continued
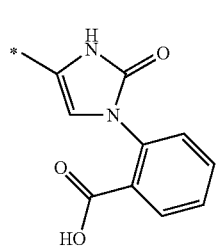 (4.8.28)
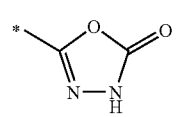 (4.8.29)
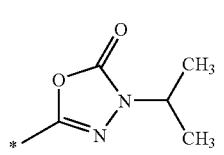 (4.8.30)
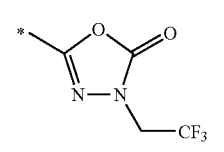 (4.8.31)
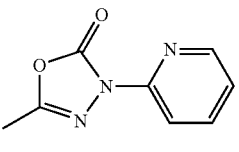 (4.8.32)
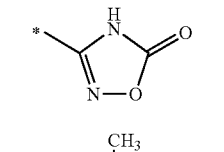 (4.8.33)
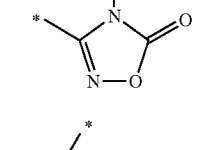 (4.8.34)
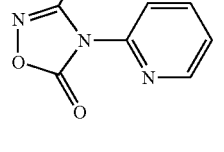 (4.8.35)
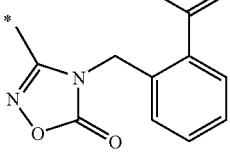 (4.8.36)
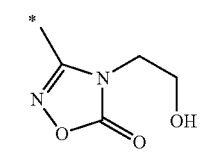 (4.8.37)
-continued
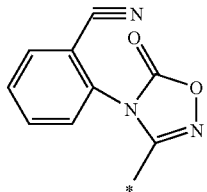 (4.8.38)
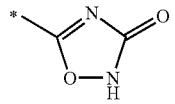 (4.8.39)
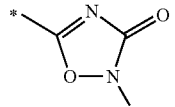 (4.8.40)
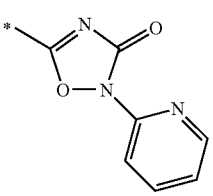 (4.8.41)
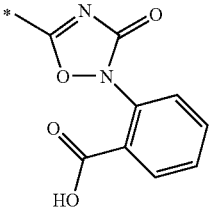 (4.8.42)
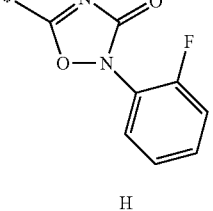 (4.8.43)
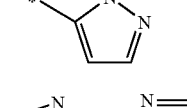 (4.8.44)
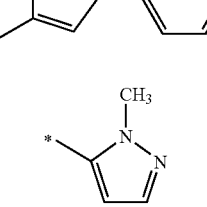 (4.8.45)
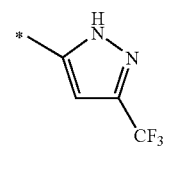 (4.8.46)
(4.8.47)

-continued
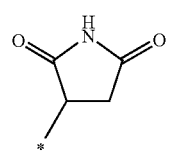 (4.8.48)
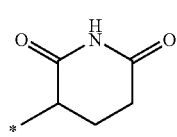 (4.8.49)
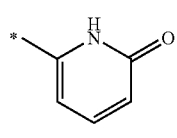 (4.8.50)
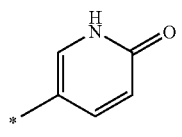 (4.8.51)
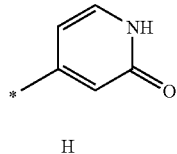 (4.8.52)
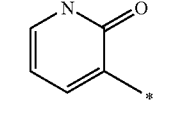 (4.8.53)
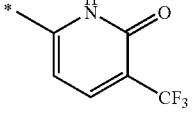 (4.8.54)
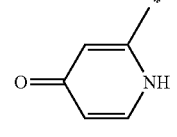 (4.8.55)
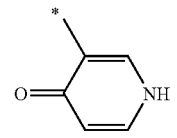 (4.8.56)
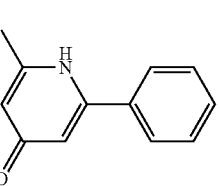 (4.8.57)
-continued
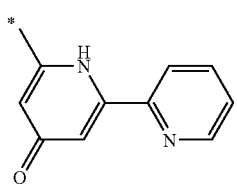 (4.8.58)
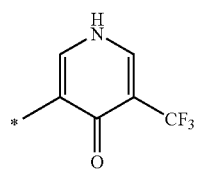 (4.8.59)
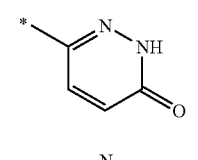 (4.8.60)
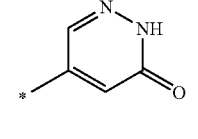 (4.8.61)
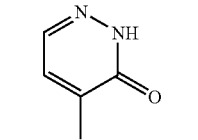 (4.8.62)
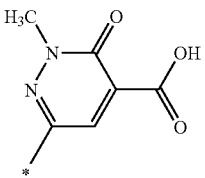 (4.8.63)
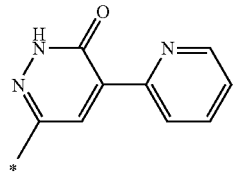 (4.8.64)
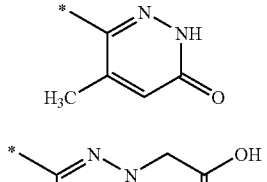 (4.8.65)
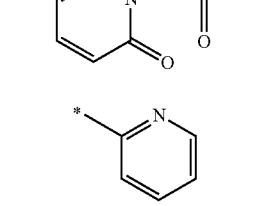 (4.8.66)
(4.8.67)

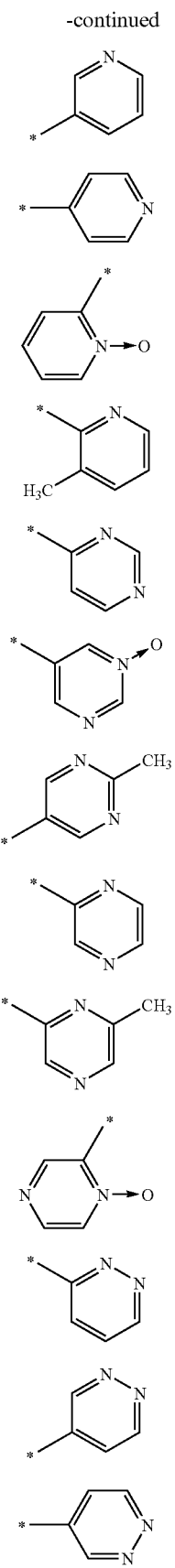

(4.8.68)
(4.8.69)
(4.8.70)
(4.8.71)
(4.8.72)
(4.8.73)
(4.8.74)
(4.8.75)
(4.8.76)
(4.8.77)
(4.8.78)
(4.8.79)
(4.8.80)

Preferred embodiments of the present invention where the group D is a moiety of partial Formula (1.1.4) and v is 0 or 1, also include those wherein the moiety $R^8$ is a bicyclic heterocyclic group selected from the group consisting of indolyl; indolinyl; isoindolinyl; benzo[b]furanyl; 2,3-dihydrobenzofuranyl; 1,3-dihydroisobenzofuranyl; 2H-1-benzopyranyl; 2-H-chromenyl; chromanyl; benzothienyl; 1H-indazolyl; benzimidazolyl; benzoxazolyl; benzisoxazolyl; benzothiazolyl; benzotriazolyl; benzotriazinyl; phthalazinyl; 1,8-naphthyridinyl; quinolinyl; isoquinolinyl; quinazolinyl; quinoxalinyl; pyrazolo[3,4-d]pyrimidinyl; pyrimido[4,5-d]pyrimidinyl; imidazo[1,2-a]pyridinyl; pyridopyridinyl; pteridinyl; and 1H-purinyl.

In order to provide a still further demonstration of preferred embodiments of the compounds of Formula (1.0.0) with reference to the D group where it is a moiety of partial Formula (1.1.4), v is 0 or 1, and $R^8$ is a bicyclic heterocyclic group, there is set out below the groups consisting of partial Formulas (5.0.1) through (5.0.28) from which the D moiety is selected in such preferred embodiments:

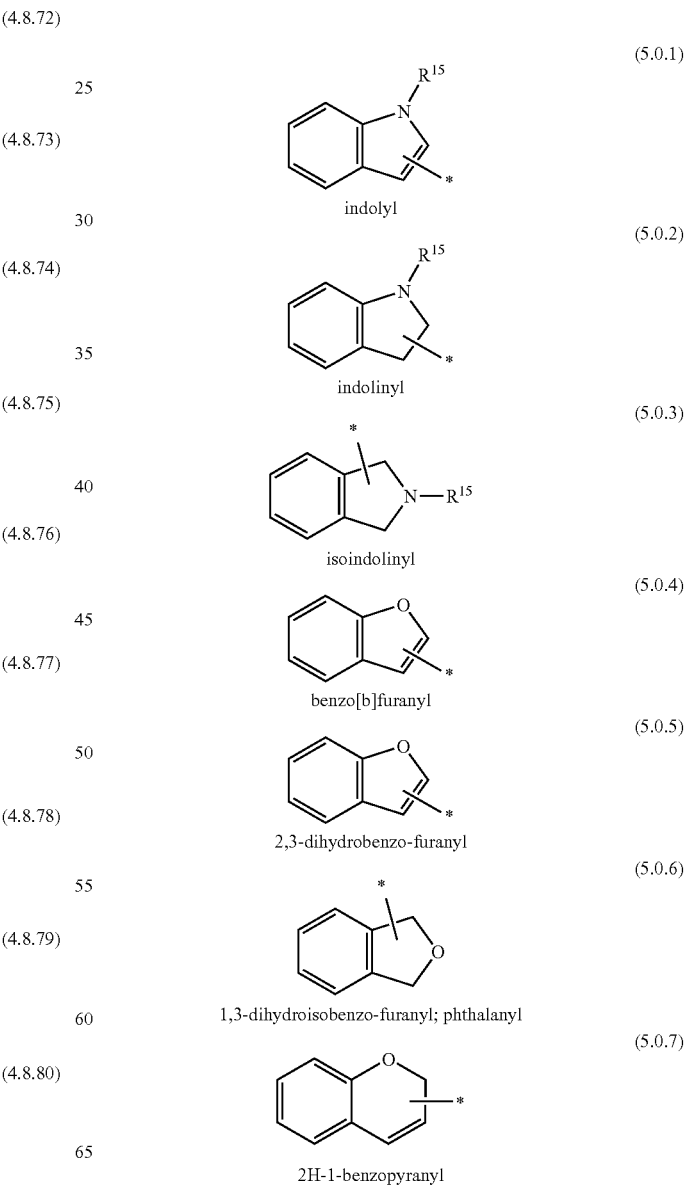

-continued
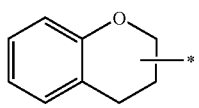 (5.0.8)
chromanyl
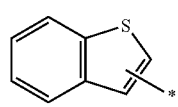 (5.0.9)
benzothienyl
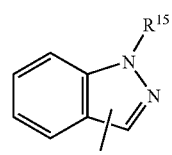 (5.0.10)
1H-indazolyl
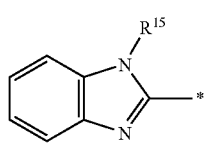 (5.0.11)
benzimidazolyl
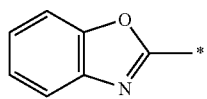 (5.0.12)
benzoxazolyl
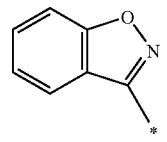 (5.0.13)
benzisoxazolyl
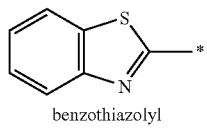 (5.0.14)
benzothiazolyl
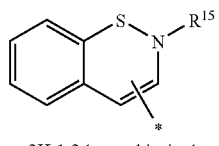 (5.0.15)
2H-1,2-benzothiazinyl
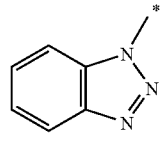 (5.0.16)
benzotriazolyl
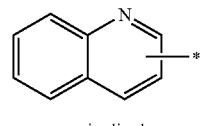 (5.0.17)
quinolinyl
-continued
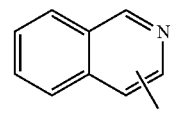 (5.0.18)
isoquinolinyl
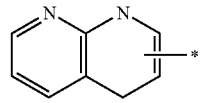 (5.0.19)
1,8-naphthyridinyl
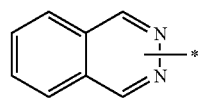 (5.0.20)
phthalazinyl
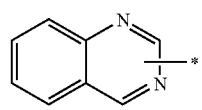 (5.0.21)
quinazolinyl
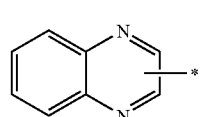 (5.0.22)
quinoxalinyl
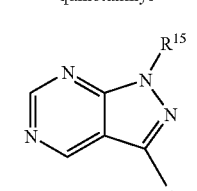 (5.0.23)
1H-pyrazolo[3,4-d]-pyrimidinyl
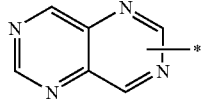 (5.0.24)
pyrimido[5,4-d]-pyrimidinyl
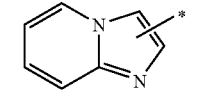 (5.0.25)
imidazo-[1,2-a]-pyridinyl
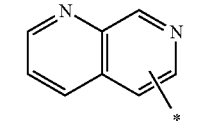 (5.0.26)
pyridopyridinyl
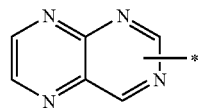 (5.0.27)
pteridinyl -continued (5.0.28)

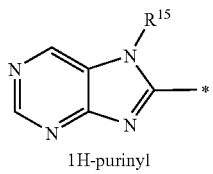

1H-purinyl where "*" indicates the point of attachment to the remaining portion of Formula (1.0.0); and where each carbon atom is optionally substituted by a substituent $R^{14}$; and where $R^{14}$ and $R^{15}$ have the same meaning as defined above; and all tautomer forms, and optionally N-oxide forms, thereof.

5.1.3 D is a Moiety of Partial Formula (1.1.5)

There are further embodiments of the compounds of Formula (1.0.0) in which the D moiety comprises a group falling within the scope of partial Formula (1.1.5):

(1.1.5)

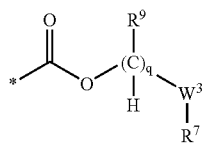

wherein q is 1, 2, or 3, provided that where q is 2 or 3, $R^9$ has the meaning of —H in at least one instance, or two instances, respectively; $W^3$ is —O—; —N($R^9$)—; or —OC(=O)— where $R^9$ has the same meaning as defined above; and $R^7$ has the same meaning as defined above.

In preferred embodiments of the compounds of partial Formula (1.1.5), q is 1 or 2, $R^9$ is —H, or —CH$_3$; $W^3$ is —O—, —O(C=O)—, or —NH—; and $R^7$ is one of the preferred moieties already described above.

Representative embodiments of the compounds of Formula (1.0.0) in which the D moiety falls within the scope of partial Formula (1.1.5) are those illustrated by partial Formulas (6.0.1) through (6.0.6):

(6.0.1)
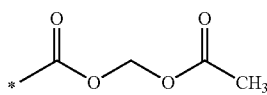

(6.0.2)
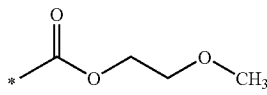

(6.0.3)
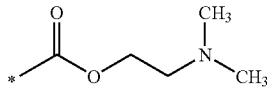

(6.0.4)
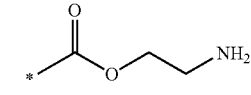

(6.0.5)
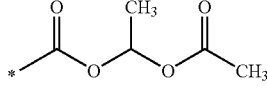

-continued (6.0.6)
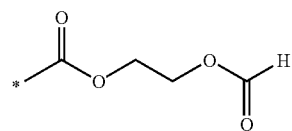

5.1.4 D is Other than a Carboxylic Acid

Embodiments of the compounds of Formula (1.0.0) include those wherein the D moiety is other than a carboxylic acid and is, instead, a phosphorus or sulfur acid or a derivative thereof. There are a significant number of such derivatives from which the D moiety may be selected, and they include the following: —O—P(=O)(OH)$_2$ (phosphoric); —PH(=O)OH (phosphinic); —P(=O)(OH)$_2$ (phosphonic); —[P(=O)(OH)—O(C$_1$–C$_4$)alkyl] (alkylphosphono); —P(=O)(OH)—O(C$_1$–C$_4$)alkyl) (alkylphosphinyl); —P(=O)(OH)NH$_2$ (phosphoramido); —P(=O)(OH)NH(C$_1$–C$_4$)alkyl and —P(=O)(OH)NHR$^{25}$ (substituted phosphoramido); —O—S(=O)$_2$OH (sulfuric); —S(=O)$_2$OH (sulfonic); —S(=O)$_2$NHR$^{26}$ or —NHS(=O)$^2$R$^{26}$ (sulfonamido) where $R^{26}$ is —CH$_3$, —CF$_3$, or o-toluyl; and acylsulfonamido selected from the group consisting of —C(=O)NHS(=O)$_2$R$^{25}$; —C(=O)NHS(=O)$_2$NH$_2$; —C(=O)NHS(=O)$_2$(C$_1$–C$_4$)alkyl; —C(=O)NHS(=O)$_2$NH(C$_1$–C$_4$)alkyl; —C(=O)NHS(=O)$_2$N[(C$_1$–C$_4$)alkyl]$_2$; —S(=O)$_2$NHC(=O)(C$_1$–C$_4$)alkyl; —S(=O)$_2$NHC(=O)NH$_2$; —S(=O)$_2$NHC(=O)NH(C$_1$–C$_4$)alkyl; —S(=O)$_2$NHC(=O)N[(C$_1$–C$_4$)alkyl]$_2$; —S(=O)$_2$NHC(=S)NH(C$_1$–C$_4$)alkyl; —S(=O)$_2$NHCN; —S(=O)$_2$NHC(=S)NH$_2$; —S(=O)$_2$NHC(=S)NH(C$_1$–C$_4$)alkyl; —S(=O)$_2$NHC(=S)N[(C$_1$–C$_4$)alkyl]$_2$; and —S(=O)$_2$NHS(=O)$_2$R$^{25}$; where $R^{25}$ is —H; —(C$_1$–C$_4$)alkyl; phenyl; or —OR$^{16}$, where $R^{16}$ has the same meaning as defined above.

Preferred embodiments of the compounds of Formula (1.0.0) wherein D is a phosphorus or sulfur acid or a derivative thereof, are those wherein D is —P(=O)(OH)NHR$^{25}$ (substituted phosphoramido); —S(=O)$_2$NHR$^{26}$ or —NHS(=O)$^2$R$^{26}$ (sulfonamido); or —C(=O)NHS(=O)$_2$R$^{25}$ (acylsulfonamido); where $R^{26}$ and $R^{25}$ has the same meaning as defined above. Some of these preferred embodiments may be illustrated by partial Formulas (6.5.1) through (6.5.9):

(6.5.1)
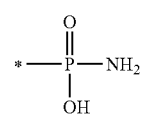

(6.5.2)
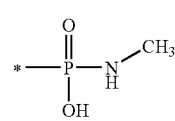

(6.5.3)
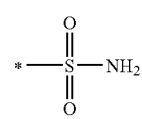

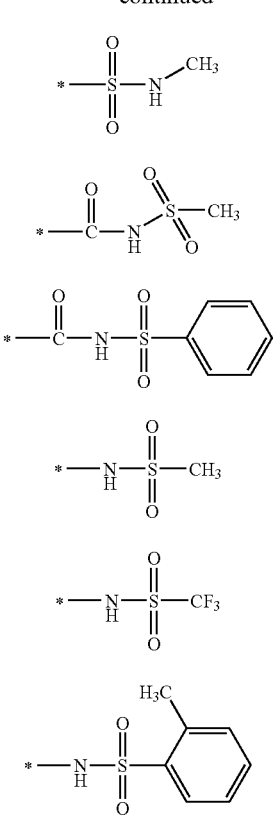

5.1.5 D is a Moiety of Partial Formulas (1.1.6) through (1.1.9)

There are further embodiments of the compounds of Formula (1.0.0) in which the D moiety comprises a group falling within the scope of partial Formulas (1.1.6) through (1.1.9):

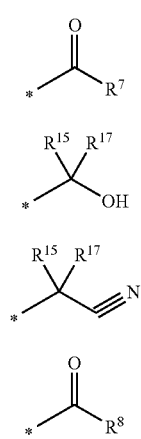

where $R^7$, $R^8$, $R^{16}$, and $R^{17}$ have the same meaning as defined above. For example, $R^{16}$ and $R^{17}$ are each independently selected from —H; —($C_1$–$C_4$)alkyl; —($C_2$–$C_4$)alkenyl; —($C_3$–$C_6$)cycloalkyl; phenyl; benzyl; and pyridyl; wherein said alkyl, alkenyl, cycloalkyl, phenyl, benzyl, or pyridyl is substituted by 0 to 3 substituents selected from the group consisting of —F, —Cl, —$CF_3$, —CN, and —($C_1$–$C_3$) alkyl.

The keto groups of partial Formulas (1.1.6) and (1.1.9) are the same with respect to the carbonyl linking entity, but differ with respect to the attached group, $R^7$ or $R^8$:

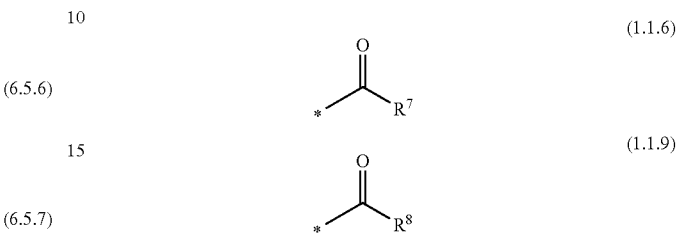

$R^7$ in the moiety of partial Formula (1.1.6) has the same meaning as defined further above, but in preferred embodiments of the compounds of Formula (1.0.0) $R^7$ has especially the meaning of —H; —($C_1$–$C_6$)alkyl, preferably methyl, ethyl, iso-propyl, or tert-butyl; —($C_2$–$C_6$)alkenyl, preferably 2-propenyl; —($C_2$–$C_6$)alkynyl, preferably ethynyl. Each of these meanings of $R^7$ is optionally substituted by up to 3 substituents $R^{10}$. The meaning of $R^{10}$ is the same as defined above, but is preferably phenyl or pyridyl optionally substituted by up to 3 $R^{11}$ where $R^{11}$ is preferably —F, —$CF_3$, —CN, —$CH_3$, or —$OCH_3$. $R^{10}$ also preferably has the meaning of —F, —$CF_3$, —$OR^{16}$, —CN; —C(=O)$OR^{16}$, —C(=O)$NR^{16}R^{17}$, —$NR^{16}R^{17}$; or —$NR^{16}S$(=O)$_2$$R^{17}$, where $R^{16}$ and $R^{17}$ are preferably —H, methyl, ethyl, cyclopropyl, phenyl, benzyl, or pyridyl optionally substituted by up to 3 of —F, or 1 of —$CF_3$, —CN, or —$CH_3$.

$R^7$ also has the meaning of —$(CH_2)_u$—($C_3$–$C_7$)cycloalkyl where u is preferably 0 or 1 and where ($C_3$–$C_7$)cycloalkyl is preferably cyclopropyl, cyclopentyl, or cyclohexyl optionally substituted by up to 3 substituents $R^{10}$ where $R^{10}$ has the same preferred meanings as defined in the paragraph immediately above.

$R^7$ also has the meaning of phenyl or benzyl, where said phenyl or benzyl optionally substituted by up to 3 substituents $R^{10}$ where $R^{10}$ has the same preferred meanings as defined in the paragraph immediately above.

$R^8$ in the moiety of partial Formula (1.1.9) has the same meaning as defined further above, but in preferred embodiments of the compounds of Formula (1.0.0) $R^8$ has especially the meaning of tetrazol-5-yl; 1,2,4-triazol-3-yl; 1,2,3-triazol-5-yl; imidazol-2-yl; imidazol-4-yl; 1,3,4-oxadiazolyl; 1,2,4-oxadiazol-3-yl; 1,2,4-oxadiazol-5-yl; 1,2,5-thiadiazolyl; 1,3,4-thiadiazolyl; morpholinyl; oxazolyl; isoxazolyl; thiazolyl; isothiazolyl; pyrrolyl; pyrazolyl; pyridyl; indolyl; benzo[b]furanyl; 2,3-dihydrobenzofuranyl; 1H-indazolyl; benzimidazolyl; benzoxazolyl; benzisoxazolyl; benzothiazolyl; benzotriazolyl; quinolinyl; isoquinolinyl; quinazolinyl; or quinoxalinyl.

Any of the above-recited especially preferred meanings of $R^8$ is optionally substituted on a carbon atom by $R^{14}$ where $R^{14}$ has the same meaning as defined above; and on a nitrogen atom by $R^{15}$ where $R^{15}$ has the same meaning as defined above. Especially included in the case of such nitrogen atom substituents, are all tautomer forms of the moieties of partial Formula (1.1.9). Sulfur atoms of said moieties are optionally substituted by 1 or 2 oxygen atoms.

In order to illustrate further meanings of D that fall within the scope of partial Formulas (1.1.6), (1.1.7), (1.1.8), and (1.1.9), there are depicted below moieties of partial Formulas (3.3.1) through (3.3.15) that represent different meanings that fall within the scope partial Formula (1.1.7):

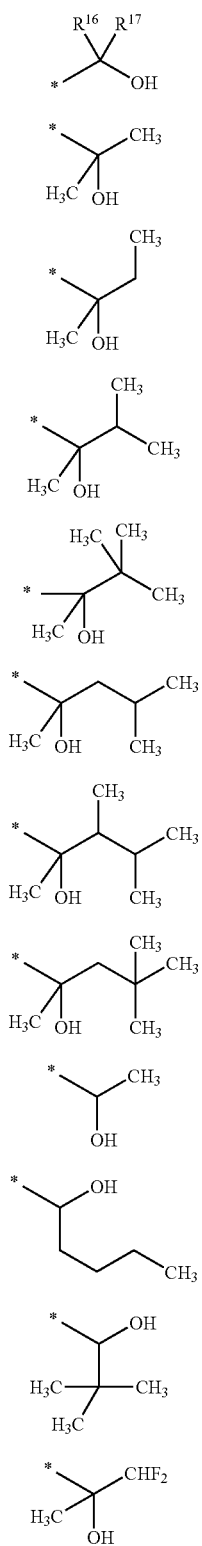

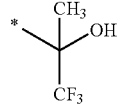

(3.3.12)

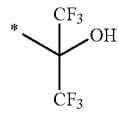

(3.3.13)

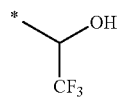

(3.3.14)

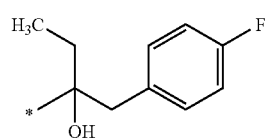

(3.3.15)

Further meanings of D are those that fall within the scope of partial Formula (1.1.8), in which a nitrile group, —C≡N, serves as a bioisosteric replacement for the hydroxyl group of partial Formula (1.1.7). Accordingly, there are depicted below moieties of partial Formulas (3.8.1) through (3.8.10) that represent different meanings that fall within the scope partial Formula (1.1.8):

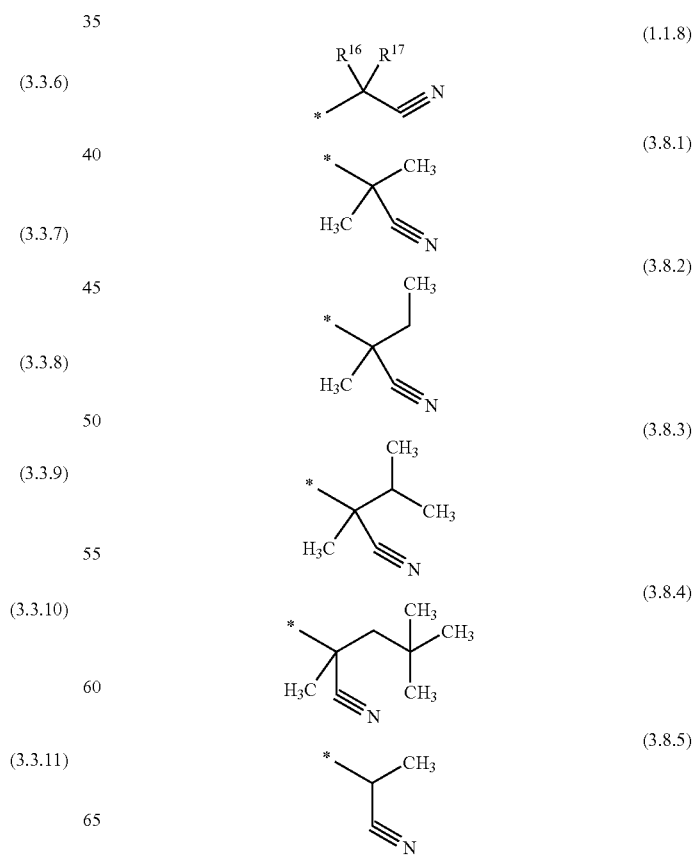

-continued
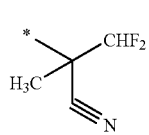 (3.8.6)
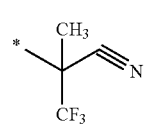 (3.8.7)
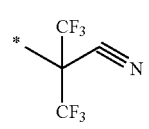 (3.8.8)
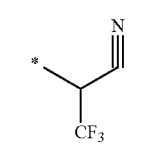 (3.8.9)
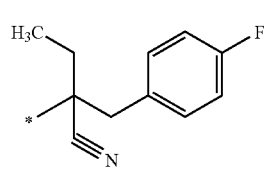 (3.8.10)
In order to illustrate additional meanings of D that fall within the scope of partial Formulas (1.1.6), (1.1.7), (1.1.8), and (1.1.9), there are depicted below moieties of partial Formulas (3.9.1) through (3.9.9) that represent different meanings that fall within the scope partial Formulas (1.1.6) and (1.1.9):
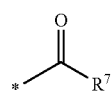 (1.1.6)
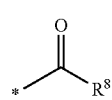 (1.1.9)
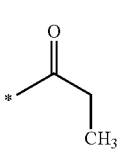 (3.9.1)
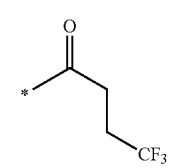 (3.9.2)
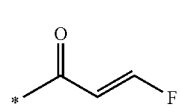 (3.9.3)
-continued
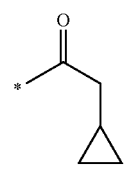 (3.9.4)
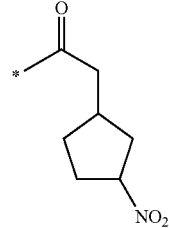 (3.9.5)
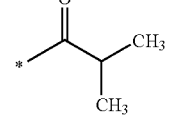 (3.9.6)
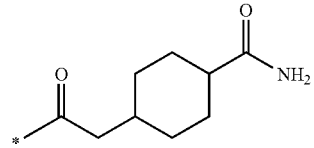 (3.9.7)
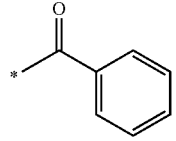 (3.9.8)
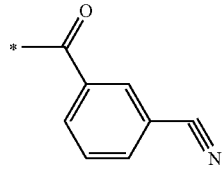 (3.9.9)
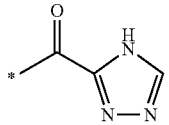 (3.9.10)
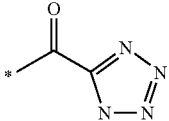 (3.9.11)
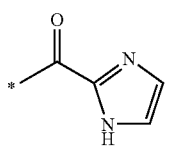 (3.9.12)

-continued
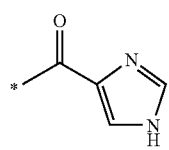 (3.9.13)
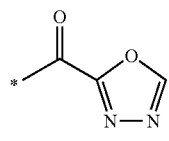 (3.9.14)
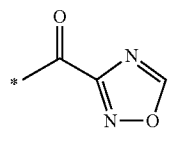 (3.9.15)
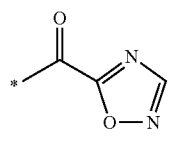 (3.9.16)
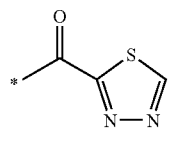 (3.9.17)
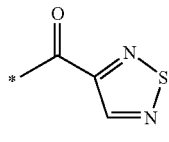 (3.9.18)
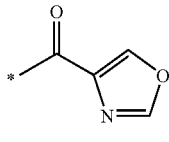 (3.9.19)
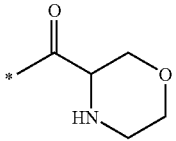 (3.9.20)
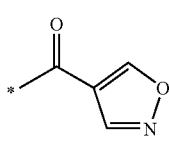 (3.9.21)
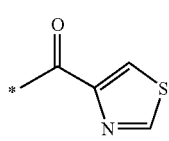 (3.9.22)
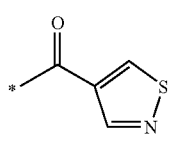 (3.9.23)
-continued
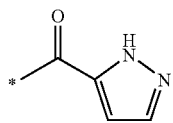 (3.9.24)
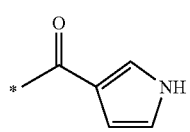 (3.9.25)
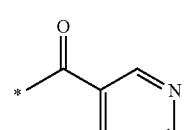 (3.9.26)
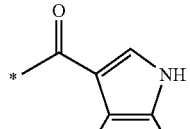 (3.9.27)
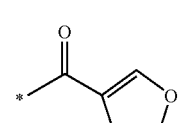 (3.9.28)
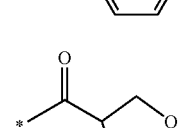 (3.9.29)
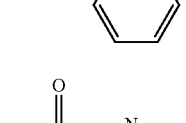 (3.9.30)
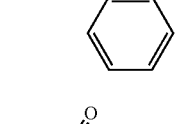 (3.9.31)
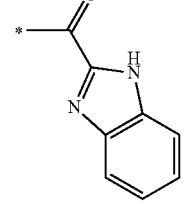

-continued (3.9.32) 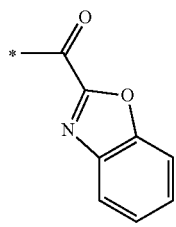

(3.9.33) 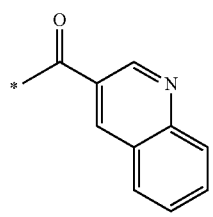

(3.9.34) 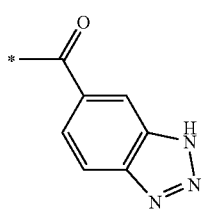

(3.9.35) 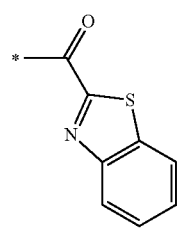

(3.9.36) 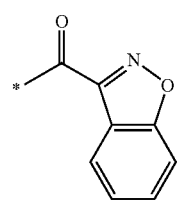

(3.9.37) 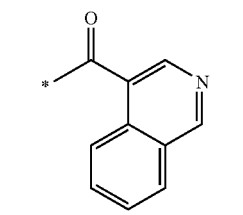

(3.9.38) 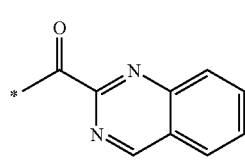

-continued (3.9.39) 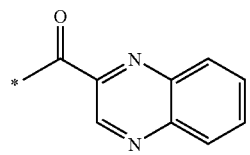

5.2 Linkage $W^1$ and ($R^4$—, $R^5$—, and $R^6$)-Substituted Moiety $*^1$

The nicotinamide core nucleus is further elaborated by allowing the 2-carbon atom in the pyridyl or pyrimidinyl ring of said nucleus to form a linkage to a ring comprising the moiety $*^1$. In preferred embodiments, the moiety $*^1$ has the meaning of a phenyl ring which is para-substituted by a moiety $R^6$, meta-substituted by a moiety $R^5$, or substituted on any of the remaining positions by a moiety $R^4$, resulting in a moiety of partial Formula (1.0.3):

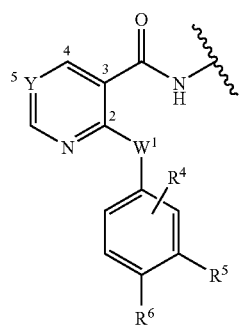

(1.0.3)

where $W^1$ has the meaning —O—; —S(=O)$_t$—, where t is 0, 1, or 2; or —N(R$^3$)— where R$^3$ is —H; —(C$_1$–C$_3$)alkyl; phenyl; benzyl; or —OR$^{16}$; and is preferably —H or —CH$_3$.

In other embodiments of the present invention, $W^1$ has the meaning —S(=O)$_t$—, where t is 0, 1, or 2; and preferably has the meaning —S— whereby a thioether linkage is formed. Where the sulfur atom of the thioether linkage is oxygenated, a sulfinyl or a sulfonyl linkage results. In still further embodiments, where $W^1$ has the meaning of —N(R$^3$)—, an amino linkage is formed, which preferably will be —NH—. Nevertheless, the nitrogen atom may be substituted and where this is the case, it is preferred that said substituent be —CH$_3$.

The meanings of the $R^4$, $R^5$ and $R^6$ substituents are selected from the same set of definitions, but it will be understood that said meanings are selected on an independent basis from each other. $R^5$ and $R^6$ may also be —H. Accordingly, where the moiety $*^1$ has the meaning of a phenyl ring, the para-($R^6$), meta-($R^5$), or ortho-($R^4$)-position of the phenyl ring may be substituted, or all three positions may be substituted, or any combination of said positions may be substituted. It is preferred, however, in the compounds of Formula (1.0.0) that the para- and/or meta-positions be substituted, rather than the ortho-position.

Where the moiety *¹ has the preferred meaning of a phenyl ring, $R^5$ and $R^6$ may also be taken together to form a member selected from a group of partial formulas described in more detail further below. Some of these meanings of $R^5$ and $R^6$ taken together also constitute preferred embodiments of the compounds of Formula (1.0.0)

$R^5$ and $R^6$ may be —H. In addition to —H, $R^5$ and $R^6$ may, inter alia, be —F; —Cl; —CN; —NO$_2$; —C(=O)R$^{16}$; —OR$^{16}$; —C(=O)OR$^{16}$; or —NR$^{16}$R$^{17}$. Where $R^5$ is —H and $R^6$ is —F, preferred embodiments of the present invention result. In a further preferred embodiment of the present invention, $R^5$ and $R^6$ may also be —OR$^{16}$, where $R^{16}$ is hydrogen; (C$_1$–C$_4$)alkyl; or (C$_3$–C$_6$)cycloalkyl; wherein said alkyl and cycloalkyl are substituted by 0 to 3 substituents selected from the group consisting of —F and —Cl. Other preferred embodiments are those wherein $R^{16}$ is methyl; difluoromethyl; ethyl; or cyclopentyl.

The medicinal chemist will appreciate that the choice of substituents from those described above will be influenced by the effect which such substituents have in turn on the physico-chemical properties of the overall molecules which result. The present state of the art provides the capability of quickly and facilely synthesizing a very large number of chemically very similar compounds based on the substituent choices outlined above, and of thereafter testing the relative effectiveness of the resulting molecules in rapid in vitro testing methods. Combinatorial chemistry synthesis and testing procedures currently available in the art have even more considerably expanded the number of substituent combinations which can be rapidly evaluated. The information which has thereby been produced through use of these techniques permits a reasonable prediction herein of certain preferences which exist as to various embodiments of the present invention. Such preferred embodiments are described in detail herein.

Preferred embodiments of the present invention further include those wherein both $R^5$ and $R^6$ are both —F; wherein $R^5$ is —H and $R^6$ is —F; and wherein $R^6$ is —H and $R^5$ is —F; —OR$^{16}$, e.g., —OCH$_3$, —OCH$_2$F, —OCHF$_2$, or —OCF$_3$; —CN; —COOH; —COOCH$_3$; —CONH$_2$; —OCOCH$_3$; or NH$_2$. The most preferred embodiments are those wherein $R^5$ is —H and $R^6$ is —F; $R^5$ is —CN and $R^6$ is —H; and $R^5$ is —NO$_2$, —NH$_2$, —CN, —OCH$_3$, or —C(=O)CH$_3$, and $R^6$ is —H.

$R^5$ and $R^6$ may also be selected from substituents comprising —(C$_1$–C$_4$)alkyl and —(C$_1$–C$_4$)alkoxy wherein said alkyl and alkoxy are substituted with 0 to 3 substituents —F or —Cl; or 0 or 1 substituent (C$_1$–C$_2$)alkoxycarbonyl-; (C$_1$–C$_2$)alkylcarbonyl-; or (C$_1$–C$_2$)alkylcarbonyloxy-.

5.3.0 *¹ is Phenyl and $R^5$ and $R^6$ are Taken Together

Where the moiety *¹ has the preferred meaning of a phenyl ring, $R^5$ and $R^6$ may also be taken together to form a moiety which is a member selected from the group consisting of partial Formulas (1.3.1) through (1.3.15):

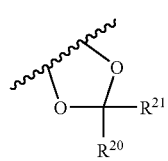
(1.3.1)

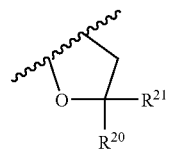
(1.3.2)

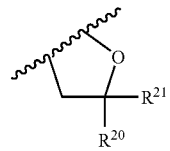
(1.3.3)

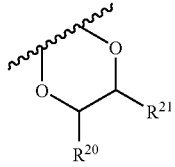
(1.3.4)

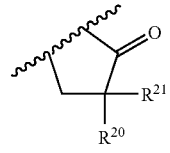
(1.3.5)

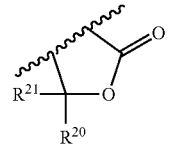
(1.3.6)

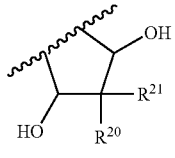
(1.3.7)

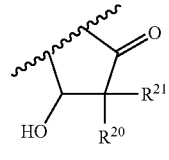
(1.3.8)

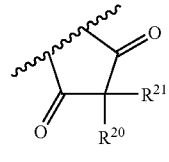
(1.3.9)

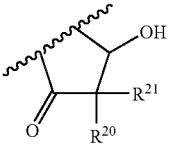
(1.3.10)

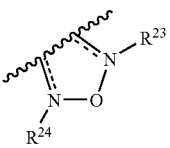
(1.3.11)

-continued

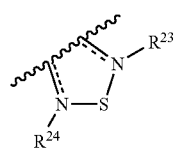 (1.3.12)

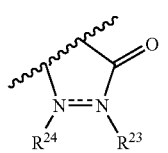 (1.3.13)

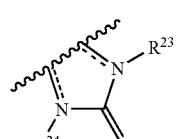 (1.3.14)

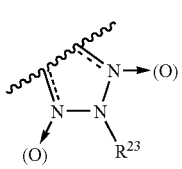 (1.3.15)

wherein $R^{20}$ and $R^{21}$ are each a member independently selected from the group consisting of —H; —F; —Cl; —CH$_3$; —CH$_2$F; —CHF$_2$; —CF$_3$; —OCH$_3$; and —OCF$_3$; and $R^{23}$ and $R^{24}$ are each independently —H; —CH$_3$; —OCH$_3$; —CH$_2$CH$_3$; —OCH$_2$CH$_3$; —CH$_2$CH$_2$CH$_3$; —CH$_2$(CH$_3$)$_2$; —CH$_2$CH$_2$CH$_2$CH$_3$; —CH(CH$_3$)CH$_2$CH$_3$; —CH$_2$CH(CH$_3$)$_2$; —C(CH$_3$)$_3$; or absent, in which case the dashed line - - - - represents a double bond. For the moiety of partial Formula (1.3.13) the nitrogen atom components thereof are represented as —[N(⇒O)]— and thus comprise optional nitrogen oxide forms of said nitrogen atoms, selected independently of each other. It will be appreciated that said nitrogen oxide form may also be represented as —N(⇒O)$_j$]— where j is 0 or 1, as in Formula (1.0.0).

Where the moiety *$^1$ has the preferred meaning of a phenyl ring, and where $R^5$ and $R^6$ are taken together to form the moiety of partial Formula (1.3.1), and $R^{20}$ and $R^{21}$ are both hydrogen, there is formed together with the phenyl group to which it is attached, a 1,3-benzodioxole group. Analogously, the structure of partial Formula (1.3.4) forms a 1,4-benzodioxan group.

Where the moiety *$^1$ has the preferred meaning of a phenyl ring, and where $R^5$ and $R^6$ are taken together to form the moieties of partial Formulas (1.3.1) through (1.3.15), and $R^{23}$ and $R^{24}$ are as defined, benzofurazan, benzothiazan, triazole, and other analogous groups, as well as substituted derivatives thereof are formed, including, inter alia, the following moieties of partial Formulas: (2.1.1) through (2.1.20):

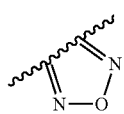 (2.1.1)

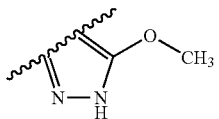 (2.1.2)

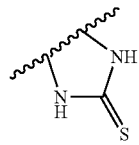 (2.1.3)

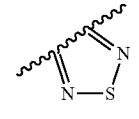 (2.1.4)

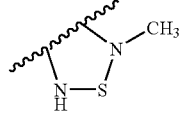 (2.1.5)

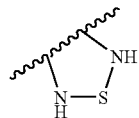 (2.1.6)

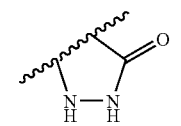 (2.1.7)

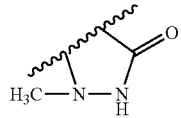 (2.1.8)

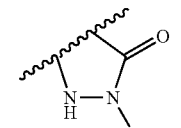 (2.1.9)

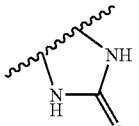 (2.1.10)

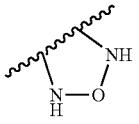 (2.1.11)

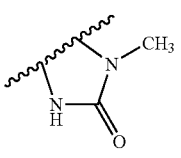 (2.1.12)

-continued

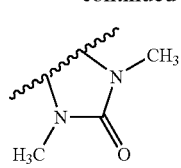
(2.1.13)

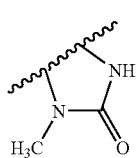
(2.1.14)

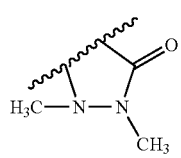
(2.1.15)

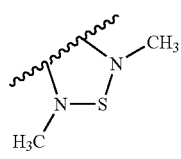
(2.1.16)

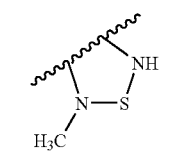
(2.1.17)

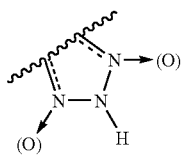
(2.1.18)

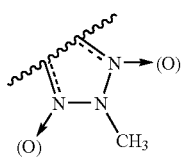
(2.1.19)

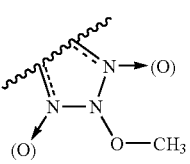
(2.1.20)

wherein the dashed line - - - - in partial Formulas (2.1.18), (2.1.19), and (2.1.20) represents a double bond where no oxygen atom is attached to the corresponding nitrogen atom, and represents a single bond where an oxygen atom is attached to said corresponding nitrogen atom.

The artisan of ordinary skill in the preparation of organic molecules will appreciate that the compounds of Formula (1.0.0) wherein $R^5$ and $R^6$ are taken together to form moieties of the above-illustrated partial Formulas (2.1.2), (2.1.3), (2.1.7), (2.1.8), (2.1.10), (2.1.12), and (2.1.14) exist in tautomeric form, and each moiety of said partial Formulas (2.1.2), (2.1.3), (2.1.7), (2.1.8), (2.1.10), (2.1.12), and (2.1.14) has a tautomer counterpart. These tautomers are related by the shift of a hydrogen and one or more π-bonds, and whenever necessary, the skilled artisan will be able to readily discern or determine which tautomeric form is present or is the most stable.

Still more preferred embodiments of the type comprising the moieties of partial Formulas (2.1.1) through (2.1.20) illustrated above are those wherein $R^5$ and $R^6$ are taken together to form a moiety which is a member selected from the group consisting of partial Formulas (2.1.1), (2.1.4) through (2.1.6), (2.1.11), and (2.1.16) through (2.1.20):

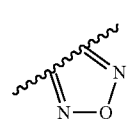
(2.1.1)

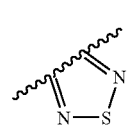
(2.1.4)

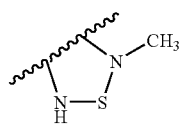
(2.1.5)

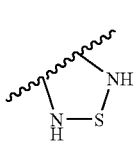
(2.1.6)

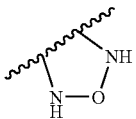
(2.1.11)

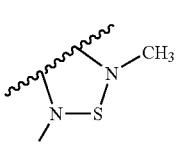
(2.1.16)

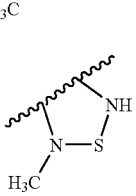
(2.1.17)

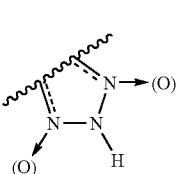
(2.1.18)

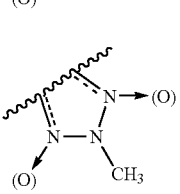
(2.1.19)

-continued (2.1.20)

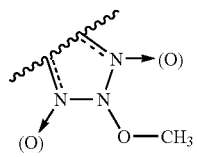

wherein the dashed line - - - - in partial Formulas (2.1.18), (2.1.19), and (2.1.20) represents a double bond where no oxygen atom is attached to the corresponding nitrogen atom, and represents a single bond where an oxygen atom is attached to said corresponding nitrogen atom.

Preferred embodiments of the present invention result directly from the definition of $R^5$ and $R^6$ as taken together to form a moiety which is a member selected from the group consisting of partial Formulas (1.3.1), (1.3.11), (1.3.12), and (1.3.15):

(1.3.1)

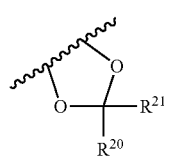

(1.3.11)

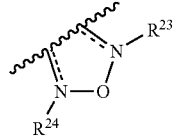

(1.3.12)

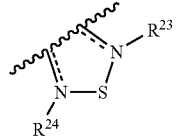

(1.3.15)

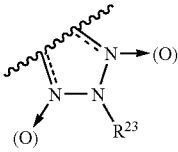

Accordingly, there further results moieties of partial Formulas (1.0.15) through (1.0.18):

(1.0.15)

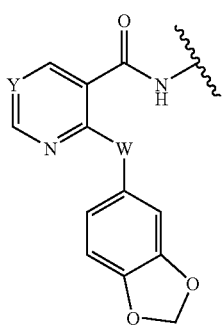

-continued (1.0.16)

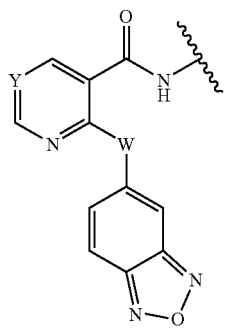

(1.0.17)

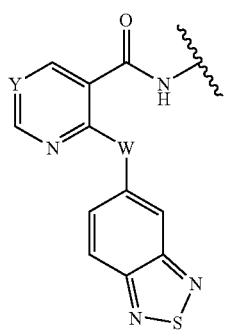

(1.0.18)

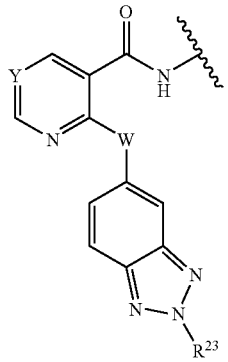

where $R^{23}$ is —H or —CH$_3$; and W has the meaning of —O—; —S(=O)$_t$— where t is 0, 1, or 2; or —N(R$^3$) where $R^3$ is as defined herein and is preferably —H or —CH$_3$. In preferred compounds of Formula (1.0.0), W has the meaning of —O— whereby an ether linkage is created to attach the benzo-fused, bicyclic heterocycle to the nicotinamide core nucleus.

In preferred embodiments of the compounds of Formula (1.0.0), $R^{23}$ and $R^{24}$ are both absent, except in compounds of the type illustrated by partial Formula (1.3.11), where only one of $R^{23}$ or $R^{24}$ may be absent. It will be recognized that where $R^{23}$ and $R^{24}$ are both absent, and the dashed lines: - - - accordingly represent double bonds, that the phenyl portion of the resulting benzo-fused bicyclic heterocycles depicted cannot have all of the double bonds depicted in said partial Formulas, since the result would be prohibited pentavalent carbon atoms in said phenyl portion.

Accordingly, where $R^{23}$ and $R^{24}$ are both absent, the resulting compounds are characterized by such structures as those shown in partial Formulas (1.0.16) and (1.0.17) above.

In other embodiments of the compounds of Formula (1.0.0) the substituents $R^{20}$ and $R^{21}$ on the benzo-fused, bicyclic heterocycles represented by partial Formula (1.3.1)

are —H, —F, —Cl, —CH$_3$, —CH$_2$F, —CHF$_2$, or —CF$_3$. Preferably, R$^{20}$ and R$^{21}$ are both —H or —F, in which case the resulting compounds are characterized by the structure shown in partial Formula (1.0.15) above, or its corresponding difluoro analog (not shown). The substituents R$^{23}$ and R$^{24}$ on the benzo-fused, bicyclic heterocycles represented by the moieties of partial Formulas (1.3.9) through (1.3.13) are each independently —H; —CH$_3$; —OCH$_3$; or absent in which case the dashed line - - - - represents a double bond. It will be understood, of course, that where R$^{23}$ and R$^{24}$ are absent; there are no pentavalent carbon atoms in the phenyl portion of said benzo-fused, bicyclic heterocycles. The resulting benzo-fused, bicyclic heterocyclic structures are shown in partial Formulas (1.0.16) through (1.0.18) above.

5.3.1 *$^1$ is Other than Phenyl

In addition to those embodiments of the present invention where *$^1$ has the preferrred meaning of phenyl, the present invention has also been defined above as being concerned with a compound of Formula (1.0.0) wherein *$^1$ has the meaning defined above as a moiety comprising a saturated or unsaturated carbon ring system that is 3- to 7-membered monocyclic, or that is 7- to 12-membered, fused or discontinuous, polycyclic; wherein optionally one carbon atom thereof may be replaced by a heteroatom selected from N, O, or S, and where N is selected, optionally a second carbon atom thereof may be replaced by a heteroatom selected from N, O, or S. The present invention is further concerned with a compound of Formula (1.0.0) wherein *$^1$ comprises especially a member selected from the group consisting of phenyl; pyrrolyl; pyrrolidinyl; furanyl; thienyl; pyridyl; pyrimidinyl; piperidinyl; piperazinyl; imidazolyl; imidazolidinyl; oxazolyl; isoxazolyl; morpholinyl; thiazolyl; indolyl; quinolinyl; isoquinolinyl; benzimidazolyl; benzoxazolyl; quinuclidinyl; and azabicyclo[3.3.0]octanyl; a monocyclic —(C$_3$–C$_7$)cycloalkyl moiety; a monocyclic —(C$_5$–C$_7$)cycloalkenyl moiety that is a member selected from the group consisting of cyclopentenyl, cyclohexenyl, and cycloheptenyl; and a bicyclic —(C$_7$–C$_{10}$)cycloalkyl or —(C$_7$–C$_{10}$)cycloalkenyl moiety that is a member selected from the group consisting of norbornanyl, norbornenyl, bicyclo[2.2.2]octanyl, bicyclo[3.2.1]octanyl, bicyclo[3.3.0]octanyl, bicyclo[2.2.2]oct-5-enyl, bicyclo[2.2.2]oct-7-enyl, bicyclo[3.3.1]nonanyl, cyclodecanyl, and adamantanyl.

The present invention is still further concerned especially with a compound of Formula (1.0.0) wherein particularly *$^1$ and the substituents R$^4$, R$^5$, and R$^6$ are selected in such a way that the left-hand terminus of said compound of Formula (1.0.0) is represented by the following partial Formulas (1.8.1) through (1.8.72):

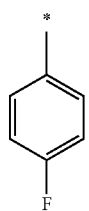
(1.8.1)

-continued

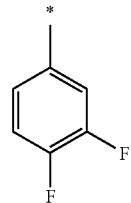
(1.8.2)

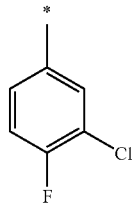
(1.8.3)

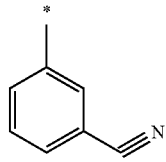
(1.8.4)

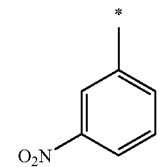
(1.8.5)

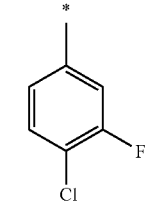
(1.8.6)

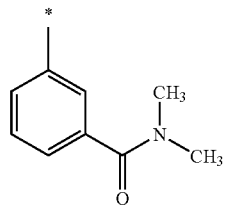
(1.8.7)

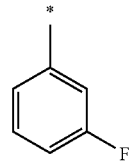
(1.8.8)

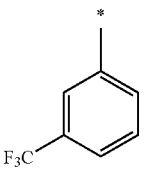
(1.8.9)

-continued
(1.8.10)
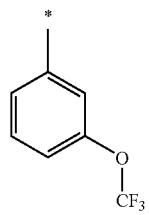
(1.8.11)
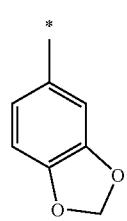
(1.8.12)
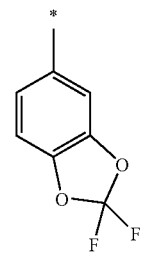
(1.8.13)
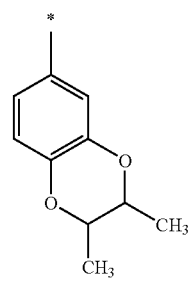
(1.8.14)
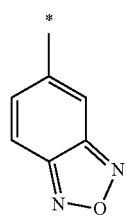
(1.8.15)
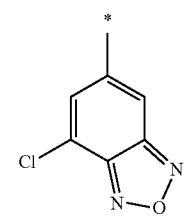
(1.8.16)
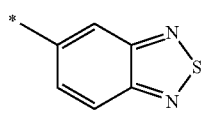
-continued
(1.8.17)
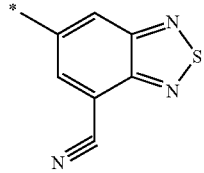
(1.8.18)
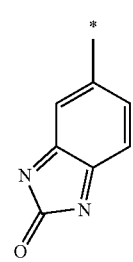
(1.8.19)
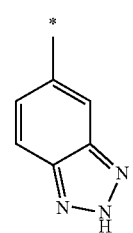
(1.8.20)
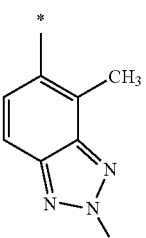
(1.8.21)
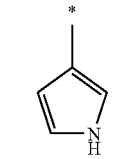
(1.8.22)
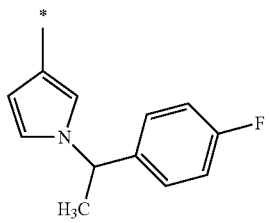
(1.8.23)
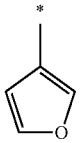

-continued
(1.8.24) 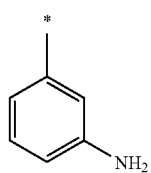
(1.8.25) 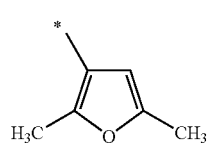
(1.8.26) 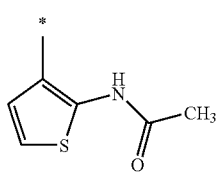
(1.8.27) 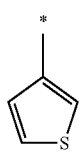
(1.8.28) 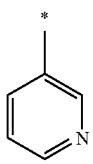
(1.8.29) 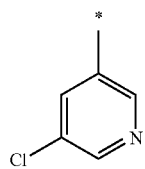
(1.8.30) 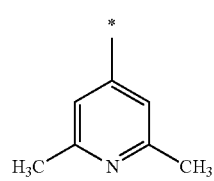
(1.8.31) 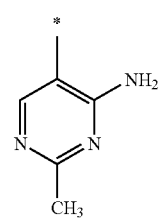
-continued
(1.8.32) 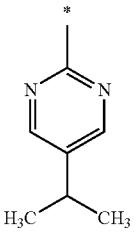
(1.8.33) 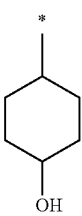
(1.8.34) 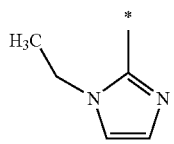
(1.8.35) 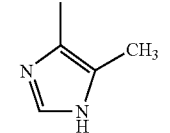
(1.8.36) 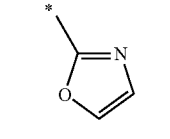
(1.8.37) 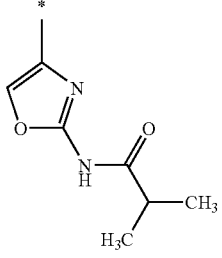
(1.8.38) 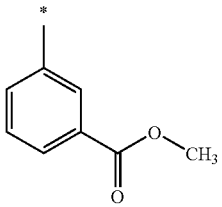
(1.8.39) 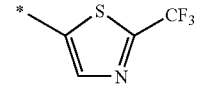
(1.8.40) 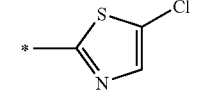

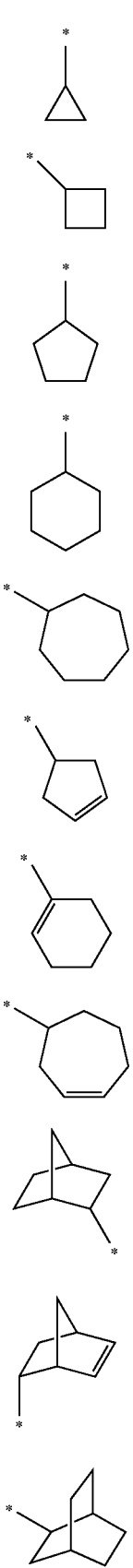
-continued
(1.8.41)
(1.8.42)
(1.8.43)
(1.8.44)
(1.8.45)
(1.8.46)
(1.8.47)
(1.8.48)
(1.8.49)
(1.8.50)
(1.8.51)
-continued
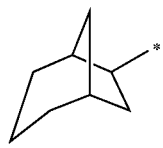 (1.8.52)
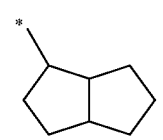 (1.8.53)
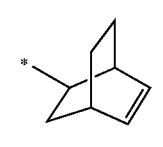 (1.8.54)
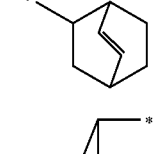 (1.8.55)
 (1.8.56)
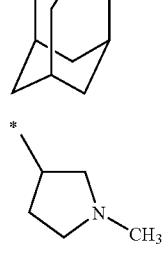 (1.8.57)
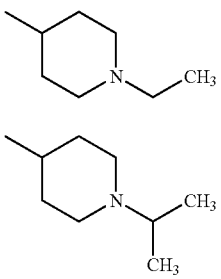 (1.8.58)
(1.8.59)
(1.8.60)
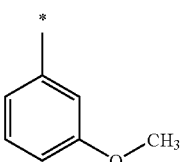 (1.8.61)
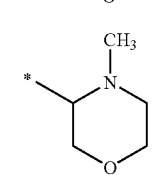 (1.8.62)

-continued

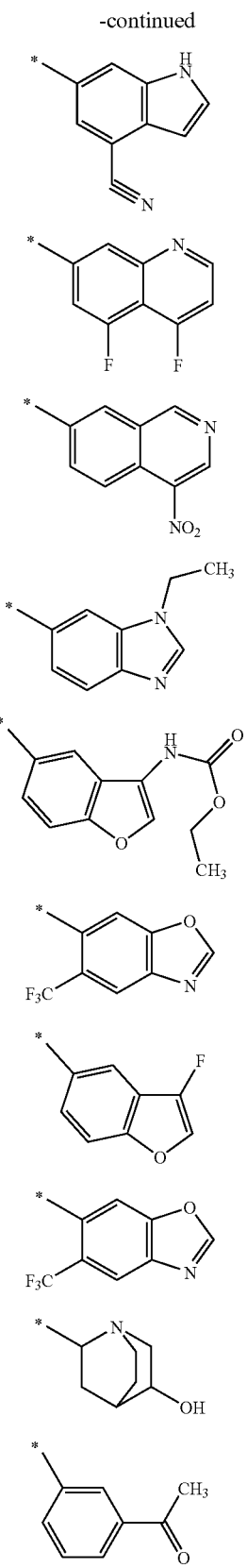

(1.8.63)
(1.8.64)
(1.8.65)
(1.8.66)
(1.8.67)
(1.8.68)
(1.8.69)
(1.8.70)
(1.8.71)
(1.8.72)

The character of the nicotinamide nucleus with an ether, thioether or sulfonyl linkage to a substituted phenyl group, which forms the left-hand-side of the compound of Formula (1.0.0), has been discussed above. The right-hand-side of the compound of Formula (1.0.0) comprises, in preferred embodiments where $*^2$ has the preferrred meaning of phenyl, a benzyl group which is substituted by substituents $R^1$ and $R^{12}$. Preferably, only a single substituent, $R^1$ or $R^2$ is present, the single substituent $R^1$ or $R^2$ is in the 2'-position, and the benzyl group is substituted in the 4-position by the moiety containing the substituents $R^A$, $R^B$, and D. This preferred right-hand-side of the compound of Formula (1.0.0) may be represented by Formula (1.0.4):

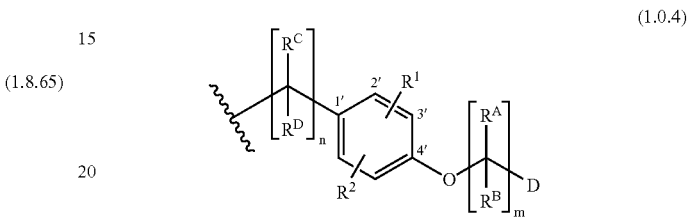

(1.0.4)

5.4.0 $*^1$ is Phenyl Substituted by $R^1$ and $R^2$

The $R^1$ and $R^2$ substituents are each a member independently selected from the group consisting of —H; —F; —Cl; $(C_1-C_3)$alkyl; fluorinated- and/or chlorinated-$(C_1-C_3)$alkyl; fluorinated- and/or chlorinated-$(C_1-C_3)$alkoxy; $(C_2-C_4)$ alkynyl; —CN; —NO$_2$; —OR$^{16}$; and —C(=O)NH$_2$. Where $R^1$ and/or $R^2$ is —H there will be no substituent at any position, especially the 2-position of the phenyl group, attached to the remainder of the left-hand side of the molecule of Formula (1.0.0). Such embodiments are not as preferred as those compounds of the present invention which have a substituent, especially one at the 2-position of the phenyl group. Thus, in some preferred embodiments of the compounds of the present invention, the meaning of $R^1$ and $R^2$ is defined as —H; —Cl; —F; chlorinated- and/or fluorinated-$(C_1-C_3)$alkyl; chlorinated- and/or fluorinated-$(C_1-C_3)$alkoxy; or $(C_2-C_4)$alkynyl.

Where a 6-membered carbon ring system is involved, e.g., as in the case of cyclohexyl, phenyl, or pyridyl, it is preferred in particular that such a moiety defining $*^2$ be attached at its 1- and 4-positions, i.e., that the points of attachment of said moiety be in para relationship to each other. However, other configurations of such a 6-membered carbon ring system defining $*^2$ are within the scope of the compounds of Formula (1.0.0), e.g., where the points of attachment are at the 1- and 2-positions, or at the 1- and 3-positions of said 6-membered carbon ring system.

It is preferred to have a halogen group at the point of the molecule occupied by the $R^1$ or $R^2$ substituent, since it usually results in improved performance. It is contemplated to be within the scope of the present invention that $R^1$ or $R^2$ is a small lipophilic group comprising —Cl or —F; chlorinated- and/or fluorinated-$(C_1-C_3)$alkyl; or chlorinated- and/or fluorinated-$(C_1-C_3)$alkoxy. Thus, the meaning of the $R^1$ or $R^2$ substituent, as well as of any other substituent of a compound of Formula (1.0.0) that includes the definitions —Cl or —F; chlorinated- and/or fluorinated-$(C_1-C_3)$alkyl; or chlorinated- and/or fluorinated-$(C_1-C_3)$alkoxy, is selected from the group consisting of the following:

—F —CH$_2$F —CHF$_2$ —CF$_3$ —CH$_2$CHF$_2$
—CH$_2$CHCF$_2$ —CH$_2$CF$_3$ —CHFCH$_2$F —CHFCHF$_2$
—CHFCF$_3$

—CF₂CF₂CF₃  —O—CH₂F  —O—CHF₂  —O—CF₃
—O—CH₂CH₂F
—O—CH₂CHF₂  —O—CH₂CF₃  —O—CHFCH₂F
—O—CHFCHF₂ —O—CHFCF₃
—O—CF₂CH₂F —O—CF₂CHF₂  —O—CF₂CF₃

The selectivity of the overall molecule which is achieved by utilizing a moiety of this type as the R¹ and R² substituent may be due to the conformational alignment of the lipophilic moiety with a corresponding lipophilic zone in the PDE4 or PDE4D enzyme substrate, or it may be due to the change in the lipophilicity of the overall molecule which results. Whatever the actual mechanism by which such selectivity is achieved, all such embodiments are contemplated to be within the scope of the present invention.

5.4.1 *² is Other than Phenyl

The present invention has also been defined above as being concerned with a compound of Formula (1.0.0) wherein *² has the meaning defined above as a moiety comprising a saturated or unsaturated carbon ring system that is 3- to 7-membered monocyclic, or that is 7- to 12-membered, fused or discontinuous, polycyclic; wherein optionally one carbon atom thereof may be replaced by a heteroatom selected from N, O, or S, and where N is selected, optionally a second carbon atom thereof may be replaced by a heteroatom selected from N, O, or S. The present invention is further concerned with a compound of Formula (1.0.0) wherein *² comprises especially a member selected from the group consisting of phenyl; pyrrolyl; pyrrolidinyl; furanyl; thienyl; pyridyl; pyrimidinyl; piperidinyl; piperazinyl; imidazolyl; imidazolidinyl; oxazolyl; isoxazolyl; thiazolyl; indolyl; quinolinyl; isoquinolinyl; benzimidazolyl; benzoxazolyl; morpholinyl; quinuclidinyl; and azabicyclo[3.3.0]octanyl; a monocyclic —(C₃–C₇)cycloalkyl moiety; a monocyclic —(C₅–C₇)cycloalkenyl moiety that is a member selected from the group consisting of cyclopentenyl, cyclohexenyl, and cycloheptenyl; and a bicyclic —(C₇–C₁₀)cycloalkyl or —(C₇–C₁₀)cycloalkenyl moiety that is a member selected from the group consisting of norbornanyl, norbornenyl, bicyclo[2.2.2]octanyl, bicyclo[3.2.1]octanyl, bicyclo[3.3.0]octanyl, bicyclo[2.2.2]oct-5-enyl, bicyclo[2.2.2]oct-7-enyl, bicyclo[3.3.1]nonanyl, cyclodecanyl, and adamantanyl.

The present invention is also further concerned especially with a compound of Formula (1.0.0) wherein particularly *² and the substituents R¹ and R² are selected in such a way that this portion of the right-hand terminus of said compound of Formula (1.0.0) is represented by the following partial Formulas (3.0.1) through (3.0.47) set out below.

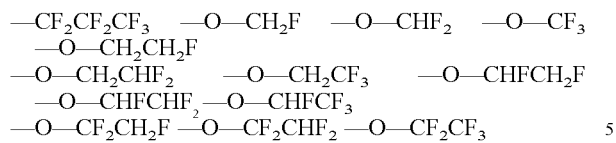
(3.0.1)

(3.0.2)

-continued

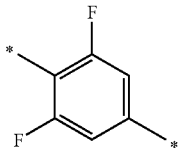
(3.0.3)

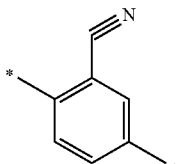
(3.0.4)

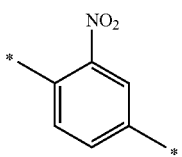
(3.0.5)

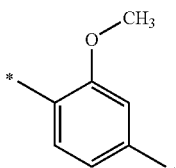
(3.0.6)

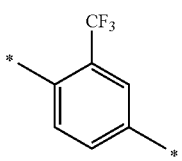
(3.0.7)

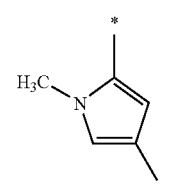
(3.0.8)

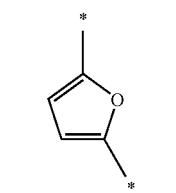
(3.0.9)

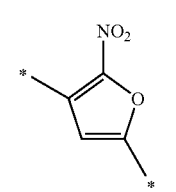
(3.0.10)

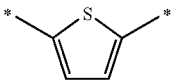
(3.0.11)

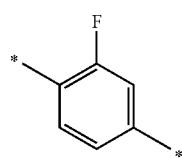

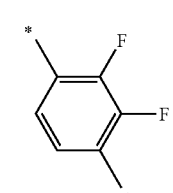

-continued
(3.0.12)
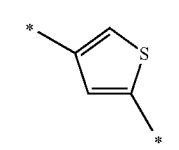
(3.0.13)
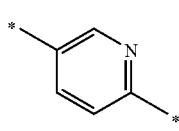
(3.0.14)
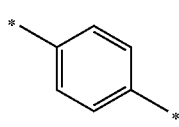
(3.0.15)
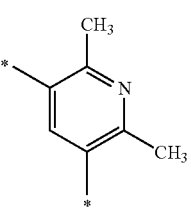
(3.0.16)
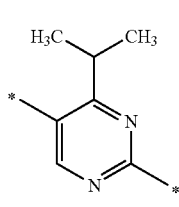
(3.0.17)
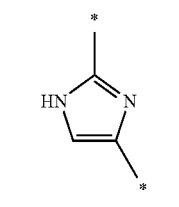
(3.0.18)
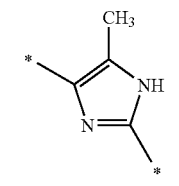
(3.0.19)
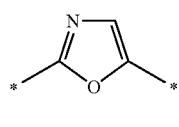
(3.0.20)
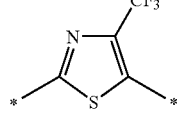
(3.0.21)
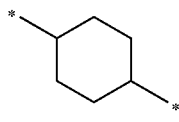
-continued
(3.0.22)
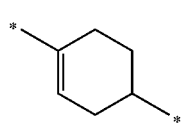
(3.0.23)
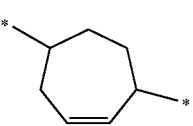
(3.0.24)
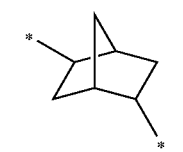
(3.0.25)
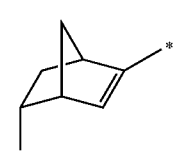
(3.0.26)
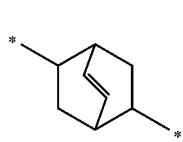
(3.0.27)
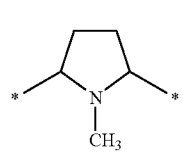
(3.0.28)
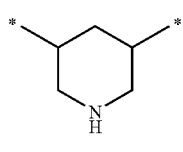
(3.0.29)
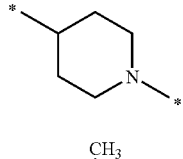
(3.0.30)
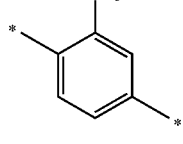
(3.0.31)
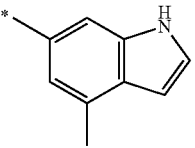
(3.0.32)
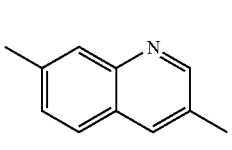

(3.0.33) 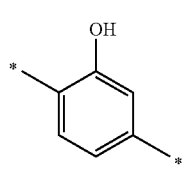

(3.0.34) 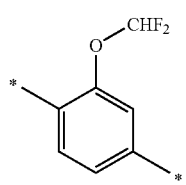

(3.0.35) 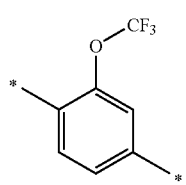

(3.0.36) 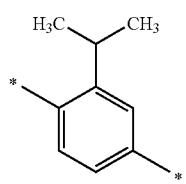

(3.0.37) 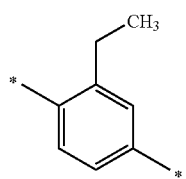

(3.0.38) 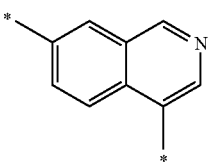

(3.0.39) 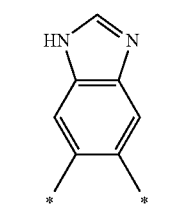

(3.0.40) 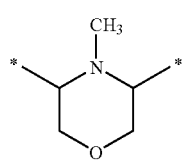

(3.0.41) 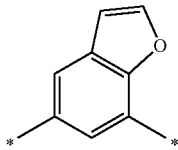

(3.0.42) 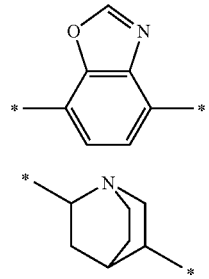

(3.0.43) 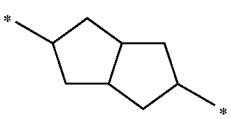

(3.0.44) 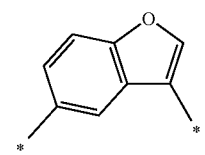

(3.0.45) 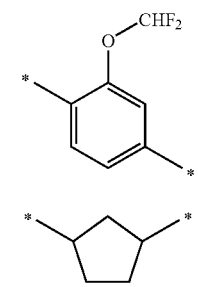

(3.0.46)

(3.0.47) 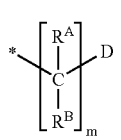

5.5 The $R^A$ and $R^B$ Substituents

The group of partial Formula (1.0.4) above is substituted in the 4-position by a moiety containing the substituents D, $R^A$, and $R^B$, which may be represented by partial Formula (1.1.8):

$$\left[ \begin{matrix} R^A \\ | \\ *-C-D \\ | \\ R^B \end{matrix} \right]_m \quad (1.1.8)$$

where m is 1, 2, or 3. In the more preferred embodiments of the compounds of the present invention, m has the meaning of 0 or 1. When m is 1 the moiety —[$R^A$—C—$R^B$]$_m$— is present, and $R^A$ and $R^B$ are preferably each a member independently selected from the group consisting of —H and ($C_1$–$C_4$)alkyl; more preferably —H and —$CH_3$.

In other preferred embodiments of the present invention $R^A$ and $R^B$ may be taken together, but only in the case where m is 1, to form a spiro moiety of Formula (1.2.0):

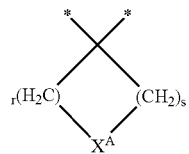
(1.2.0)

where r and s are independently 0 to 4 provided that the sum of r+s is at least 1, but not greater than 5; $X^A$ is —CH$_2$, —CHR$^{11}$, or —C(R$^{11}$)$_2$— where each R$^{11}$ is selected independently of the other and each R$^{11}$ has the same meaning as defined herein; —NR$^{15}$— where R$^{15}$ has the same meaning as defined herein; —O—; or —S(=O)$_t$, where t is 0, 1, or 2; and said spiro moiety is substituted as to any one or more carbon atoms thereof by 0 to 3 substituents R$^{14}$, as to a nitrogen atom thereof by 0 or 1 substituent R$^{15}$, and as to a sulfur atom thereof by 0 or 2 oxygen atoms. Accordingly, there results, inter alia, the moieties illustrated by partial Formulas (1.2.1) through (1.2.12):

(1.2.1)

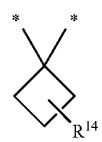
(1.2.2)

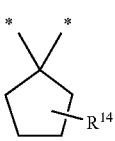
(1.2.3)

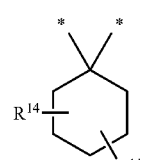
(1.2.4)

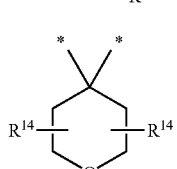
(1.2.5)

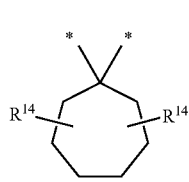
(1.2.6)

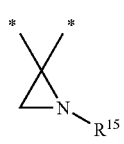
(1.2.7)

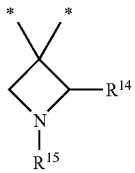
(1.2.8)

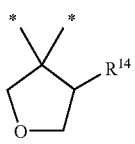
(1.2.9)

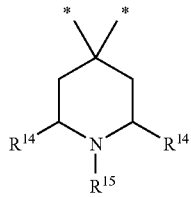
(1.2.10)

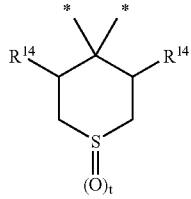
(1.2.11)

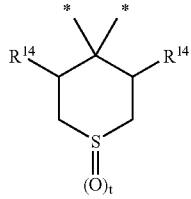
(1.2.12)

where t is 0, 1, or 2; and R$^{14}$ and R$^{15}$ have the same meaning as defined herein.

Preferred meanings of the R$^{14}$ substituent include —F; —Cl; =O; —OH; —CH$_3$; —OCH$_3$; —C(=O)OH; —C(=O)NH$_2$; —NH$_2$; —NHCH(CH$_3$)$_2$; —NHC(=O)CH$_3$; —NHC(=O)OCH$_2$CH$_3$; —NHS(=O)$_2$CH$_3$; and —S(=O)$_2$NH$_2$, resulting in moieties such as those of partial Formulas (3.1.1) through (3.1.34):

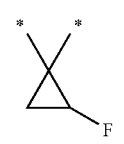
(3.1.1)

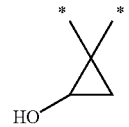
(3.1.2)

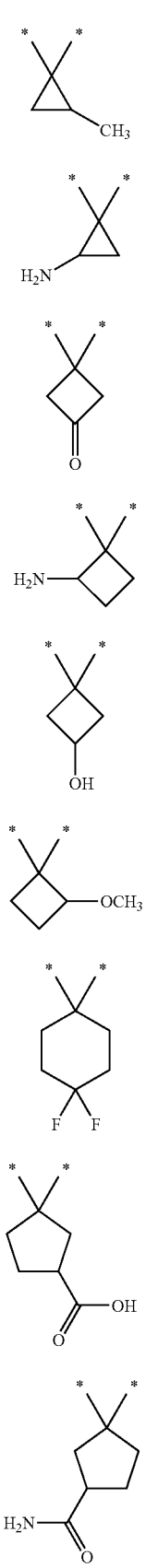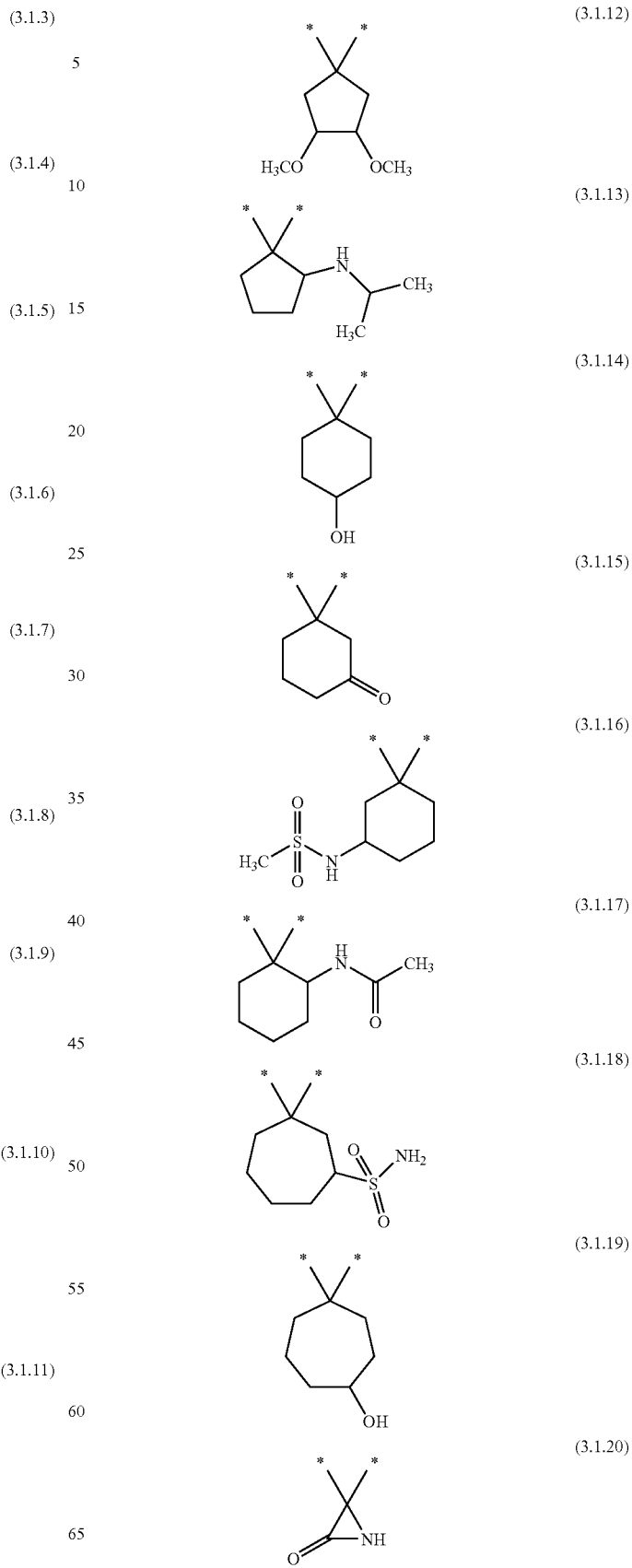

-continued (3.1.21) 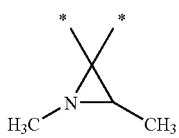

(3.1.22) 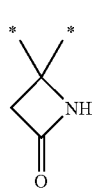

(3.1.23) 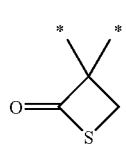

(3.1.24) 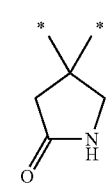

(3.1.25) 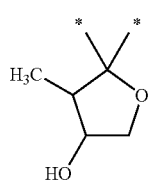

(3.1.26) 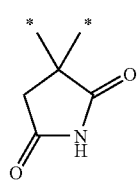

(3.1.27) 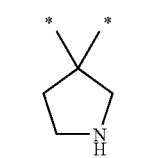

(3.1.28) 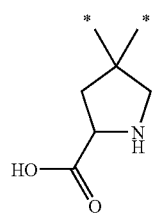

(3.1.29) 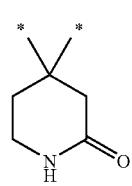

-continued (3.1.30) 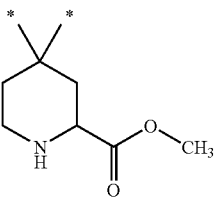

(3.1.31) 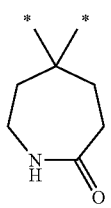

(3.1.32) 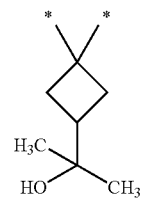

(3.1.33) 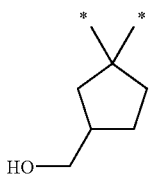

(3.1.34) 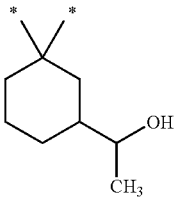

5.6 The $R^C$ and $R^D$ Substituents

As already described, $R^C$ and $R^D$ have the same meaning as defined above for $R^A$ and $R^B$, except that one of them must be —H, and they are selected independently of each other and of $R^A$ and $R^B$. Accordingly, all of the particular and preferred embodiments of the compounds of Formula (1.0.0) detailed above with regard to the $R^A$ and $R^B$ substituents, are for the most part also particular and preferred embodiments of the compounds of Formula (1.0.0) with regard to the $R^C$ and $R^D$ substituents.

5.7 The Moiety —[N(R³)]$_j$—

The subscript j has the meaning of 0 or 1. Where j has the meaning of 1, which is the preferred meaning, the moiety —N(R³)— is present and the compounds of Formula (1.0.0) are essentially nicotinamides in structure with respect to the left-hand side of the core nucleus. The nitrogen atom substituent R³ is preferably selected from —H; —(C₁–C₃)alkyl;

and —(C$_1$–C$_3$)alkoxy; and is more preferably —H; —CH$_3$; or —OCH$_3$. In the most preferred embodiments of the compounds of Formula (1.0.0), R$^3$ has the meaning of —H.

Where ✻$^1$ and ✻$^2$ both have the prefered meaning of phenyl; and j has the meaning of 0, which is a less preferred meaning than where j is 1, the moiety —N(R$^3$) is absent and the compounds of Formula (1.0.0) are essentially nicotinoyl moieties, i.e., ketones in structure with respect to the left-hand side of the core nucleus. Such a ketone structure in the left-hand side of the core nucleus, together with benzyl as a preferred meaning of the ✻ moiety, is represented by Formula (1.0.7):

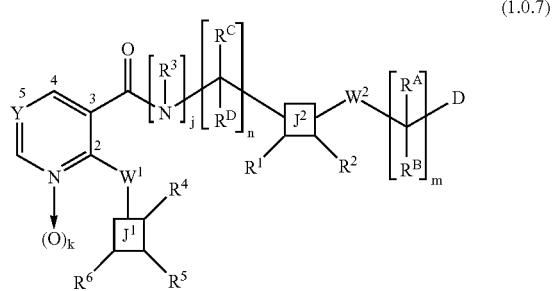

(1.0.7)

where all of the substituents and components thereof, i.e., D; W; Y; k, m, and n; R$^1$, R$^2$, R$^4$, R$^5$, and R$^6$; and R$^A$, R$^B$, R$^C$, and R$^D$; have, for the most part, the same particular and preferred meanings described in detail herein as in the case where j is 1 and the left-hand side of the core nucleus of the compounds is a nicotinamide in structure.

5.8 Preferred Subgenus and Species Embodiments of Formula (1.0.0)

In the above description various preferred aspects of the compounds of Formula (1.0.0) have been set forth. As a further demonstration of the scope and the content of the present invention, subgeneric embodiments of the compounds of Formula (1.0.0) are presented. Such preferred embodiments include, but are not limited to, those recited in the following paragraphs (i) through (viii):

(i) A compound according to Formula (1.0.0) wherein where m is 1 or 2, and n is 1; ♦ R$^A$ and R$^B$ are —H, —CF$_3$, or —(C$_1$–C$_6$)alkyl substituted by 0 or 1 of —F, —Cl, —CF$_3$, —CN, —NH$_2$, or —C(=O)NH$_2$, or both taken together are spiro —(C$_3$–C$_6$)cycloalkyl-substituted by 0 or 1 of —F, —Cl, —CF$_3$, or —CN; ♦ one of R$^C$ and R$^D$ is —H, and the other is —H, —(C$_1$–C$_4$)alkyl, or phenyl, each substituted by 0 or 1 of—F, —Cl, or —CN; ♦ W$^1$ is —O— or —S—; ♦ W$^2$ is —O—; ♦ Y is =C(R$^1_a$)— where R$^1_a$ is —H, —F, —Cl, —CN, —CH$_3$, or —OCH$_3$; ♦ R$^1$ and R$^2$ are —H, —F, —Cl, —CN, —NO$_2$, —OH, —CH$_3$, —OCH$_3$, —OCHF$_2$, or —OCF$_3$; ♦ R$^3$ is —H or —CH$_3$; ♦ R$^4$ are —H, —F, —CN, —NO$_2$, —OH, —CH$_3$, or —OCH$_3$; ♦ ✻$^1$ is phenyl; ♦ R$^5$ and R$^6$ are taken together to form a moiety of partial Formula (1.3.1) where R$^{20}$ and R$^{21}$ are —H or —CH$_3$; or a moiety of partial Formula (1.3.11), (1.3.12), or (1.3.15) where R$^{23}$ and R$^{24}$ are absent or are —H, or —CH$_3$; ♦ ✻$^2$ is phenyl, norbornanyl, furanyl, thienyl, pyrimidinyl, or cyclohexyl; ♦ and D is —C(=O)OR$^7$ where R$^7$ is —H or —CH$_3$; —C(=O)NH$_2$; or tetrazol-5-yl;

(ii) A compound according to paragraph (i) wherein R$^A$ and R$^B$ are both —CH$_3$, or one is —CH$_3$ and the other is —CH(CH$_3$)$_2$ or —C(CH$_3$)$_3$, or one is —H and the other is —CH$_3$ or —CF$_3$, or both taken together are spiro cyclopropyl or spiro cyclobutyl; ♦ one of R$^C$ and R$^D$ is —H and the other is —H or —CH$_3$; W$^1$ is —O—; ♦ Y is =C(R$^1_a$) where R$^1_a$ is —H, —F, or —Cl; ♦ R$^1$ and R$^2$ are —H, —F, or Cl; ♦ R$^3$ is —H; ♦ R$^4$ is —H; ♦ R$^5$ and R$^6$ are taken together to form a moiety of partial Formula (1.3.1) or (1.3.11) where R$^{23}$ and R$^{24}$ are both absent; ♦ ✻$^2$ is phenyl, thienyl, or cyclohexyl; ♦ and D is —C(=O)OR$^7$ where R$^7$ is —H or —CH$_3$; —C(=O)NH$_2$; or tetrazol-5-yl;

(iii) A compound according to paragraph (ii) wherein R$^A$ and R$^B$ are both —CH$_3$, or both taken together are spiro cyclopropyl; ♦ one of R$^C$ and R$^D$ is —H and the other is —H or —CH$_3$; ♦ Y is =C(R$^1_a$)— where R$^1_a$ is —H, —F, or —Cl; ♦ R$^1$ and R$^2$ are —H, —F, or Cl; ♦ R$^3$ is —H; ♦ R$^4$ is —H; ♦ R$^5$ and R$^6$ are taken together to form a moiety of partial Formula (1.3.11) where R$^{23}$ and R$^{24}$ are both absent; ♦ ✻$^2$ is phenyl; ♦ and D is —C(=O)OR$^7$ where R$^7$ is —H or —CH$_3$; —C(=O)NH$_2$; or tetrazol-5-yl;

(iv) A compound according to paragraph (iii) wherein R$^A$ and R$^B$ are both —CH$_3$; ♦ R$^C$ and R$^D$ are both —H; ♦ Y is =C(R$^1_a$)— where R$^1_a$ is —H; ♦ and one of R$^1$ and R$^2$ is —H and the other is —F;

(v) A compound according to paragraph (iii) wherein Y is =C(R$^1_a$)— where R$^1_a$ is —F; ♦ and R$^1$ and R$^2$ are both —H;

(vi) A compound according to paragraph (ii) wherein R$^A$ and R$^B$ are both —CH$_3$, or both taken together are spiro cyclopropyl; ♦ one of R$^C$ and R$^D$ is —H and the other is —H or —CH$_3$; ♦ Y is =C(R$^1_a$)— where R$^1_a$ is —H, —F, or —Cl; ♦ R$^1$ and R$^2$ are —H, —F, or Cl; ♦ R$^3$ is —H; ♦ R$^4$ is —H; R$^5$ and R$^6$ are taken together to form a moiety of partial Formula (1.3.1) where R$^{20}$ and R$^{21}$ are both —H; ♦ ✻$^2$ is phenyl; ♦ and D is —C(=O)OR$^7$ where R$^7$ is —H or —CH$_3$; —C(=O)NH$_2$; or tetrazol-5-yl;

(vii) A compound according to paragraph (vi) wherein R$^A$ and R$^B$ are both —CH$_3$; ♦ R$^C$ and R$^D$ are both —H; ♦ Y is =C(R$^1_a$)— where R$^1_a$ is —H; ♦ and one of R$^1$ and R$^2$ is —H and the other is —F; and (viii) A compound according to paragraph (vii) wherein Y is =C(R$^1_a$)— where R$^1_a$ is —F; ♦ and R$^1$ and R$^2$ are both —H.

The above description various preferred aspects of the compounds of Formula (1.0.0) have been set forth. As a further demonstration of the scope and the content of the present invention, specific compounds comprising embodiments of the compounds of Formula (1.0.0) are presented. Such species of Formula (1.0.0) include, but are not limited to the following compounds of Formulas (5.5.1) through (5.5.106):

| NOMENCLATURE | STRUCTURAL FORMULA |
|---|---|
| [4-({[2-(Benzo[1,3]dioxol-5-yloxy)-pyridine-3-carbonyl]-amino}-methyl)-3-fluoro-phenoxy]-acetic acid of Formula (5.5.1); | 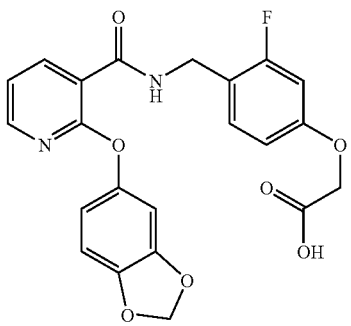 |
| (±)-2-[4-({[2-(Benzo[1,3]dioxol-5-yloxy)-pyridine-3-carbonyl]-amino}-methyl)-3-fluoro-phenoxy]-propionic acid of Formula (5.5.2); | 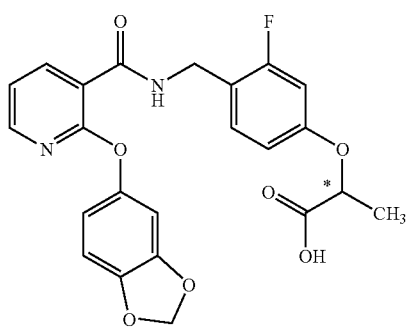 |
| (±)-2-[4-({[2-(Benzo[2,1,3]oxadiazol-5-yloxy)-pyridine-3-carbonyl]-amino}-methyl)-3-fluoro-phenoxy]-propionic acid of Formula (5.5.3); | 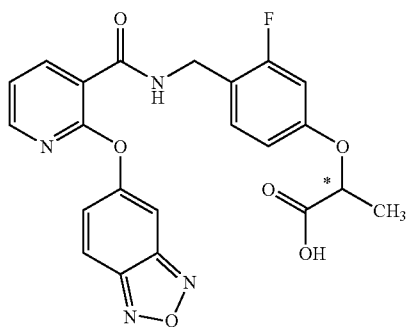 |
| (±)-2-[3-Fluoro-4-({[2-(4-fluoro-phenoxy)-pyridine-3-carbonyl]-amino}-methyl)-phenoxy]-propionic acid of Formula (5.5.4); | 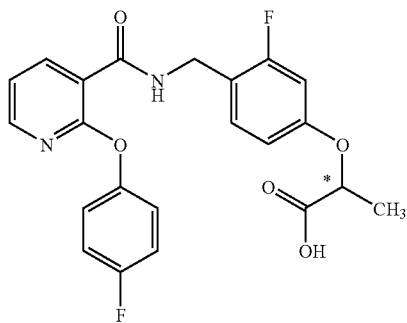 |

-continued

| NOMENCLATURE | STRUCTURAL FORMULA |
|---|---|
| (±)-2-[3-Fluoro-4-({[2-(3-cyano-phenoxy)-pyridine-3-carbonyl]-amino}-methyl)-phenoxy]-propionic acid of Formula (5.5.5); | 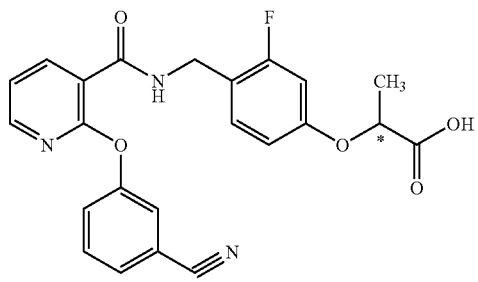 |
| (±)-2-[4-({[2-(Benzo[1,3]dioxol-5-yloxy)-5-fluoro-pyridine-3-carbonyl]-amino}-methyl)-3-fluoro-phenoxy]-propionic acid of Formula (5.5.6); | 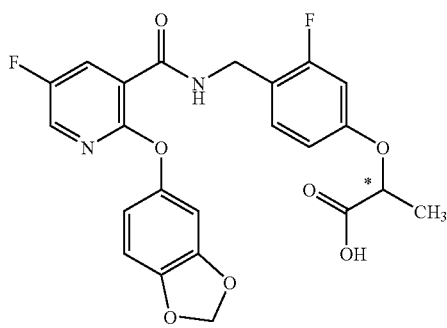 |
| (±)-2-[4-({[2-(Benzo[2,1,3]thiadiazol-5-yloxy)-pyridine-3-carbonyl]-amino}-methyl)-3-fluoro-phenoxy]-propionic acid of Formula (5.5.7); | 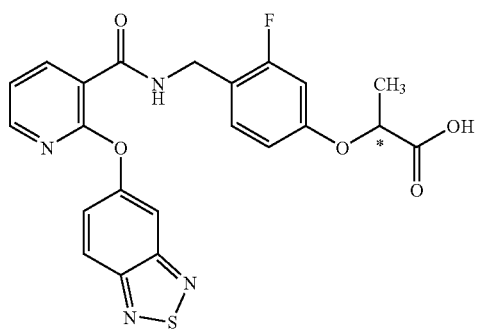 |
| (R)-2-[4-({[2-(Benzol[1,3]dioxol-5-yloxy)-pyridine-3-carbonyl]-amino}-methyl)-3-fluoro-phenoxy]-propionic acid of Formula (5.5.8); | 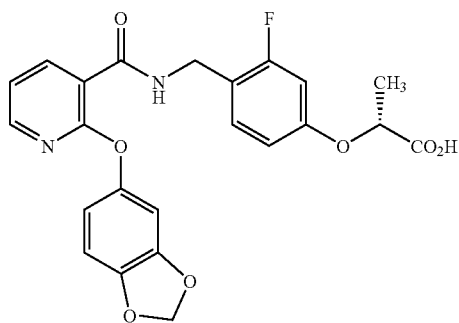 |

-continued

| NOMENCLATURE | STRUCTURAL FORMULA |
|---|---|
| (S)-2-[4-({[2-(Benzo[1,3]dioxol-5-yloxy)-pyridine-3-carbonyl]-amino}-methyl)-3-fluoro-phenoxy]-propionic acid of Formula (5.5.9); | 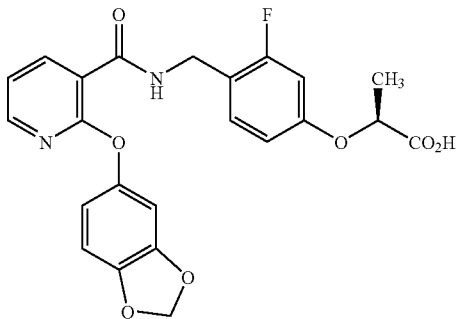 |
| (R)-2-[4-({[2-(Benzo[2,1,3]oxadiazol-5-yloxy)-pyridine-3-carbonyl]-amino}-methyl)-3-fluoro-phenoxy]-propionic acid of Formula (5.5.10); | 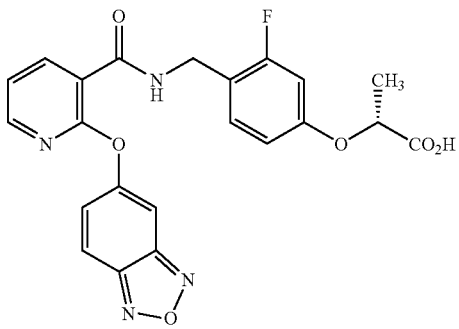 |
| (R)-2-[3-Fluoro-4-({[2-(3-cyano-phenoxy)-pyridine-3-carbonyl]-amino}-methyl)-phenoxy]-propionic acid of Formula (5.5.11); | 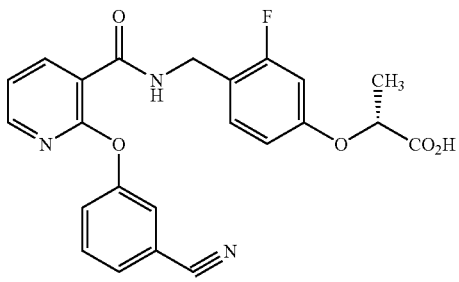 |
| (R)-2-[4-({[2-(Benzo[1,3]dioxol-5-yloxy)-5-fluoro-pyridine-3-carbonyl]-amino}-methyl)-3-fluoro-phenoxy]-propionic acid of Formula (5.5.12); | 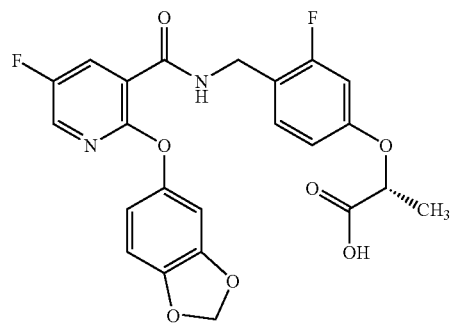 |

| NOMENCLATURE | STRUCTURAL FORMULA |
|---|---|
| (R)-2-[4-({[2-(Benzo[2,1,3]thiadiazol-5-yloxy)-pyridine-3-carbonyl]-amino}-methyl)-3-fluoro-phenoxy]-propionic acid of Formula (5.5.13); | 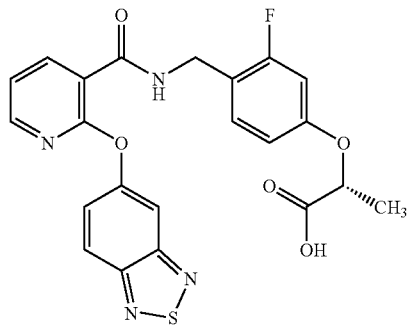 |
| (R)-2-(Benzo[1,3]dioxol-5-yloxy)-N-[4-(1-carbamoyl-ethoxy)-2-fluoro-benzyl]-nicotinamide of Formula (5.5.14); | 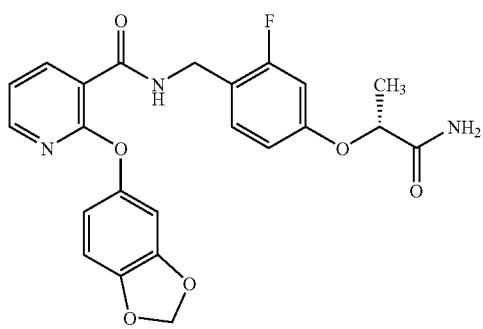 |
| (R)-2-(Benzo[2,1,3]oxadiazol-5-yloxy)-N-[4-(1-carbamoyl-ethoxy)-2-fluoro-benzyl]-nicotinamide of Formula (5.5.15); | 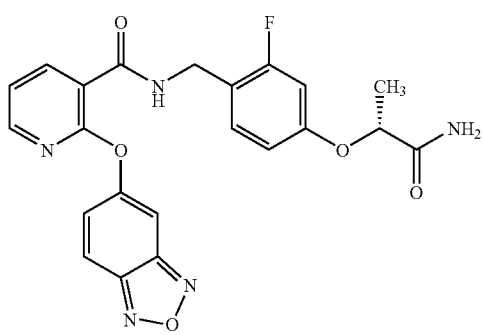 |
| (R)-2-(Benzo[2,1,3]thiadiazol-5-yloxy)-N-[4-(1-carbamoyl-ethoxy)-2-fluoro-benzyl]-nicotinamide of Formula (5.5.16); | 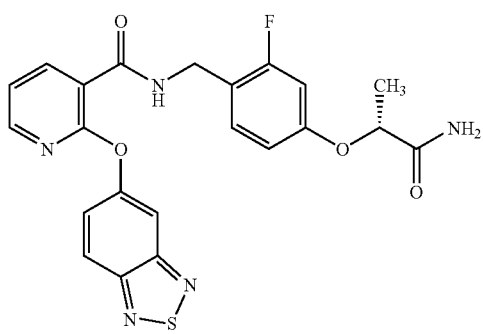 |

| NOMENCLATURE | STRUCTURAL FORMULA |
|---|---|
| (R)-N-[4-(1-Carbamoyl-ethoxy)-2-fluoro-benzyl]-2-(3-cyano-phenoxy)-nicotinamide of Formula (5.5.17); | 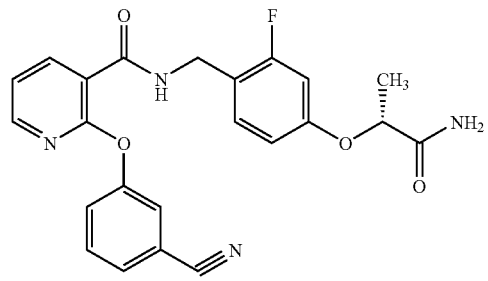 |
| (R)-2-(Benzo[1,3]dioxol-5-yloxy)-N-[4-(1-carbamoyl-ethoxy)-2-fluoro-benzyl]-5-fluoro-nicotinamide of Formula (5.5.18); | 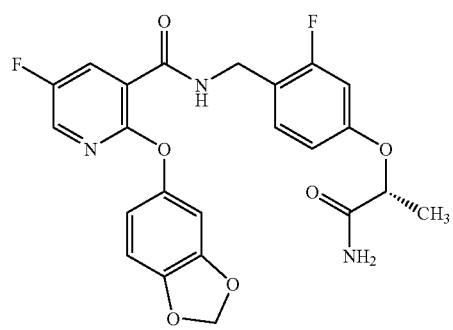 |
| (±)-2-(Benzo[1,3]dioxol-5-yloxy)-N-{2-fluoro-4-[1-(1H-tetrazol-5-yl)-ethoxy]-benzyl}-nicotinamide of Formula (5.5.19); | 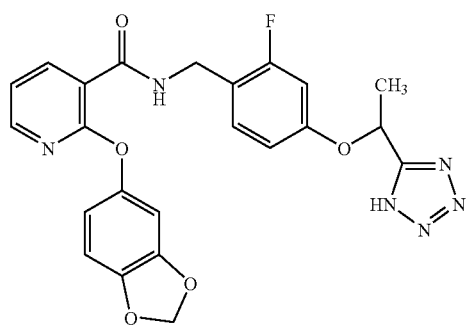 |
| (R)-2-(Benzo[1,3]dioxol-5-yloxy)-N-{2-fluoro-4-[1-(5-methyl-4H-[1,2,4]triazol-3-yl)-ethoxy]-benzyl}-nicotinamide of Formula (5.5.20); | 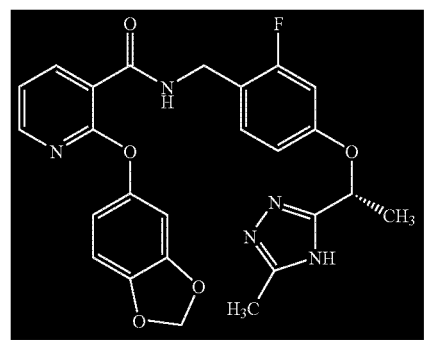 |

-continued

| NOMENCLATURE | STRUCTURAL FORMULA |
|---|---|
| (R)-2-(Benzo[1,3]dioxol-5-yloxy)-5-fluoro-N-{2-fluoro-4-[1-(5-methyl-4H-[1,2,4]triazol-3-yl)-ethoxy]-benzyl}-nicotinamide of Formula (5.5.21); | 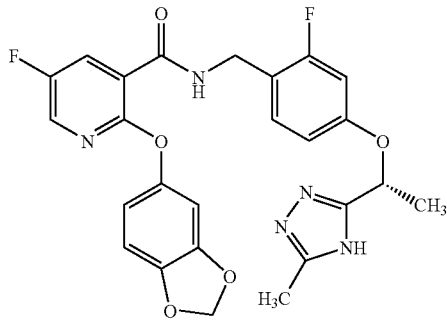 |
| (±)-2-(Benzo[1,3]dioxol-5-yloxy)-N-{2-fluoro-4-[1-(1H-tetrazol-5-yl)-ethoxy]-benzyl}-nicotinamide of Formula (5.5.22); | 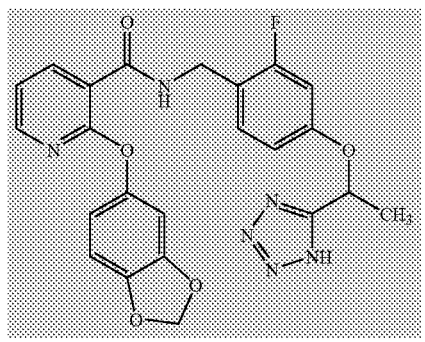 |
| (R)-2-(Benzo[1,3]dioxol-5-yloxy)-N-[2-fluoro-4-(2-hydroxy-1,2-dimethyl-propoxy)-benzyl]-nicotinamide of Formula (5.5.23); | 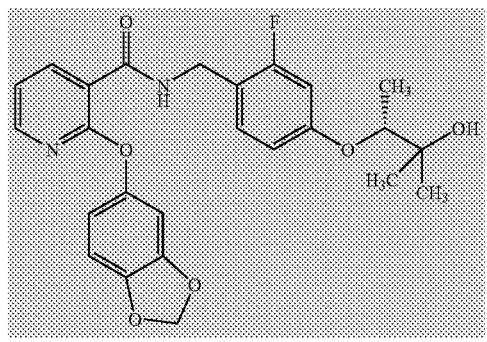 |
| (R)-2-(Benzo[1,3]dioxol-5-yloxy)-5-fluoro-N-[2-fluoro-4-(2-hydroxy-1,2-dimethyl-propoxy)-benzyl]-nicotinamide of Formula (5.5.24); | 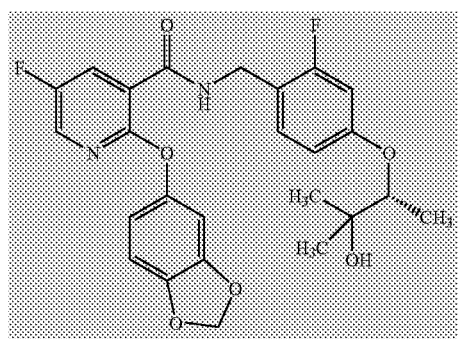 |

| NOMENCLATURE | STRUCTURAL FORMULA |
|---|---|
| (S)-3-[4-({[2-(Benzo[1,3]dioxol-5-yloxy)-pyridine-3-carbonyl]-amino}-methyl)-3-fluoro-phenoxy]-2-methyl-propionic acid of Formula (5.5.25); | 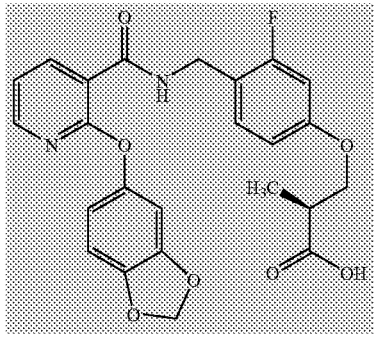 |
| 2-(Benzo[1,3]dioxol-5-yloxy)-5-fluoro-N-[2-fluoro-4-(pyridin-2-ylmethoxy)-benzyl]-nicotinamide of Formula (5.5.26); | 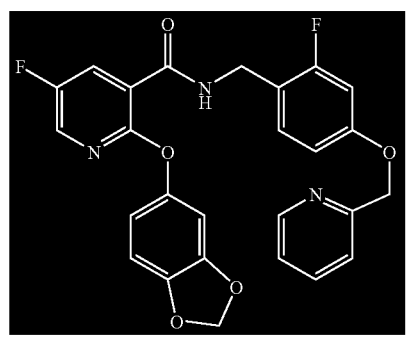 |
| 2-(Benzo[1,3]dioxol-5-yloxy)-5-fluoro-N-[2-fluoro-4-(pyridin-4-ylmethoxy)-benzyl]-nicotinamide of Formula (5.5.27); | 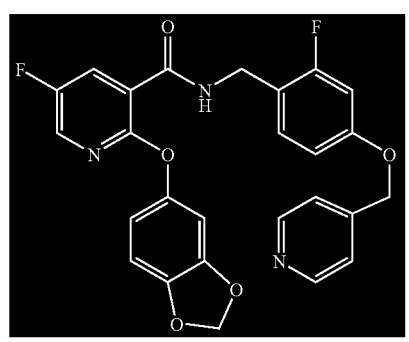 |
| 2-(Benzo[1,3]dioxol-5-yloxy)-5-fluoro-N-[2-fluoro-4-(pyridin-3-ylmethoxy)-benzyl]-nicotinamide of Formula (5.5.28); | 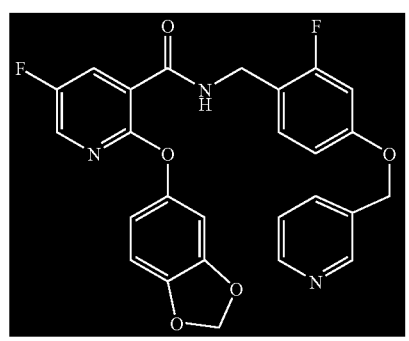 |

| NOMENCLATURE | STRUCTURAL FORMULA |
|---|---|
| [4-({[2-(3-Cyano-phenoxy)-pyridine-3-carbonyl]-amino}-methyl)-cyclohex-3-enyloxy]-acetic acid of Formula (5.5.29); | 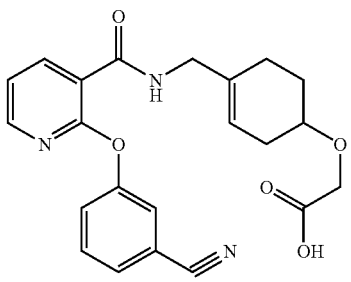 |
| [4-({[2-(2-Methyl-2H-benzotriazol-5-yloxy)-pyridine-3-carbonyl]-amino}-methyl)-cyclohex-3-enyloxy]-acetic acid of Formula (5.5.30); | 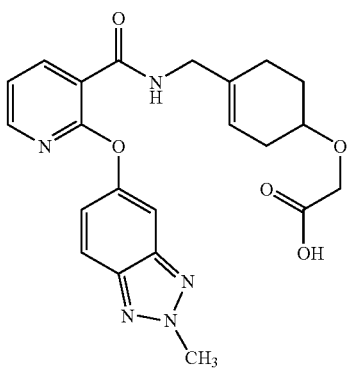 |
| (±)-2-[4-({[2-(Benzo[2,1,3]thiadiazol-5-yloxy)-pyridine-3-carbonyl]-amino}-methyl)-cyclohex-3-enyloxy]-propionic acid of Formula (5.5.31); | 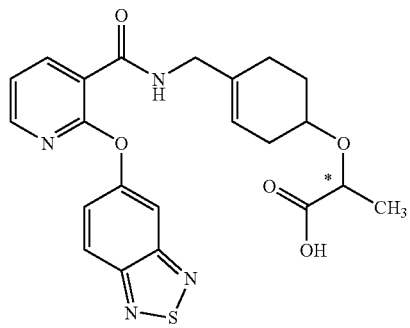 |
| (±)-2-[4-({[2-(Benzo[2,1,3]oxadiazol-5-yloxy)-pyridine-3-carbonyl]-amino}-methyl)-cyclohex-3-enyloxy]-propionic acid of Formula (5.5.32); | 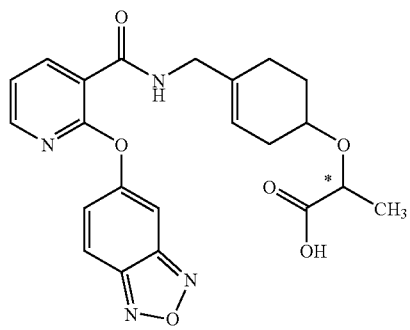 |

| NOMENCLATURE | STRUCTURAL FORMULA |
|---|---|
| (±)-2-[4-({[2-(Benzo[1,3]dioxol-5-yloxy)-pyridine-3-carbonyl]-amino}-methyl)-cyclohex-3-enyloxy]-propionic acid of Formula (5.5.33); | 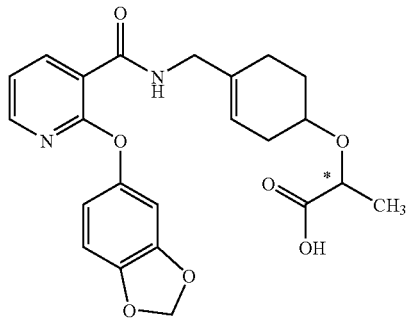 |
| (±)-2-[4-({[2-(4-Fluoro-phenoxy)-pyridine-3-carbonyl]-amino}-methyl)-cyclohex-3-enyloxy]-propionic acid of Formula (5.5.34); | 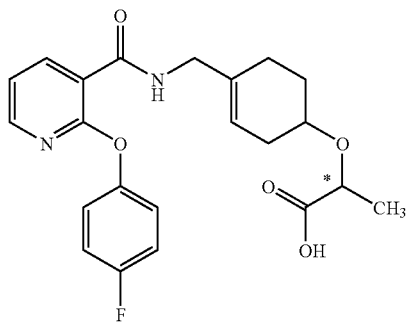 |
| (±)-2-[4-({[2-(3-Cyano-phenoxy)-pyridine-3-carbonyl]-amino}-methyl)-cyclohex-3-enyloxy]-propionic acid of Formula (5.5.35); | 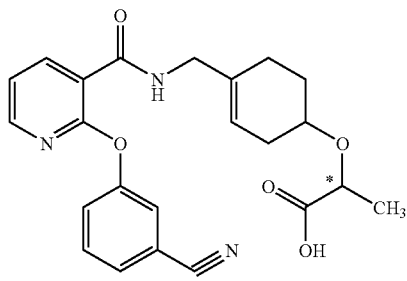 |
| (±)-2-[4-({[2-(2-Methyl-2H-benzotriazol-5-yloxy)-pyridine-3-carbonyl]-amino}-methyl)-cyclohex-3-enyloxy]-propionic acid of Formula (5.5.36); | 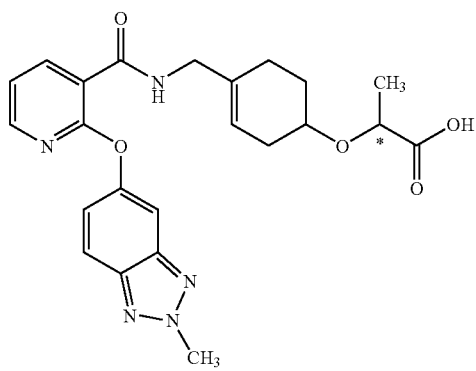 |

| NOMENCLATURE | STRUCTURAL FORMULA |
|---|---|
| (R)-2-[4-({[2-(Benzo[2,1,3]thiadiazol-5-yloxy)-pyridine-3-carbonyl]-amino}-methyl)-cyclohex-3-enyloxy]-propionic acid of Formula (5.5.37); | 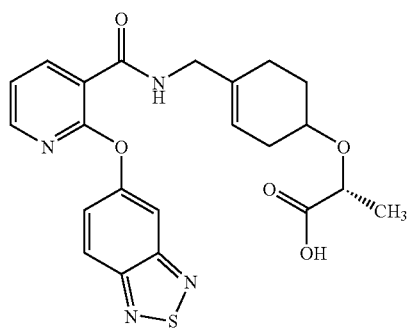 |
| (R)-2-[4-({[2-(Benzo[2,1,3]oxadiazol-5-yloxy)-pyridine-3-carbonyl]-amino}-methyl)-cyclohex-3-enyloxy]-propionic acid of Formula (5.5.38); | 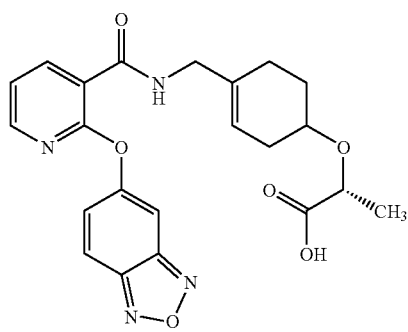 |
| (R)-2-[4-({[2-(Benzo[1,3]dioxol-5-yloxy)-pyridine-3-carbonyl]-amino}-methyl)-cyclohex-3-enyloxy]-propionic acid of Formula (5.5.39); | 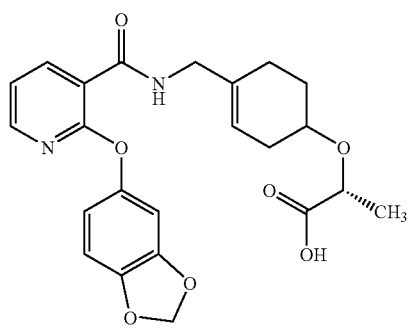 |
| (R)-2-[4-({[2-(4-Fluoro-phenoxy)-pyridine-3-carbonyl]-amino}-methyl)-cyclohex-3-enyloxy]-propionic acid of Formula (5.5.40); | 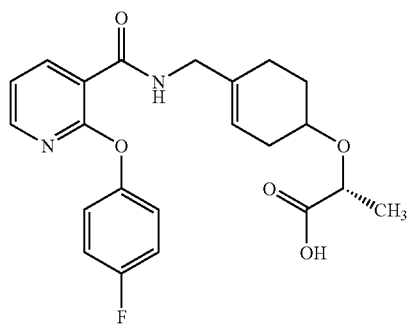 |

-continued

| NOMENCLATURE | STRUCTURAL FORMULA |
|---|---|
| (R)-2-[4-({[2-(3-Cyano-phenoxy)-pyridine-3-carbonyl]-amino}-methyl)-cyclohex-3-enyloxy]-propionic acid of Formula (5.5.41); | 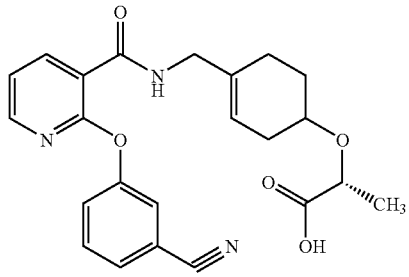 |
| (R)-2-[4-({[2-(2-Methyl-2H-benzotriazol-5-yloxy)-pyridine-3-carbonyl]-amino}-methyl)-cyclohex-3-enyloxy]-propionic acid of Formula (5.5.42); | 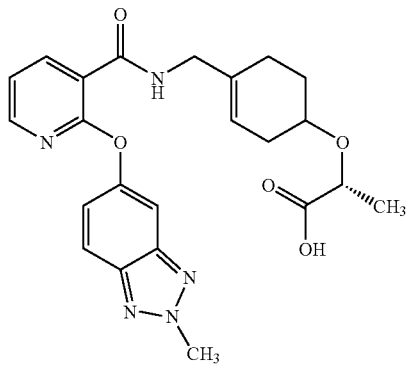 |
| [4-({[2-(Benzo[2,1,3]thiadiazol-5-yloxy)-pyridine-3-carbonyl]-amino}-methyl)-cyclohexyloxy]-acetic acid of Formula (5.5.43); | 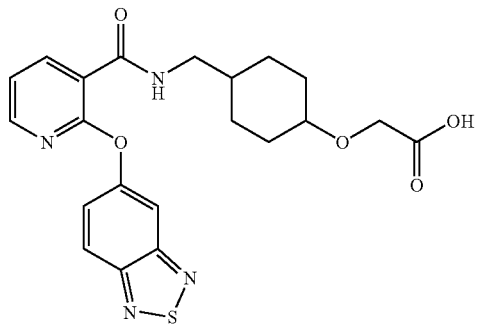 |
| [4-({[2-(Benzo[2,1,3]oxadiazol-5-yloxy)-pyridine-3-carbonyl]-amino}-methyl)-cyclohexyloxy]-acetic acid of Formula (5.5.44); | 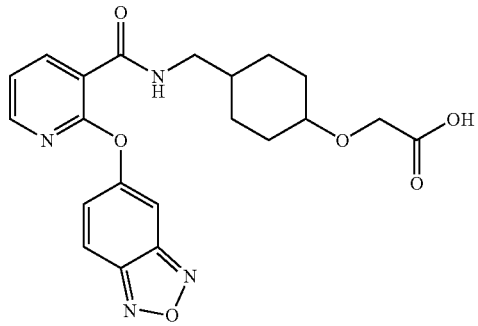 |

| NOMENCLATURE | STRUCTURAL FORMULA |
|---|---|
| [4-({[2-(Benzo[1,3]dioxol-5-yloxy)-pyridine-3-carbonyl]-amino}-methyl)-cyclohexyloxy]-acetic acid of Formula (5.5.45); | 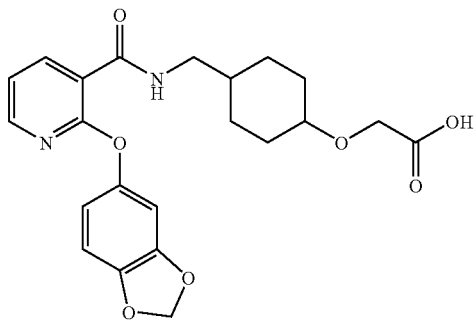 |
| [4-({[2-(4-Fluoro-phenoxy)-pyridine-3-carbonyl]-amino}-methyl)-cyclohexyloxy]-acetic acid of Formula (5.5.46); | 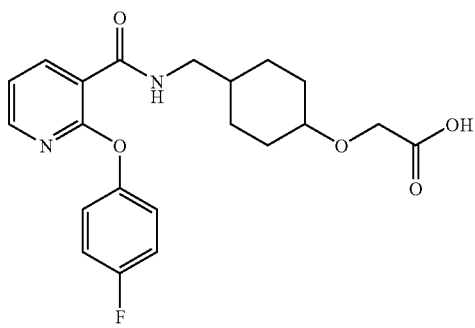 |
| [4-({[2-(3-Cyano-phenoxy)-pyridine-3-carbonyl]-amino}-methyl)-cyclohexyloxy]-acetic acid of Formula (5.5.47); | 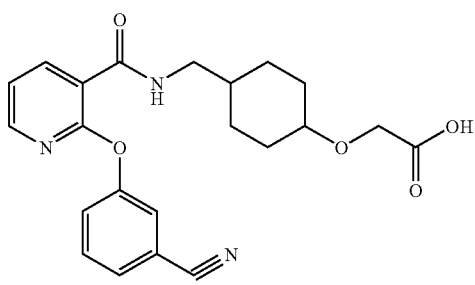 |
| [4-({[2-(2-Methyl-2H-benzotriazol-5-yloxy)-pyridine-3-carbonyl]-amino}-methyl)-cyclohexyloxy]-acetic acid of Formula (5.5.48); | 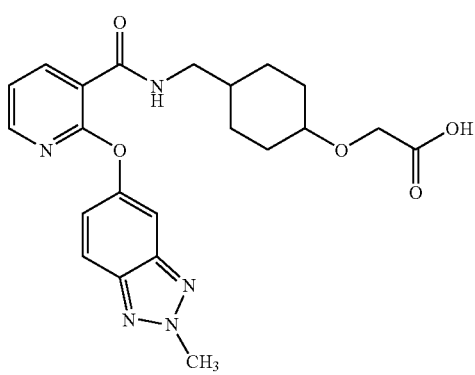 |

| NOMENCLATURE | STRUCTURAL FORMULA |
|---|---|
| (±)-2-[4-({[2-(Benzo[2,1,3]thiadiazol-5-yloxy)-pyridine-3-carbonyl]-amino}-methyl)-cyclohexyloxy]-propionic acid of Formula (5.5.49); | 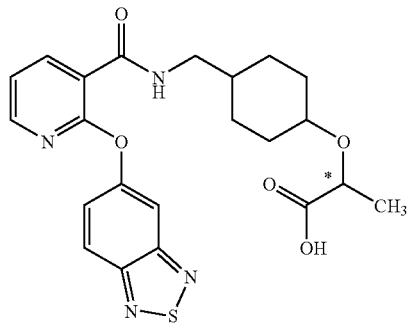 |
| (±)-2-[4-({[2-(Benzo[2,1,3]oxadiazol-5-yloxy)-pyridine-3-carbonyl]-amino}-methyl)-cyclohexyloxy]-propionic acid of Formula (5.5.50); | 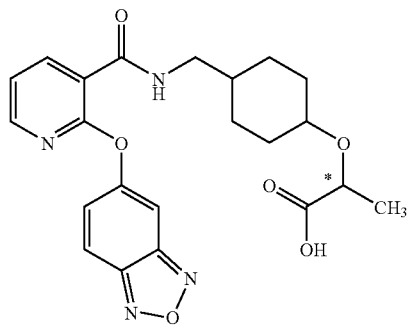 |
| (±)-2-[4-({[2-(4-Fluoro-phenoxy)-pyridine-3-carbonyl]-amino}-methyl)-cyclohexyloxy]-propionic acid of Formula (5.5.51); | 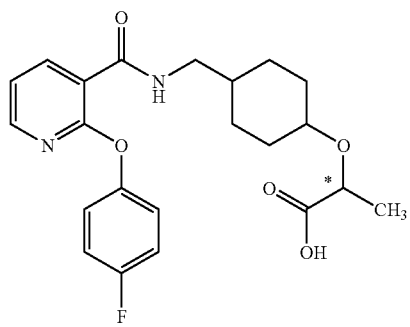 |
| (±)-2-[4-({[2-(3-Cyano-phenoxy)-pyridine-3-carbonyl]-amino}-methyl)-cyclohexyloxy]-propionic acid of Formula (5.5.52); | 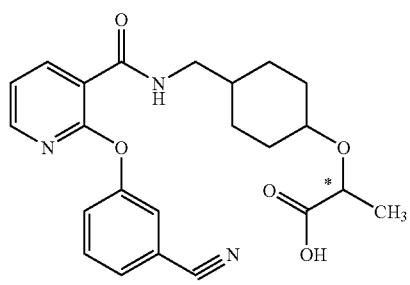 |

-continued

| NOMENCLATURE | STRUCTURAL FORMULA |
|---|---|
| (±)-2-[4-({[2-(2-Methyl-2H-benzotriazol-5-yloxy)-pyridine-3-carbonyl]-amino}-methyl)-cyclohexyloxy]-propionic acid of Formula (5.5.53); | 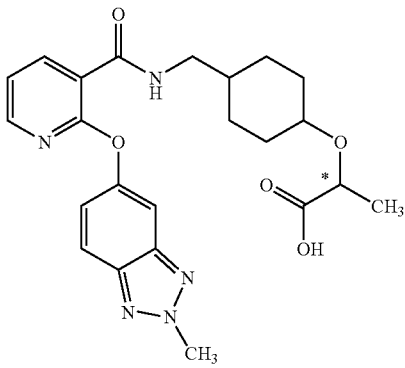 |
| (R)-2-[4-({[2-(Benzo[2,1,3]thiadiazol-5-yloxy)-pyridine-3-carbonyl]-amino}-methyl)-cyclohexyloxy]-propionic acid of Formula (5.5.54); | 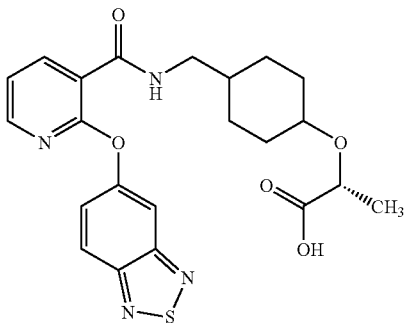 |
| (R)-2-[4-({[2-(Benzo[2,1,3]oxadiazol-5-yloxy)-pyridine-3-carbonyl]-amino}-methyl)-cyclohexyloxy]-propionic acid of Formula (5.5 55); | 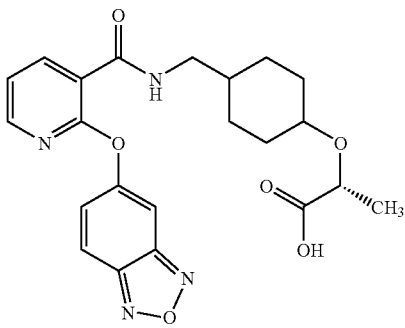 |
| (R)-2-[4-({[2-(Benzo[1,3]dioxol-5-yloxy)-pyridine-3-carbonyl]-amino}-methyl)-cyclohexyloxy]-propionic acid of Formula (5.5.56); | 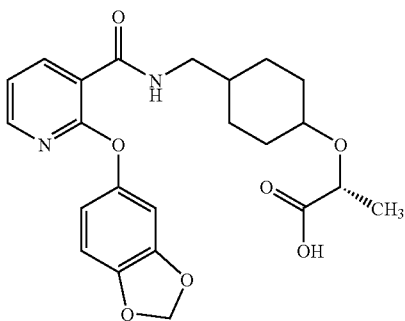 |

| NOMENCLATURE | STRUCTURAL FORMULA |
|---|---|
| (R)-2-[4-({[2-(4-Fluoro-phenoxy)-pyridine-3-carbonyl]-amino}-methyl)-cyclohexyloxy]-propionic acid of Formula (5.5.57); | 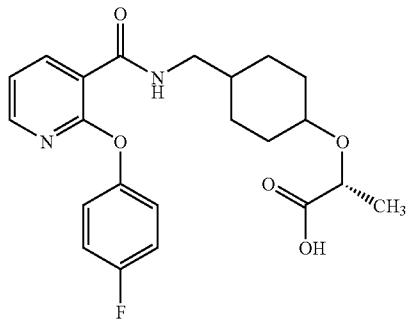 |
| (R)-2-[4-({[2-(3-Cyano-phenoxy)-pyridine-3-carbonyl]-amino}-methyl)-cyclohexyloxy]-propionic acid of Formula (5.5.58); | 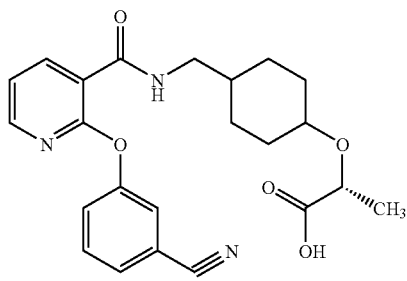 |
| (R)-2-[4-({[2-(2-Methyl-2H-benzotriazol-5-yloxy)-pyridine-3-carbonyl]-amino}-methyl)-cyclohexyloxy]-propionic acid of Formula (5.5.59); | 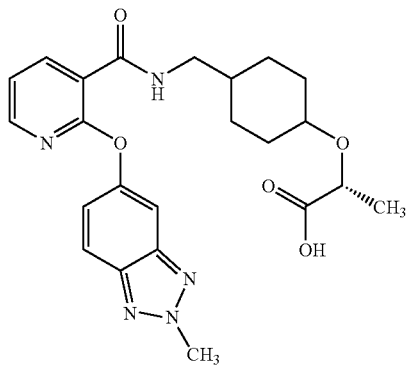 |
| 2-[4-({[2-(Benzo[2,1,3]thiadiazol-5-yloxy)-pyridine-3-carbonyl]-amino}-methyl)-cyclohexyloxy]-2-methyl-propionic acid of Formula (5.5.60); | 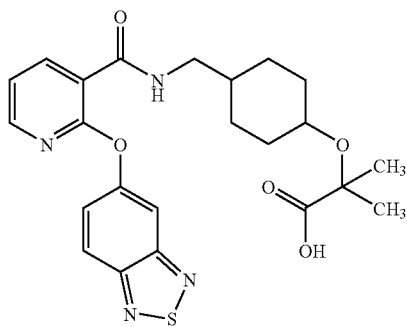 |

| NOMENCLATURE | STRUCTURAL FORMULA |
|---|---|
| 2-[4-({[2-(Benzo[2,1,3]oxadiazol-5-yloxy)-pyridine-3-carbonyl]-amino}-methyl)-cyclohexyloxy]-2-methyl-propionic acid of Formula (5.5.61); | 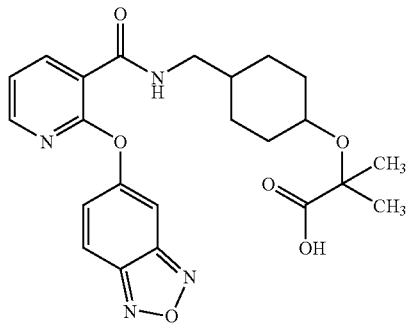 |
| 2-[4-({[2-(Benzo[1,3]dioxol-5-yloxy)-pyridine-3-carbonyl]-amino}-methyl)-cyclohexyloxy]-2-methyl-propionic acid of Formula (5.5.62); | 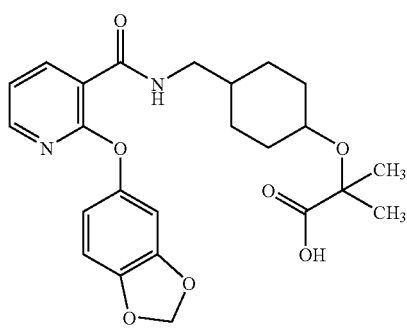 |
| 2-[4-({[2-(4-Fluoro-phenoxy)-pyridine-3-carbonyl]-amino}-methyl)-cyclohexyloxy]-2-methyl-propionic acid of Formula (5.5.63); | 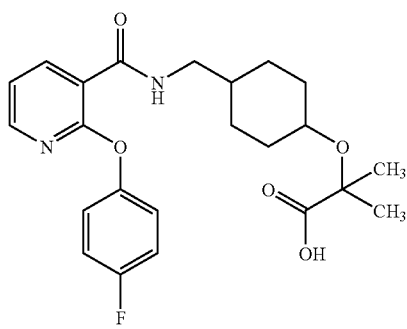 |
| 2-[4-({[2-(3-Cyano-phenoxy)-pyridine-3-carbonyl]-amino}-methyl)-cyclohexyloxy]-2-methyl-propionic acid of Formula (5.5.64); | 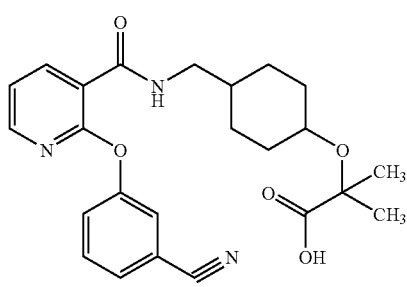 |

| NOMENCLATURE | STRUCTURAL FORMULA |
|---|---|
| 2-Methyl-2-[4-({[2-(2-methyl-2H-benzotriazol-5-yloxy)-pyridine-3-carbonyl]-amino}-methyl)-cyclohexyloxy]-propionic acid of Formula (5.5.65); | 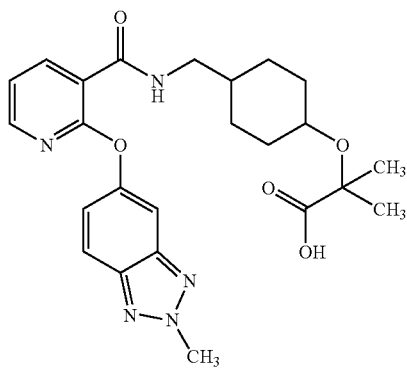 |
| [5-({[2-(Benzo[2,1,3]thiadiazol-5-yloxy)-pyridine-3-carbonyl]-amino}-methyl)-bicyclo[2.2.2]oct-2-yloxy]-acetic acid of Formula (5.5.66); | 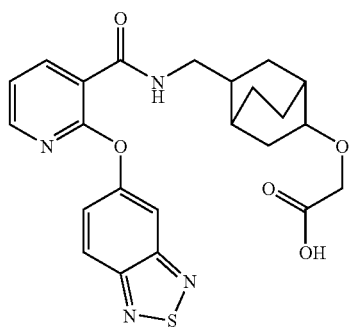 |
| (±)-2-[5-({[2-(Benzo[2,1,3]oxadiazol-5-yloxy)-pyridine-3-carbonyl]-amino}-methyl)-bicyclo[2.2.2]oct-2-yloxy]-propionic acid of Formula (5.5.67); | 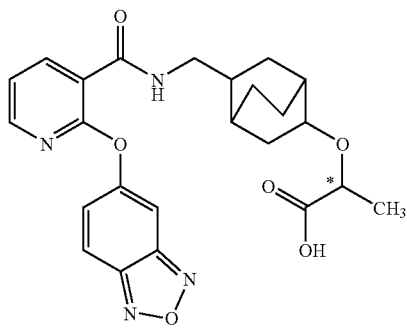 |
| (R)-2-[5-({[2-(Benzo[1,3]dioxol-5-yloxy)-pyridine-3-carbonyl]-amino}-methyl)-bicyclo[2.2.2]oct-2-yloxy]-propionic acid of Formula (5.5.68); | 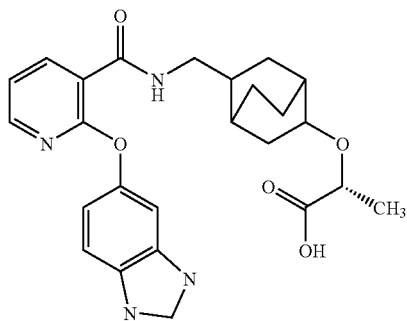 |

| NOMENCLATURE | STRUCTURAL FORMULA |
|---|---|
| 2-[5-({[2-(4-Fluoro-phenoxy)-pyridine-3-carbonyl]-amino}-methyl)-bicyclo[2.2.2]oct-2-yloxy]-2-methyl-propionic acid of Formula (5.5.69); | 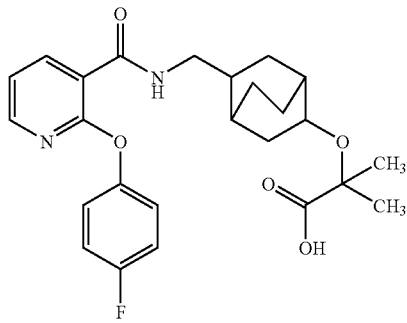 |
| 2-[5-({[2-(3-Cyano-phenoxy)-pyridine-3-carbonyl]-amino}-methyl)-bicyclo[2.2.2]oct-2-yloxy]-2-methyl-propionic acid of Formula (5.5.70); | 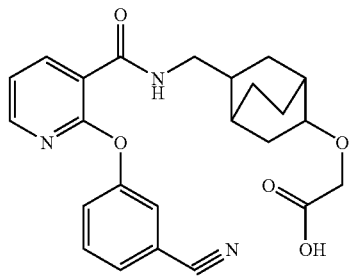 |
| (R)-2-[5-({[2-(2-Methyl-2H-benzotriazol-5-yloxy)-pyridine-3-carbonyl]-amino}-methyl)-bicyclo[2.2.2]oct-2-yloxy]-propionic acid of Formula (5.5.71); | 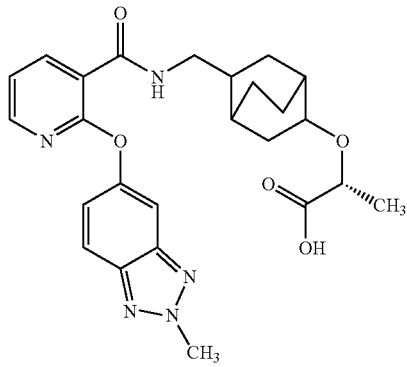 |
| [5-({[2-(Benzo[2,1,3]oxadiazol-5-yloxy)-pyridine-3-carbonyl]-amino}-methyl)-bicyclo[2.2.2]oct-2-yloxy]-acetic acid of Formula (5.5.72); | 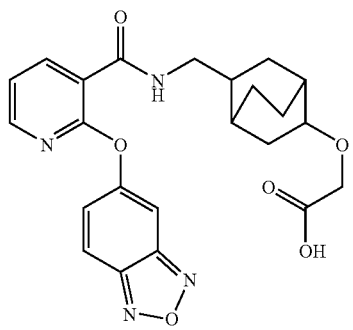 |

| NOMENCLATURE | STRUCTURAL FORMULA |
|---|---|
| 2-[8-({[2-(Benzo[2,1,3]oxadiazol-5-yloxy)-pyridine-3-carbonyl]-amino}-methyl)-bicyclo[2.2.2]oct-5-en-2-yloxyl-2-methyl-propionic acid of Formula (5.5.73); | 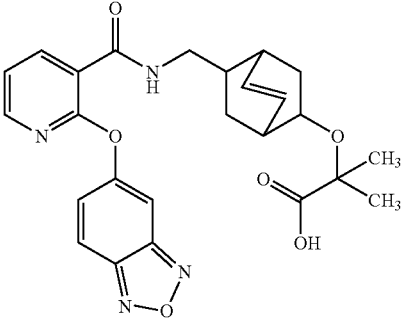 |
| (R)-2-[3-({[2-(Benzo[2,1,3]oxadiazol-5-yloxy)-pyridine-3-carbonyl]-amino}-methyl)-bicyclo[3.2.1]oct-8-yloxy]-propionic acid of Formula (5.5.74); | 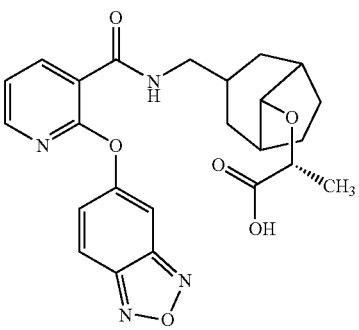 |
| 2-[3-({[2-(Benzo[1,3]dioxol-5-yloxy)-pyridine-3-carbonyl]-amino}-methyl)-cyclopent-3-enyloxy]-propionic acid of Formula (5.5.75); | 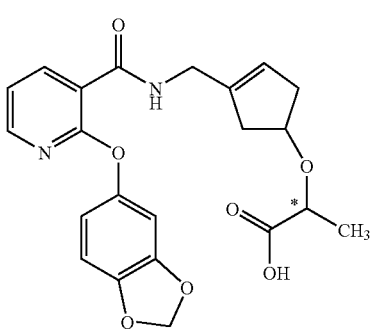 |
| [5-({[2-(2-Methyl-2H-benzotriazol-5-yloxy)-pyridine-3-carbonyl]-amino}-methyl)-bicyclo[2.2.1]hept-2-yloxy]-acetic acid of Formula (5.5.76); | 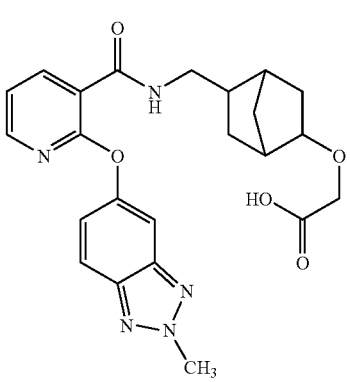 |

| NOMENCLATURE | STRUCTURAL FORMULA |
|---|---|
| 2-[5-({[2-(Benzo[2,1,3]oxadiazol-5-yloxy)-pyrdine-3-carbonyl]-amino}-methyl)-7-fluoro-bicyclo[2.2.1]hept-5-en-2-yloxy]-2-methyl-propionic acid of Formula (5.5.77); | 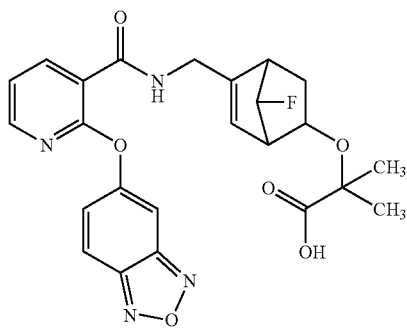 |
| (R)-2-[5-({[2-(Benzo[2,1,3]oxadiazol-5-yloxy)-pyridine-3-carbonyl]-amino}-methyl)-furan-2-yloxy]-propionic acid of Formula (5.5.78); | 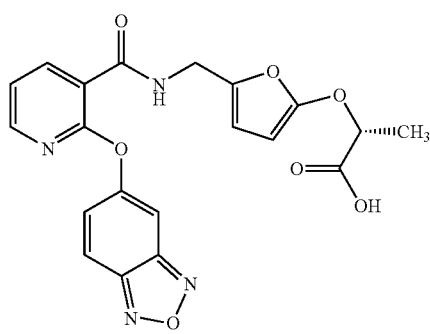 |
| (±)-2-[6-({[2-(Benzo[2,1,3]oxadiazol-5-yloxy)-pyridine-3-carbonyl]-amino}-methyl)-pyridin-3-yloxy]-propionic acid of Formula (5.5.79); | 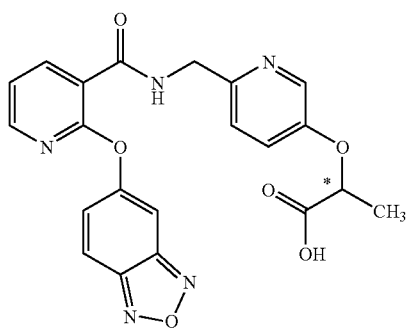 |
| [2-({[2-(Benzo[2,1,3]oxadiazol-5-yloxy)-pyridine-3-carbonyl]-amino}-methyl)-oxazol-5-yloxy]-acetic acid of Formula (5.5.80); | 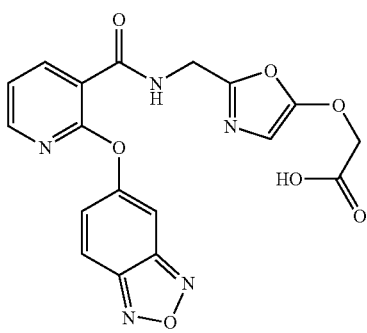 |

| NOMENCLATURE | STRUCTURAL FORMULA |
|---|---|
| 2-[2-({[2-(Benzo[2,1,3]oxadiazol-5-yloxy)-pyridine-3-carbonyl]-amino}-methyl)-thiazol-5-yloxy]-2-methyl-propionic acid of Formula (5.5.81); | 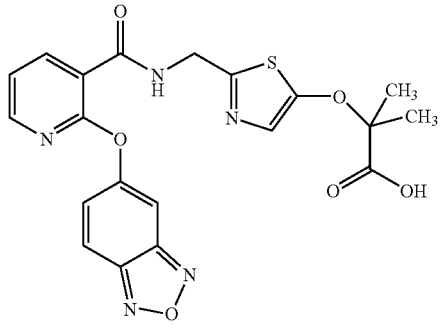 |
| (±)-2-[5-(1-{[2-(Benzo[2,1,3]oxadiazol-5-yloxy)-pyridine-3-carbonyl]-amino}-ethyl)-pyridin-2-yloxy]-propionic acid of Formula (5.5.82); | 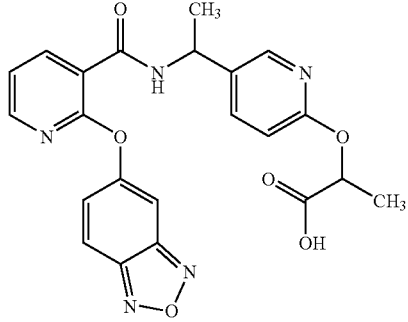 |
| 2-[4-({[2-(Benzo[2,1,3]oxadiazol-5-yloxy)-pyridine-3-carbonyl]-amino}-methyl)-phenoxy]-2-methyl-propionic acid of Formula (5.5.83); | 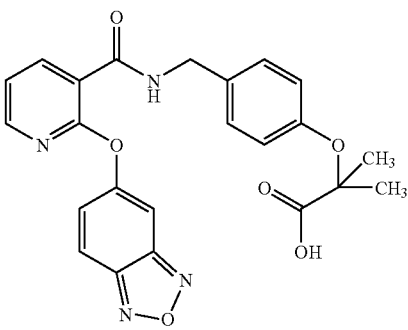 |
| 2-[4-({[2-(Benzo[2,1,3]oxadiazol-5-yloxy)-pyridine-3-carbonyl]-amino}-methyl)-3-fluoro-phenoxy]-2-methyl-propionic acid of Formula (5.5.84); | 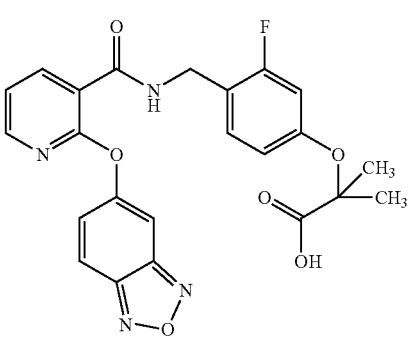 |

-continued

| NOMENCLATURE | STRUCTURAL FORMULA |
|---|---|
| 2-[4-({[2-(Benzo[2,1,3]thiadiazol-5-yloxy)-pyridine-3-carbonyl]-amino}-methyl)-3-fluoro-phenoxy]-2-methyl-propionic acid of Formula (5.5.85); | 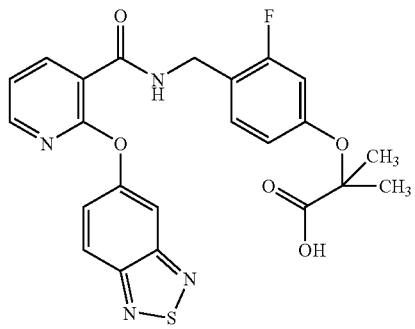 |
| 2-[4-({[2-(Benzo[1,3]dioxol-5-yloxy)-pyridine-3-carbonyl]-amino}-methyl)-3-fluoro-phenoxy]-2-methyl-propionic acid of Formula (5.5.86); | 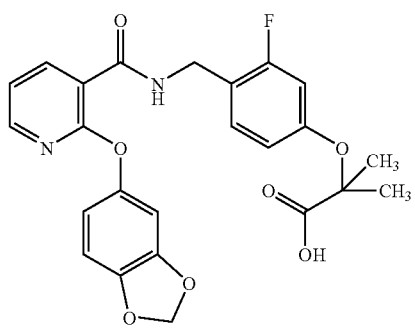 |
| 2-[3-Fluoro-4-({[2-(4-fluoro-phenoxy)-pyridine-3-carbonyl]-amino}-methyl)-phenoxy]-2-methyl-propionic acid of Formula (5.5.87); | 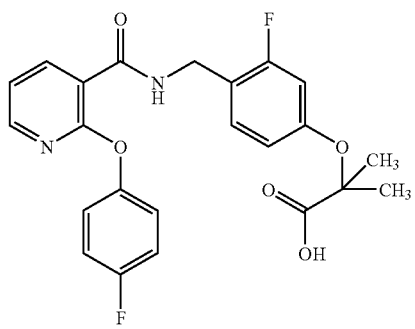 |
| 2-[4-({[2-(3-Cyano-phenoxy)-pyridine-3-carbonyl]-amino}-methyl)-3-fluoro-phenoxy]-2-methyl-propionic acid of Formula (5.5.88); | 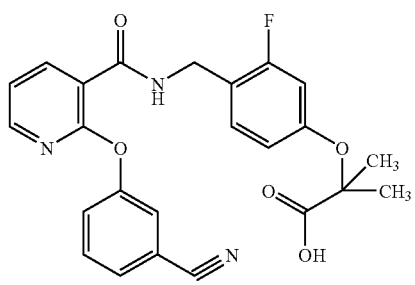 |

| NOMENCLATURE | STRUCTURAL FORMULA |
|---|---|
| [4-({[2-(Benzo[2,1,3]thiadiazol-5-yloxy)-pyridine-3-carbonyl]-amino}-methyl)-cyclohex-3-enyloxy]-acetic acid of Formula (5.5.89); | 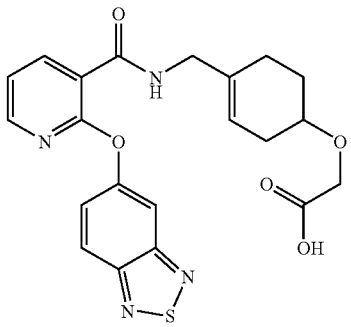 |
| (±)-2-(3-Cyano-phenoxy)-N-{4-[1-(5-methyl-4H-[1,2,4]triazol-3-yl)-ethoxy]-cyclohexylmethyl}-nicotinamide of Formula (5.5.90); | 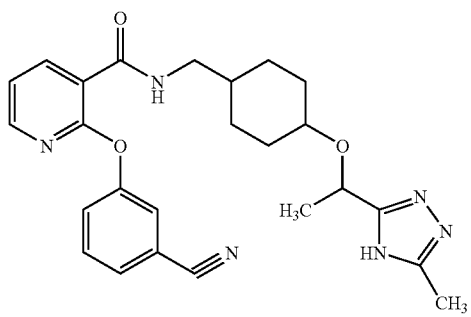 |
| (±)-2-(3-Cyano-phenoxy)-N-{4-[1-(1H-tetrazol-5-yl)-ethoxy]-cyclohexylmethyl}-nicotinamide of Formula (5.5.91); | 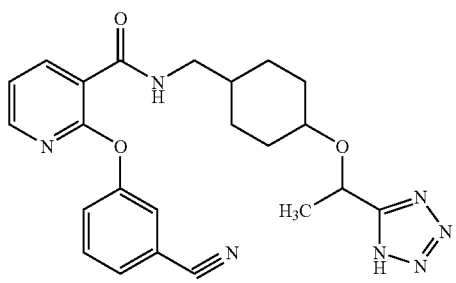 |
| (±)-N-{2-Fluoro-4-[1-(5-methyl-4H-[1,2,4]triazol-3-yl)-ethoxy]-benzyl}-2-(3-methoxy-phenoxy)-nicotinamide of Formula (5.5.92); | 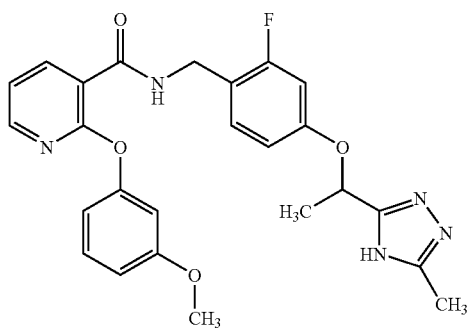 |
| N-[2-Fluoro-4-(pyridin-2-ylmethoxy)-benzyl]-2-(3-methoxy-phenoxy)-nicotinamide of Formula (5.5.93); | 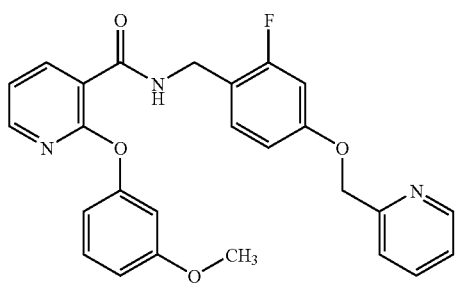 |

-continued

| NOMENCLATURE | STRUCTURAL FORMULA |
|---|---|
| (±)-2-[3-Fluoro-4-({[2-(3-nitro-phenoxy)-pyridine-3-carbonyl]-amino}-methyl)-phenoxy]-propionic acid of Formula (5.5.94); | 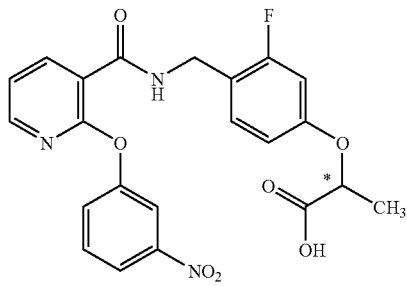 |
| (±)-N-{2-Fluoro-4-[1-(1H-tetrazol-5-yl)-ethoxy]-benzyl}-2-(3-nitro-phenoxy)-nicotinamide of Formula (5.5.95); | 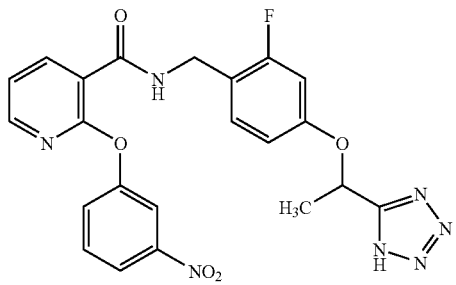 |
| (±)-N-{2-Fluoro-4-[1-(5-methyl-4H-[1,2,4]triazol-3-yl)-ethoxy]-benzyl}-2-(3-nitro-phenoxy)-nicotinamide of Formula (5.5.96); | 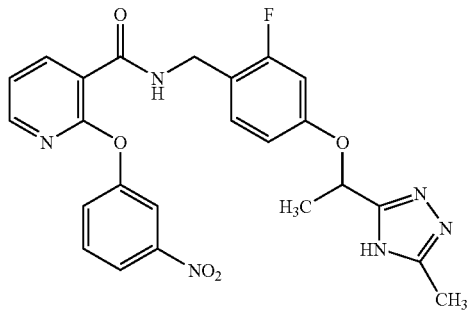 |
| [4-({[2-(Benzo[2,1,3]oxadiazol-5-yloxy)-pyridine-3-carbonyl]-amino}-methyl)-cyclohex-3-enyloxy]-acetic acid of Formula (5.5.97); | 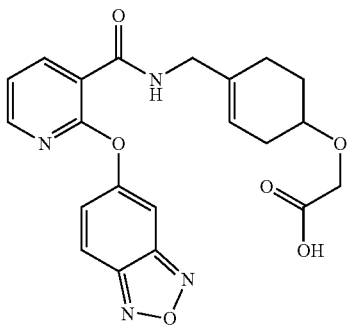 |

| NOMENCLATURE | STRUCTURAL FORMULA |
|---|---|
| [4-({[2-(Benzo[1,3]dioxol-5-yloxy)-pyridine-3-carbonyl]-amino}-methyl)-cyclohex-3-enyloxy]-acetic acid of Formula (5.5.98); | 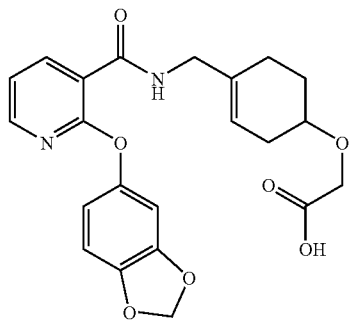 |
| [4-({[2-(4-Fluoro-phenoxy)-pyridine-3-carbonyl]-amino}-methyl)-cyclohex-3-enyloxy]-acetic acid of Formula (5.5.99); | 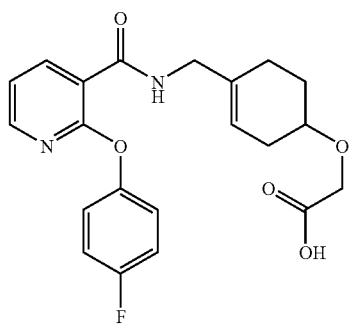 |
| (R)-2-[4-({[2-(3-Methoxy-phenoxy)-pyridine-3-carbonyl]-amino}-methyl)-phenoxy]-propionic acid of Formula (5.5.100); | 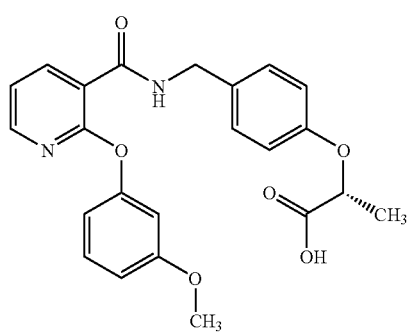 |
| (R)-2-[3-Fluoro-4-({[2-(3-methoxy-phenoxy)-pyridine-3-carbonyl]-amino}-methyl)-phenoxy]-propionic acid of Formula (5.5.101); | 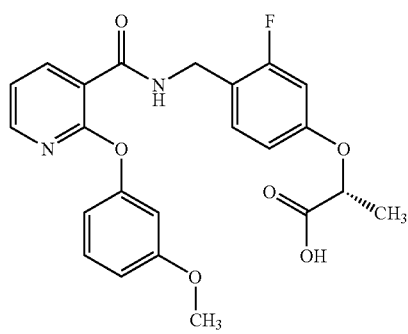 |

| NOMENCLATURE | STRUCTURAL FORMULA |
|---|---|
| (R)-2-[3-Fluoro-4-({[5-fluoro-2-(3-methoxy-phenoxy)-pyridine-3-carbonyl]-amino}-methyl)-phenoxy]-propionic acid of Formula (5.5.102); | 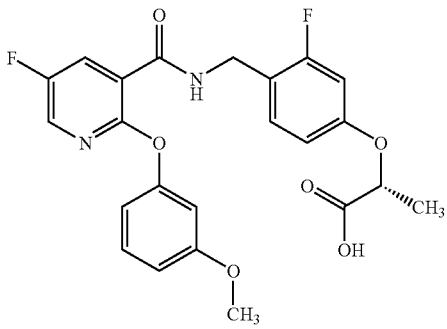 |
| (R)-2-[4-({[2-(3-Nitro-phenoxy)-pyridine-3-carbonyl]-amino}-methyl)-phenoxy]-propionic acid of Formula (5.5.103); | 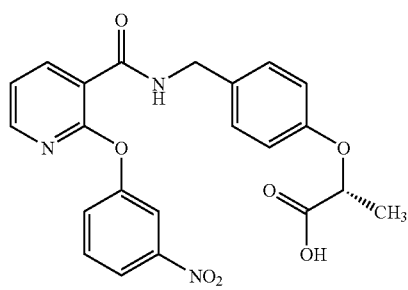 |
| (R)-2-[4-({[2-(3-Chloro-4-fluoro-phenoxy)-pyridine-3-carbonyl]-amino}-methyl)-phenoxy]-propionic acid of Formula (5.5.104); | 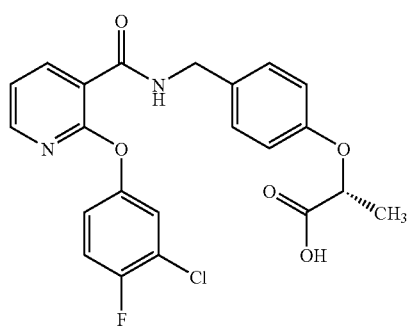 |
| (R)-2-[4-({[2-(3,4-Difluoro-phenoxy)-pyridine-3-carbonyl]-amino}-methyl)-phenoxy]-propionic acid of Formula (5.5.105); | 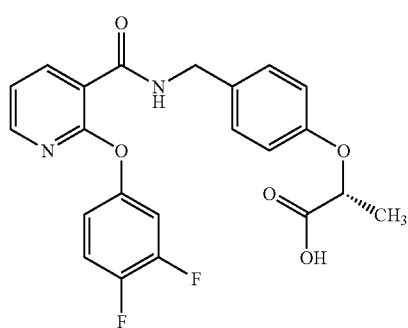 |

| NOMENCLATURE | STRUCTURAL FORMULA |
|---|---|
| (R)-2-[4-({[2-(2,3-Dihydro-benzofuran-5-yloxy)-pyridine-3-carbonyl]-amino}-methyl)-phenoxy]-propionic acid of Formula (5.5.106); | 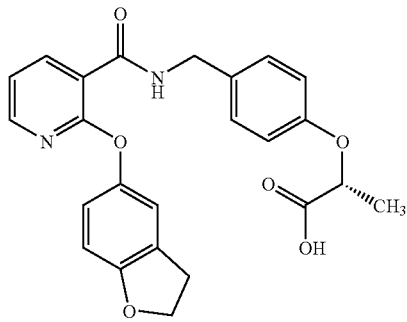 |
| (R)-2-[4-({[2-(2,3-Dihydro-benzofuran-6-yloxy)-pyridine-3-carbonyl]-amino}-methyl)-phenoxy]-propionic acid of Formula (5.5.107); | 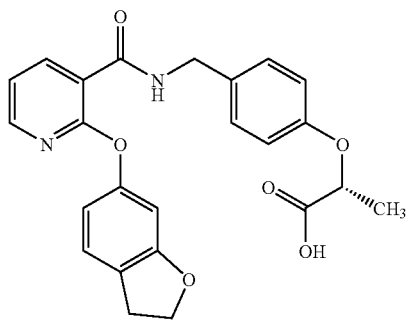 |
| (S)-2-(Benzo[1,3]dioxol-5-yloxy)-N-{2-fluoro-4-[1-(1H-tetrazol-5-yl)-ethoxy]-benzyl}-nicotinamide of Formula (5.5.108); | 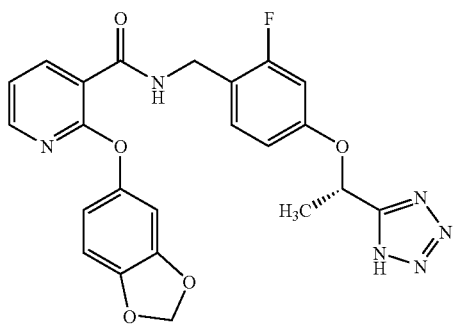 |
| (R)-2-(Benzo[1,3]dioxol-5-yloxy)-N-{2-fluoro-4-[1-(1H-tetrazol-5-yl)-ethoxy]-benzyl}-nicotinamide of Formula (5.5.109); | 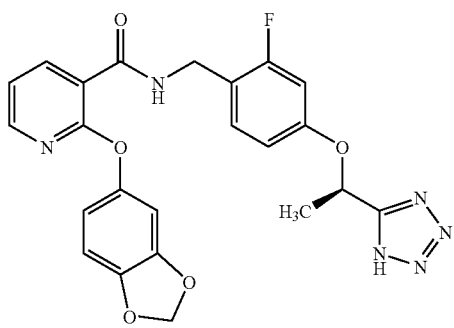 |

-continued

| NOMENCLATURE | STRUCTURAL FORMULA |
|---|---|
| (R)-3-[4-({[2-(Benzo[1,3]dioxol-5-yloxy)-pyridine-3-carbonyl]-amino}-methyl)-3-fluoro-phenoxy]-2-methyl-propionic acid of Formula (5.5.110); | 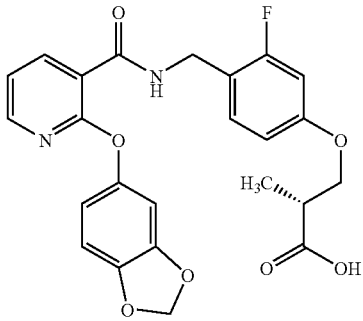 |
| (S)-2-(Benzo[1,3]dioxol-5-yloxy)-N-[4-(2-carbamoyl-propoxy)-2-fluoro-benzyl]-nicotinamide of Formula (5.5.111); | 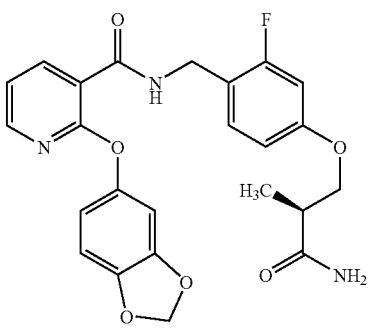 |
| (R)-2-(Benzo[1,3]dioxol-5-yloxy)-5-fluoro-N-{2-fluoro-4-[1-(1H-tetrazol-5-yl)-ethoxy]-benzyl}-nicotinamide of Formula (5.5.112); | 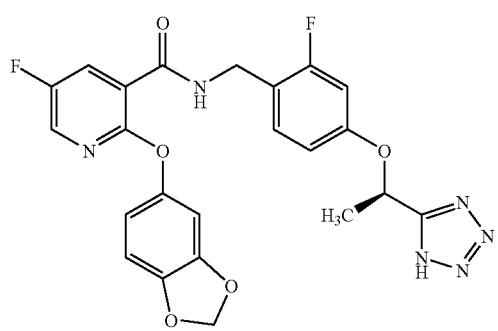 |
| (±)-2-(3-Methoxy-phenoxy)-N-{4-[1-(1H-tetrazol-5-yl)-ethoxy]-benzyl}-nicotinamide of Formula (5.5.113); | 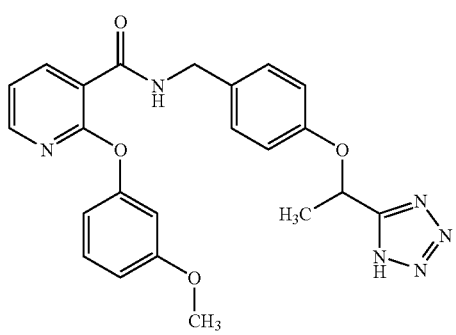 |

| NOMENCLATURE | STRUCTURAL FORMULA |
|---|---|
| 2-[5-({[2-(Benzo[1,3]dioxol-5-yloxy)-pyridine-3-carbonyl]-amino}-methyl)-thiophen-2-yloxy]-propionic acid of Formula (5.5.114); | 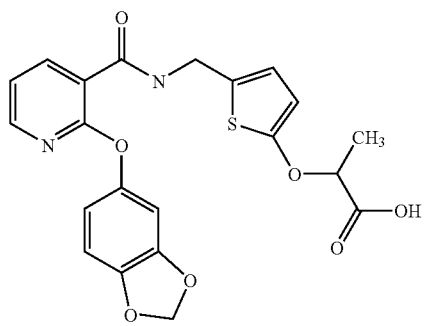 |
| (±)-2-(Benzo[1,3]dioxol-5-yloxy)-N-{2-fluoro-4-[1-methyl-2-oxo-2-(4H-[1,2,4]triazol-3-yl)-ethoxy]-benzyl}-nicotinamide of Formula (5.5.115) | 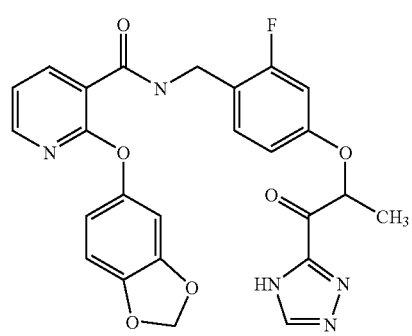 |

DETAILED DESCRIPTION OF THE INVENTION 6.0 Processes for Making the Compounds of Formula (1.0.0)

A suitable method for preparing a compound of Formula (1.0.0) that belongs to the class of ether acids, where $W^1$ and $W^2$ are both —O—, $*^2$ is phenyl, and D is a moiety of partial Formula (1.1.1), is illustrated in Synthesis Scheme (10.0.0) below.

SYNTHESIS SCHEME (10.0.0)

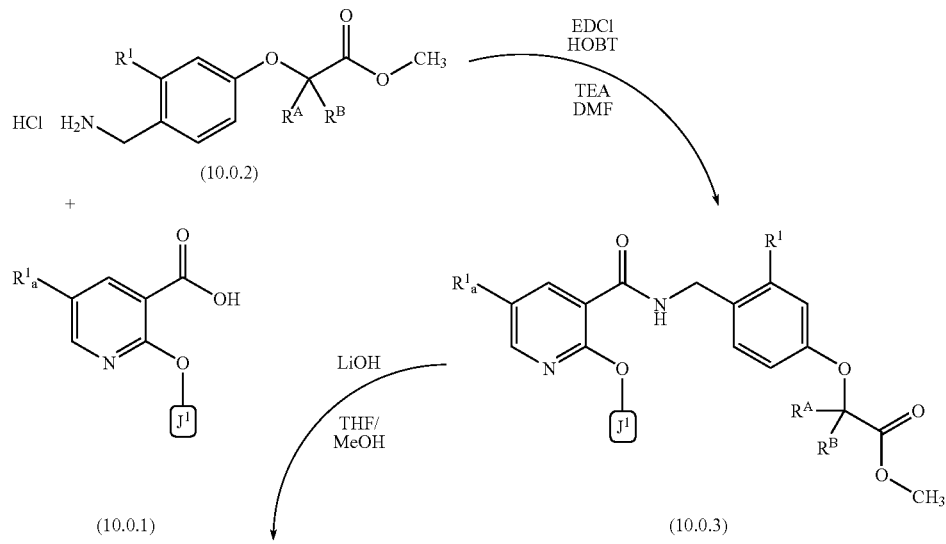

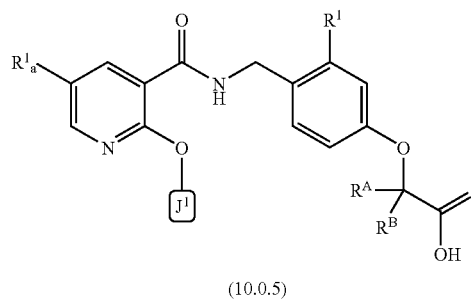

(10.0.5)

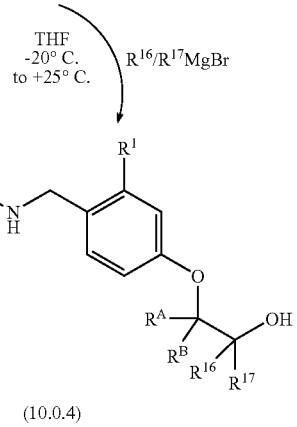

(10.0.4)

where $R^1$ is —H or —F; $R^A$ and $R^B$ are —H or $(C_1–C_4)$alkyl; $R^1_a$ and $*^1$ have the same meanings as defined above; and $R^{16}$ and $R^{17}$ must have the same meaning.

A suitable method for preparing a compound of Formula (1.0.0) that belongs to the class of triazoles, where $W^1$ and $W^2$ are both —O—, $*^2$ is phenyl, and D is a moiety of partial Formula (1.1.4) where v is 0 and $R^8$ is triazole, is illustrated in Synthesis Scheme (10.1.0) below. The first step of Synthesis Scheme (10.1.0) illustrates the preparation of ether amides of Formula (1.0.0).

SYNTHESIS SCHEME (10.1.0)

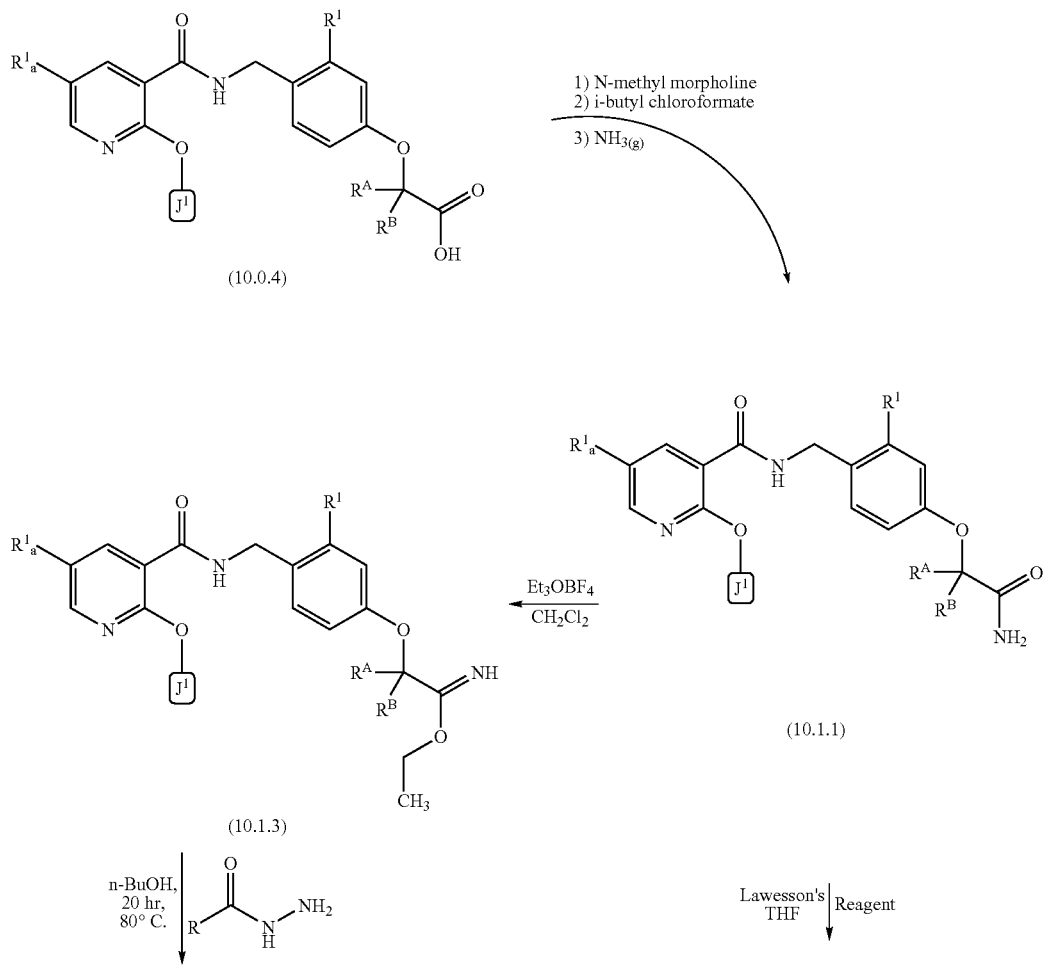

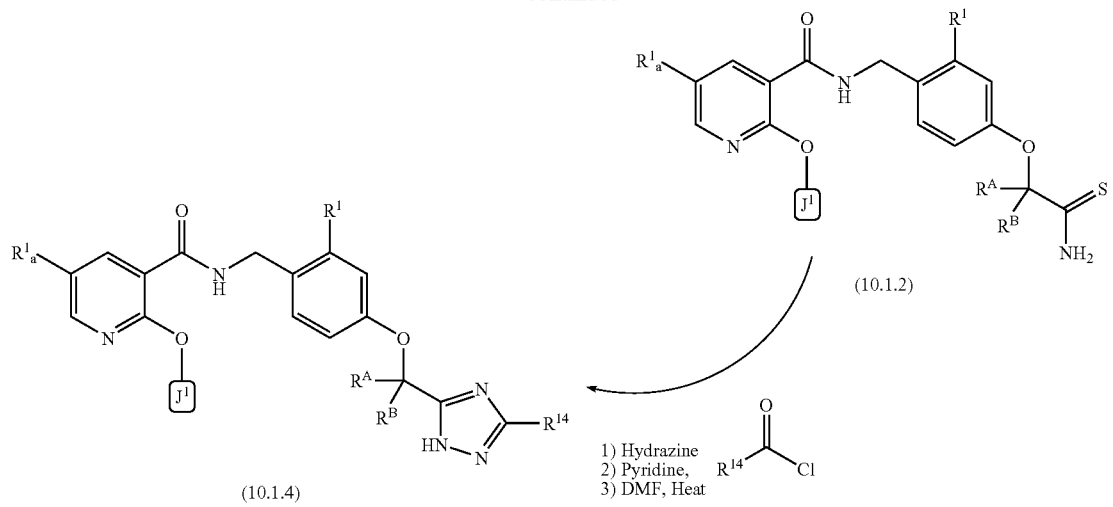

where $R^1$ is —H or —F; $R^A$ and $R^B$ are —H or $(C_1-C_4)$alkyl; $R^1_a$ and $*^1$ have the same meanings as defined above; and $R^{14}$ has the same meaning as above, and is preferably methyl, phenyl, or iso-propyl.

A suitable method for preparing racemic amino ether ester compounds of Formula (1.0.0) where $W^1$ and $W^2$ are both —O—, $*^2$ is phenyl, and D is a moiety of partial Formula (1.1.1), is illustrated in Synthesis Scheme (10.2.0) below.

SYNTHESIS SCHEME (10.2.0)

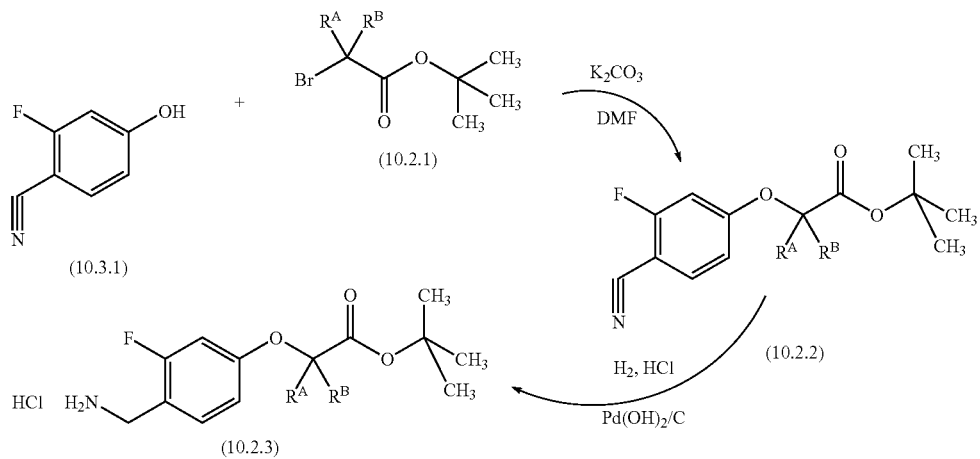

where $R^A$ and $R^B$ have the same meanings as defined above.

A suitable method for preparing enantiomeric amino ether ester compounds of Formula (1.0.0) where $W^1$ and $W^2$ are both —O—, $*^2$ is phenyl, and D is a moiety of partial Formula (1.1.1), is illustrated in Synthesis Scheme (10.3.0) below.

SYNTHESIS SCHEME (10.3.0)
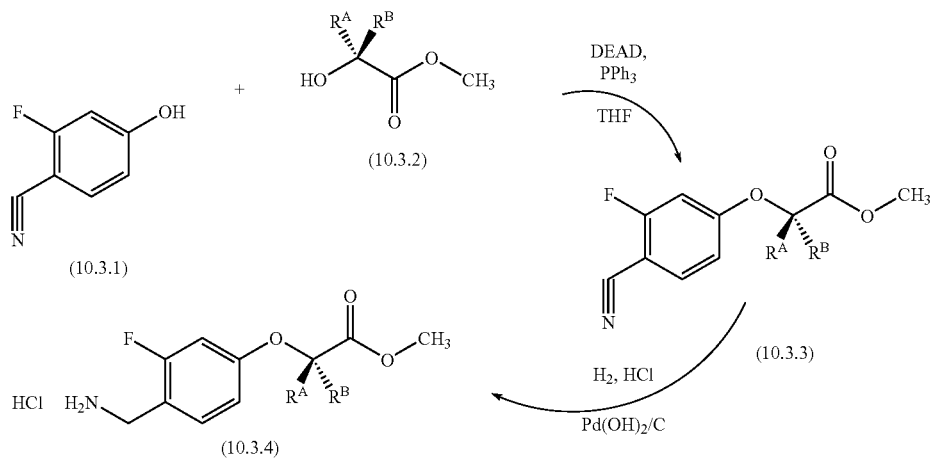
where $R^A$ and $R^B$ have the same meanings as defined above.
Other suitable methods for preparing phenyl, pyridyl, and tetrazolyl ether compounds of Formula (1.0.0) where $W^1$ and $W^2$ are both —O—, $*^2$ is phenyl, and D is a moiety of partial Formula (1.1.4), where v is 0 and $R^8$ is pyridyl or tetrazolyl, are illustrated in Synthesis Scheme (10.4.0) below.
SYNTHESIS SCHEME (10.4.0)
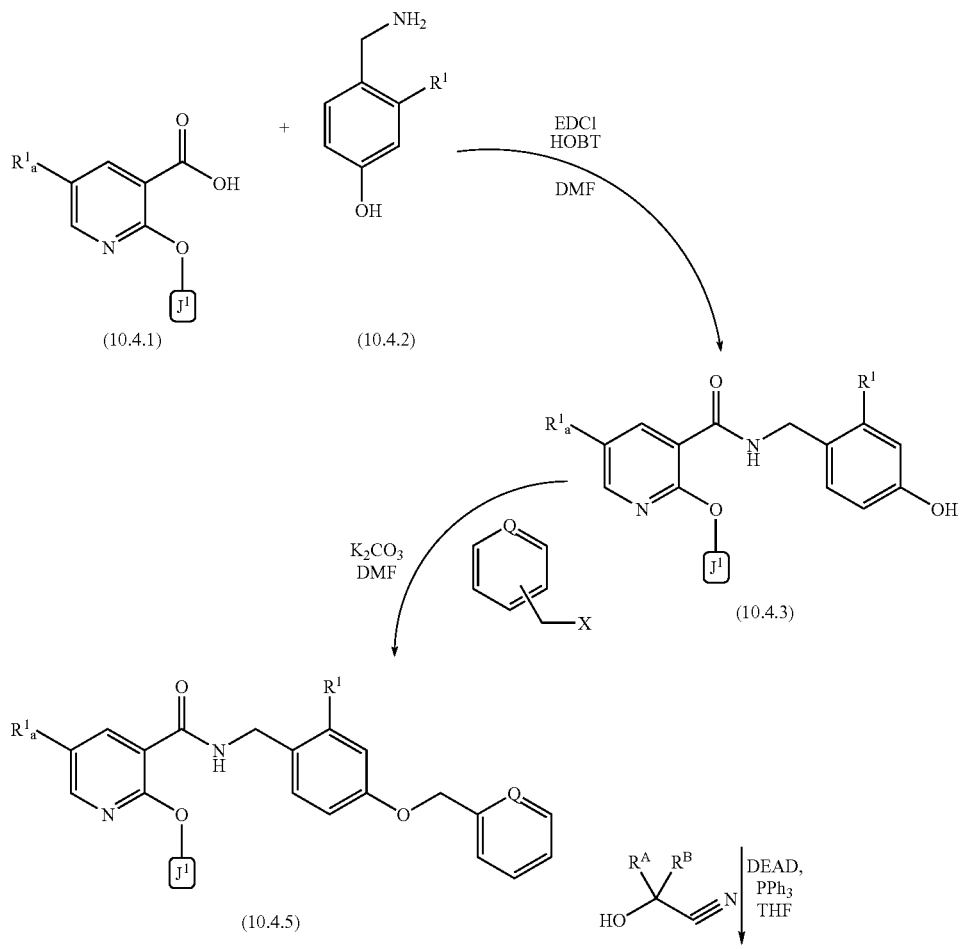

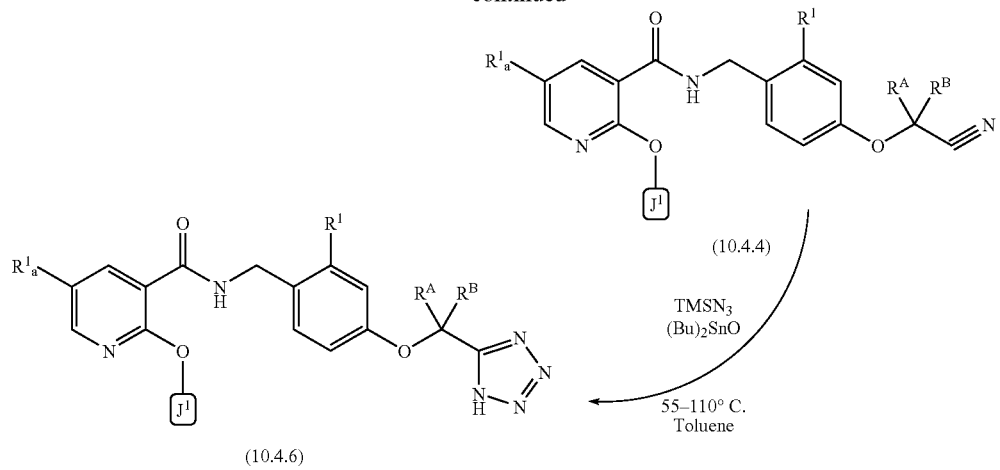

where $R^1$ is —H or —F; $R^A$ and $R^B$ are —H or ($C_1$-$C_4$)alkyl; Q is CH or N; X is halo; and $R^1_a$ $*^1$ have the same meanings as defined above.

DETAILED DESCRIPTION OF THE INVENTION

7.0 Pharmaceutical Salts and Other Forms

The above-described compounds of the present invention may be utilized in the form of acids, esters, or other chemical classes of compounds to which the compounds described belong. It is also within the scope of the present invention to utilize those compounds in the form of their pharmaceutically acceptable salts derived from various organic and inorganic acids and bases in accordance with procedures well known in the art.

Pharmaceutically acceptable salt forms of the compounds of Formula (1.0.0) are prepared for the most part by conventional means. Where the compound of Formula (1.0.0) contains a carboxylic acid group, a suitable salt thereof may be formed by reacting the compound with an appropriate base to provide the corresponding base addition salt. Examples of such bases are alkali metal hydroxides including potassium hydroxide, sodium hydroxide, and lithium hydroxide; alkaline earth metal hydroxides such as barium hydroxide and calcium hydroxide; alkali metal alkoxides, e.g., potassium ethanolate and sodium propanolate; and various organic bases such as piperidine, diethanolamine, and N-methylglutamine. Also included are the aluminum salts of the compounds of Formula (1.0.0).

For certain compounds of Formula (1.0.0) acid addition salts may be formed by treating said compounds with pharmaceutically acceptable organic and inorganic acids, e.g., hydrohalides such as hydrochloride, hydrobromide, hydroiodide; other mineral acids and their corresponding salts such as sulfate, nitrate, phosphate, etc.; and alkyl- and mono-arylsulfonates such as ethanesulfonate, toluenesulfonate, and benzenesulfonate; and other organic acids and their corresponding salts such as acetate, tartrate, maleate, succinate, citrate, benzoate, salicylate, ascorbate, etc.

Accordingly, the pharmaceutically acceptable acid addition salts of the compounds of Formula (1.0.0) include, but are not limited to: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, phthalate,.

Further, base salts of the compounds of the present invention include, but are not limited to aluminum, ammonium, calcium, copper, ferric, ferrous, lithium, magnesium, manganic, manganous, potassium, sodium, and zinc salts. Preferred among the above-recited salts are ammonium; the alkali metal salts sodium and potassium; and the alkaline earth metal salts calcium and magnesium. Salts of the compounds of Formula (1.0.0) derived from pharmaceutically acceptable organic non-toxic bases include, but are not limited to salts of primary, secondary, and tertiary amines, substituted amines including naturally occurring substituted amines, cyclic amines, and basic ion exchange resins, e.g., arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine(tromethamine).

Compounds of the present invention which comprise basic nitrogen-containing groups may be quaternized with such agents as ($C_1$-$C_4$)alkyl halides, e.g., methyl, ethyl, iso-propyl and tert-butyl chlorides, bromides and iodides; di($C_1$-$C_4$)alkyl sulfate, e.g., dimethyl, diethyl and diamyl sulfates; ($C_{10}$-$C_{18}$)alkyl halides, e.g., decyl, dodecyl, lauryl, myristyl and stearyl chlorides, bromides and iodides; and aryl-$(C_1-C_4)$alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

The acid addition salts of basic compounds of Formula (1.0.0) are prepared by contacting the free base form with a sufficient amount of the desired acid to produce the salt in the conventional manner. The free base may be regenerated by contacting the salt form with a base and isolating the free base in the conventional manner. The free base forms differ from their respective salt forms somewhat in certain physical properties such as solubility in polar solvents, but otherwise the salts are equivalent to their respective free base forms for purposes of the present invention.

As indicated, the pharmaceutically acceptable base addition salts of the compounds of Formula (1.0.0) are formed with metals or amines, such as alkali metals and alkaline earth metals, or organic amines. Preferred metals are sodium, potassium, magnesium, and calcium. Preferred organic amines are N,N'-dibenzylethylenediamine, chloroprocaine, choline, diethanolamine, ethylenediamine, N-methyl-D-glucamine, and procaine The base addition salts of acidic compounds of the present invention are prepared by contacting the free acid form with a sufficient amount of the desired base to produce the salt in the conventional manner. The free acid form may be regenerated by contacting the salt form with an acid and isolating the free acid form in the conventional manner. The free acid forms differ from their respective salt forms somewhat in physical properties such as solubility in polar solvents, but otherwise the salts are equivalent to their respective free acid forms for purposes of the present invention.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

In light of the above, it can be seen that the expression "pharmaceutically acceptable salt" as used herein is intended to mean an active ingredient comprising a compound of Formula (1.0.0) utilized in the form of a salt thereof, especially where said salt form confers on said active ingredient improved pharmacokinetic properties as compared to the free form of said active ingredient or some other salt form of said active ingredient utilized previously. The pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation and excretion of said active ingredient. While the route of administration of the pharmaceutical composition is important, and various anatomical, physiological and pathological factors can critically affect bioavailability, the solubility of said active ingredient is usually dependent upon the character of the particular salt form thereof which it utilized. Further, as the artisan will appreciate, an aqueous solution of said active ingredient will provide the most rapid absorption of said active ingredient into the body of a patient being treated, while lipid solutions and suspensions, as well as solid dosage forms, will result in less rapid absorption of said active ingredient.

Oral ingestion of an active ingredient of Formula (1.0.0) is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different pharmaceutically acceptable salt forms may be effective in overcoming or alleviating one or more of the above-recited problems encountered with absorption of oral dosage forms.

A compound of Formula (1.0.0) prepared in accordance with the methods described herein can be separated from the reaction mixture in which it is finally produced by any ordinary means known to the chemist skilled in the preparation of organic compounds. Once separated said compound can be purified by known methods. Various methods and techniques can be used as the means for separation and purification, and include, e.g., distillation; recrystallization; column chromatography; ion-exchange chromatography; gel chromatography; affinity chromatography; preparative thin-layer chromatography; and solvent extraction.

7.1 Stereoisomers

A compound within the scope of Formula (1.0.0) may be such that its constituent atoms are capable of being arranged in space in two or more different ways, despite having identical connectivities. As a consequence, said compound exists in the form of stereoisomers. Sys-trans isomerism is but one type of stereoisomerism. Where the stereoisomers are nonsuperimposable mirror images of each other, they are enantiomers which have chirality or handedness, because of the presence of one or more asymmetric carbon atoms in their constituent structure. Enantiomers are optically active and therefore distinguishable because they rotate the plane of polarized light by equal amounts, but in opposite directions.

Where two or more asymmetric carbon atoms are present in a compound of Formula (1.0.0), there are two possible configurations at each said carbon atom. Where two asymmetric carbon atoms are present, for example, there are four possible stereoisomers. Further, these four possible stereoisomers may be arranged into six possible pairs of stereoisomers that are different from each other. In order for a pair of molecules with more than one asymmetric carbon to be enantiomers, they must have different configurations at every asymmetric carbon. Those pairs that are not related as enantiomers have a different stereochemical relationship referred to as a diastereomeric relationship. Stereoisomers that are not enantiomers are called diastereoisomers, or more commonly, diastereomers.

All of these well known aspects of the stereochemistry of the compounds of Formula (1.0.0) are contemplated to be a part of the present invention. Within the scope of the present invention there is thus included compounds of Formula (1.0.0) that are stereoisomers, and where these are enantiomers, the individual enantiomers, racemic mixtures of said enantiomers, and artificial, i.e., manufactured mixtures containing proportions of said enantiomers that are different from the proportions of said enantiomers found in a racemic mixture. Where a compound of Formula (1.0.0) comprises stereoisomers that are diastereomers, there is included within the scope of said compound the individual diastereomers as well as mixtures of any two or more of said diastereomers in any proportions thereof.

By way of illustration, in the case where there is a single asymmetric carbon atom in a compound of Formula (1.0.0), resulting in the (−)(R) and (+)(S) enantiomers thereof; there is included within the scope of said compound all pharmaceutically acceptable salt forms, prodrugs and metabolites thereof which are therapeutically active and useful in treating or preventing the diseases and conditions described further herein. Where a compound of Formula (1.0.0) exists in the form of (−)(R) and (+)(S) enantiomers, there is also included within the scope of said compound the (+)(S) enantiomer alone, or the (−)(R) enantiomer alone, in the case where all, substantially all, or a predominant share of the therapeutic activity resides in only one of said enantiomers, and/or unwanted side effects reside in only one of said enantiomers. In the case where there is substantially no difference between the biological activities of both enantiomers, there is further included within the scope of said compound of Formula (1.0.0) the (+)(S) enantiomer and the (−)(R) enantiomer present together as a racemic mixture or as a non-racemic mixture in any ratio of proportionate amounts thereof.

For example, the particular biological activities and/or physical and chemical properties of a pair or set of enantiomers of a compound of Formula (1.0.0) where such exist, may suggest use of said enantiomers in certain ratios to constitute a final therapeutic product. By way of illustration, in the case where there is a pair of enantiomers, they may be employed in ratios such as 90% (R)-10% (S); 80% (R)-20% (S); 70% (R)-30% (S); 60% (R)-40% (S); 50% (R)-50% (S); 40% (R)-60% (S); 30% (R)-70% (S); 20% (R)-80% (S); and 10% (R)-90% (S). After evaluating the properties of the various enantiomers of a compound of Formula (1.0.0) where such exist, the proportionate amount of one or more of said enantiomers with certain desired properties that will constitute the final therapeutic product can be determined in a straightforward manner.

7.2 Isotopes

There is further contemplated to be included within the scope of a compound of Formula (1.0.0) isotopically-labelled forms thereof. An isotopically-labelled form of a compound of Formula (1.0.0) is identical to said compound but for the fact that one or more atoms of said compound have been replaced by an atom or atoms having an atomic mass or mass number different from the atomic mass or mass number of said atom which is usually found in nature. Examples of isotopes which are readily available commercially and which can be incorporated into a compound of Formula (1.0.0) in accordance with well established procedures, include isotopes of hydrogen, carbon, nitrogen, oxygen, phosphorous, sulfur, fluorine and chlorine, e.g., $^2H$, $^3H$, $^{13}C$, $^{14}C$, $^{15}N$, $^{18}O$, $^{17}O$, $^{31}P$, $^{32}P$, $^{35}$, $^{18}F$, and $^{36}Cl$, respectively. A compound of Formula (1.0.0), a prodrug thereof, or a pharmaceutically acceptable salt of either which contains one or more of the above-mentioned isotopes and/or other isotopes of other atoms is contemplated to be within the scope of the present invention.

An isotopically-labelled compound of Formula (1.0.0) may be used in a number of beneficial ways. For example, an isotopically-labelled compound of Formula (1.0.0), e.g., one in which a radioactive isotope such as $^3H$ or $^{14}C$ has been incorporated, will be useful in drug and/or substrate tissue distribution assays. These radioactive isotopes, i.e., tritium, $^3H$, and carbon-14, $^{14}C$, are especially preferred for their ease of preparation and eminent detectability. Incorporation of heavier isotopes, e.g., deuterium, $^2H$, into a compound of Formula (1.0.0) will provide therapeutic advantages based on the greater metabolic stability of said isotopically-labelled compound. Greater metabolic stability translates directly into increased in vivo half-life or reduced dosage requirements, which under most circumstances would constitute a preferred embodiment of the present invention. An isotopically-labelled compound of Formula (1.0.0) can usually be prepared by carrying out the procedures disclosed in the Synthesis Schemes and related description, Examples, and Preparations herein, substituting a readily available isotopically-labelled reagent for its corresponding non-isotopically-labelled reagent.

Deuterium, $^2H$, can also be incorporated into a compound of Formula (1.0.0) for the purpose of manipulating the oxidative metabolism of said compound by way of the primary kinetic isotope effect. The primary kinetic isotope effect is a change of rate for a chemical reaction that results from substitution of isotopic nuclei, which in turn is caused by the change in ground state energies required for covalent bond formation subsequent to said isotopic substitution. Substitution of a heavier isotope will usually result in a lowering of the ground state energy for a chemical bond, thereby causing a reduction in rate for a rate-limiting bond breaking step. If the bond-breaking event occurs on or near a saddle-point region along the coordinate of a multi-product reaction, the product distribution ratios can be altered substantially. By way of illustration, when deuterium is bound to a carbon atom at a non-exchangeable site, rate differences of $k_M/k_D=2-7$ are typical. This difference in rate, applied successfully to an oxidatively labile compound of Formula (1.0.0), can dramatically affect the profile of said compound in vivo and result in improved pharmacokinetic properties.

In discovering and developing therapeutic agents, the skilled artisan seeks to optimize pharmacokinetic parameters while retaining desirable in vitro properties. It is a reasonable surmise that many compounds with poor pharmacokinetic profiles suffer from a lability to oxidative metabolism. In vitro liver microsomal assays now available provide valuable information about the course of this oxidative metabolism, which in turn permits the rational design of deuterated compounds of Formula (1.0.0) with improved stability through resistance to such oxidative metabolism. Significant improvements in the pharmacokinetic profiles of compounds of Formula (1.0.0) are thereby obtained, and can be expressed quantitatively in terms of increases in in vivo half-life (t/2), concentration at maximum therapeutic effect ($C_{max}$), area under the dose response curve (AUC), and F; and in terms of decreases in clearance, dose, and cost-of-goods.

By way of illustration of the above, a compound of Formula (1.0.0) which has multiple potential sites for oxidative metabolism, e.g., benzylic hydrogen atoms and hydrogen atoms a to a nitrogen atom, is prepared as a series of analogs in which various combinations of hydrogen atoms are replaced by deuterium atoms so that some, most or all of said hydrogen atoms are replaced with deuterium atoms. Half-life determinations provide an expedient and accurate determination of the extent of improvement in resistance to oxidative metabolism. In this manner it is determined that the half-life of the parent compound can be extended by as much as 100% as the result of such deuterium-for-hydrogen substitution.

Deuterium-for-hydrogen substitution in a compound of Formula (1.0.0) can also be used to achieve a favorable alteration in the metabolite profile of the parent compound as a way of diminishing or eliminating unwanted toxic metabolites. For example, where a toxic metabolite arises through an oxidative carbon-hydrogen, C—H, bond scission, the deuterated analog is reasonably expected to greatly diminish or eliminate production of the unwanted metabolite, even in the case where the particular oxidation is not a rate-determining step.

Further information concerning the state of the art with respect to deuterium-for-hydrogen substitution may be found, e.g., in Hanzlik et al., *J. Org. Chem.* 55 3992–3997, 1990; Reider et al., *J. Org. Chem.* 52 3326–3334, 1987; Foster, Adv. Drug Res. 14 1–40, 1985; Gillette et al., *Biochemistry* 33(10) 2927–2937, 1994; and Jarman et al., *Carcinogenesis* 16(4) 683–688, 1993.

DETAILED DESCRIPTION OF THE INVENTION 8.0 Therapeutic Applications and Clinical Endpoints The description which follows concerns the therapeutic applications to which the compounds of Formula (1.0.0) may be put, and where applicable an explanation of the clinical endpoints associated with such therapeutic applications. There is also set forth a disclosure of various in vitro assays and animal model experiments, which are capable of providing data sufficient to define and demonstrate the therapeutic utility of the compounds of Formula (1.0.0).

The therapeutic utility of the compounds of Formula (1.0.0) is applicable to a patient or subject afflicted with a disease or condition as herein set forth and therefore in need of such treatment. The beneficial results are therapeutic whether administered to animals or humans. As used herein the terms "animal" and "animals" is used merely for the purpose of pointing out human beings as opposed to other members of the animal kingdom. The compounds of Formula (1.0.0) have therapeutic applicability in the treatment of mammals, and in particular of humans. All of the major subdivisions of the class of mammals (Mammalia) are included within the scope of the present invention with regard to being recipients of therapeutic treatment as described herein. Mammals have value as pets to humans and are therefore likely to be subjects of treatment. This applies especially to the canine and feline groups of mammals. Other mammals are valued as domesticated animals and their treatment in accordance with the present invention is likely in view of the adverse economic impact of not treating the diseases and conditions described herein. This applies especially to the equine, bovine, porcine, and ovine groups of mammals.

The compounds of Formula (1.0.0) inhibit the PDE4 isozyme and thereby have a wide range of therapeutic applications, as described further below, because of the essential role which the PDE4 family of isozymes plays in the physiology of all mammals. The enzymatic role performed by the PDE4 isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE4 inhibition plays a significant role in a variety of physiological processes. There is extensive literature in the art describing the effects of PDE inhibitors on various inflammatory cell responses, which in addition to cAMP elevation, include inhibition of superoxide production, degranulation, chemotaxis and tumor necrosis factor (TNF) release in eosinophils, neutrophils and monocytes.

PDE4 was first identified in 1985, Nemoz et al. *Biochem. Pharmacol.* 34 2997–3000, 1985, and the PDE4 inhibitors rolipram and denbufylline were studied early on in clinical trials for CNS indications such as depression. Subsequently, it was established that PDE4 is the principal phosphodiesterase in inflammatory leukocytes. The four subtypes of PDE4, i.e., PDE4A, PDE4B, PDE4C, and PDE4D, are widely distributed in human tissues, as determined by the presence of their mRNAs. PbE4D is expressed in kidney, thymus, small intestine, and colon tissues, and is strongly expressed in brain, lung, skeletal muscle, prostate, and peripheral blood leukocyte (PBL) tissues. It is only weakly expressed in heart, placenta, liver, pancreas, spleen, testes, and ovary tissues. PDE4A and PDE4B are also strongly expressed in brain and skeletal muscle tissues, and only weakly expressed in placenta, liver, and ovary tissues. PDE4C is strongly expressed in skeletal muscle tissue as well, and is also weakly expressed in ovary tissue. PDE4C is usually not detectable in the majority of the above-mentioned tissues.

The PDE4 family of isozymes is the predominant form of phosphodiesterase found in cell types implicated in chronic inflammatory diseases, and among bone-marrow derived cell types, only platelets do not express PDE. PDE4 is the major cAMP-metabolizing enzyme in immune and inflammatory cells, and is one of two major cAMP-metabolizing enzymes in airway smooth muscle. PDE4 is exclusively present in neutrophils, eosinophils, basophils, and monocyctes, while in macrophages PDE3 and PDE1 activity, and in T lymphocytes PDE7 activity has also been demonstrated. The beneficial anti-inflammatory effects of inhibitors of PDE have been demonstrated heretofore using in vitro experiments, which have established that such compounds inhibit superoxide generation in human monocytes, eosinophils, and neutrophils; mediator release in basophils, macrophages, and neutrophils; and TNFα release in monocytes and macrophages. PDE inhibitors also inhibit mediator release of inflammatory cells like monocytes and monocyte-derived macrophages, lung mast cells, T lymphocytes, B lymphocytes, alveolar macrophages, and eosinophils.

Beneficial anti-inflammatory effects have also been observed in vivo heretofore, including inhibition of microvascular leakage into the lungs of sensitized guinea pigs, and reduction of bronchial hyper-reactivity and eosinophilia in cynomolgus monkeys following repeated antigen challenge. It has also been demonstrated heretofore that PDE4 inhibitors potently suppress TNFα release from mononuclear phagocytes.

8.1 Asthma

One of the most important respiratory diseases treatable with PDE4, especially PDE4D inhibitors of the type within the scope of the compounds of Formula (1.0.0) is asthma, a chronic, increasingly common disorder encountered worldwide and characterized by intermittent reversible airway obstruction, airway hyper-responsiveness and inflammation. The cause of asthma has yet to be determined, but the most common pathological expression of asthma is inflammation of the airways, which may be significant even in the airways of patients with mild asthma. Based on bronchial biopsy and lavage studies it has been clearly shown that asthma involves infiltration by mast cells, eosinophils, and T-lymphocytes into a patient's airways. Bronchoalveolar lavage (BAL) in atopic asthmatics shows activation of interleukin (IL)-3, IL-4, IL-5 and granulocyte/macrophage-colony stimulating factor (GM-CSF) that suggests the presence of a T-helper 2 (Th-2)-like T-cell population.

Compounds of Formula (1.0.0) inhibit PDE4 in human eosinophils and are therefore useful in the treatment of atopic and non-atopic asthma. The term "atopy" refers to a genetic predisposition toward the development of type I (immediate) hypersensitivity reactions against common environmental antigens. The most common clinical manifestation is allergic rhinitis, while bronchial asthma, atopic dermatitis, and food allergy occur less frequently. Accordingly, the expression "atopic asthma" as used herein is intended to be synonymous with "allergic asthma", i.e., bronchial asthma which is an allergic manifestation in a sensitized person. The term "non-atopic asthma" as used herein is intended to refer to all other asthmas, especially essential or "true" asthma, which is provoked by a variety of factors, including vigorous exercise, irritant particles, psychologic stresses, etc.

The use of the compounds of Formula (1.0.0) to treat atopic asthma or non-atopic asthma is established and demonstrated by the models of PDE inhibition, inhibition of eosinophil activation, and the cell infiltration models described below.

Pulmonary Inflammation in Allergic Cynomolgus Monkeys—The ability of the combinations of therapeutic agents of the present invention to inhibit *Ascaris* antigen induced increases in the inflammatory cell content of bronchial alveolar lavage fluid from cynomolgus monkey subjects is evaluated in this method. Using a cross-over design, 8–10 Ascaris-sensitive cynomolgus monkeys are treated with vehicle or drug. At appropriate pretreatment time, each monkey is anesthetized (ketamine 10 m/kg+xylazine 1 mg/kg, i.m.) and intubated with a cuffed endotracheal tube. Bronchoalveolar lavage (BAL) is performed using one 15 ml wash of phosphate buffered saline (PBS) delivered through a pediatric fiberoptic bronchoscope inserted through the endotracheal tube and wedged into a third to fifth generation bronchus. Lavage fluid is gently aspirated and collected in a syringe. After BAL is complete, each animal receives a 2 min exposure to a concentration of *Ascaris suum* aerosol which doubles respiratory system resistance determined in previous experiments. Each monkey is returned to its cage and 24 hr later a second lavage is performed, using 15 ml PBS, on the opposite side of the lung. One week after the first trial, control and treated monkeys are reversed and the experiment repeated. To determine the percent composition of each leukocyte type, two slides from each monkey BAL sample is obtained by centrifuging 2×150 ul lavage fluid for 2 min @ 500 rpm in Cytospin centrifuge. Slides are stained in Diff-Quick for differential cell count and cells identified by standard morphological criteria. Total leukocyte numbers per milliliter of BAL fluid are determined by diluting 20 ul of sample in 20 ml Isoton, adding 3 drops of Zapoglobin to lyse erythrocytes and reading the sample using a Coulter Counter. Comparisons are made between the ratio of increase in bronchial alveolar lavage eosinophil, cytokine or mediator levels, pre-antigen challenge versus 24 hours post antigen challenge, with and without drug treatment.

In the above test model the combinations of therapeutic agents of the present invention exhibit anti-inflammatory activity at dosages in the range of from 0.001 to 0.1 mg/kg i.v. or 0.01 to 10.0 mg/kg p.o. or 0.001 to 0.1 mg/kg i.t.

Another useful assay, based on the use of primates, is that described in Turner et al., "Characterization of a primate model of asthma using anti-allergy/anti-asthma agents," *Inflammation Research* 45 239–245, 1996.

Anti-inflammatory Activity—The anti-inflammatory activity of the combinations of therapeutic agents of the present invention is demonstrated by the inhibition of eosinophil activation as measured by sephadex bead stimulated LTE4 production in whole human blood. Whole Blood Assay for LTE4 using Sephadex Beads as Stimulant. On the day before the assay, siliconize glass tubes with Sigmacote (Sigma, Cat# SL-2). Before Drawing the blood, dilute compounds in DMSO 1000×, add 1 μl of either DMSO or compound to each respective tube, and place rack of tubes in 37° C. water bath. Have Blood drawn into heparinized Vacutainer tube #6480 (143USP units sodium heparin, 10 ml), 10 tubes=100 ml blood. Pool Blood tubes in two 50 ml conical tubes. Add 1 ml of whole blood to each siliconized tube containing DMSO or compound VORTEX and then incubate at 37° C. for 15 minutes. To prepare the Sephadex G-15 beads (Pharmacia, Cat# 17-0020-01) suspension, add 3.3 g. of Sephadex G-15, mix with 20 mls of PBS in a 100 ml beaker then mix with a magnetic stir bar. After 15 minutes, add 100 μl of Sephadex G-15 beads to each tube except the Sephadex tubes which will provide the baseline value for LTE4 release. Vortex and incubate for 90 minutes at 37° C. At the end of 90 minutes incubation, add 20 μl of 15% EDTA, VORTEX and centrifuge for 5 minutes at 1000 rpm. Then remove and save the plasma sample for analysis. LTE4 levels are determined by Cayman's Cysteinyl-LT ELISA kit (Cat # 520501). Percent inhibition is calculated as 100×1−(LTE4 concentration in the drug treated sample divided by the LTE4 concentration in the non-drug treated control samples).

Compounds of Formula (1.0.0) are active in the above test method at concentrations in the range of from 0.0001 μM to 20.0 μM, with preferred embodiments being active at concentrations in the range of from 0.5 nM to 1000 nM.

From the above it may be seen that compounds of Formula (1.0.0) are useful for the treatment of inflammatory or obstructive airways diseases or other conditions involving airways obstruction. In particular they are useful for the treatment of bronchial asthma.

In view of their anti-inflammatory activity, their influence on airways hyper-reactivity, and their profile in relation to PDE isoenzyme inhibition, in particular as selective PDE4 inhibitors, the compounds of Formula (1.0.0) are useful for the treatment, in particular prophylactic treatment, of obstructive or inflammatory airways diseases. Thus, by continued and regular administration over prolonged periods of time the compounds of Formula (1.0.0) are useful in providing advance protection against the recurrence of bronchoconstriction or other symptomatic attack consequential to obstructive or inflammatory airways diseases. The compounds of Formula (1.0.0) are also useful for the control, amelioration or reversal of the basal status of such diseases.

Having regard to their bronchodilator activity the compounds of Formula (1.0.0) are useful as bronchodilators, e.g., in the treatment of chronic or acute bronchoconstriction, and for the symptomatic treatment of obstructive or inflammatory airways diseases.

The words "treatment" and "treating" as used throughout the present specification and claims in relation to obstructive or inflammatory airways diseases are to be understood, accordingly, as embracing both prophylactic and symptomatic modes of therapy.

In light of the above description, it may be seen that the present invention also relates to a method for the treatment of airways hyper-reactivity in mammals; to a method of effecting bronchodilation in mammals; and in particular, to a method of treating obstructive or inflammatory airways diseases, especially asthma, in a mammal subject in need thereof, which method comprises administering to said subject mammal an effective amount of a compound of Formula (1.0.0).

Obstructive or inflammatory airways diseases to which the present invention applies include asthma; pneumoconiosis; chronic eosinophilic pneumonia; chronic obstructive airways or pulmonary disease (COAD or COPD); and adult respiratory distress syndrome (ARDS), as well as exacerbation of airways hyper-reactivity consequent to other drug therapy, e.g., aspirin or β-agonist therapy.

The compounds of Formula (1.0.0) are useful in the treatment of asthma of whatever type, etiology, or pathogenesis; including intrinsic asthma attributed to pathophysiologic disturbances, extrinsic asthma caused by some factor in the environment, and essential asthma of unknown or inapparent cause. The compounds of Formula (1.0.0) are useful in the treatment of allergic (atopic/bronchial/IgE-mediated) asthma; and they are useful as well in the treatment of non-atopic asthma, including e.g. bronchitic, emphysematous, exercise-induced, and occupational asthma; infective asthma that is a sequela to microbial, especially bacterial, fungal, protozoal, or viral infection; and other non-allergic asthmas, e.g., incipient asthma (wheezy infant syndrome).

The compounds of Formula (1.0.0) are further useful in the treatment of pneumoconiosis of whatever type, etiology, or pathogenesis; including, e.g., aluminosis (bauxite workers' disease); anthracosis (miners' asthma); asbestosis (steam-fitters' asthma); chalicosis (flint disease); ptilosis caused by inhaling the dust from ostrich feathers; siderosis caused by the inhalation of iron particles; silicosis (grinders' disease); byssinosis (cotton-dust asthma); and talc pneumoconiosis.

8.2 Chronic Obstructive Pulmonary Disease (COPD)

The compounds of Formula (1.0.0) are still further useful in the treatment of COPD or COAD including chronic bronchitis, pulmonary emphysema or dyspnea associated therewith. COPD is characterized by irreversible, progressive airways obstruction. Chronic bronchitis is associated with hyperplasia and hypertrophy of the mucus secreting glands of the submucosa in the large cartilaginous airways. Goblet cell hyperplasia, mucosal and submucosal inflammatory cell infiltration, edema, fibrosis, mucus plugs and increased smooth muscle are all found in the terminal and respiratory bronchioles. The small airways are known to be a major site of airway obstruction. Emphysema is characterized by destruction of the alveolar wall and loss of lung elasticity. A number of risk factors have also been identified as linked to the incidence of COPD. The link between tobacco smoking and COPD is well established. Other risk factors include exposure to coal dust and various genetic factors. See Sandford et al., "Genetic risk factors for chronic obstructive pulmonary disease," *Eur. Respir. J.* 10 1380–1391, 1997. The incidence of COPD is increasing and it represents a significant economic burden on the populations of the industrialized nations. COPD also presents itself clinically with a wide range of variation from simple chronic bronchitis without disability to patients in a severely disabled state with chronic respiratory failure.

COPD is characterized by inflammation of the airways, as is the case with asthma, but the inflammatory cells that have been found in the bronchoalveolar lavage fluid and sputum of patients neutrophils rather than eosinophils. Elevated levels of inflammatory mediators are also found in COPD patients, including IL-8, $LTB_4$, and TNF-α, and the surface epithelium and sub-epithelium of the bronchi of such patients has been found to be infiltrated by T-lymphocytes and macrophages. Symptomatic relief for COPD patients can be provided by the use of β-agonist and anticholinergic bronchodilators, but the progress of the disease remains unaltered. COPD has been treated using theophylline, but without much success, even though it reduces neutrophil counts in the sputum of COPD patients. Steroids have also failed to hold out much promise as satisfactory treatment agents in COPD.

Accordingly, the use of the compounds of Formula (1.0.0) to treat COPD and its related and included obstructed airways diseases, represents a significant advance in the art. The present invention is not limited to any particular mode of action or any hypothesis as to the way in which the desired therapeutic objectives have been obtained by utilizing the compounds of Formula (1.0.0). However, it is recognized in the art that PDE4 is the predominant PDE in neutrophils and macrophages; Cheng et al., "Synthesis and in vitro profile of a novel series of catechol benzimidazoles. The discovery of potent, selective phosphodiesterase Type IV inhibitors with greatly attenuated affinity for the [3H] rolipram binding site," *Bioorg. Med. Chem. Lett.* 5 1969–1972, 1995; Wright et al. "Differential inhibition of human neutrophil functions: role of cyclic AMP-specific, cyclic GMP-insensitive phosphodiesterase," *Biochem. Pharmacol.* 40 699–707, 1990; Schudt et al., "Influence of selective phosphodiesterase inhibitors on human neutrophil functions and levels of cAMP and Cai," *Naunyn Schmiedebergs Arch. Pharmacol.* 344 682–690, 1991; and Tenor et al., "Cyclic nucleotide phosphodiesterase isoenzyme activities in human alveolar macrophages," *Clin. Exp. Allergy* 25 625–633,1995.

In order to provide a better understanding of the present invention, the inference is made here that the compounds of Formula (1.0.0) inhibit PDE4s in neutrophils, resulting in reduced chemotaxis, activation, adherence, and degranulation; Schudt et al., Ibid.; Nelson et al., "Effect of selective phosphodiesterase inhibitors on the polymorphonuclear leukocyte respiratory burst," *J. Allergy Clin. Immunol.* 86 801–808, 1990; and Bloeman et al., "Increased cAMP levels in stimulated neutrophils inhibit their adhesion to human bronchial epithelial cells," *Am. J. Physiol.* 272 L580–587, 1997.

It is also inferred that the compounds of Formula (1.0.0) reduce superoxide anion production mediated by PDE4s in peripheral blood neutrophils, and that they regulate leukotriene synthesis mediated by PDE4s; Wright et al., Ibid.; Schudt et al., Ibid.; Bloeman et al., Ibid.; Al Essa, et al., "Heterogeneity of circulating and exudated polymorphonuclear leukocytes in superoxide-generating response to cyclic AMP and cyclic AMP-elevating agents: investigation of the underlying mechanism," *Biochem. Pharmacol.* 49 315–322, 1995; Ottonello et al., "Cyclic AMP-elevating agents down-regulate the oxidative burst induced by granulocyte-macrophage colony stimulating factor (GM-CSF) in adherent neutrophils," *Clin. Exp. Immunol.* 101 502–506, 1995; and Ottonello et al., "Tumor necrosis factor alpha-induced oxidative burst in neutrophils adherent to fibronectin: effects of cyclic AMP-elevating agents," *Br. J. Haematol.* 91 566–570, 1995.

It is further inferred that the compounds of Formula (1.0.0) inhibit CD11b/CD18 expression; Berends et al., "Inhibition of PAF-induced expression of CD11b and shedding of L-selectin on human neutrophils and eosinophils by the type-IV selective PDE inhibitor, rolipram," *Eur. Respir. J.* 10 1000–1007, 1997; and Derian et al., "Inhibition of chemotactic peptide-induced neutrophil adhesion to vascular endothelium by cAMP modulators," *J. Immunol.* 154 308–317, 1995.

It is still further inferred that the compounds of Formula (1.0.0) inhibit alveolar macrophage PDE4s, thereby reducing the release of chemotactic factors and TNF-α; and that the compounds of Formula (1.0.0) increase synthesis and facilitate release from monocytes of the anti-inflammatory cytokine IL-10, which in turn is capable of decreasing the generation of TNF-α, IL-1β, and GM-CSF by synovial fluid mononuclear cells, thereby augmenting the overall anti-inflammatory profile of the PDE4 inhibitors of Formula (1.0.0); Schudt et al., "PDE isoenzymes as targets for anti-asthma drugs," *Eur. Respir. J.* 8 1179–1183, 1995; and Kambayashi et al., "Cyclic nucleotide phosphodiesterase Type IV participates in the regulation of IL-10 and the subsequent inhibition of TNF-alpha and IL-6 release by endotoxin-stimulated macrophages," *J. Immunol.* 155 4909–4916, 1995.

The application of PDE4 inhibitors to the treatment of COPD in human patients has been demonstrated in clinical trials. Treatment with SB-207,499, represented by Formula (0.1.9) above, at a dose of 15 mg twice a day for six weeks has been shown to result in increrases in FEV, and forced vital capacity (FVC); Brown, W. M., "SB-207499," *Antiinflamm. Immunomodulatory Invest. Drugs* 1 39–47, 1999. The clinical efficacy of SB-207,499 has also been demonstrated in a four week trial that has provided evidence of improved $FEV_1$; and in a six week study in COPD patients receiving 15 mg twice a day that has also provided evidence of improved $FEV_1$; Brown, Ibid. SB-207,499 has already been described further above and represented by Formula (0.1.9):

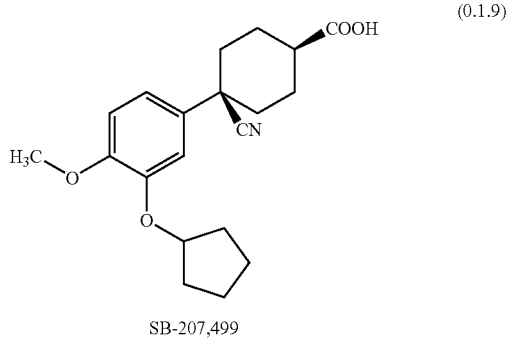

SB-207,499

8.3 Bronchitis and Bronchiectasis

In accordance with the particular and diverse inhibitory activities described above that are possessed by the compounds of Formula (1.0.0), they are useful in the treatment of bronchitis of whatever type, etiology, or pathogenesis, including, e.g., acute bronchitis which has a short but severe course and is caused by exposure to cold, breathing of irritant substances, or an acute infection; acute laryngotracheal bronchitis which is a form of nondiphtheritic croup; arachidic bronchitis which is caused by the presence of a peanut kernel in a bronchus; catarrhal bronchitis which is a form of acute bronchitis with a profuse mucopurulent discharge; chronic bronchitis which is a long-continued form of bronchitis with a more or less marked tendency to recurrence after stages of quiescence, due to repeated attacks of acute bronchitis or chronic general diseases, characterized by attacks of coughing, by expectoration either scanty or profuse, and by secondary changes in the lung tissue; croupus bronchitis which is characterized by violent cough and paroxysms of dyspnea; dry bronchitis which is characterized by a scanty secretion of tough sputum; infectious asthmatic bronchitis which is a syndrome marked by the development of symptoms of bronchospasm following respiratory tract infections in persons with asthma; productive bronchitis which is bronchitis associated with a productive cough; *staphylococcus* or streptococcal bronchitis which are caused by staphylococci or streptococci; and vesicular bronchitis in which the inflammation extends into the alveoli, which are sometimes visible under the pleura as whitish-yellow granulations like millet seeds.

Bronchiectasis is a chronic dilatation of the bronchi marked by fetid breath and paroxysmal coughing with the expectoration of mucopurulent matter. It may affect the tube uniformly, in which case it is referred to as cylindric bronchiectasis, or it may occur in irregular pockets, in which case it is called sacculated bronchiectasis. When the dilated bronchial tubes have terminal bulbous enlargements, the term fusiform bronchiectasis is used. In those cases where the condition of dilatation extends to the bronchioles, it is referred to as capillary bronchiectasis. If the dilatation of the bronchi is spherical in shape, the condition is referred to as cystic bronchiectasis. Dry bronchiectasis occurs where the infection involved is episodic and it may be accompanied by hemoptysis, the expectoration of blood or of blood-stained sputum. During quiescent periods of dry bronchiectasis, the coughing which occurs is nonproductive. Follicular bronchiectasis is a type of bronchiectasis in which the lymphoid tissue in the affected regions becomes greatly enlarged, and by projection into the bronchial lumen, may seriously distort and partially obstruct the bronchus. Accordingly, the compounds of Formula (1.0.0) are useful in the beneficial treatment of the various above-described types of bronchiectasis as a direct result of their inhibition of PDE4 isozymes.

The utility of the compounds of Formula (1.0.0) as bronchodilaors or bronchospasmolytic agents for treating bronchial asthma, chronic bronchitis and related diseases and disorder described herein, is demonstrable through the use of a number of different in vivo animal models known in the art, including those described in the paragraphs below.

Bronchospasmolytic Activity In Vitro—The ability of the compounds of Formula (1.0.0) to cause relaxation of guinea-pig tracheal smooth muscle is demonstrated in the following test procedure. Guinea-pigs (350–500 g) are killed with sodium pentothal (100 mg/kg i.p.). The trachea is dissected and a section 2–3 cm in length is excised. The trachea is transected in the transverse plane at alternate cartilage plates so as to give rings of tissue 3–5 mm in depth. The proximal and distal rings are discarded. Individual rings are mounted vertically on stainless steel supports, one of which is fixed at the base of an organ bath, while the other is attached to an isometric transducer. The rings are bathed in Krebs solution (composition μM: $NaHCO_3$ 25; NaCl 113; KCl 4.7; $MgSO_4 \cdot 7H_2O$ 1.2; $KH_2PO_4$ 1.2; $CaCl_2$ 2.5; glucose 11.7) at 37° C. and gassed with $O_2/CO_2$ (95:5, v/v). Rings prepared in this manner, preloaded to 1 g, generate spontaneous tone and, after a period of equilibration (45–60 m), relax consistently on addition of spasmolytic drugs. To ascertain spasmolytic activity, test compounds of Formula (1.0.0) are dissolved in physiological saline and added in increasing quantities to the organ bath at 5 m intervals to provide a cumulative concentration-effect curve.

In the above test model, compounds of Formula (1.0.0) produce concentration-related relaxation of guinea-pig tracheal ring preparations at concentrations in the range of from 0.001 to 1.0 PM.

The anti-inflammatory activity of the combinations of therapeutic agents of the present invention is demonstrated by the inhibition of TNFα production in human whole blood stimulated with Lipopolysacharide (LPS). Compounds are analyzed in the presence of beta agonist (10 ng/ml) and Indomethacin (1 uM). Prepare 250 ml assay buffer 200 mM HEPES in RPMI 1640 filtered. The following are performed at room temperature at the bench. Prepare "IP" cocktail in 50 ml polypropylene tube by adding 0.4 ml of Indomethacin (stock 4 mM) and 0.4 ml of beta agonist (stock 0.04 mg/ml) for f.v. 40 ml with assay buffer. Prepare compounds from powder stocks into DMSO to either 200 or 60 mM stock solutions. Make eight-point half-log serial dilutions in glass vials or microtubes. Add 0.01 ml of each compound dilution to the 5 ml polypropylene tubes where 0.490 ml assay buffer and 0.50 ml "IP" cocktail is added for f.v. 1.0 ml. (The compounds' assay f.c. 100–0.1 uM.) Prepare LPS solution such that 0.08 ml LPS (stock 1 mg/ml) is added to 40 ml assay buffer for f.c. 2 ug/ml. 6. Prepare a 2% DMSO solution by adding 200 ul DMSO to 9.8 ml assay buffer. Add 10 ml of IP cocktail to the 2% DMSO solution. This cocktail is used for control wells such that Indomethacin assay f.c. is 1 uM and beta agonist f.c. is 10 ng/ml. The following are performed under the tissue culture hood. Add 0.0125 ml of diluted compound to appropriate well in U-bottom sterile Costar 96-well plate #3790. Add 0.0125 ml LPS to all wells (f.c. 0.1 ug/ml) except negative control wells. Fresh human whole blood is drawn (~22 ml per 96-well plate) usually four green tops per donor into sterile heparin tubes kept at 37° C. Add 0.225 ml of whole blood to the plates. Cover, incubate at 37° C., and rock for four hours. Centrifuge the plates at 2000 rpm for 10 minutes. Prepare ELISA standards. Remove 100 ul serum into flat bottom plate. Dilute 1:20 by removing 15 ul and adding 285 ul RD6 diluent. Freeze @-20° C. For analysis, thaw and add 200 ul to R & D Systems TNFα ELISA. Process the plates according to R & D Systems protocol. Read plate at 450 nm using SoftMax Pro. Analyze and interpret with Java Fitter in order to determine IC50 values. A dose response curve of data expressed as percent control is plotted. A minimum of six triplicate points are generated for each compound. The IC50 values are calculated using the Java Fitter curve-fitting program under the "IC50 fix both" parameter.

In the above test model, combinations of therapeutic agents of the present invention produce concentration-related inhibition of TNFα production at concentrations in the range of from 0.001 to 1.0 μM.

8.4 Allergic and Other Types of Rhinitis; Sinusitis

Allergic rhinitis is characterized by nasal obstruction, itching, watery rhinorrhea, sneezing and occasional anosmia. Allergic rhinitis is divided into two disease categories, seasonal and perennial, in which the former is attributed to pollen or outdoor mould spores, while the latter is attributed to common allergens such as house dust mites, animal danders, and mould spores. Allergic rhinitis generally exhibits an early phase response and a late phase response. The early phase response is associated with mast cell degranulation, while the late phase response is characterized by infiltration of eosinophils, basophils, monocytes, and T-lymphocytes. A variety of inflammatory mediators is also released by these cells, all of which may contribute to the inflammation exhibited in the late phase response.

A particularly prevalent form of seasonal allergic rhinitis is hay fever, which is marked by acute conjunctivitis with lacrimation and itching, swelling of the nasal mucosa, nasal catarrh, sudden attacks of sneezing, and often with asthmatic symptoms. The compounds of Formula (1.0.0) are especially useful in the beneficial treatment of hay fever.

Other types of rhinitis for which the compounds of Formula (1.0.0) may be used as therapeutic agents include acute catarrhal rhinitis which is a cold in the head involving acute congestion of the mucous membrane of the nose, marked by dryness and followed by increased mucous secretion from the membrane, impeded respiration through the nose, and some pain; atrophic rhinitis which is a chronic form marked by wasting of the mucous membrane and the glands; purulent rhinitis which is chronic rhinitis with the formation of pus; and vasomotor rhinitis which is a nonallergic rhinitis in which transient changes in vascular tone and permeability with the same symptoms as allergic rhinitis, are brought on by such stimuli as mild chilling, fatigue, anger, and anxiety.

There is a recognized link between allergic rhinitis and asthma. Allergic rhinitis is a frequent accompaniment to asthma, and it has been demonstrated that treating allergic rhinitis will improve asthma. Epidemiologic data has also been used to show a link between severe rhinitis and more severe asthma. For example, the compound D-22888, under preclinical development for the treatment of allergic rhinitis, has been shown to exhibit a strong anti-allergic affect and to inhibit rhinorrhea in the antigen-challenged pig. See, Marx et 30 al "D-22888—a new PDE4 inhibitor for the treatment of allergic rhinitis and other allergic disorders," *J. Allergy Clin. Immunol.* 99 S444, 1997. Another experimental compound, AWD-12,281 has been shown to be active in a rat model of allergic rhinitis. See Poppe et al "Effect of AWD 12–281, a new selective PDE-4 inhibitor, loteprednol and beclomethasone in models of allergic rhinitis and airway inflammation in brown norway-rats," *Am. J. Respir. Crit. Care Med.* A95, 1999. The compounds D-22888 and AWD-12,281 have already been described further above and represented by Formulas (0.0.28) and (0.0.34), respectively:

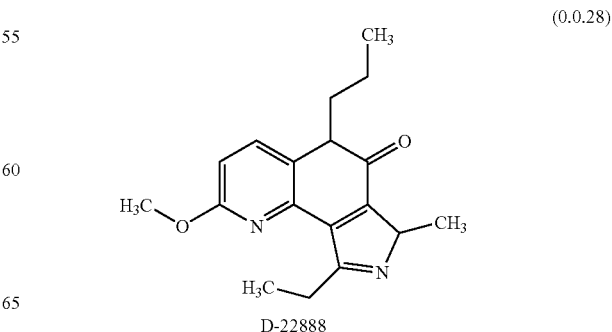

(0.0.28)

D-22888

-continued (0.0.34)

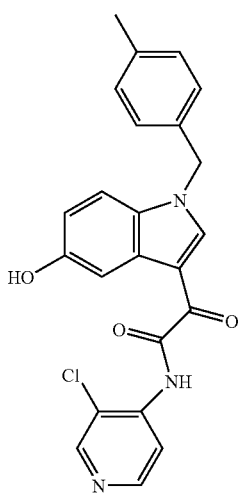

Loteprednol (AWD-12,281)

Sinusitis is related to rhinitis in terms of anatomical proximity as well as a shared etiology and pathogenesis in some cases. Sinusitis is the inflammation of a sinus and this condition may be purulent or nonpurulent, as well as acute or chronic. Depending upon the sinus where the inflammation is located, the condition is known as ethmoid, frontal, maxillary, or sphenoid sinusitis. The ethmoidal sinus is one type of paranasal sinus, located in the ethmoid bone. The frontal sinus is one of the paired paranasal sinuses located in the frontal bone. The maxillary sinus is one of the paired paranasal sinuses located in the body of the maxilla. Accordingly, the compounds of Formula (1.0.0) are useful in the beneficial treatment of acute or chronic sinusitis, but especially of chronic sinusitis.

8.5 Rheumatoid Arthritis, Osteoarthritis, Pain, Fever, and Gout

Arthritis is defined as inflammation of the joints, and rheumatoid arthritis is a chronic systemic disease primarily of the joints, usually polyarticular, marked by inflammatory changes in the synovial membranes and articular structures, and by muscular atrophy and rarefaction of the bones. Late stages of rheumatoid arthritis are marked by ankylosis and deformity. Rheumatoid arthritis is a crippling autoimmune disease of unknown etiology which affects over 1% of the population.

As used herein, the term "rheumatoid arthritis" is intended to include within its scope where applicable related and associated forms of arthritis well known in the art, since these may also be treated with the compounds of Formula (1.0.0). Accordingly, the term "rheumatoid arthritis" includes acute arthritis, which is arthritis marked by pain, heat, redness, and swelling due to inflammation, infection, or trauma; acute gouty arthritis, which is acute arthritis associated with gout; chronic inflammatory arthritis, which is inflammation of the joints in chronic disorders such as rheumatoid arthritis; degenerative arthritis, which is osteoarthritis; infectious arthritis, which is arthritis caused by bacteria, rickettsiae, mycoplasmas, viruses, fungi, or parasites; Lyme arthritis, which is arthritis of the large joints associated with Lyme 20 disease; proliferative arthritis, which is inflammation of the joints with proliferation of the synovium, seen in rheumatoid arthritis; psoriatic arthritis, which is a syndrome in which psoriasis occurs in association with inflammatory arthritis; and vertebral arthritis, which is inflammation involving the intervertebral disks.

The three major pathological features of rheumatoid arthritis that are responsible for progressive joint destruction are inflammation, abnormal cellular and humoral responses, and synovial hyperplasia. The particular cellular pathology of rheumatoid arthritis includes the presence of T-cells and monocytes. The T-cells, which are predominantly memory T-cells, constitute up to 50% of the cells recovered from the synovial tissue of rheumatoid arthritis patients; and of the monocytes found in the same tissue, 30–50% are antigen presenting cells, which is indicative of the autoimmune character of the disease. Pro-inflammatory cytokines, e.g., IL-1, IL-4, IL-5, IL-6, IL-9, IL-13, and TNF-α, are the major contributors to joint tissue damage, inflammation, hyperplasia, pannus formation and bone resorption. See Firestein, G. S. and Zvaifier, W. J., "How important are T-cells in chronic rheumatoid synovitis?" Arth. Rheum. 33 768–773, 1990. This has been demonstrated, e.g., by the fact that monoclonal antibodies (Mabs) to TNF-α have shown promise in $R^A$ clinical trials; Maini el al, "Beneficial effects of tumor necrosis factor-alpha (TNF-α blockade in rheumatoid arthritis (RA)," Clin. Exp. Immunol. 101 207–212, 1995.

The PDE4 inhibitors of Formula (1.0.0) are useful in the treatment of rheumatoid arthritis as a result of their ability to suppress the activity of a variety of inflammatory cells, including basophils, eosinophils, and mast cells. These inhibitory activities of the compounds of Formula (1.0.0) have already been described further above, as has their wide range of in vitro anti-inflammatory action via the release of reactive oxygen species, prostaglandins, and inflammatory cytokines, e.g., IL-5, IFN-γ, and TNF-α. See further Cohan et al, "In vitro pharmacology of the novel phosphodiesterase Type IV inhibitor, CP-80,633," J. Pharm. Exp. Ther. 278 1356–1361, 1996; and Barnette et al., "SB207499 (Ariflo), a potent and selective second generation phosphodiesterase 4 inhibitor: in vitro anti-inflammatory actions," J. Pharm. Exp. Ther. 284 420–426, 1998. The PDE4 inhibitors of Formula (1.0.0) are also useful in the treatment of rheumatoid arthritis as a result of their effectiveness in inhibiting T-cell proliferation mediated via a number of different agents, including antigens such as house dust mite, which has been demonstrated in the art; Barnette et al, Ibid. The ability of the compounds of Formula (1.0.0) to facilitate the release of cytokine IL-10 from monocytes, which in turn is capable of decreasing the generation of TNF-α, IL-1, IL-4, IL-5, IL-6, IL-9, IL-13, and GM-CSF by synovial fluid mononuclear cells, further augments the overall anti-inflammatory profile of the PDE4 inhibitors of Formula (1.0.0); Kambayashi et al, Ibid. Further, the ability of the compounds of Formula (1.0.0) to inhibit TNF-α release from stimulated monocytes can be correlated with animal models of inflammation in which anti-inflammatory effects can be shown to correspond to suppression of TNF-α accumulation. One such animal model involves inhibition of LPS induced TNF-α release in mice by oral administration of a PDE4 inhibitor; Cheng et al, "The phosphodiesterase Type 4 (PDE4) inhibitor CP-80,633 elevates cyclic AMP levels and decreases TNF-α production in mice: effect of adrenalectomy," J. Pharm. Exp. Ther. 280 621–626, 1997. Another such animal model involves the inhibition of rat paw edema, induced by carageenan, by oral administration of rolipram; Singh et al, "Synovial fluid levels of tumor necrosis factor a in the inflamed rat knee: Modulation by dexamethasone and inhibitors of matrix metalloproteinases and phosphodiesterases," Inflamm. Res. 46(Suppl. 2) S153–S154, 1997.

Gout refers to a group of disorders of purine metabolism, and fully developed gout is manifested by various combinations of hyperuricemia, recurrent, characteristic acute inflammatory arthritis induced by crystals of monosodium urate monohydrate, tophaceous deposits of said crystals in and around the joints of the extremities, which may lead to joint destruction and severe crippling, and uric acid urolithiasis. Rheumatic gout is another name for rheumatoid arthritis. Tophaceous gout is gout in which there are tophi or chalky deposits of sodium urate. Some therapeutic agents are useful in treating both gout and its attendant inflammation, e.g., phenylbutazone and colchicine; while other therapeutic agents possess only uricosuric properties, e.g., sulfinpyrazone and benzbromarone Fever, or pyrexia, may be the result of any one of a large number of different factors, but with regard to the present invention such fever is either that manifested in pharyngoconjunctival fever or rheumatic fever, or that manifested during inflammation. A concomitant of inflammation is pain, especially that experienced in the joints and connective tissue of those suffering from rheumatoid arthritis and gout.

Accordingly, the PDE4 inhibitory compounds of Formula (1.0.0) provide beneficial results in the treatment of gout, and fever and pain associated with inflammation.

Animal models of rheumatoid arthritis have also been used in the art for the purpose of demonstrating the correlation between in vivo modulation of TNF-α by PDE4 inhibitors and their utility in the treatment of rheumatoid arthritis. The activity of rolipram in animal models of acute inflammation such as the mouse adjuvant arthritis model, has been demonstrated in the art; Sekut et al, "Anti-inflammatory activity of phosphodiesterase (PDE) IV inhibitors in acute and chronic models of inflammation," Olin. Exp. Immunol. 100(1) 126–132, 1995. The ability of rolipram to reduce disease severity in the collagen 11 induced arthritis (CIA) model after sc. or ip. injection has been demonstrated in the art; Nyman et al., "Amelioration of collagen 11 induced arthritis in rats by Type IV phosphodiesterase inhibitor rolipram," Olin. Exp. Immunol. 108 415–419, 1997. In this study the dosing regimen for rolipram was 2 mg/kg twice daily for five days before the onset of arthritis, and it significantly delayed the appearance of arthritic symptoms. After the cessation of treatment the test animals developed arthritis and reached the same arthritis top score as the control group. In the same study rolipram was also administered at 3 mg/kg twice daily at the time point when arthritis was apparent. This treatment drastically changed the development of the disease whereby progression of severity was halted and even after the cessation of treatment, the arthritis score did not reach the levels observed in untreated animals. The investigators were also able to demonstrate a strong down-regulation of TNF-α and IFN-γ mRNA expression in regional lymph nodes, which suggests that the major effect of rolipram is exerted in the effector phase of the inflammatory process. Nyman et al, Ibid.

Inhibition of TNF-α Production by Human Monocytes In Vitro—The inhibitory effect of the compounds of Formula (1.0.0) on in vitro TNF-α production by human monocytes may be determined in accordance with the protocol described in EP 411 754 (Badger et al) and WO 90/15534 (Hanna). The referenced publications also describe two models of endotoxic shock which may be used to determine in vivo inhibitory activity of the compounds of Formula (1.0.0). The protocols used in these models are detailed and test compounds demonstrate a positive result by reducing serum levels of TNF-α induced by the injection of endotoxin.

Selective PDE4 inhibitors such as RP73401 have been shown to exhibit significant amelioration of disease, especially improvements in joint destruction, synovitis, and fibrosis, in animal models such as those involving streptococcal cell wall (SCW)-induced arthritis; Souness et al, "Potential of phosphodiesterase Type IV inhibitors in the treatment of rheumatoid arthritis," Drugs 1 541–553, 1998.

Of particular interest to the treatment of rheumatoid arthritis is the observation that PDE4 inhibitors have positive effects at the site of action of the disease. For example, RP73401 has been demonstrated to decrease TNF-α mRNA expression at the pannus/cartilage interface of paw joints of collagen 11 treated mice. Souness et al, Ibid. RP73401 has also been studied clinically in rheumatoid arthritis patients in a placebo-controlled, double-blind Phase II study of 35 rheumatoid arthritis patients administered 400 pg of the compound t.i.d. The compound was able to induce a positive trend towards clinical improvement associated with a reduction in C-reactive protein and IL-6 serum levels. Chikanza et al, "The clinical effects of RP73401 phosphodiesterase Type 4 inhibitor in patients with rheumatoid arthritis," Br. J. RheumatoL 36:Abstr. Suppl. I, 186, 1997.

Assaying Increased cAMP Accumulation in Intact Tissues Using U-937 Cells—Another assay suitable for demonstrating the PDE4 inhibiting activity of the compounds of Formula (1.0.0) is one which utilizes U-937 cells from a human monocyte cell line that has been shown to contain a large amount of PDE4. In order to assess the inhibition of PDE4 activity in intact cells, non-differentiated U-937 cells at a density of approximately $10^5$ cells per reaction tube are incubated with concentrations ranging from 0.01 to 1000 pM of test compound for one minute, and with 1 μM of prostaglandin E2 for an additional four minutes. Five minutes after initiating the reaction, cells are lysed by the addition of 17.5% perchloric acid, after which the pH is brought to neutral by the addition of 1 M potassium carbonate. The cAMP content of the reaction tube is measured using RIA techniques. A detailed protocol for carrying out this assay is described in Brooker et al., "Radioimmunoassay of cyclic AMP and cyclic GMP," Adv. Cyclic Nucleotide Res. 10 1–33, 1979.

8.6 Eosinophil-Related Disorders

The ability of the PDE4 inhibitory compounds of Formula (1.0.0) to inhibit eosinophil activation as part of their overall anti-inflammatory activity has been described above. Accordingly, the compounds of Formula (1.0.0) are useful in the therapeutic treatment of eosinophil-related disorders. Such disorders include eosinophilia, which is the formation and accumulation of an abnormally large number of eosinophils in the blood. The name of the disorder derives from "eosin", a rose-colored stain or dye comprising a bromine derivative of fluorescein which readily stains "eosinophilic leukocytes" in the blood of patients who are thus readily identified. A particular eosinophilic disorder that can be treated in accordance with the present invention is pulmonary infiltration eosinophilia, which is characterized by the infiltration of the pulmonary parenchyma by eosinophils. This disorder includes especially Loffler's syndrome, which is a condition characterized by transient infiltrations of the lungs, accompanied by cough, fever, dyspnea, and eosinophilia.

Other eosinophilic disorders include chronic eosinophilic pneumonia, which is a chronic interstitial lung disease characterized by cough, dyspnea, malaise, fever, night sweats, weight loss, eosinophilia, and a chest film revealing non-segmental, non-migratory infiltrates in the lung periphery; tropical pulmonary eosinophilia, which is a subacute or chronic form of occult filariasis, usually involving *Brugia malayi, Wuchereria bancrofti*, or filariae that infect animals, occurs in the tropics, and is characterized by episodic nocturnal wheezing and coughing, strikingly elevated eosinophilia, and diffuse reticulonodular infiltrations of the lungs; bronchopneumonic aspergillosis, which is an infection of the bronchi and lungs by *Aspergillus* funga resulting in a diseased condition marked by inflammatory granulomatous lesions in the nasal sinuses and lungs, but also in the skin, ear, orbit, and sometimes in the bones and meninges, and leading to aspergilloma, the most common type of fungus ball formed by colonization of *Aspergillus* in a bronchus or lung cavity.

The term "granulomatous" means containing granulomas, and the term "granuloma" refers to any small nodular delimited aggregation of mononuclear inflammatory cells or such a collection of modified macrophages resembling epithelial cells, usually surrounded by a rim of lymphocytes, with fibrosis commonly seen around the lesion. Some granulomas contain eosinophils. Granuloma formation represents a chronic inflammatory response initiated by various infectious and noninfectious agents. A number of such granulomatous conditions are treatable using a compound of Formula (1.0.0), e.g., allergic granulomatous angiitis, also called Churg-Strauss syndrome, which is a form of systemic necrotizing vasculitis in which there is prominent lung involvement, generally manifested by eosinophilia, granulomatous reactions, and usually severe asthma. A related disorder is polyarteritis nodosa (PAN), which is marked by multiple inflammatory and destructive arterial lesions and is a form of systemic necrotizing vasculitis involving the small and medium-sized arteries with signs and symptoms resulting from infarction and scarring of the affected organ system, in particular the lungs. Other eosinophil-related disorders which may be treated in accordance with the present invention are those affecting the airways which are induced or occasioned by a reaction to a therapeutic agent unrelated to any compound of Formula (1.0.0).

8.7 Atopic Dermatitis, Urticaria, Conjunctivitis, and Uveitis

Atopic dermatitis is a chronic inflammatory skin disorder seen in individuals with a hereditary predisposition to a lowered cutaneous threshold to pruritis, that is often accompanied by allergic rhinitis, hay fever, and asthma, and that is principally characterized by extreme itching. Atopic dermatitis is also called allergic dermatitis, and allergic or atopic eczema.

Atopic dermatitis (AD) is the most common chronic inflammatory skin disease in young children, and it affects from 10% to 15% of the population during childhood. Atopic dermatitis is frequently associated with asthma and allergies and it has therefore become known as a component of the so-called "atopic triad", since it occurs frequently in individuals with asthma and/or allergic rhinitis. See Leung Dym, *Atopic Dermatitis: From Pathogenesis To Treatment*, R.G. Landes Co., Austin, Tex., 1–226, 1996. Accordingly, the immune dysfunction associated with atopic dermatitis is treatable with therapeutic agents that are inhibitors of PDE4. For example, rolipram, Ro-201724, and denbufylline have been reported to produce a concentration-related inhibition of the proliferation of human peripheral blood mononuclear cells (HPBM) from normal patients as well as from subjects with atopic dermatitis. See, respectively, Torphy et al., *Drugs and the Lung*, Eds. Page and Metzger, Raven Press, New York, 1994; and O'Brien, *Mol. Medicine Today*, 369, 1997. These studies also determined that the proliferative response of HPBM from atopic dermatitis patients was more sensitive to PDE4 inhibition than was the proliferation observed in HPBM from normal subjects.

Th2 type cytokine secreting T-cells expressing the cutaneous lymphocyte associated antigen play a central role in the induction of local IgE responses and the recruitment of eosinophils in this disease. The chronic inflammation seen in atopic dermatitis is considered to be the result of several interdependent factors, such as repeated or persistent allergen exposure, which can lead to Th2 cell expansion. It has been demonstrated that there is an increased frequency of allergen specific T-cells producing increased IL-4, IL-5, and IL-3 levels in the blood of atopic dermatitis patients. See Leung Dym et al., "Allergic and immunological skin disorders," *JAMA* 278(22) 1914–1923, 1997. This is significant because IL-4 and IL-3 induce the expression of vascular adhesion molecule-1 (VCAM-1), an adhesion molecule involved in the migration of mononuclear cells and eosinophils into sites of tissue inflammation. Further, IL-5 is a key mediator of eosinophil activation, which is a common feature of atopic disease.

Increased concentration of cAMP in lymphocytes and basophils has long been known to be associated with decreased mediator release from those cells, and more recently it has been reported that histamine acting on H2 receptors increases cAMP levels and inhibits IL-4 production in murine Th2 cells. It is surmised, accordingly, that there is present in atopic diseases such as atopic dermatitis, impaired β-adrenergic responses or enhanced PDE4 activity of leukocyte inflammatory responses. A diminished cAMP response may result from an enhanced PDE4 activity that has a genetic basis or that is an acquired condition.

Studies have been carried out which compare different cell types from atopic patients with those from healthy volunteers, and the results have shown that increased cAMP-PDE activity in atopic cells correlates with abnormal inflammatory and immune cell function in atopic dermatitis. Further, the PDE4 enzyme from atopic leukocytes is more sensitive to PDE4 inhibitors than the PDE4 enzyme from normal leukocytes, and up to a 14-fold difference has been demonstrated. See Chan and Hanifin, "Differential inhibitory effects of cAMP phosphodiesterase isoforms in atopic and normal leukocytes," *J. Lab. Clin. Med.*, 121(1) 44–51, 1993. An increased sensitivity can also be seen in the inhibition of proliferation of peripheral blood mononuclear cells from atopic donors on treatment with PDE4 inhibitors. For example, rolipram has been found to be more effective at inhibiting PHA stimulated atopic dermatitis PBMC proliferation than at inhibiting PHA stimulated normal PBMC proliferation, with an $IC_{50}=280$ nM compared to an $IC_{50}=2600$ nM, respectively.

Further, it has been shown that a structurally diverse range of selective PDE4 inhibitors are effective in reducing skin eosinophilia in the guinea pig which has been mediated via a range of agents such as PAF, arachidonic acid, zymosan activated plasma, and protein of cutaneous anaphylaxis. See Beasley et al., "Synthesis and evaluation of a novel series of phosphodiesterase 4 inhibitors. A potential treatment for asthma," *Bioorg. Med. Chem. Letts.* 8 2629–2634, 1998. Such data shows the utility of PDE4 inhibitors in treating eosinophil driven skin diseases. Such treatment is by means of topical administration, e.g., topical atizoram applied bilaterally over eight days to twenty patients in a clinical trial has been found to effectively inhibit all of the inflammatory parameters tested, showing both qualitative and quantitative improvements with no adverse effects. See Hanifin et al., "Type 4 phosphodiesterase inhibitors have clinical and in vitro anti-inflammatory effects in atopic dermatitis," *J. Invest. Dermatol.* 107 51–56, 1996.

Accordingly, the PDE4 inhibitors of Formula (1.0.0) are useful for the beneficial treatment of atopic dermatitis as described above. A related area of therapeutic application for which the compounds of Formula (1.0.0) also produce beneficial results is in the treatment of urticaria. Urticaria is a vascular reaction, usually transient, involving the upper dermis, representing localized edema caused by dilatation and increased permeability of the capillaries, and marked by the development of wheals or hives. Many different stimuli are capable of inducing an urticarial reaction, and it may be classified according to precipitating causes, as: immune-mediated, complement-mediated which may involve immunologic or nonimmunologic mechanisms, urticariogenic material-induced, physical agent-induced, stress-induced, or idiopathic. The condition may also be designated acute or chronic depending on the duration of an attack. Angioedema is the same response in the deep dermis or subcutaneous or submucosal tissues.

The most common types of urticaria which are treatable with the compounds of Formula (1.0.0) are cholinergic urticaria which is characterized by the presence of distinctive punctate wheals surrounded by areas of erythema, thought to be a nonimmunologic hypersensitivity reaction in which acetylcholine released from parasympathetic or motor nerve terminals induces release of mediators from mast cells, and evoked by conditions of exertion, stress, or increased environmental heat; cold urticaria which is urticaria precipitated by cold air, water, or objects, occurring in two forms: In the autosomal dominant form which is associated with fevers, arthralgias, and leukocytosis, the lesions present are erythematous, burning papules and macules, and in the more common acquired form which is usually idiopathic and self-limited; contact urticaria which is a localized or generalized transient wheal-and-flare response elicited by exposure to rapidly absorbable urticariogenic agents; giant urticaria which is angioedema; and papular urticaria which is a persistent cutaneous eruption representing a hypersensitivity reaction to insect bites.

Accordingly, the PDE4 inhibitors of Formula (1.0.0) are useful for the beneficial treatment of the various types of urticaria as described above. A related area of therapeutic application for which the compounds of Formula (1.0.0) also produce beneficial results is in various ophthalmic uses, in particular in the treatment of conjunctivitis and uveitis.

The conjunctiva is a delicate membrane that lines the eyelids and covers the exposed surface of the sclera. Conjunctivitis is an inflammation of the conjunctiva that generally consists of conjunctival hyperemia associated with a discharge. The most common types of conjunctivitis, which are treatable with the compounds of Formula (1.0.0), are actinic conjunctivitis produced by ultraviolet light; acute catarrhal conjunctivitis which is an acute, infectious conjunctivitis associated with cold or catarrh and characterized by vivid hyperemia, edema, loss of translucence, and mucous or mucopurulent discharge; acute contagious conjunctivitis which is a mucopurulent, epidemic conjunctivitis caused by *Haemophilus aegyptius* that has the same symptoms as acute catarrhal conjunctivitis and is also called "pinkeye"; allergic conjunctivitis which is a component of hay fever; atopic conjunctivitis which is allergic conjunctivitis of the immediate type caused by airborne allergens, e.g., pollens, dusts, spores, and animal dander; chronic catarrhal conjunctivitis which is a mild, chronic conjunctivitis with only slight hyperemia and mucous discharge; purulent conjunctivitis which is an acute conjunctivitis caused by bacteria or viruses, particularly gonococci, meningococci, pneumococci, and streptococci, and characterized by severe inflammation of the conjunctiva and copious discharge of pus; and vernal conjunctivitis which is a bilateral conjunctivitis of seasonal occurrence, of unknown cause, affecting children especially boys and characterized by flattened papules and a thick, gelatinous exudate. Accordingly, the PDE4 inhibitors of Formula (1.0.0) are useful for the beneficial treatment of the various types of conjunctivitis as described above. A related area of therapeutic application for which the compounds of Formula (1.0.0) also produce beneficial results is in the treatment of uveitis.

The uvea is the vascular middle coat or tunic of the eye, comprising the iris, ciliary body, and choroid. Uveitis is an inflammation of all or part of the uvea and commonly involves the other tunics of the eye, i.e., the sclera and the cornea, and the retina as well. The most common types of uveitis, which are treatable with the compounds of Formula (1.0.0), are anterior uveitis which is uveitis involving the structures of the iris and/or ciliary body, including iritis, cyclitis, and iridocyclitis; granulomatous uveitis which is uveitis of any part of the uveal tract but particularly of the posterior portion, characterized by nodular collections of epithelioid cells and giant cells surrounded by lymphocytes; nongranulomatous uveitis which is inflammation of the anterior portion of the uveal tract, i.e., the iris and ciliary body; phacoantigenic uveitis which is one of the lens-induced uveitides is a severe anterior uveitis similar to sympathetic ophthalmia, observed weeks or even months after extracapsular lens surgery or other trauma to the capsule; and posterior uveitis which is uveitis involving the posterior segment of the eye, including choroiditis and chorioretinitis. Accordingly, the PDE4 inhibitors of Formula (1.0.0) are useful for the beneficial treatment of the various types of unveitis as described above.

8.8 Psoriasis

Psoriasis is a common chronic, squamous dermatosis with polygenic inheritance and a fluctuating course that is characterized by microabscesses and spongiform pustules, as well as erythematous, dry, scaling patches of various sizes. Psoriasis is a common skin disease that affects approximately 2% of the population, and more than 1½ million patients in the US annually consult physicians for treatment. Psoriasis is usually recurrent and in some instances can be very debilitating. The etiology of psoriasis is unknown, but it appears to be an autoimmune disease with genetic predisposition.

Psoriasis involves a large T-cell infiltration in the affected regions of the skin, with CD4+ lymphocytes in the dermis and CD8+ lymphocytes in the epidermis. These lymphocytes secrete IL-2, IFN-γ, and TNF-α, which alter keratinocyte proliferation and differentiation. Further, from 5% to 10% of psoriasis patients develop psoriatic arthritis, the symptoms of which are very similar to those of rheumatoid arthritis. The broad spectrum of anti-inflammatory activities displayed by PDE4 inhibitors, already discussed above, enables such inhibitors to be used beneficially in the treatment of psoriasis.

It has been demonstrated that treatment of epidermal basal cells, in primary culture, with the PDE4 inhibitor Ro 20-1724 leads to a three-fold increase in cAMP concentrations. It has also been shown that treatment of psoriatic epidermal slices and keratomed psoriatic epidermal slices with Ro 20-1724 results in a very marked elevation of cAMP concentrations over controls. Specifically, a 1395% increase in cAMP concentration in keratomed psoriatic epidermis has been observed. PDE4 inhibitors have also been shown to inhibit the inflammatory response of a number of mediators via either topical or systemic administration. For example, rolipram has been shown to inhibit *croton* oil-induced ear inflammation in the mouse at topical doses as low as 0.03 mg per ear. The selective PDE4 inhibitor Ro 20-1724 has also been investigated in two double-blind studies comparing its effectiveness to vehicle, where it has been shown to improve psoriatic lesions without adverse systemic or cutaneous effects.

8.9 Multiple Sclerosis and Other Inflammatory Autoimmune Diseases

A sclerosis is an induration, or hardening, and refers especially to hardening of a part from inflammation, and from increased formation of connective tissue and in diseases of the interstitial substance. The term "sclerosis" is used chiefly for such a hardening of the nervous system due to the deposition of connective tissue, or to designate hardening of the blood vessels. Multiple sclerosis (MS) is a disease in which there are foci of demyelination of various sizes throughout the white matter of the central nervous system, sometimes extending into the gray matter, resulting in weakness, incoordination, paresthesias, speech disturbances, and visual complaints. Multiple sclerosis is a disease of unknown etiology with a prolonged course involving many remissions and relapses.

Multiple sclerosis is an autoimmune disease that in addition to chronic inflammation and demyelination, also results in gliosis within the central nervous system. There are several disease subtypes, including primary progressive multiple sclerosis, and relapsing remitting multiple sclerosis. These disease subtypes may be distinguished from each other on the basis of the course of the disease, of the type of inflammation involved, and through the use of magnetic resonance imaging (MRI). It is also possible for the basic disease mechanism to change during the course of multiple sclerosis, with an inflammation-based process being replaced later by one which involves demyelination and axonal damage. See Weilbach and Gold, "Disease modifying treatments for multiple sclerosis. What is on the horizon?" *CNS Drugs* 11 133–157, 1999.

In multiple sclerosis inflammatory lesions are localized to, but prevalent throughout the white matter of the central nervous system, although sclerotic plaques characterized by demyelination are a hallmark of the disease. The development of demyelination, in turn, is caused by the necrosis of oligodendrocytes, and demyelination is associated with an infiltrate composed mainly of T-cells and macrophages, which together with local cells such as astrocytes, microglia and microvascular brain endothelial cells, express major histocompatibility complex (MHC) class II. These cells are thus implicated in antigen presentation and an inflammatory response, and a number of pro-inflammatory cytokines, including TNF-α, TNF-β, IL-1, IL-6 and IFN-γ have been identified in the brain tissue of multiple sclerosis patients and their presence is generally associated with active lesions. TNF-α in particular has been the focus of attention because it mediates myelin and oligodendrocyte damage in vitro, induces astrocytes to express surface adhesion molecules, and is associated with disruption of the blood-brain barrier.

Animal models have been used to demonstrate the role of TNF-α in multiple sclerosis, e.g., in experimental allergic encephalomyelitis (EAE) administration of anti-TNF antibodies or soluble TNF receptors has been shown to provide a protective effect. See Selmaj et al., "Prevention of chronic relapsing experimental autoimmune encephalomyelitis by soluble tumor necrosis factor," *J. Neuroimmunol.* 56 135–141, 1995. A direct correlation between the level of TNF-α mRNA and progression of EAE has also been reported. See Reeno et al., "TNF-alpha expression by resident microglia and infiltrating leukocytes in the central nervous system of mice with experimental allergic encephalomyelitis: regulation by the Th1 cytokines," *J. Immunol.* 154 944–953, 1995. Further evidence demonstrating that TNF-α is a mediator of multiple sclerosis is the increased concentration of TNF-α in the cerebrospinal fluid of multiple sclerosis patients during the course of the disease. Further, a transgenic mouse overexpressing TNF-α in the central nervous system has shown signs of spontaneous demyelination, while a transgenic TNF-α knockout mouse has shown a protective effect. See Probert et al., "Spontaneous inflammatory demyelinating disease in transgenic mice showing central nervous system-specific expression of tumor necrosis factor alpha," *Proc. Natl. Acad. Sci. USA* 92 11294–11298, 1995; and Liu et al., "TNF is a potent anti-inflammatory cytokine in autoimmune-mediated demyelination," *Nature Med.* 4 78–83, 1998.

Since PDE4 inhibitors also reduce TNF-α, they are beneficial in the treatment of multiple sclerosis because TNF-α plays a key role in mediating multiple sclerosis, as discussed above. For example, in a marmoset model of experimental allergic encephalomyelitis rolipram has been found to suppress the appearance of clinical signs and abolish abnormalities in MRI imaging. In another study of the effects of rolipram on chronic relapsing experimental allergic encephalomyelitis in SJL mice, it has been shown that rolipram ameliorates clinical signs and pathological changes in this model. See Genain et al., "Prevention of autoimmune demyelination in non-human primates by a cAMP-specific phosphodiesterase," *Proc. Natl. Acad. Sci. USA.* 92 3601–3605, 1995; and Sommer et al., "Therapeutic potential of phosphodiesterase Type 4 inhibition in chronic autoimmune demyelinating disease," *J. Neuroimmunol.* 79 54–61, 1997.

In addition to inhibiting PDE4 activity and the production of TNF-α, the compounds of Formula (1.0.0) also possess activity as immunosuppressive agents and are especially useful for treating autoimmune diseases in which inflammation is a component part of the autoimmune disease, or in which inflammation is part of the etiology of the autoimmune disease, or in which inflammation is otherwise involved with the autoimmune disease. Alternatively, the compounds of Formula (1.0.0) are anti-inflammatory agents useful in the treatment of inflammatory diseases in which autoimmune reactions are a component part of the inflammatory disease, or in which autoimmune reactions are part of the etiology of the inflammatory disease, or in which autoimmune reactions are otherwise involved with the inflammatory disease. Accordingly, the compounds of Formula (1.0.0) are useful in the treatment of multiple sclerosis, as discussed in detail further above.

Other autoimmune/inflammatory diseases that can be treated by therapeutic agents comprising the compounds of Formula (1.0.0) include, but are not limited to, autoimmune hematological disorders such as hemolytic anemia, aplastic anemia, pure red cell anemia, and idiopathic thrombocytopenic purpura; systemic lupus erythematosus; polychondritis; scleroderma; Wegner's granulomatosis; dermatomyositis; chronic active hepatitis; myasthenia gravis; Stevens-Johnson syndrome; idiopathic sprue; autoimmune inflammatory bowel diseases such as ulcerative colitis and Crohn's disease; endocrin opthamopathy; Grave's disease;

sarcoidosis; alveolitis; chronic hypersensitivity pneumonitis; primary biliary cirrhosis; juvenile diabetes (diabetes mellitus type I); anterior uveitis and granulomatous (posterior) uveitis; keratoconjunctivitis sicca and epidemic keratoconjunctivitis; diffuse interstitial pulmonary fibrosis (interstitial lung fibrosis); idiopathic pulmonary fibrosis; cystic fibrosis; psoriatic arthritis; glomerulonephritis with and without nephrotic syndrome, including acute glomerulonephritis, idiopathic nephrotic syndrome, and minimal change nephropathy; inflammatory/hyperproliferative skin diseases including psoriasis and atopic dermatitis discussed in detail further above, contact dermatitis, allergic contact dermatitis, benign familial pemphigus, pemphigus erythematosus, pemphigus foliaceus, and pemphigus vulgaris.

Further, the compounds of Formula (1.0.0) may be used as immunosuppressant agents for the prevention of allogeneic graft rejection following organ transplantation, where such organs typically include tissue from bone marrow, bowel, heart, kidney, liver, lung, pancreas, skin and cornea.

8.10 Inflammatory Bowel Disease

Ulcerative colitis (UC) is a chronic, recurrent ulceration in the colon, chiefly of the mucosa and submucosa, which is of unknown cause, and which is manifested clinically by cramping abdominal pain, rectal bleeding, and loose discharges of blood, pus, and mucus with scanty fecal particles. Related diseases of the bowel include collagenous colitis, which is a type of colitis of unknown etiology that is characterized by deposits of collagenous material beneath the epithelium of the colon, and marked by crampy abdominal pain with a conspicuous reduction in fluid and electrolyte absorption that leads to watery diarrhea; colitis polyposa, which is ulcerative colitis associated with the formation of pseudopolyps, i.e., edematous, inflamed islands of mucosa between areas of ulceration; and transmural colitis, which is inflammation of the full thickness of the bowel, rather than mucosal and submucosal disease, usually with the formation of noncaseating granulomas, that clinically resembles ulcerative colitis but in which the ulceration is often longitudinal or deep, the disease is often segmental, stricture formation is common, and fistulas, particularly in the perineum, are a frequent complication.

Crohn's disease (CD) is a chronic granulomatous inflammatory disease of unknown etiology involving any part of the gastrointestinal tract, but commonly involving the terminal ileum with scarring and thickening of the bowel wall, frequently leading to intestinal obstruction, and fistula and abscess formation, and having a high rate of recurrence after treatment. Ulcerative colitis, Crohn's disease and the related diseases discussed above are collectively referred to as inflammatory bowel disease (IBD). These diseases are chronic, spontaneously relapsing disorders of unknown cause that are immunologically mediated and whose pathogenesis has been established through the use of animal models and advanced immunological techniques. See Bickston and Caminelli, "Recent developments in the medical therapy of IBD," *Curr. Opin. Gastroenterol.* 14 6–10, 1998; and Murthy et al., "Inflammatory bowel disease: A new wave of therapy," *Exp. Opin. Ther. Patents* 8(7) 785–818, 1998. While the incidence of ulcerative colitis has remained relatively stable, the incidence of Crohn's disease has increased significantly.

Current therapy for inflammatory bowel disease includes 5-aminosalicylic acid, corticosteroids, and immunomodulators such as azathioprine, 6-mercaptopurine, and methotrexate. These agents have a wide range of adverse side effects and do not modify the disease itself, and there is thus an ongoing need for more effective treatment agents. The compounds of Formula (1.0.0) are able to beneficially treat inflammatory bowel diseases as a result of their ability to inhibit the production of TNF-α, because TNF-α causes immune cell activation, proliferation, and mediator release in inflammatory bowel disease. See Radford-Smith and Jewell, "Cytokines and inflammatory bowel disease." *Baillieres Clin. Gasteroenterol.* 10 151–164, 1996. TNF-α has also been detected in the stools and intestinal mucosa of patients with inflammatory bowel disease. Further, early clinical studies in Crohn's disease using TNF monoclonal antibodies have shown significant promise.

As already detailed further above, selective PDE4 inhibitors have a marked effect on the inhibition of TNF-α release from peripheral blood mononuclear cells after those cells have been stimulated with a wide range of mediators, both in vitro and in vivo. The selective PDE4 inhibitor arofylline has been shown to provide beneficial effects when tested in models of colitis in the rat. Further, in a dextran sulfate induced colitis model in the rat, rolipram and the selective PDE4 inhibitor LAS31025 have demonstrated beneficial effects comparable to prednisolone. Both test compounds have been shown to ameliorate bleeding and inflammatory markers. See Puig et al. "Curative effects of phosphodiesterase 4 inhibitors in dextran sulfate sodium induced colitis in the rat," *Gastroenterology* 114(4) A1064, 1998. Other workers have used additional models to demonstrate the ability of selective PDE4 inhibitors to provide gastrointestinal protection. For example, it has been shown that lipopolysaccharide induced erythrocyte extravasation in rats and intestinal hypoperfusion in dogs can be attenuated with the selective PDE4 inhibitors rolipram and denbufylline. See Cardelus et al., "Inhibiting LPS induced bowel erythrocyte extravasation in rats, and of mesenteric hypoperfusion in dogs, by phosphodiesterase inhibitors," *Eur. J. Pharmacol.* 299 153–159, 1996; and Cardelus et a!., "Protective effects of denbufylline against endotoxin induced bowel hyperplasia," *Met. Find. Exp. Clin. Pharmacol.* 17 (Suppl. A) 142, 1995.

8.11 Septic Shock, Renal Failure, Cachexia, and Infection

Septic shock is shock associated with overwhelming infection, most commonly infection with gram negative-bacteria, although it may be produced by other bacteria, viruses, fungi and protozoa. Septic shock is deemed to result from the action of endotoxins or other products of the infectious agent on the vascular system, causing large volumes of blood to be sequestered in the capillaries and veins. Activation of the complement and kinin systems and the release of histamine, cytokines, prostaglandins, and other mediators is also involved.

It has been shown in a model of endotoxin-induced acute renal failure in rats that the selective PDE4 inhibitor, Ro-201724, given as a post-treatment at 10 µg/kg/min significantly increases urinary cAMP excretion, markedly attenuates endotoxin-induced increases in renal vascular resistance and decreases in renal blood flow and glomerular filtration rate. Ro-201724 has also been shown to improve survival rates for endotoxin-treated rats. See Carcillo et al., *Pharmacol. Exp. Ther.* 279 1197, 1996. Pentoxifylline has also been studied in patients suffering from septic shock. In this study twenty-four individuals fulfilling the criteria for septic shock have been selected, twelve of which have received pentoxifylline at 1 mg/kg/hr over a 24-hour period, while the other twelve have served as a control group. After 24 hours it has been found that the TNF-α levels in the therapy group have been significantly lowered, while the IL-6 levels have been significantly increased.

In another study, it has been shown that pretreatment with pentoxifylline at 5 to 50 mg/kg i.p. 3×, or with the selective PDE4 inhibitors rolipram at 10 to 30 mg/kg i.p. 3×, and debufylline at 0.1 to 3 mg/kg i.p. 3×, reduces lipopolysaccharide-induced bowel erythrocyte extravasation in rats, and that denbufylline is 100-fold more potent than pentoxifylline in inhibiting lipopolysaccharide-induced mesenteric blood flow fall, without affecting renal blood flow or cardiac index. See Cardelus et al., Ibid., *Eur. J. Pharmacol.*

Renal failure is the inability of the kidney to excrete metabolites at normal plasma levels under conditions of normal loading, or the inability to retain electrolytes under conditions of normal intake. In the acute form, it is marked by uremia and usually by oliguria or anuria, with hyperkalemia and pulmonary edema. On the basis of the above-described activities of selective PDE4 inhibitors, it has been demonstrated that selective PDE4 inhibitors are useful in the treatment of renal failure, especially acute renal failure. See Begany et al., "Inhibition of Type IV phosphodiesterase by Ro-20-1724 attenuates endotoxin-induced acute renal failure," *J. Pharmacol Exp. Thera.* 278 37–41, 1996. See also WO 98/00135 assigned to the University of Pittsburgh. Accordingly, the compounds of Formula (1.0.0) are useful in the treatment of renal failure, particularly acute renal failure.

Cachexia is a profound and marked state of constitutional disorder characterized by general ill health and malnutrition. Cachexia may be the end result of a number of causative factors, e.g., it may result from infection by any one of a number of different unicellular organisms or microorganisms including bacteria, viruses, fungi, and protozoans. Malarial cachexia is representative and comprises a group of signs of a chronic nature that result from antecedent attacks of severe malaria, the principal signs being anemia, sallow skin, yellow sclera, splenomegaly, and hepatomegaly. Another cause of cachexia is the deprivation or deterioration of humoral or other organic functions, e.g., hypophysial cachexia comprises a train of symptoms resulting from total deprivation of function of the pituitary gland, including phthisis, loss of sexual function, atrophy of the pituitary target glands, bradycardia, hypothermia, apathy, and coma. Uremic cachexia is cachexia associated with other systemic symptoms of advanced renal failure. Cardiac cachexia comprises the emaciation due to heart disease. Cachexia suprarenalis, or Addison's disease, is a disorder characterized by hypotension, weight loss, anorexia, and weakness, caused by adrenocortical hormone deficiency. It is due to tuberculosis- or autoimmune-induced destruction of the adrenal cortex that results in deficiency of aldosterone and cortisol.

Cachexia may also be the result of disease states of various types. Cancerous cachexia comprises the weak, emaciated condition seen in cases of malignant tumor. Cachexia can also be a consequence of infection by the human immunodeficiency virus (HIV), and comprises the symptoms commonly referred to as acquired immune deficiency syndrome (AIDS). The compounds of Formula (1.0.0) are useful in treating cachexia of the different types described above as a result of their ability to provide down-regulation or inhibition of TNF-α release. The selective PDE4 inhibitors of the present invention have a marked effect on the inhibition of TNF-α release from peripheral blood mononuclear cells after those cells have been stimulated with a wide range of mediators. TNF-α release is implicated or plays a mediating role in diseases or conditions whose etiology involves or comprises morbid, i.e., unhealthy, excessive or unregulated TNF-α release.

The PDE4 inhibitory compounds of Formula (1.0.0) are further useful in the treatment of infection, especially infection by viruses wherein such viruses increase the production of TNF-α in their host, or wherein such viruses are sensitive to upregulation of TNF-α in their host so that their replication or other vital activities are adversely impacted. Such viruses include, e.g., HIV-1, HIV-2, and HIV-3; cytomegalovirus, CMV; influenza; adenoviruses; and Herpes viruses, especially Herpes zoster and Herpes simplex.

The PDE4 inhibitory compounds of Formula (1.0.0) are further useful in the treatment of yeast and fungus infections wherein said yeast and fungi are sensitive to upregulation by TNF-α or elicit TNF-α production in their host. A particular disease which is treatable in this way is fungal meningitis. The compounds of Formula (1.0.0) also provide beneficial effects when combined with, i.e., administered in conjunction with other drugs of choice for the treatment of systemic yeast and fungus infections. Such drugs of choice include, but are not limited to polymixins, e.g., Polymycin B; imidazoles, e.g., clotrimazole, econazole, miconazole, and ketoconazole; triazoles, e.g., fluconazole and itranazole; and amphotericins, e.g., Amphotericin B and liposomal Amphotericin B. The term "co-administration" as used herein with reference to the compounds of Formula (1.0.0) and drugs of choice for the treatment of systemic yeast and fungus infections, is intended to mean and include (a) simultaneous administration of such compound(s) and drug(s) to a subject when formulated together into a single dosage form; (b) substantially simultaneous administration of such compound(s) and drug(s) to a subject when formulated apart from each other into separate dosage forms; and (c) sequential administration of such compound(s) and drug(s) to a subject when formulated apart from each other and administered consecutively with some significant time interval between.

8.12 Liver Injury

In addition to the above-described adverse effects of TNF-α, it also causes hepatic failure in humans, a phenomenon which has been shown in a number of animal models. For example, in an acute model of T-cell mediated hepatic failure, rolipram administered at 0.1 to 10 mg/kg i.p. 30 minutes before challenge with either concanavalin A or staphylococcal enterotoxin B, has been shown to significantly reduce plasma TNF-α and INF-γ concentrations, whereas it also significantly elevates IL-10 levels. See Gantner et al., *J. Pharmacol. Exp. Ther.* 280 53, 1997. In this same study, rolipram has also been shown to suppress concanavalin A-induced IL-4 release. The plasma activities of the liver specific enzymes ALT, AST, and SDH have also been assessed in this study, since any increase in their levels would indicate massive liver cell destruction. It has been found that in pretreatment of naïve mice receiving concanavalin A, or galactosamine-sensitized mice receiving galactosamine/staphylococcal enterotoxin B, with rolipram at 0.1 to 10 mg/kg i.p., that rolipram has dose-dependently inhibited the above-mentioned plasma enzyme activities. Accordingly, the compounds of Formula (1.0.0) are useful in the treatment of T-cell disorders such as liver failure.

8.13 Pulmonary Hypertension

It is known that the activity of phosphodiesterases, which hydrolyze the vasodilatory second messengers cAMP and cGMP, may be increased by hypoxia-induced pulmonary hypertension (HPH). Hypoxia is a reduction of oxygen supply to tissue below physiological levels despite adequate perfusion of the tissue by blood. The resulting pulmonary hypertension is characterized by increased pressure, ie., above 30 mm Hg systolic and above 12 mm. Hg diastolic, within the pulmonary arterial circulation. Using a model which utilizes isolated pulmonary artery rings from normal rats and from rats with hypoxia-induced pulmonary hypertension, it has been shown that the selective PDE4 inhibitor rolipram potentiates the relaxant activities of isoproterenol and forskolin. The same effect has been observed with milrinone, which is a selective PDE3 inhibitor, thereby supporting inhibition of both PDE3 and PDE4 in order to significantly improve pulmonary artery relaxation in hypoxia-induced pulmonary hypertension. See Wagner et al., *J. Pharmacol. Exp. Ther.* 282 1650, 1997. Accordingly, the compounds of Formula (1.0.0) are useful in the treatment of pulmonary hypertension, especially hypoxia-induced pulmonary hypertension.

8.14 Bone Loss Disease

Bone loss disease, more commonly referred to as osteoporosis, is a condition of low bone mass and microarchitectural disruption that results in fractures with minimal trauma. Secondary osteoporosis is due to systemic illness or medications such as glucocorticoids. Primary osteoporosis, it has been contended, should be viewed as comprising two conditions: Type I osteoporosis which is loss of trabecular bone due to estrogen deficiency at menopause, and Type II osteoporosis which is loss of cortical and trabecular bone due to long-term remodeling inefficiency, dietary inadequacy, and activation of the parathyroid axis with age. The primary regulators of adult bone mass include physical activity, reproductive endocrine status, and calcium intake, and optimal maintenance of bone requires sufficiency in all three areas.

It has been demonstrated that selective PDE4 inhibitors are useful in the beneficial treatment of bone loss disease, particularly osteoporosis. The effect of denbufylline on bone loss in Walker 256/S-bearing rats and on mineralized nodule formation and osteoclast-like cell formation has been studied in bone marrow culture systems. It has been discovered that serial oral administrations of denbufylline inhibit the decrease in the bone mineral density of femurs from Walker 256/S-bearing rats, and restore the bone mass and the number of osteoclasts and osteoblasts per trabecular surface in the femur metaphysis. The administration of denbufylline has also been found to result in an increase in the number of mineralized nodules and a decrease in the number of osteoclast-like cells in the in vitro bone marrow culture system. These beneficial effects are specific for PDE4 inhibition and are mimicked by dibutyryl cAMP, demonstrating that the PDE4 isozyme plays an important role in bone turnover through cAMP. See Miyamoto et al., *Biochem. Pharmacol.* 54 613, 1997; Waki et al., "Effects of XT-44, a phosphodiesterase 4 inhibitor, in osteoblastgenesis and osteoclastgenesis in culture and its therapeutic effects in rat osteopenia models," *Jpn. J. Pharmacol.* 79 477–483, 1999; and JP 9169665 assigned to Miyamoto (1997). Consequently, the selective PDE4 inhibitors of Formula (1.0.0) are useful in the treatment of diseases involving bone loss, especially osteoporosis.

8.15 CNS Disorders

The PDE4 selective inhibitor rolipram was initially developed as an antidepressant and continues to be studied in clinical trials for that indication. Further, it has been demonstrated that selective PDE4 inhibitors provide beneficial effects in other central nervous system disorders, including Parkinson's disease, Hulley et al., "Inhibitors of Type IV phosphodiesterases reduce the toxicity of MPTP in substantia nigra neurons in vivo," *Eur. J. Neurosci.* 7 2431–2440, 1995; as well as learning and memory impairment, Egawa et al., "Rolipram and its optical isomers, phosphodiesterase 4 inhibitors, attenuate the scopolamine-induced impairments of learning and memory in rats," *Jpn. J. Pharmacol.* 75 275–281, 1997; Imanishi et al., "Ameliorating effects of rolipram on experimentally induced impairments of learning and memory in rodents," *Eur. J. Pharmacol.* 321 273–278, 1997; and Barad et al., "Rolipram, a Type IV-specific phosphodiesterase inhibitor, facilitates the establishment of long-lasting long-term potentiation and improves memory," *Proc. Natl. Acad. Sci. USA* 95 15020–15025, 1998.

The use of PDE4 inhibitors to treat tardive dyskinesia and drug dependence has also been disclosed in the art, WO 95/28177 and JP 92221423 (1997), both assigned to Meiji Seika Kaisha Ltd. The PDE4 isozyme has been found to play a major role in controlling dopamine biosynthesis in mesencephalic neurons; accordingly PDE4 inhibitors are useful in the treatment of disorders and diseases which are associated with or mediated by dopamine within and around mesencephalic neurons, Yamashita et al., "Rolipram, a selective inhibitor of phosphodiesterase Type 4, pronouncedly enhances the forskolin-induced promotion of dopamine biosynthesis in primary cultured rat mesencephalic neurons," *Jpn. J. Pharmacol.* 75 91–95, 1997.

The PDE4 inhibitory compounds of Formula (1.0.0) are further useful in the treatment of arteriosclerotic dementia and subcortical dementia. Arteriosclerotic dementia, also called vascular dementia and multi-infarct dementia, is a dementia with a stepwise deteriorating course in the form of a series of small strokes, and an irregular distribution of neurological deficits caused by cerebrovascular disease. Subcortical dementia are caused by lesions affecting subcortical brain structures and are characterized by memory loss with slowness in processing information or making intellectual responses. Included are dementias that accompany Huntington's chorea, Wilson's disease, paralysis agitans, and thalamic atrophies.

8.16 Other Therapeutic Applications

It has been demonstrated that PDE4 inhibitors are useful in the treatment of ischemia-reperfusion injury, Block et al., "Delayed treatment with rolipram protects against neuronal damage following global ischemia in rats," *NeuroReport* 8 3829–3832, 1997 and Belayev et al. "Protection against blood-brain barrier disruption in focal cerebral ischemia by the Type IV phosphodiesterase inhibitor BBB022: a quantitative study," *Brain Res.* 787 277–285, 1998; in the treatment of autoimmune diabetes, Liang et al., "The phosphodiesterase inhibitors pentoxifylline and rolipram prevent diabetes in NOD mice," *Diabetes* 47 570–575, 1998; in the treatment of retinal autoimmunity, Xu et al., "Protective effect of the Type IV phosphodiesterase inhibitor rolipram in EAU: protection is independent of the IL-10-inducing activity," *Invest. Ophthalmol. Visual Sci.* 40 942–950, 1999; in the treatment of chronic lymphocytic leukemia, Kim and Lerner, "Type 4 cyclic adenosine monophosphate phosphodiesterase as a therapeutic agent in chronic lymphocytic leukemia," *Blood* 92 2484–2494, 1998; in the treatment of HIV infections, Angel et al., "Rolipram, a specific Type IV phosphodiesterase inhibitor, is a potent inhibitor of HIV-1 replication," *AIDS* 9 1137–1144, 1995 and Navarro et al., "Inhibition of phosphodiesterase Type IV suppresses human immunodeficiency virus Type 1 replication and cytokine production in primary T cells: involvement of NF-kappaB and NFAT," *J. Virol.* 72 4712–4720, 1998; in the treatment of lupus erythematosus, JP 10067682 (1998) assigned to Fujisawa Pharm. Co. Ltd.; in the treatment of kidney and ureter disease, DE 4230755 (1994) assigned to Schering A G; in the treatment of urogenital and gastrointestinal disorders, WO 94/06423 assigned to Schering A G; and in the treatment of prostate diseases, WO 99/02161 assigned to Porssmann and WO 99/02161 assigned to Stief.

In accordance with the above descriptions, it will be understood that the compounds of Formula (1.0.0) are useful in the beneficial treatment of any one or more members selected from the group consisting of the following diseases, disorders, and conditions:

asthma of whatever type, etiology, or pathogenesis; or asthma that is a member selected from the group consisting of atopic asthma; non-atopic asthma; allergic asthma; atopic, bronchial, IgE-mediated asthma; bronchial asthma; essential asthma; true asthma; intrinsic asthma caused by pathophysiologic disturbances; extrinsic asthma caused by environmental factors; essential asthma of unknown or inapparent cause; non-atopic asthma; bronchitic asthma; emphysematous asthma; exercise-induced asthma; occupational asthma; infective asthma caused by bacterial, fungal, protozoal, or viral infection; non-allergic asthma; incipient asthma; wheezy infant syndrome;

chronic or acute bronchoconstriction; chronic bronchitis; small airways obstruction; and emphysema;

obstructive or inflammatory airways diseases of whatever type, etiology, or pathogenesis; or an obstructive or inflammatory airways disease that is a member selected from the group consisting of asthma; pneumoconiosis; chronic eosinophilic pneumonia; chronic obstructive pulmonary disease (COPD); COPD that includes chronic bronchitis, pulmonary emphysema or dyspnea associated therewith; COPD that is characterized by irreversible, progressive airways obstruction; adult respiratory distress syndrome (ARDS), and exacerbation of airways hyper-reactivity consequent to other drug therapy;

pneumoconiosis of whatever type, etiology, or pathogenesis; or pneumoconiosis that is a member selected from the group consisting of aluminosis or bauxite workers' disease; anthracosis or miners' asthma; asbestosis or steam-fitters' asthma; chalicosis or flint disease; ptilosis caused by inhaling the dust from ostrich feathers; siderosis caused by the inhalation of iron particles; silicosis or grinders' disease; byssinosis or cotton-dust asthma; and talc pneumoconiosis;

bronchitis of whatever type, etiology, or pathogenesis; or bronchitis that is a member selected from the group consisting of acute bronchitis; acute laryngotracheal bronchitis; arachidic bronchitis; catarrhal bronchitis; croupus bronchitis; dry bronchitis; infectious asthmatic bronchitis; productive bronchitis; staphylococcus or streptococcal bronchitis; and vesicular bronchitis;

bronchiectasis of whatever type, etiology, or pathogenesis; or bronchiectasis that is a member selected from the group consisting of cylindric bronchiectasis; sacculated bronchiectasis; fusiform bronchiectasis; capillary bronchiectasis; cystic bronchiectasis; dry bronchiectasis; and follicular bronchiectasis;

seasonal allergic rhinitis; or perennial allergic rhinitis; or sinusitis of whatever type, etiology, or pathogenesis; or sinusitis that is a member selected from the group consisting of purulent or nonpurulent sinusitis; acute or chronic sinusitis; and ethmoid, frontal, maxillary, or sphenoid sinusitis;

rheumatoid arthritis of whatever type, etiology, or pathogenesis; or rheumatoid arthritis that is a member selected from the group consisting of acute arthritis; acute gouty arthritis; chronic inflammatory arthritis; degenerative arthritis; infectious arthritis; Lyme arthritis; proliferative arthritis; psoriatic arthritis; and vertebral arthritis;

gout, and fever and pain associated with inflammation;

an eosinophil-related disorder of whatever type, etiology, or pathogenesis; or an eosinophil-related disorder that is a member selected from the group consisting of eosinophilia; pulmonary infiltration eosinophilia; Loffler's syndrome; chronic eosinophilic pneumonia; tropical pulmonary eosinophilia; bronchopneumonic aspergillosis; aspergilloma; granulomas containing eosinophils; allergic granulomatous angiitis or Churg-Strauss syndrome; polyarteritis nodosa (PAN); and systemic necrotizing vasculitis;

atopic dermatitis; or allergic dermatitis; or allergic or atopic eczema;

urticaria of whatever type, etiology, or pathogenesis; or urticaria that is a member selected from the group consisting of immune-mediated urticaria; complement-mediated urticaria; urticariogenic material-induced urticaria; physical agent-induced urticaria; stress-induced urticaria; idiopathic urticaria; acute urticaria; chronic urticaria; angioedema; cholinergic urticaria; cold urticaria in the autosomal dominant form or in the acquired form; contact urticaria; giant urticaria; and papular urticaria;

conjunctivitis of whatever type, etiology, or pathogenesis; or conjunctivitis that is a member selected from the group consisting of actinic conjunctivitis; acute catarrhal conjunctivitis; acute contagious conjunctivitis; allergic conjunctivitis; atopic conjunctivitis; chronic catarrhal conjunctivitis; purulent conjunctivitis; and vernal conjunctivitis;

uveitis of whatever type, etiology, or pathogenesis; or uveitis that is a member selected from the group consisting of inflammation of all or part of the uvea; anterior uveitis; iritis; cyclitis; iridocyclitis; granulomatous uveitis; nongranulomatous uveitis; phacoantigenic uveitis; posterior uveitis; choroiditis; and chorioretinitis;

psoriasis;

multiple sclerosis of whatever type, etiology, or pathogenesis; or multiple sclerosis that is a member selected from the group consisting of primary progressive multiple sclerosis; and relapsing remitting multiple sclerosis;

autoimmune/inflammatory diseases of whatever type, etiology, or pathogenesis; or an autoimmune/inflammatory disease that is a member selected from the group consisting of autoimmune hematological disorders; hemolytic anemia; aplastic anemia; pure red cell anemia; idiopathic thrombocytopenic purpura; systemic lupus erythematosus; polychondritis; scleroderma; Wegner's granulomatosis; dermatomyositis; chronic active hepatitis; myasthenia gravis; Stevens-Johnson syndrome; idiopathic sprue; autoimmune inflammatory bowel diseases; ulcerative colitis; Crohn's disease; endocrin opthamopathy; Grave's disease; sarcoidosis; alveolitis; chronic hypersensitivity pneumonitis; primary biliary cirrhosis; juvenile diabetes or diabetes mellitus type I; anterior uveitis; granulomatous or pos terior uveitis; keratoconjunctivitis sicca; epidemic keratoconjunctivitis; diffuse interstitial pulmonary fibrosis or interstitial lung fibrosis; idiopathic pulmonary fibrosis; cystic fibrosis; psoriatic arthritis; glomerulonephritis with and without nephrotic syndrome; acute glomerulonephritis; idiopathic nephrotic syndrome; minimal change nephropathy; inflammatory/hyperproliferative skin diseases; psoriasis; atopic dermatitis; contact dermatitis; allergic contact dermatitis; benign familial pemphigus; pemphigus erythematosus; pemphigus foliaceus; and pemphigus vulgaris;

prevention of allogeneic graft rejection following organ transplantation;

inflammatory bowel disease (IBD) of whatever type, etiology, or pathogenesis; or inflammatory bowel disease that is a member selected from the group consisting of ulcerative colitis (UC); collagenous colitis; colitis polyposa; transmural colitis; and Crohn's disease (CD);

septic shock of whatever type, etiology, or pathogenesis; or septic shock that is a member selected from the group consisting of renal failure; acute renal failure; cachexia; malarial cachexia; hypophysial cachexia; uremic cachexia; cardiac cachexia; cachexia suprarenalis or Addison's disease; cancerous cachexia; and cachexia as a consequence of infection by the human immunodeficiency virus (HIV);

liver injury;

pulmonary hypertension; and hypoxia-induced pulmonary hypertension;

bone loss diseases; primary osteoporosis; and secondary osteoporosis;

central nervous system disorders of whatever type, etiology, or pathogenesis; or a central nervous system disorder that is a member selected from the group consisting of depression; Parkinson's disease; learning and memory impairment; tardive dyskinesia; drug dependence; arteriosclerotic dementia; and dementias that accompany Huntington's chorea, Wilson's disease, paralysis agitans, and thalamic atrophies;

infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3; cytomegalovirus, CMV; influenza; adenoviruses; and Herpes viruses, including Herpes zoster and Herpes simplex;

yeast and fungus infections wherein said yeast and fungi are sensitive to upregulation by TNF-α or elicit TNF-α production in their host, e.g., fungal meningitis; particularly when administered in conjunction with other drugs of choice for the treatment of systemic yeast and fungus infections, including but are not limited to, polymixins, e.g., Polymycin B; imidazoles, e.g., clotrimazole, econazole, miconazole, and ketoconazole; triazoles, e.g., fluconazole and itranazole; and amphotericins, e.g., Amphotericin B and liposomal Amphotericin B; and ischemia-reperfusion injury; autoimmune diabetes; retinal autoimmunity; chronic lymphocytic leukemia; HIV infections; lupus erythematosus; kidney and ureter disease; urogenital and gastrointestinal disorders; and prostate diseases.

DETAILED DESCRIPTION OF THE INVENTION 9.0 Combination with Other Drugs and Therapies The present invention contemplates embodiments in which a compound of Formula (1.0.0) is the only therapeutic agent which is employed in a method of treatment described herein, whether used alone or more commonly, together with a pharmaceutically acceptable carrier to produce a suitable dosage form for administration to a patient. Other embodiments of the present invention contemplate a combination of a compound of Formula (1.0.0) together with one or more additional therapeutic agents to be co-administered to a patient to obtain some particularly desired therapeutic end result. The second, etc. therapeutic agent may also be one or more compounds of Formula (1.0.0), or one or more PDE4 inhibitors known in the art and described in detail herein. More typically, the second, etc. therapeutic agent will be selected from a different class of therapeutic agents. These selections are described in detail below.

As used herein, the terms "co-administration", "co-administered", and "in combination with", referring to the compounds of Formula (1.0.0) and one or more other therapeutic agents, is intended to mean, and does refer to and include the following: (a) simultaneous administration of such combination of compound(s) and therapeutic agent(s) to a patient in need of treatment, when such components are formulated together into a single dosage form which releases said components at substantially the same time to said patient; (b) substantially simultaneous administration of such combination of compound(s) and therapeutic agent(s) to a patient in need of treatment, when such components are formulated apart from each other into separate dosage forms which are ingested at substantially the same time by said patient, whereupon said components are released at substantially the same time to said patient; (c) sequential administration of such combination of compound(s) and therapeutic agent(s) to a patient in need of treatment, when such components are formulated apart from each other into separate dosage forms which are ingested at consecutive times by said patient with a significant time interval between each ingestion, whereupon said components are released at substantially different times to said patient; and (d) sequential administration of such combination of compound(s) and therapeutic agent(s) to a patient in need of treatment, when such components are formulated together into a single dosage form which releases said components in a controlled manner whereupon they are concurrently, consecutively, and/or overlappingly ingested at the same and/or different times by said patient.

9.1 With Leukotriene Biosynthesis Inhibitors: 5-Lipoxygenase (5-LO) Inhibitors and 5-Lipoxygenase Activating Protein (FLAP) Antagonists One or more compounds of Formula (1.0.0) is used in combination with leukotriene biosynthesis inhibitors, i.e., 5-lipoxygenase inhibitors and/or 5-lipoxygenase activating protein antagonists, to form embodiments of the present invention. As already adverted to above, 5-lipoxygenase (5-LO) is one of two groups of enzymes that metabolize arachidonic acid, the other group being the cyclooxygenases, COX-1 and COX-2. The 5-lipoxygenase activating protein is an 18 kDa membrane-bound, arachidonate-binding protein which stimulates the conversion of cellular arachidonic acid by 5-lipoxygenase. The arachidonic acid is converted into 5-hydroperoxyeicosatetraenoic acid (5-HPETE), and this pathway eventually leads to the production of inflammatory leukotrienes; consequently, blocking the 5-lipoxygenase activating protein or the 5-lipoxygenase enzyme itself provides a desirable target for beneficially interfering with that pathway. One such 5-lipoxygenase inhibitor is zileuton represented by Formula (0.1.14), which may be found both above and following. Among the classes of leukotriene synthesis inhibitors which are useful for forming therapeutic combinations with the compounds of Formula (1.0.0) are the following:

(a) redox-active agents which include N-hydroxyureas; N-alkylhydroxamic acids; selenite; hydroxybenzofurans; hydroxylamines; and catechols; see Ford-Hutchinson et al., "5-Lipoxygenase," *Ann. Rev. Biochem.* 63 383–417, 1994; Weitzel and Wendel, "Selenoenzymes regulate the activity of leukocyte 5-lipoxygenase via the peroxide tone," *J. Biol. Chem.* 268 6288–92, 1993; Björnstedt et al. "Selenite incubated with NADPH and mammalian thioredoxin reductase yields selenide, which inhibits lipoxygenase and changes the electron spin resonance spectrum of the active site iron," *Biochemistry* 35 8511–6, 1996; and Stewart et al., "Structure-activity relationships of N-hydroxyurea 5-lipoxygenase inhibitors," *J. Med. Chem.* 40 1955–68, 1997;

(b) alkylating agents and compounds which react with SH groups have been found to inhibit leukotriene synthesis in vitro; see Larsson et al., "Effects of 1-chloro-2,4,6-trinitrobenzene on 5-lipoxygenase activity and cellular leukotriene synthesis," *Biochem. Pharmacol.* 55 863–71, 1998; and (c) competitive inhibitors of 5-lipoxygenase, based on thiopyranoindole and methoxyalkyl thiazole structures which may act as non-redox inhibitors of 5-lipoxygenase; see Ford-Hutchinson et al., Ibid.; and Hamel et al., "Substituted (pyridylmethoxy)naphthalenes as potent and orally active 5-lipoxygenase inhibitors—synthesis, biological profile, and pharmacokinetics of L-739,010," *J. Med. Chem.* 40 2866–75, 1997.

The observation that arachidonoyl hydroxyamate inhibits 5-lipoxygenase has led to the discovery of clinically useful selective 5-lipoxygenase inhibitors such as the N-hydroxyurea derivatives zileuton and ABT-761, represented by Formulas (0.1.14) and (5.2.1):

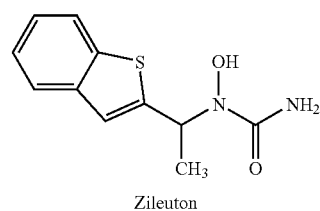

(0.1.14)

Zileuton

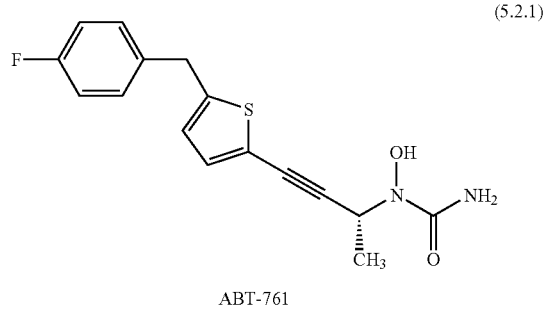

(5.2.1)

ABT-761

Another N-hydroxyurea compound is fenleuton (Abbott-76745) which is represented by Formula (5.2.2):

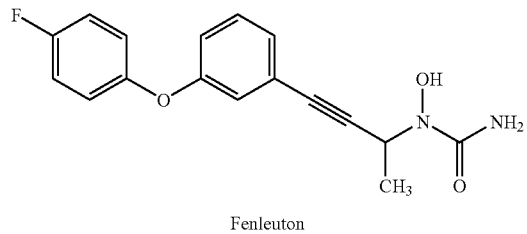

(5.2.2)

Fenleuton

Zileuton is covered by U.S. Pat. No. 4,873,259 (Summers et al.) assigned to Abbott Laboratories, which discloses indole, benzofuran, and benzothiophene containing lipoxygenase inhibiting compounds which may be represented by Formula (5.2.3):

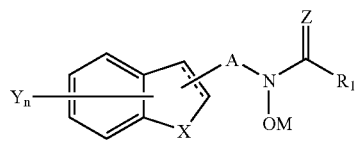

(5.2.3)

where $R_1$ is H; $(C_1-C_4)$alkyl; $(C_2-C_4)$alkenyl; or $NR_2R^3$ where $R_2$ and $R_3$ are H; $(C_1-C_4)$alkyl; or OH; X is O; S; $SO_2$; or $NR_4$ where $R^4$ is H; $(C_1-C_6)$alkyl; $(C_1-C_6)$alkanoyl; aroyl; or alkylsulfonyl; A is $(C_1-C_6)$alkylene; or $(C_2-C_6)$alkenylene; n is 1–5; and Y is H; halo; OH; CN; halo substituted alkyl; $(C_1-C_{12})$alkyl; $(C_2-C_{12})$alkenyl; $(C_1-C_{12})$alkoxy; $(C_3-C_8)$cycloalkyl; $(C_1-C_8)$thioalkyl; aryl; aryloxy; aroyl; $(C_1-C_{12})$arylalkyl; $(C_2-C_{12})$arylalkenyl; $(C_1-C_{12})$arylalkoxy; $(C_1-C_{12})$arylthioalkoxy; or substituted derivatives of aryl; aryloxy; aryoyl; $(C_1-C_{12})$arylalkyl; $(C_2-C_{12})$arylalkenyl; $(C_1-C_{12})$arylalkoxy; $(C_1-C_{12})$arylthioalkoxy; where said substituent is halo; $NO_2$; CN; or $(C_1-C_{12})$-alkyl -alkoxy and -halosubstitutedalkyl; Z is O or S; and M is H; pharmaceutically acceptable cation; aroyl; or $(C_1-C_{12})$alkanoyl.

Related compounds are disclosed in U.S. Pat. No. 4,769,387 (Summers et al.); U.S. Pat. No. 4,822,811 (Summers); U.S. Pat. No. 4,822,809 (Summers and Stewart); U.S. Pat. No. 4,897,422 (Summers); U.S. Pat. No. 4,992,464 (Summers et al.); and U.S. Pat. No. 5,250,565 (Brooks and Summers); each of which is incorporated herein by reference in its entirety as though fully set out herein.

Zileuton or any of the above-described derivatives thereof are combined with the compounds of Formula (1.0.0) to form embodiments of the present invention.

Fenleuton is disclosed in U.S. Pat. Nos. 5,432,194; 5,446,062; 5,484,786; 5,559,144; 5,616,596; 5,668,146; 5,668,150; 5,843,968; 5,407,959; 5,426,111; 5,446,055; 5,475,009; 5,512,581; 5,516,795; 5,476,873; 5,714,488; 5,783,586; 5,399,699; 5,420,282; 5,459,150; and 5,506,261; each of which is incorporated herein by reference in its entirety as though fully set out herein. Further descriptions of such N-hydroxyurea and related inhibitors of 5-lipoxygenase and the synthesis of inflammatory leukotrienes may be found in WO 95/30671; WO 96/02507; WO 97/12865; WO 97/12866; WO 97/12867; WO 98/04555; and WO 98/14429.

Tepoxalin is a dual COX/5-LO inhibitor with short-lived in vivo activity that has led to the development of two series of hybrid compounds which are N-hydroxyureas and hydroxamic acids of Formulas (5.2.4) and (5.2.5), respectively:

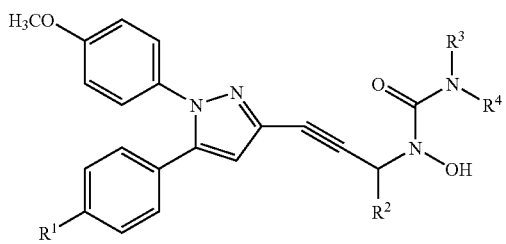

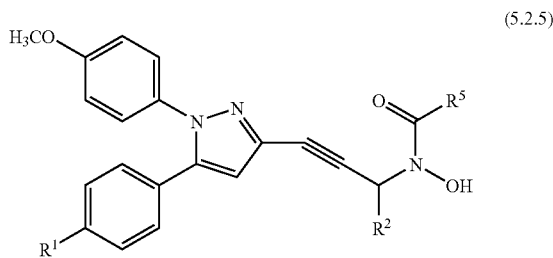

where $R^1$ through $R^4$ are H; Cl; $CH_3$; ethyl; iso-propyl; or n-propyl; or $R^3$ and $R^4$ together are $(CH_2)_5$ or $(CH_2)_2O(CH_2)_2$; and $R^5$ is methyl; ethyl; iso-propyl; methoxy; trifluoromethyl; chloromethyl; ethyl propionate; phenyl; 2-furyl; 3-pyridyl; or 4-pyridyl. See Connolly et al., "N-Hydroxyurea and hydroxamic acid inhibitors of cyclooxygenase and 5-lipoxygenase," *Bioorganic & Medicinal Chemistry Letters* 9 979–984, 1999.

Another N-hydroxyurea compound is Abbott-79175 which is represented by Formula (5.2.6):

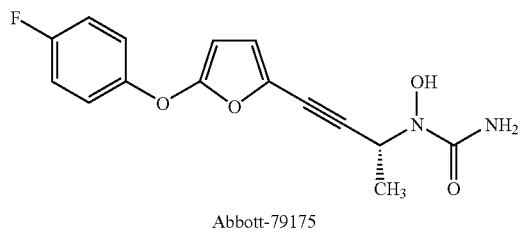

Abbott-79175

Abbott-79175 has a longer duration of action than zileuton; Brooks et al., *J. Pharm. Exp. Therapeut.* 272 724, 1995.

A still further N-hydroxyurea compound is Abbott-85761 which is represented by Formula (5.2.7):

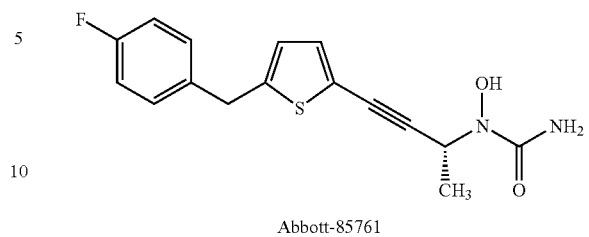

Abbott-85761

Abbott-85761 is delivered to the lung by aerosol administration of a homogeneous, physically stable and nearly monodispersed formulation; Gupta et al., "Pulmonary delivery of the 5-lipoxygenase inhibitor, Abbott-85761, in beagle dogs," *International Journal of Pharmaceutics* 147 207–218, 1997.

Fenleuton, Abbott-79175, Abbott-85761 or any of the above-described derivatives thereof or of tepoxalin, are combined with the compounds of Formula (1.0.0) to form embodiments of the present invention.

Since the elucidation of the 5-LO biosynthetic pathway, there has been an ongoing debate as to whether it is more advantageous to inhibit the 5-lipoxygenase enzyme or to antagonize peptido- or non-peptido leukotriene receptors. Inhibitors of 5-lipoxygenase are deemed to be superior to LT-receptor antagonists, since 5-lipoxygenase inhibitors block the action of the full spectrum of 5-LO products, whereas LT-antagonists produce narrower effects. Nevertheless, embodiments of the present invention include combinations of the compounds of Formula (1.0.0) with LT-antagonists as well as 5-LO inhibitors, as described below. Inhibitors of 5-lipoxygenase having chemical structures that differ from the classes of N-hydroxyureas and hydroxamic acids described above are also used in combination with the compounds of Formula (1.0.0) to form further embodiments of the present invention. An example of such a different class is the N-(5-substituted)-thiophene-2-alkylsulfonamides of Formula (5.2.8):

where X is O or S; R' is methyl, iso-propyl, n-butyl, n-octyl, or phenyl; and R is n-pentyl, cyclohexyl, phenyl, tetrahydro-1-naphthyl, 1- or 2-naphthyl, or phenyl mono- or di-substituted by Cl, F, Br, $CH_3$, $OCH_3$, $SCH_3$, $SO_2CH_3$, $CF_3$, or iso-propyl. A preferred compound is that of Formula (5.2.9):

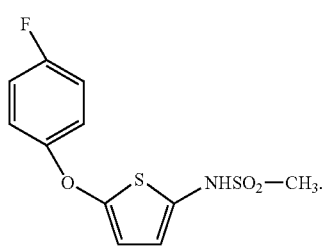

A further description of these compounds may be found in Beers et al., "N-(5-substituted)thiophene-2-alkylsulfonamides as potent inhibitors of 5-lipoxygenase," *Bioorganic & Medicinal Chemistry* 5(4) 779–786, 1997.

Another distinct class of 5-lipoxygenase inhibitors is that of the 2,6-di-tert-butylphenol hydrazones described in Cuadro et al., "Synthesis and biological evaluation of 2,6-di-tert-butylphenol hydrazones as 5-lipoxygenase inhibitors," *Bioorganic & Medicinal Chemistry* 6 173–180, 1998. Compounds of this type are represented by Formula (5.2.10):

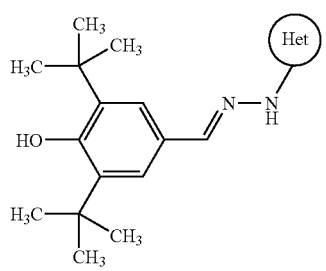

(5.2.10)

where "Het" is benzoxazol-2-yl; benzothizazol-2-yl; pyridin-2-yl; pyrazin-2-yl; pyrimidin-2-yl; 4-phenylpyrimidin-2-yl; 4,6-diphenylpyrimidin-2-yl; 4-methylpyrimidin-2-yl; 4,6-dimethylpyrimidin-2-yl; 4-butylpyrimidin-2-yl; 4,6-dibutylpyrimidin-2-yl; and 4-methyl-6-phenylpyrimidin-2-yl.

The N-(5-substituted)-thiophene-2-alkylsulfonamides of Formula (5.2.8), or the 2,6-di-tert-butylphenol hydrazones of Formula (5.2.10), or any of the above-described derivatives thereof, are combined with the compounds of Formula (1.0.0) to form embodiments of the present invention.

A further distinct class of 5-lipoxygenase inhibitors is that of methoxytetrahydropyrans to which Zeneca ZD-2138 belongs. ZD-2138 is represented by Formula (5.2.11):

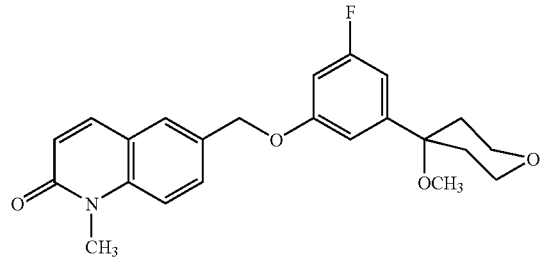

(5.2.11)

ZD-2138 is highly selective and highly active orally in a number of species and has been evaluated in the treatment of asthma and rheumatoid arthritis by oral admininstration. Further details concerning ZD-2138 and derivatives thereof are disclosed in Crawley et al., *J. Med. Chem.*, 35 2600, 1992; and Crawley et al., *J. Med. Chem.* 36 295, 1993.

Another distinct class of 5-lipoxygenase inhibitors is that to which the SmithKline Beecham compound SB-210661 belongs. SB-210661 is represented by Formula (5.2.12):

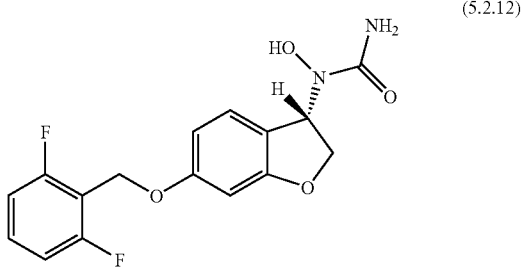

(5.2.12)

Two further distinct and related classes of 5-lipoxygenase inhibitors comprise a series of pyridinyl-substituted 2-cyanonaphthalene compounds and a series of 2-cyanoquinoline compounds discovered by Merck Frosst. These two classes of 5-lipoxygenase inhibitors are exemplified by L-739,010 and L-746,530, represented by Formulas (5.2.13) and (5.2.14) respectively:

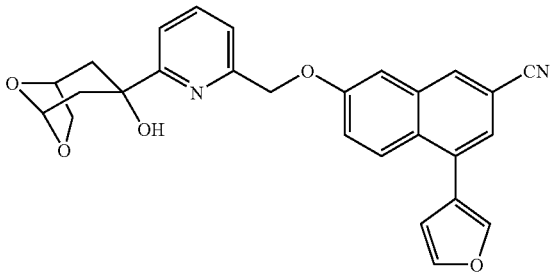

(5.2.13)

L-739,010

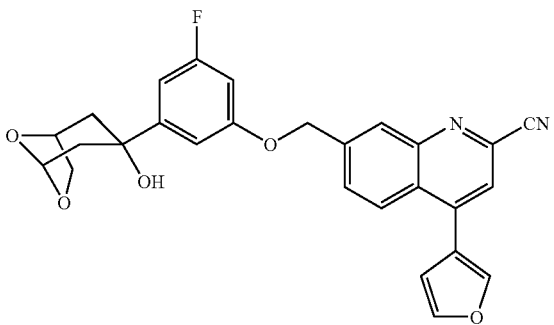

(5.2.14)

L-746,530

Details concerning L-739,010 and L-746,530 are disclosed in Dube et al., "Quinolines as potent 5-lipoxygenase inhibitors: synthesis and biological profile of L-746,530," *Bioorganic & Medicinal Chemistry* 8 1255–1260, 1998; and in WO 95/03309 (Friesen et al.).

The class of methoxytetrahydropyrans including Zeneca ZD-2138 of Formula (5.2.11); or the lead compound SB-210661 of Formula (5.2.12) and the class to which it belongs; or the series of pyridinyl-substituted 2-cyanonaphthalene compounds to which L-739,010 belongs, or the series of 2-cyanoquinoline compounds to which L-746,530 belongs; or any of the above-described derivatives of any of the above-mentioned classes, are combined with the compounds of Formula (1.0.0) to form embodiments of the present invention.

In addition to the 5-lipoxygenase enzyme, the other endogenous agent which plays a significant role in the biosynthesis of the leukotrienes is the 5-lipoxygenase activating protein (FLAP). This role is an indirect one, in contrast to the direct role of the 5-lipoxygenase enzyme. Nevertheless, antagonists of the 5-lipoxygenase activating protein are employed to inhibit the cellular synthesis of leukotrienes, and as such are also used in combination with the compounds of Formula (1.0.0) to form embodiments of the present invention.

Compounds which bind to the 5-lipoxygenase activating protein and thereby block utilization of the endogenous pool of archidonic acid which is present have been synthesized from indole and quinoline structures; see Ford-Hutchinson et al., Ibid.; Rouzer et al. "MK-886, a potent and specific leukotriene biosynthesis inhibitor blocks and reverses the membrane association of 5-lipoxygenase in ionophore-challenged leukocytes," *J. Biol. Chem.* 265 143–42, 1990; and Gorenne et al., "{(R)-2-quinolin-2-yl-methoxy)phenyl)-2-cyclopentyl acetic acid} (BAY x1005), a potent leukotriene synthesis inhibitor: effects on anti-IgE challenge in human airways," *J. Pharmacol. Exp. Ther.* 268 868–72, 1994

MK-591, which has been designated quiflipon sodium, is represented by Formula (5.2.15):

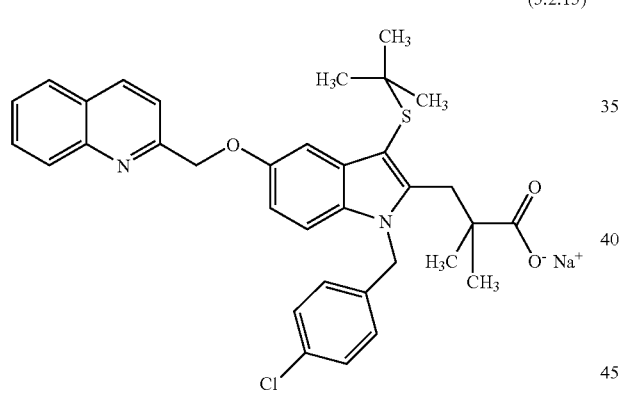

(5.2.15)

The above-mentioned indole and quinoline classes of compounds and the specific compounds MK-591, MK-886, and BAY x 1005 to which they belong, or any of the above-described derivatives of any of the above-mentioned classes, are combined with the compounds of Formula (1.0.0) to form embodiments of the present invention.

9.2 With Receptor Antagonists for Leukotrienes $LTB_4$, $LTC_4$, $LTD_4$, and $LTE_4$ One or more compounds of Formula (1.0.0) is used in combination with receptor antagonists for leukotrienes $LTB_4$, $LTC_4$, $LTD_4$, and $LTE_4$. The most significant of these leukotrienes in terms of mediating inflammatory response, are $LTB_4$ and $LTD_4$. Classes of antagonists for the receptors of these leukotrienes are described in the paragraphs which follow.

4-Bromo-2,7-diemethoxy-3H-phenothiazin-3-ones, including L-651,392, are potent receptor antagonists for $LTB_4$ that are described in U.S. Pat. No. 4,939,145 (Guindon et al.) and U.S. Pat. No. 4,845,083 (Lau et al.). L-651,392 is represented by Formula (5.2.16):

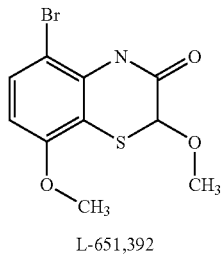

L-651,392

A class of amidino compounds that includes CGS-25019c is described in U.S. Pat. No. 5,451,700 (Morrissey and Suh); U.S. Pat. No. 5,488,160 (Morrissey); and U.S. Pat. No. 5,639,768 (Morrissey and Suh). These receptor antagonists for $LTB_4$ are typified by CGS-25019c, which is represented by Formula (5.2.17):

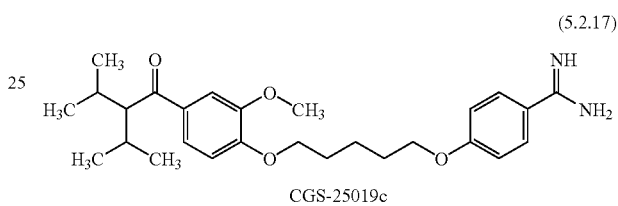

CGS-25019c

Ontazolast, a member of a class of benzoxaolamines that are receptor antagonists for $LTB_4$, is described in EP 535 521 (Anderskewitz et al.); and is represented by Formula (5.2.18)

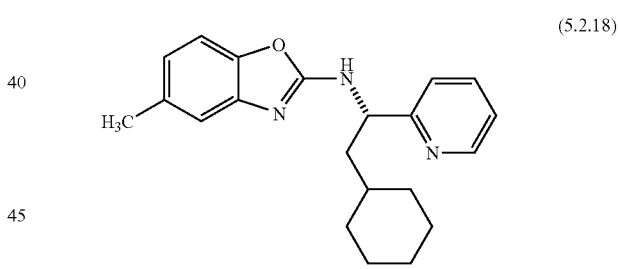

Ontazolast

The same group of workers has also discovered a class of benzenecarboximidamides which are receptor antagonists for $LTB_4$, described in WO 97/21670 (Anderskewitz et al.); and WO 98/11119 (Anderskewitz et al.); and which are typified by BIIL 284/260, represented by Formula (5.2.19):

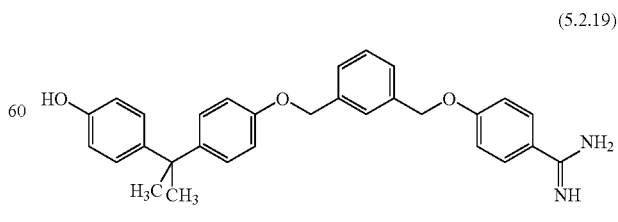

BIIL 284/260

Zafirlukast is a receptor antagonist for $LTC_4$, $LTD_4$, and $LTE_4$ which is sold commercially under the name Accolate®. It belongs to a class of heterocyclic amide derivatives described in U.S. Pat. No. 4,859,692 (Bernstein et al.); U.S. Pat. No. 5,319,097 (Holohan and Edwards); U.S. Pat. No. 5,294,636 (Edwards and Sherwood); U.S. Pat. No. 5,482,963; U.S. Pat. No. 5,583,152 (Bernstein et al.); and U.S. Pat. No. 5,612,367 (Timko et al.). Zafirlukast is represented by Formula (5.2.20):

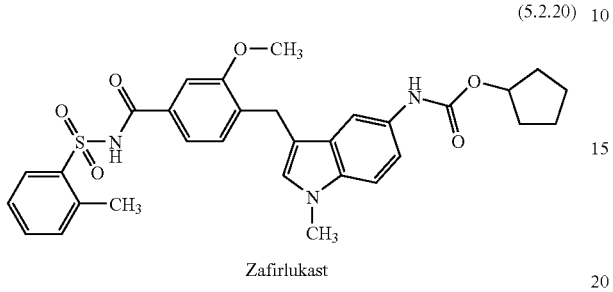

Zafirlukast

Ablukast is a receptor antagonist for $LTD_4$ that is designated Ro 23-3544/001, and is represented by Formula (5.2.21):

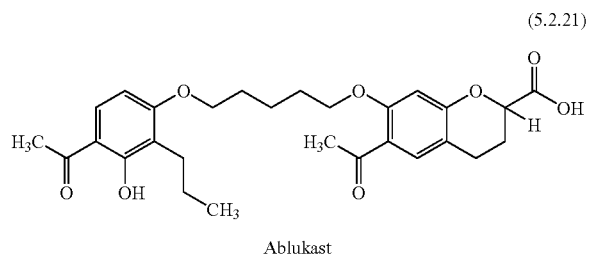

Ablukast

Montelukast is a receptor antagonist for $LTD_4$ which is sold commercially under the name Singulair® and is described in U.S. Pat. No. 5,565,473. Montelukast is represented by Formula (5.2.22):

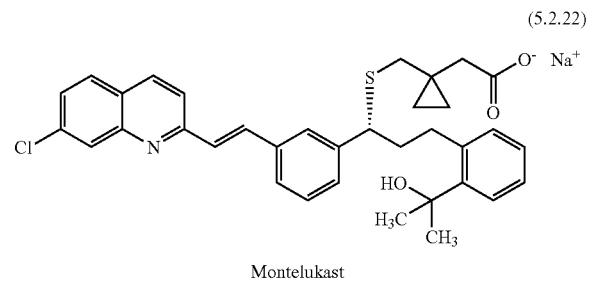

Montelukast

Other receptor antagonists for $LTD_4$ include pranlukast, verlukast (MK-679), RG-12525, Ro-245913, iralukast (CGP 45715A), and BAY x 7195.

The above-mentioned phenothiazin-3-one class of compounds, including L-651,392; the class of amidino compounds that includes CGS-25019c; the class of benzoxaolamines which includes Ontazolast; the class of benzenecarboximidamides which is typified by BIIL 284/260; the heterocyclic amide derivatives including Zafirlukast; Ablukast and Montelukast and the classes of compounds to which they belong; or any of the above-described derivatives of any of the above-mentioned classes, are combined with the compounds of Formula (1.0.0) to form embodiments of the present invention.

9.3 With Other Therapeutic Agents to Form Further Combinations

One or more compounds of Formula (1.0.0) are used together with other therapeutic agents as well as non-therapeutic agents to form combinations that are further embodiments of the present invention and that are useful in the treatment of a significant number of different diseases, disorders, and conditions described herein. Said embodiments comprise one or more compounds of Formula (1.0.0) together with one or more of the following:

(a) PDE4 inhibitors including inhibitors of the isoform PDE4D;
(b) 5-Lipoxygenase (5-LO) inhibitors; or 5-lipoxygenase activating protein (FLAP) antagonists;
(c) Dual inhibitors of 5-lipoxygenase (5-LO) and antagonists of platelet activating factor (PAF);
(d) Leukotriene antagonists (LTRAs) including antagonists of $LTB_4$, $LTC_4$, $LTD_4$, and $LTE_4$;
(e) Antihistaminic $H_1$ receptor antagonists including cetirizine, loratadine, desloratadine, fexofenadine, astemizole, azelastine, and chlorpheniramine;
(f) Gastroprotective $H_2$ receptor antagonists;
(g) $\alpha_1$- and $\alpha_2$-adrenoceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride;
(h) $\alpha_1$- and $\alpha_2$-adrenoceptor agonists in combination with inhibitors of 5-lipoxygenase (5-LO);
(i) Anticholinergic agents including ipratropium bromide;
(j) $\beta_1$- to $\beta_4$-adrenoceptor agonists including isoprenaline, albuterol, salbutamol, formoterol, salmeterol, terbutaline, orciprenaline, bitolterol mesylate, and pirbuterol;
(k) Theophylline and aminophylline;
(l) Sodium cromoglycate;
(m) Muscarinic receptor (M1, M2, and M3) antagonists;
(n) COX-1 inhibitors (NSAIDs); COX-2 selective inhibitors including rofecoxib; and nitric oxide NSAIDs;
(o) Insulin-like growth factor type I (IGF-1) mimetics;
(p) Ciclesonide;
(q) Inhaled glucocorticoids with reduced systemic side effects, including flunisolide, triamcinolone acetonide, beclomethasone dipropionate, budesonide, fluticasone propionate, and mometasone furoate;
(r) Tryptase inhibitors;
(s) Platelet activating factor (PAF) antagonists;
(t) Monoclonal antibodies against endogenous inflammatory entities;
(u) IPL 576;
(v) Anti-tumor necrosis factor (TNFα) agents including Etanercept, Infliximab, and D2E7;
(w) DMARDs including Leflunomide;
(x) TCR peptides;
(y) Interleukin converting enzyme (ICE) inhibitors;
(z) IMPDH inhibitors;
(aa) Adhesion molecule inhibitors including VLA-4 antagonists;
(bb) Cathepsins;
(cc) MAP kinase inhibitors;
(dd) Glucose-6 phosphate dehydrogenase inhibitors;
(ee) Kinin-$B_1$- and $B_2$-receptor antagonists;

(ff) Gold in the form of an aurothio group together with various hydrophilic groups;
(gg) Immunosuppressive agents, e.g., cyclosporine, azathioprine, and methotrexate;
(hh) Anti-gout agents, e.g., colchicine;
(ii) Xanthine oxidase inhibitors, e.g., allopurinol;
(jj) Uricosuric agents, e.g., probenecid, sulfinpyrazone, and benzbromarone;
(kk) Antineoplastic agents, especially antimitotic drugs including the vinca alkaloids such as vinblastine and vincristine;
(ll) Growth hormone secretagogues;
(mm) Inhibitors of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11);
(nn) Transforming growth factor (TGFβ);
(o) Platelet-derived growth factor (PDGF);
(pp) Fibroblast growth factor, e.g., basic fibroblast growth factor (bFGF);
(qq) Granulocyte macrophage colony stimulating factor (GM-CSF);
(rr) Capsaicin cream;
(ss) Anti-emetic agents including NK-1 receptor antagonists and D-4418; and
(tt) Anti-depressants.

DETAILED DESCRIPTION OF THE INVENTION 10.0 Pharmaceutical Compositions and Formulations The description which follows concerns the manner in which the compounds of Formula (1.0.0), together with other therapeutic agents or non-therapeutic agents where these are desired, are combined with what are for the most part conventional pharmaceutically acceptable carriers to form dosage forms suitable for the different routes of administration which are utilized for any given patient, as well as appropriate to the disease, disorder, or condition for which any given patient is being treated.

The preferred routes of administration for the compounds of Formula (1.0.0) are by way of oral and aerosol formulations prepared and delivered in a conventional fashion. Detailed information regarding the preparation of such formulations and the manner in which they are to be given to a patient in need of treatment are discussed further below.

The pharmaceutical compositions of the present invention comprise any one or more of the above-described inhibitory compounds of the present invention, or a pharmaceutically acceptable salt thereof as also above-described, together with a pharmaceutically acceptable carrier in accordance with the properties and expected performance of such carriers which are well-known in the pertinent art.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The above-described compounds of the present invention may be utilized in the form of acids, esters, or other chemical classes of compounds to which the compounds described belong. It is also within the scope of the present invention to utilize those compounds in the form of pharmaceutically acceptable salts derived from various organic and inorganic acids and bases in accordance with procedures described in detail above and well known in the art. An active ingredient comprising a compound of Formula (1.0.0) is often utilized in the form of a salt thereof, especially where said salt form confers on said active ingredient improved pharmacokinetic properties as compared to the free form of said active ingredient or some other salt form of said active ingredient utilized previously. The pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation and excretion of said active ingredient. While the route of administration of the pharmaceutical composition is important, and various anatomical, physiological and pathological factors can critically affect bioavailability, the solubility of said active ingredient is usually dependent upon the character of the particular salt form thereof which it utilized. Further, as the artisan understands, an aqueous solution of said active ingredient will provide the most rapid absorption of said active ingredient into the body of a patient being treated, while lipid solutions and suspensions, as well as solid dosage forms, will result in less rapid absorption of said active ingredient. Oral ingestion of said active ingredient is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different pharmaceutically acceptable salt forms may be effective in overcoming or alleviating one or more of the above-recited problems encountered with absorption of oral dosage forms.

Among the pharmaceutical salts recited further above, those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described inhibitory compounds of the present invention, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipients, adjuvants, vehicles, solubilization aids, viscosity modifiers, preservatives and other agents well known to the artisan for providing favorable properties in the final pharmaceutical composition. In order to illustrate such carriers, there follows a brief survey of pharmaceutically acceptable carriers that may be used in the pharmaceutical compositions of the present invention, and thereafter a more detailed description of the various types of ingredients. Typical carriers include but are by no means limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; hydrogenated palm oils; water; salts or electrolytes, e.g., prolamine sulfate, disodium hydrogen phosphate, potassium hydrogen phosphate, sodium chloride, and zinc salts; colloidal silica; magnesium trisilicate; polyvinyl pyrrolidone; cellulose-based substances; e.g., sodium carboxymethylcellulose; polyethylene glycol; polyacrylates; waxes; polyethylene-polyoxypropylene-block polymers; and wool fat.

More particularly, the carriers used in the pharmaceutical compositions of the present invention comprise various classes and species of additives which are members independently selected from the groups consisting essentially of those recited in the following paragraphs.

Acidifying and alkalizing agents are added to obtain a desired or predetermined pH and comprise acidifying agents, e.g., acetic acid, glacial acetic acid, malic acid, and propionic acid. Stronger acids such as hydrochloric acid, nitric acid and sulfuric acid may be used but are less preferred. Alkalizing agents include, e.g., edetol, potassium carbonate, potassium hydroxide, sodium borate, sodium carbonate, and sodium hydroxide. Alkalizing agents which contain active amine groups, such as diethanolamine and trolamine, may also be used.

Aerosol propellants are required where the pharmaceutical composition is to be delivered as an aerosol under significant pressure. Such propellants include, e.g., acceptable fluorochlorohydrocarbons such as dichlorodifluoromethane, dichlorotetrafluoroethane, and trichloromonofluoromethane; nitrogen; or a volatile hydrocarbon such as butane, propane, isobutane or mixtures thereof.

Antimicrobial agents including antibacterial, antifungal and antiprotozoal agents are added where the pharmaceutical composition is topically applied to areas of the skin which are likely to have suffered adverse conditions or sustained abrasions or cuts which expose the skin to infection by bacteria, fungi or protozoa. Antimicrobial agents include such compounds as benzyl alcohol, chlorobutanol, phenylethyl alcohol, phenylmercuric acetate, potassium sorbate, and sorbic acid. Antifungal agents include such compounds as benzoic acid, butylparaben, ethylparaben, methylparaben, propylparaben, and sodium benzoate.

Antimicrobial preservatives are added to the pharmaceutical compositions of the present invention in order to protect them against the growth of potentially harmful microorganisms, which usually invade the aqueous phase, but in some cases can also grow in the oil phase of a composition. Thus, preservatives with both aqueous and lipid solubility are desirable. Suitable antimicrobial preservatives include, e.g., alkyl esters of p-hydroxybenzoic acid, propionate salts, phenoxyethanol, methylparaben sodium, propylparaben sodium, sodium dehydroacetate, benzalkonium chloride, benzethonium chloride, benzyl alcohol, hydantoin derivatives, quaternary ammonium compounds and cationic polymers, imidazolidinyl urea, diazolidinyl urea, and trisodium ethylenediamine tetracetate (EDTA). Preservatives are preferably employed in amounts ranging from about 0.01% to about 2.0% by weight of the total composition.

Antioxidants are added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols.

Buffering agents are used to maintain a desired pH of a composition once established, from the effects of outside agents and shifting equilibria of components of the composition. The buffering may be selected from among those familiar to the artisan skilled in the preparation of pharmaceutical compositions, e.g., calcium acetate, potassium metaphosphate, potassium phosphate monobasic, and tartaric acid.

Chelating agents are used to help maintain the ionic strength of the pharmaceutical composition and bind to and effectively remove destructive compounds and metals, and include, e.g., edetate dipotassium, edetate disodium, and edetic acid.

Dermatologically active agents are added to the pharmaceutical compositions of the present invention where they are to be applied topically, and include, e.g., wound healing agents such as peptide derivatives, yeast, panthenol, hexylresorcinol, phenol, tetracycline hydrochloride, lamin and kinetin; retinoids for treating skin cancer, e.g., retinol, tretinoin, isotretinoin, etretinate, acitretin, and arotinoid; mild antibacterial agents for treating skin infections, e.g., resorcinol, salicylic acid, benzoyl peroxide, erythromycin-benzoyl peroxide, erythromycin, and clindamycin; antifungal agents for treating tinea corporis, tinea pedis, candidiasis and tinea versicolor, e.g., griseofulvin, azoles such as miconazole, econazole, itraconazole, fluconazole, and ketoconazole, and allylamines such as naftifine and terfinafine; antiviral agents for treating cutaneous herpes simplex, herpes zoster, and chickenpox, e.g., acyclovir, famciclovir, and valacyclovir; antihistamines for treating pruritis, atopic and contact dermatitis, e.g., diphenhydramine, terfenadine, astemizole, loratadine, cetirizine, acrivastine, and temelastine; topical anesthetics for relieving pain, irritation and itching, e.g., benzocaine, lidocaine, dibucaine, and pramoxine hydrochloride; topical analgesics for relieving pain and inflammation, e.g., methyl salicylate, camphor, menthol, and resorcinol; topical antiseptics for preventing infection, e.g., benzalkonium chloride and povidone-iodine; and vitamins and derivatives thereof such as tocopherol, tocopherol acetate, retinoic acid and retinol.

Dispersing and suspending agents are used as aids for the preparation of stable formulations and include, e.g., poligeenan, povidone, and silicon dioxide.

Emollients are agents, preferably non-oily and water-soluble, which soften and soothe the skin, especially skin that has become dry because of excessive loss of water. Such agents are used with pharmaceutical compositions of the present invention which are intended for topical applications, and include, e.g., hydrocarbon oils and waxes, triglyceride esters, acetylated monoglycerides, methyl and other alkyl esters of $C_{10}$–$C_{20}$ fatty acids, $C_{10}$–$C_{20}$ fatty acids, $C_{10}$–$C_{20}$ fatty alcohols, lanolin and derivatives, polyhydric alcohol esters such as polyethylene glycol (200–600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol-monoethylether, 1-dodecylazacycloheptan-2-one, and dimethylsulfoxide (DMSO); preservatives, e.g., benzalkonium chloride, benzethonium chloride, alkyl esters of p-hydroxybenzoic acid, hydantoin derivatives, cetylpyridinium chloride, propylparaben, quaternary ammonium compounds such as potassium benzoate, and thimerosal; sequestering agents comprising cyclodextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water; stabilizers, e.g., calcium saccharate and thymol; surfactants, e.g., lapyrium chloride; laureth 4, i.e., α-dodecyl-ω-hydroxy-poly(oxy-1,2-ethanediyl) or polyethylene glycol monododecyl ether.

Emulsifying agents, including emulsifying and stiffening agents and emulsion adjuncts, are used for preparing oil-in-water emulsions when these form the basis of the pharmaceutical compositions of the present invention. Such emulsifying agents include, e.g., non-ionic emulsifiers such as $C_{10}$–$C_{20}$ fatty alcohols and said fatty alcohols condensed with from 2 to 20 moles of ethylene oxide or propylene oxide, ($C_6$–$C_{12}$)alkyl phenols condensed with from 2 to 20 moles of ethylene oxide, mono- and di-$C_{10}$–$C_{20}$ fatty acid esters of ethylene glycol, $C_{10}$–$C_{20}$ fatty acid monoglyceride, diethylene glycol, polyethylene glycols of MW 200–6000, polypropylene glycols of MW 200–3000, and particularly sorbitol, sorbitan, polyoxyethylene sorbitol, polyoxyethylene sorbitan, hydrophilic wax esters, cetostearyl alcohol, oleyl alcohol, lanolin alcohols, cholesterol, mono- and diglycerides, glyceryl monostearate, polyethylene glycol monostearate, mixed mono- and distearic esters of ethylene glycol and polyoxyethylene glycol, propylene glycol monostearate, and hydroxypropyl cellulose. Emulsifying agents which contain active amine groups may also be used and typically include anionic emulsifiers such as fatty acid soaps, e.g., sodium, potassium and triethanolamine soaps of $C_{10}$–$C_{20}$ fatty acids; alkali metal, ammonium or substituted ammonium ($C_{10}$–$C_{30}$)alkyl sulfates, ($C_{10}$–$C_{30}$)alkyl sulfonates, and ($C_{10}$–$C_{50}$)alkyl ethoxy ether sulfonates. Other suitable emulsifying agents include castor oil and hydrogenated castor oil; lecithin; and polymers of 2-propenoic acid together with polymers of acrylic acid, both cross-linked with allyl ethers of sucrose and/or pentaerythritol, having varying viscosities and identified by product names carbomer 910, 934, 934P, 940, 941, and 1342. Cationic emulsifiers having active amine groups may also be used, including those based on quaternary ammonium, morpholinium and pyridinium compounds. Similarly, amphoteric emulsifiers having active amine groups, such as cocobetaines, lauryl dimethylamine oxide and cocoylimidazoline, may be used. Useful emulsifying and stiffening agents also include cetyl alcohol and sodium stearate; and emulsion adjuncts such as oleic acid, stearic acid, and stearyl alcohol.

Excipients include, e.g., laurocapram and polyethylene glycol monomethyl ether.

Where the pharmaceutical composition of the present invention is to be applied topically, penetration enhancers may be used, which include, e.g., dimethyl isosorbide, diethyl-glycol-monoethylether, 1-dodecylazacycloheptan-2-one, and dimethylsulfoxide (DMSO). Such compositions will also typically include ointment bases, e.g., petrolatum, polyethylene glycol, lanolin, and poloxamer, which is a block copolymer of polyoxyethylene and polyoxypropylene, which may also serve as a surfactant or emulsifying agent.

Preservatives are used to protect pharmaceutical compositions of the present invention from degradative attack by ambient microorganisms, and include, e.g., benzalkonium chloride, benzethonium chloride, alkyl esters of p-hydroxybenzoic acid, hydantoin derivatives, cetylpyridinium chloride, monothioglycerol, phenol, phenoxyethanol, methylparagen, imidazolidinyl urea, sodium dehydroacetate, propylparaben, quaternary ammonium compounds, especially polymers such as polixetonium chloride, potassium benzoate, sodium formaldehyde sulfoxylate, sodium propionate, and thimerosal.

Sequestering agents are used to improve the stability of the pharmaceutical compositions of the present invention and include, e.g., the cyclodextrins which are a family of natural cyclic oligosaccharides capable of forming inclusion complexes with a variety of materials, and are of varying ring sizes, those having 6-, 7- and 8-glucose residues in a ring being commonly referred to as α-cyclodextrins, β-cyclodextrins, and γ-cyclodextrins, respectively. Suitable cyclodextrins include, e.g., α-cyclodextrin, β-cyclodextrin, γ-cyclodextrin, δ-cyclodextrin and cationized cyclodextrins.

Solvents which may be used in preparing the pharmaceutical compositions of the present invention include, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water.

Stabilizers which are suitable for use include, e.g., calcium saccharate and thymol.

Stiffening agents are typically used in formulations for topical applications in order to provide desired viscosity and handling characteristics and include, e.g., cetyl esters wax, myristyl alcohol, parafin, synthetic parafin, emulsifying wax, microcrystalline wax, white wax and yellow wax.

Sugars are often used to impart a variety of desired characteristics to the pharmaceutical compositions of the present invention and in order to improve the results obtained, and include, e.g., monosaccharides, disaccharides and polysaccharides such as glucose, xylose, fructose, reose, ribose, pentose, arabinose, allose, tallose, altrose, mannose, galactose, lactose, sucrose, erythrose, glyceraldehyde, or any combination thereof.

Surfactants are employed to provide stability for multi-component pharmaceutical compositions of the present invention, enhance existing properties of those compositions, and bestow desirable new characteristics on said compositions. Surfactants are used as wetting agents, antifoam agents, for reducing the surface tension of water, and as emulsifiers, dispersing agents and penetrants, and include, e.g., lapyrium chloride; laureth 4, i.e., α-dodecyl-ω-hydroxy-poly(oxy-1,2-ethanediyl) or polyethylene glycol monododecyl ether; laureth 9, i.e., a mixture of polyethylene glycol monododecyl ethers averaging about 9 ethylene oxide groups per molecule; monoethanolamine; nonoxynol 4, 9 and 10, i.e., polyethylene glycol mono(p-nonylphenyl)ether;

nonoxynol 15, i.e., α-(p-nonylphenyl)-ω-hydroxypentadeca(oxyethylene); nonoxynol 30, i.e., α-(p-nonylphenyl)-ω-hydroxytriaconta(oxyethylene); poloxalene, i.e., nonionic polymer of the polyethylene-polypropylene glycol type, MW=approx. 3000; poloxamer, referred to in the discussion of ointment bases further above; polyoxyl 8, 40 and 50 stearate, i.e., poly(oxy-1,2-ethanediyl), α-hydro-ω-hydroxy-; octadecanoate; polyoxyl 10 oleyl ether, i.e., poly(oxy-1,2-ethanediyl), α-[(Z)-9-octadecenyl-ω-hydroxy-; polysorbate 20, i.e., sorbitan, monododecanoate, poly(oxy-1,2-ethanediyl); polysorbate 40, i.e., sorbitan, monohexadecanoate, poly(oxy-1,2-ethanediyl); polysorbate 60, i.e., sorbitan, monooctadecanoate, poly(oxy-1,2-ethanediyl); polysorbate 65, i.e., sorbitan, trioctadecanoate, poly(oxy-1,2-ethanediyl); polysorbate 80, i.e., sorbitan, mono-9-monodecenoate, poly(oxy-1,2-ethanediyl); polysorbate 85, i.e., sorbitan, tri-9-octadecenoate, poly(oxy-1,2-ethanediyl); sodium lauryl sulfate; sorbitan monolaurate; sorbitan monooleate; sorbitan monopalmitate; sorbitan monostearate; sorbitan sesquioleate; sorbitan trioleate; and sorbitan tristearate.

The pharmaceutical compositions of the present invention may be prepared using very straightforward methodology which is well understood by the artisan of ordinary skill. Where the pharmaceutical compositions of the present invention are simple aqueous and/or other solvent solutions, the various components of the overall composition are brought together in any practical order, which will be dictated largely by considerations of convenience. Those components having reduced water solubility, but sufficient solubility in the same co-solvent with water, may all be dissolved in said co-solvent, after which the co-solvent solution will be added to the water portion of the carrier whereupon the solutes therein will become dissolved in the water. To aid in this dispersion/solution process, a surfactant may be employed.

Where the pharmaceutical compositions of the present invention are to be in the form of emulsions, the components of the pharmaceutical composition will be brought together in accordance with the following general procedures. The continuous water phase is first heated to a temperature in the range of from about 60° to about 95° C., preferably from about 70° to about 85° C., the choice of which temperature to use being dependent upon the physical and chemical properties of the components which make up the oil-in-water emulsion. Once the continuous water phase has reached its selected temperature, the components of the final composition to be added at this stage are admixed with the water and dispersed therein under high-speed agitation. Next, the temperature of the water is restored to approximately its original level, after which the components of the composition which comprise the next stage are added to the composition mixture under moderate agitation and mixing continues for from about 5 to about 60 minutes, preferably about 10 to about 30 minutes, depending on the components of the first two stages. Thereafter, the composition mixture is passively or actively cooled to from about 20° to about 55° C. for addition of any components in the remaining stages, after which water is added in sufficient quantity to reach its original predetermined concentration in the overall composition.

According to the present invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Rh, HCIX or similar alcohol.

The pharmaceutical compositions of the present invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the present invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate, cetyl esters wax, cetearyl alcohol, 2-octyldodecanol, benzyl alcohol and water.

Pharmaceutical compositions within the scope of the present invention include those wherein the therapeutically effective amount of an active ingredient comprising a compound of the present invention required for treating or preventing diseases, disorders, and conditions mediated by or associated with modulation of PDE4, especially PDE4D activity as described herein, is provided in a dosage form suitable for systemic administration. Such a pharmaceutical composition will contain said active ingredient in suitable liquid form for delivery by: (1) injection or infusion which is intraarterial, intra- or transdermal, subcutaneous, intramuscular, intraspinal, intrathecal, or intravenous, wherein said active ingredient: (a) is contained in solution as a solute; (b) is contained in the discontinuous phase of an emulsion, or the discontinuous phase of an inverse emulsion which inverts upon injection or infusion, said emulsions containing suitable emulsifying agents; or (c) is contained in a suspension as a suspended solid in colloidal or microparticulate form, said suspension containing suitable suspending agents; (2) injection or infusion into suitable body tissues or cavities as a depot, wherein said composition provides storage of said active ingredient and thereafter delayed-, sustained-, and/or controlled-release of said active ingredient for systemic distribution; (3) instillation, inhalation or insufflation into suitable body tissues or cavities of said pharmaceutical composition in suitable solid form, where said active ingredient: (a) is contained in a solid implant composition providing delayed-, sustained-, and/or controlled-release of said active ingredient; (b) is contained in a particulate composition to be inhaled into the lungs; or (c) is contained in a particulate composition to be blown into suitable body tissues or cavities, where said composition optionally provides delayed-, sustained-, and/or controlled-release of said active ingredient; or (4) ingestion of said pharmaceutical composition in suitable solid or liquid form for peroral delivery of said active ingredient, where said active ingredient is contained in a solid dosage form; or (b) is contained in a liquid dosage form.

Particular dosage forms of the above-described pharmaceutical compositions include (1) suppositories as a special type of implant, comprising bases which are solid at room temperature but melt at body temperature, slowly releasing the active ingredient with which they are impregnated into the surrounding tissue of the body, where the active ingredient becomes absorbed and transported to effect systemic administration; (2) solid peroral dosage forms selected from the group consisting of (a) delayed-release oral tablets, capsules, caplets, lozenges, troches, and multiparticulates; (b) enteric-coated tablets and capsules which prevent release and absorption in the stomach to facilitate delivery distal to the stomach of the patient being treated; (c) sustained-release oral tablets, capsules and microparticulates which provide systemic delivery of the active ingredient in a controlled manner up to a 24-hour period; (d) fast-dissolving tablets; (e) encapsulated solutions; (f) an oral paste; (g) a granular form incorporated in or to be incorporated in the food of a patient being treated; and (h) liquid peroral dosage forms selected from the group consisting of solutions, suspensions, emulsions, inverse emulsions, elixirs, extracts, tinctures, and concentrates.

Pharmaceutical compositions within the scope of the present invention include those wherein the therapeutically effective amount of an active ingredient comprising a compound of the present invention required for treating or preventing diseases, disorders, and conditions mediated by or associated with modulation of PDE4, especially PDE4D activity as described herein is provided in a dosage form suitable for local administration to a patient being treated, wherein said pharmaceutical composition contains said active ingredient in suitable liquid form for delivering said active ingredient by: (1) injection or infusion into a local site which is intraarterial, intraarticular, intrachondrial, intracostal, intracystic, intra- or transdermal, intrafasicular, intraligamentous, intramedulary, intramuscular, intranasal, intraneural, intraocular, i.e., opthalmic administration, intraosteal, intrapelvic, intrapericardial, intraspinal, intrasternal, intrasynovial, intratarsal, or intrathecal; including components which provide delayed-release, controlled-release, and/or sustained-release of said active ingredient into said local site; where said active ingredient is contained: (a) in solution as a solute; (b) in the discontinuous phase of an emulsion, or the discontinuous phase of an inverse emulsion which inverts upon injection or infusion, said emulsions containing suitable emulsifying agents; or (c) in a suspension as a suspended solid in colloidal or microparticulate form, said suspension containing suitable suspending agents; or (2) injection or infusion as a depot for delivering said active ingredient to said local site; wherein said composition provides storage of said active ingredient and thereafter delayed-, sustained-, and/or controlled-release of said active ingredient into said local site, and wherein said composition also includes components which ensure that said active ingredient has predominantly local activity, with little systemic carryover activity; or wherein said pharmaceutical composition contains said active ingredient in suitable solid form for delivering said inhibitor by: (3) instillation, inhalation or insufflation to said local site, where said active ingredient is contained: (a) in a solid implant composition which is installed in said local site, said composition optionally providing delayed-, sustained-, and/or controlled-release of said active ingredient to said local site; (b) in a particulate composition which is inhaled into a local site comprising the lungs; or (c) in a particulate composition which is blown into a local site, where said composition includes components which will ensure that said active ingredient has predominantly local activity, with insignificant systemic carryover activity, and optionally provides delayed-, sustained-, and/or controlled-release of said active ingredient to said local site. For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of the present invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

As already mentioned, the active ingredients of Formula (1.0.0) of the present invention may be administered systemically to a patient to be treated as a pharmaceutical composition in suitable liquid form by injection or infusion. There are a number of sites and organ systems in the body of the patient which will allow the properly formulated pharmaceutical composition, once injected or infused, to permeate the entire body and all of the organ system of the patient being treated. An injection is a single dose of the pharmaceutical composition forced, usually by a syringe, into the tissue involved. The most common types of injections are intramuscular, intravenous, and subcutaneous. By contrast, an infusion is the gradual introduction of the pharmaceutical composition into the tissue involved. The most common type of infusion is intravenous. Other types of injection or infusion comprise intraarterial, intra- or transdermal (including subcutaneous), or intraspinal especially intrathecal. In these liquid pharmaceutical compositions, the active ingredient may be contained in solution as the solute. This is the most common and most preferred type of such composition, but requires an active ingredient in a salt form that has reasonably good aqueous solubility. Water (or saline) is by far the most preferred solvent for such compositions. Occasionally supersaturated solutions may be utilized, but these present stability problems that make them impractical for use on an everyday basis.

If it is not possible to obtain a form of some compound of Formula (1.0.0) that has the requisite degree of aqueous solubility, as may sometimes occur, it is within the skill of the artisan to prepare an emulsion, which is a dispersion of small globules of one liquid, the discontinuous or internal phase, throughout a second liquid, the continuous or external phase, with which it is immiscible. The two liquids are maintained in an emulsified state by the use of emulsifiers which are pharmaceutically acceptable. Thus, if the active ingredient is a water-insoluble oil, it can be administered in an emulsion of which it is the discontinuous phase. Also where the active ingredient is water-insoluble but can be dissolved in a solvent which is immiscible with water, an emulsion can be used. While the active ingredient would most commonly be used as the discontinuous or internal phase of what is referred to as an oil-in-water emulsion, it could also be used as the discontinuous or internal phase of an inverse emulsion, which is commonly referred to as a water-in-oil emulsion. Here the active ingredient is soluble in water and could be administered as a simple aqueous solution. However, inverse emulsions invert upon injection or infusion into an aqueous medium such as the blood, and offer the advantage of providing a more rapid and efficient dispersion of the active ingredient into that aqueous medium than can be obtained using an aqueous solution. Inverse emulsions are prepared by using suitable, pharmaceutically acceptable emulsifying agents well known in the art. Where the active ingredient has limited water solubility, it may also be administered as a suspended solid in colloidal or microparticulate form in a suspension prepared using suitable, pharmaceutically acceptable suspending agents. The suspended solids containing the active ingredient may also be formulated as delayed-, sustained-, and/or controlled-release compositions.

While systemic administration will most frequently be carried out by injection or infusion of a liquid, there are many situations in which it will be advantageous or even necessary to deliver the active ingredient as a solid. Systemic administration of solids is carried out by instillation, inhalation or insufflation of a pharmaceutical composition in suitable solid form containing the active ingredient. Instillation of the active ingredient may entail installing a solid implant composition into suitable body tissues or cavities. The implant may comprise a matrix of bio-compatible and bio-erodible materials in which particles of a solid active ingredient are dispersed, or in which, possibly, globules or isolated cells of a liquid active ingredient are entrapped. Desirably, the matrix will be broken down and completely absorbed by the body. The composition of the matrix is also preferably selected to provide controlled-, sustained-, and/or delayed release of the active ingredient over extended periods of time, even as much as several months.

The term "implant" most often denotes a solid pharmaceutical composition containing the active ingredient, while the term "depot" usually implies a liquid pharmaceutical composition containing the active ingredient, which is deposited in any suitable body tissues or cavities to form a reservoir or pool which slowly migrates to surrounding tissues and organs and eventually becomes systemically distributed. However, these distinctions are not always rigidly adhered to in the art, and consequently, it is contemplated that there is included within the scope of the present invention liquid implants and solid depots, and even mixed solid and liquid forms for each. Suppositories may be regarded as a type of implant, since they comprise bases which are solid at room temperature but melt at a patient's body temperature, slowly releasing the active ingredient with which they are impregnated into the surrounding tissue of the patient's body, where the active ingredient becomes absorbed and transported to effect systemic administration.

Systemic administration can also be accomplished by inhalation or insufflation of a powder, i.e., particulate composition containing the active ingredient. For example, the active ingredient in powder form may be inhaled into the lungs using conventional devices for aerosolizing particulate formulations. The active ingredient as a particulate formulation may also be administered by insufflation, i.e., blown or otherwise dispersed into suitable body tissues or cavities by simple dusting or using conventional devices for aerosolizing particulate formulations. These particulate compositions may also be formulated to provide delayed-, sustained-, and/or controlled-release of the active ingredient in accordance with well understood principles and known materials.

Other means of systemic administration which may utilize the active ingredients of the present invention in either liquid or solid form include transdermal, intranasal, and opthalmic routes. In particular, transdermal patches prepared in accordance with well known drug delivery technology may be prepared and applied to the skin of a patient to be treated, whereafter the active agent by reason of its formulated solubility characteristics migrates across the epidermis and into the dermal layers of the patient's skin where it is taken up as part of the general circulation of the patient, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology, and may be prepared in such a way as to provide controlled-, sustained-, and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

In the above description of pharmaceutical compositions containing an active ingredient of Formula (1.0.0), the equivalent expressions: "administration", "administration of", "administering", and "administering a" have been used with respect to said pharmaceutical compositions. As thus employed, these expressions are intended to mean providing to a patient in need of treatment a pharmaceutical composition of the present invention by any of the routes of administration herein described, wherein the active ingredient is a compound of Formula (1.0.0) or a prodrug, derivative, or metabolite thereof which is useful in treating a disease, disorder, or condition mediated by or associated with modulation of PDE4, especially PDE4D activity in said patient. Accordingly, there is included within the scope of the present invention any other compound which, upon administration to a patient, is capable of directly or indirectly providing a compound of Formula (1.0.0). Such compounds are recognized as prodrugs, and a number of established procedures are available for preparing such prodrug forms of the compounds of Formula (1.0.0).

The dosage and dose rate of the compounds of Formula (1.0.0) effective for treating or preventing a disease, disorder, or condition mediated by or associated with modulation of PDE4, especially PDE4D activity, will depend on a variety of factors, such as the nature of the inhibitor, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the compounds of Formula (1.0.0) will be between about 0.1 μg/kg and about 50.0 mg/kg body weight per day, preferably between about 5.0 μg/kg and about 5.0 mg/kg body weight per day, more preferably between about 10.0 μg/kg and about 1.0 mg/kg of body weight per day, and most preferably between about 20.0 μg/kg and about 0.5 mg/kg of body weight per day of the active ingredient.

Where the dosage form is topically administered to the bronchia and lungs, e.g., by means of a powder inhaler or nebulizer, suitable dosage levels of the compounds of Formula (1.0.0) will be between about 0.001 μg/kg and about 10.0 mg/kg body weight per day, preferably between about 0.5 μg/kg and about 0.5 mg/kg body weight per day, more preferably between about 1.0 μg/kg and about 0.1 mg/kg of body weight per day, and most preferably between about 2.0 μg/kg and about 0.05 mg/kg of body weight per day of the active ingredient.

Using representative body weights of 10 kg and 100 kg in order to illustrate the range of daily aerosolized topical dosages which might be used as described above, suitable dosage levels of the compounds of Formula (1.0.0) will be between about 1.0–10.0 μg and 500.0–5000.0 mg per day, preferably between about 5.0–50.0 μg and 5.0–50.0 mg per day, more preferably between about 100.0–1000.0 μg and 10.0–100.0 mg per day, and most preferably between about 200.0–2000.0 μg and about 5.0–50.0 mg per day of the active ingredient comprising a compound of Formula (1.0.0). These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy Numerous other factors must also be considered in deciding upon the number of doses per day and the amount of active ingredient per dose that will be administered. Not the least important of such other factors is the individual response of the patient being treated. Thus, for example, where the active ingredient is used to treat or prevent asthma, and is administered topically via aerosol inhalation into the lungs, from one to four doses consisting of acuations of a dispensing device, i.e., "puffs" of an inhaler, will be administered each day, each dose containing from about 50.0 μg to about 10.0 mg of active ingredient.

DETAILED DESCRIPTION OF THE INVENTION 11.0 Preparations and Working Examples

Preparation 1a

2-[Benzo[2,1,3]oxadiazol-5-yloxy]-nicotinic acid ethyl ester of Formula (5.0.1)

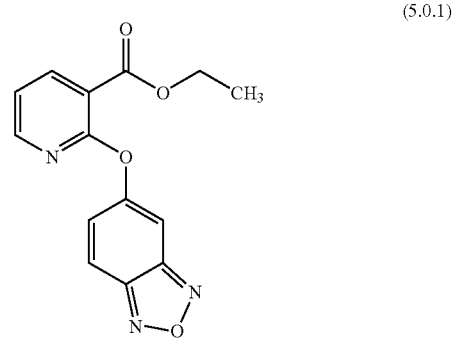

(5.0.1)

A mixture of 5.5 g (29.4 mmol.) 2-chloro nicotinic acid ethyl ester, 4.0 g (29.4 mmol.) 5-hydroxybenzofurazan and 20.1 g (61.7 mmol.) cesium carbonate in 125 ml dry dimethylforamide was heated at 90° C. for five days. The mixture was poured into water and extracted with ethyl acetate. The ethyl acetate extracts were combined, washed successively with sodium bicarbonate solution, water, brine then dried ($Na_2SO_4$) and concentrated in vacuo to give a solid. Recrystallization from diethyl ether/pentane gave 2.2 g (26%) solid.

$^1$H-NMR ($CDCl_3$): δ 8.3 (m, 2H), 7.8 (d, 1H, J=10 Hz), 7.2 (m, 3H), 4.4 (q, 2H, J=7 Hz), 1.4 (t, 3H, J=7 Hz).

GC-MS (m/z): 285 ($M^+$, 20), 122 (100).

Preparation 1b

2-[Benzo[2,1,3]oxadiazol-5-yloxy]-nicotinic acid of Formula (5.0.2)

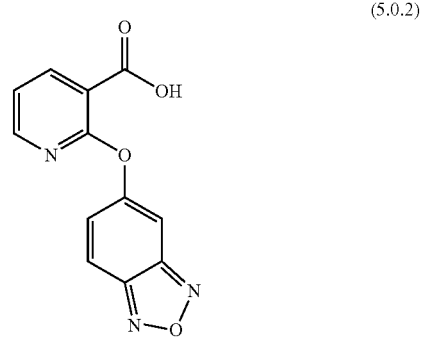

(5.0.2)

A mixture of 2.2 g (7.7 mmol.) 2-[benzo[2,1,3]oxadiazol-5-yloxy]-nicotinic acid ethyl ester and 23.1 ml (23.1 mmol.) 1M LiOH in 75 ml tetrahydrofuran was stirred overnight at room temperature. The tetrahydrofuran was evaporated in vacuo and the aqueous mixture acidified with 1N HCl. The resulting precipitate was filtered and dried to give 1.9 g (96%) solid.

¹H-NMR (CH₃OD): δ 8.4 (d, 1H, J=8 Hz), 8.3 (dd, 1H, J=2, 5 Hz), 8.0 (d, 1H, J=9 Hz), 7.6 (s, 1H), 7.5 (d, 1H, J=9 Hz), 7.2 (dd, 1H, 5, 8 Hz).

MS (m/z): 257 (M⁺, 20), 256 (100).

Preparation 2

Benzo-[2,1,3]-thiadiazol-5-ol of Formula (5.0.3)

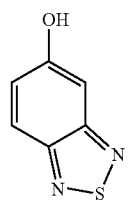

(5.0.3)

5-Methoxybenzo-2,1,3-thiadiazole (4.09 g, 24.6 mmol) was stirred with hydrobromic acid (60 mL, 165 mmol, 30% in acetic acid) at 80° C. 5 days. The mixture was cooled to 10° C. and filtered. The solids were purified by short column chromatography (50% ethyl acetate/hexane). Solvents were stripped in vacuo to afford 1.0 g of a yellow solid (27% yield).

¹H NMR (CD₃OD): δ 7.81 (d, 1H, J=2 Hz), 7.79 (d, 1H, J=2 Hz), 7.30 (s, 1H).

Preparation 3

2-(Benzo[2,1,3]thiadiazol-5-yloxy)-nicotinic acid ethyl ester of Formula (5.0.4)

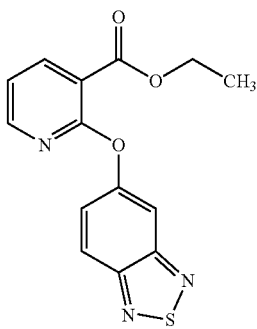

(5.0.4)

A mixture of 2-chloro-nicotinic acid ethyl ester (0.516 g, 3 mmol), benzo-[2,1,3]-thiadiazol-5-ol (0.46 g, 3 mmol) and cesium carbonate (2.07 g, 6.3 mmol) was stirred in 40 mL N,N-dimethylformamide at 80° C. for 48 hours. The dark orange mixture was cooled and poured into water (600 mL) and extracted with ethyl acetate. The combined organic layers were washed with water and brine, and dried (Na₂SO₄). The mixture was concentrated in vacuo to give 0.74 g yellow solid (82% yield).

MS (m/z): 302 (M⁺, 20), 227 (100).

Preparation 4

2-(Benzo[2,1,3]thiadiazol-5-yloxy)-nicotinic acid of Formula (5.0.5)

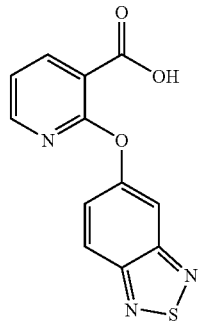

(5.0.5)

A solution of 2-(benzo[2,1,3]thiadiazol-5-yloxy)-nicotinic acid ethyl ester (0.74 g, 2.5 mmol) in tetrahydrofuran (2.78 ml) and 1 M LiOH (2.7 ml) was stirred over night. The mixture was diluted with water and acidified to pH 1 with 2 N hydrochloric acid and filtered to give a pale yellow solid (160 mg).

¹H NMR (CD₃OD): δ 8.37 (d, 1H, J=6 Hz), 8.26 (dd, 1H, J=2 Hz, 5 Hz), 8.00 (d, 1H, J=9 Hz), 7.60 (t, 1H, J=2 Hz), 7.50 (t, 1H, J=2 Hz), 7.26 (d, 1H, J=8 Hz).

Preparation 5

2-(Benzo-[1,3]dioxol-5-yloxy)-nicotinic acid of Formula (5.0.6)

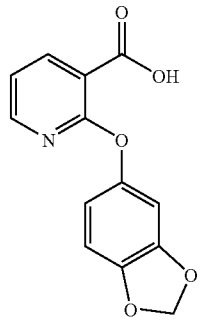

(5.0.6)

2-Chloro-nicotinic acid ethyl ester (10 g), benzo[1,3]dioxol-5-ol (sesamol, 8.2 g), and cesium carbonate (21 g) were mixed in anhydrous dioxane (40 mL) and the resulting slurry heated to reflux for 16 h. In a separate flask, lithium hydroxide (12.9 g) was dissolved in water (80 mL) with warming and then added to the refluxing mixture, which was heated for an additional 4 h. The mixture was cooled to ambient temperature and concentrated in vacuo to remove the dioxane. Concentrated hydrochloric acid was added dropwise until the pH=3. The acidified solution was then extracted with ethyl acetate (7×100 mL) to yield crude product, which was recrystallized from ethyl acetate to yield the purified title compound (10.8 g).

$^1$H NMR (CD$_3$OD): δ 8.28 (dd, J=8 and 2 Hz, 2H), 7.13 (m, 1H), 6.79 (d, J=8 Hz, 1H), 6.62 (s, J=2 Hz, 1H), 6.53 (dd, J=8 and 2 Hz, 1H), 5.95 (s, 2H).

Preparation 6

2-(Benzo[1,3]dioxol-5-yloxy)-5-fluoro-nicotinic acid of Formula (5.0.7)

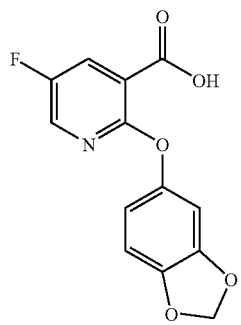
(5.0.7)

2-Chloro-5-fluoro-nicotinic acid (synthesized in accordance with the procedures described in European patent: EP 0634413 A1) was converted to the corresponding ethyl ester with anhydrous ethanol and excess thionyl chloride, then worked up in the usual manner. To 2-chloro-5-fluoro-nicotinic acid ethyl ester (5.0 g) in an oven-dried 250 mL flask was added cesium carbonate (9.60 g), sesamol (4.07 g), and 50 mL of anhydrous dioxane. The reaction was stirred overnight at 100° C. Lithium hydroxide (2.94 g) in 10 mL water was added, and the reaction was again allowed to stir overnight at 100° C. The dioxane was then evaporated under a nitrogen stream. The residue was then taken up in 50 mL water, acidified with conc. hydrochloric acid to pH=3, and extracted with ethyl acetate (3×100 mL). The combined organic extracts were dried over magnesium sulfate, filtered, and concentrated in vacuo. The dried residue was washed with ethyl acetate (20 mL) and dried under high vacuum, giving the title compound (2.96 g).

$^1$H NMR (CD$_3$OD) δ 8.09–8.04 (m, 2H), 6.76 (d, J=9 Hz, 1H), 6.61 (s, 1H), 6.51 (d, J=7, 1H), 5.93 (s, 2H).

MS m/z 278 (M+H)$^+$.

Preparation 7

2-(4-Fluoro-phenoxy)-nicotinic acid of Formula (5.0.8)

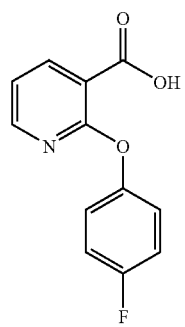
(5.0.8)

2-Chloro-nicotinic acid ethyl ester, 4-fluoro-phenol, and cesium carbonate were mixed in anhydrous dioxane and the resulting slurry heated to reflux for about 16 h. In a separate flask, lithium hydroxide was dissolved in water with warming and then added to the refluxing mixture, which was heated for an additional 4 h. The mixture was cooled to ambient temperature and concentrated in vacuo to remove the dioxane. Concentrated hydrochloric acid was added dropwise until the pH=3. The acidified solution was then extracted with ethyl acetate to yield crude product, which was recrystallized from ethyl acetate to yield the purified title compound (10.8 g).

MS m/z 232 (M–H)$^+$

Preparation 8

2-(3-Cyano-phenoxy)-nicotinic acid of Formula (5.0.9)

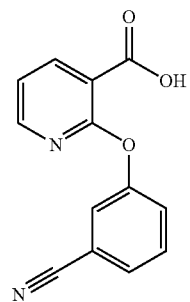
(5.0.9)

The compound of Formula (5.0.9) was prepared in a manner analogous to that described in Preparation 7 above, replacing the 4-fluoro-phenol with 3-cyano-phenol.

Preparation 9

(±)-2-(4-Cyano-3-fluoro-phenoxy)-propionic acid tert-butyl ester of Formula (5.0.10)

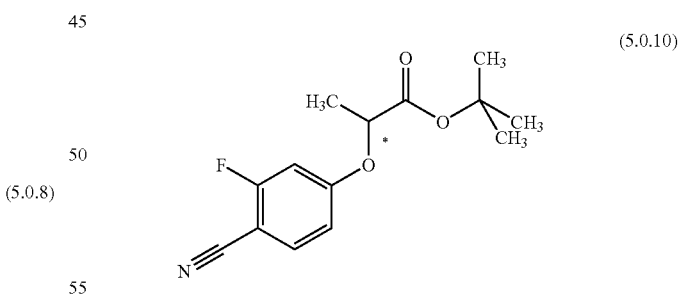
(5.0.10)

2-Fluoro-4-hydroxybenzonitrile (1 g, 7.29 mmol) was dissolved in N,N-dimethyl-formamide (20 mL) and stirred with potassium carbonate (1.1 g, 8.0 mmol) at rt for 2 h. (±) 2-Bromopropionic acid tert-butyl ester (1.67 g, 8.0 mmol) was added and the reaction was stirred at rt for 72 hours. The reaction was quenched into dilute aqueous hydrochloric acid and extracted 2× with ethyl acetate. The pooled organics were dried (Na$_2$SO$_4$) and adsorbed onto silica gel, followed by purification by flash column chromatography (20% ethyl acetate/hexane) to afford 1.8 g colorless oil (93% yield).

¹H NMR (CDCl₃): δ 7.48 (t, 1H, J=7.5 Hz), 6.68 (d, 1H, J=9 Hz), 6.64 (d, 1H, J=11 Hz), 4.55 (q, 1H, J=7 Hz), 1.58 (d, 3H, J=7 Hz), 1.41 (s, 9H).

Preparation 10

(±)-2-(4-Aminomethyl-3-fluoro-phenoxy)-propionic acid tert-butyl ester of Formula (5.0.11)

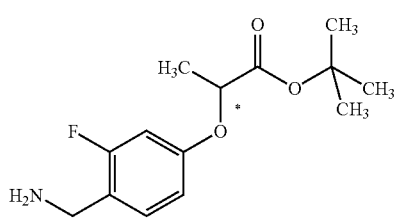

(5.0.11)

(±)-2-(4-Cyano-3-fluoro-phenoxy)-propionic acid tert-butyl ester (1.77 g, 6.7 mmol) was shaken on a Parr shaker under 40 psi hydrogen for 30 min, using palladium hydroxide on carbon (1 g, 30% Pd by wt) in 200 mL anhydrous methanol. The reaction mixture was filtered through sintered glass, and solvents removed in vacuo to afford 1.71 g colorless oil (95% yield).

MS (m/z): 269 (M⁺, 45), 168 (100).

Preparation 11

(R)-2-(4-Cyano-3-fluoro-phenoxy)-propionic acid methyl ester of Formula (5.0.12)

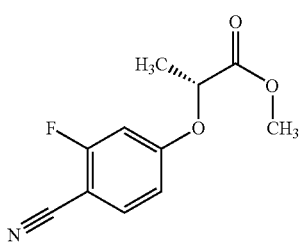

(5.0.12)

To a stirred solution of 2-fluoro-4-hydroxybenzonitrile (0.2 g, 1.5 mmol), methyl (S)-(−)-lactate (0.14 mL, 1.5 mmol) and triphenylphosphine (1.15 g, 4.4 mmol) at room temperature, diethyl azodicarboxylate (0.67 mL, 4.4 mmol) was added dropwise. The mixture was stirred at room temperature overnight, diluted with ethyl acetate and washed successively with dilute aqueous sodium hydroxide, dilute aqueous hydrochloric acid, brine, and dried (Na₂SO₄). Solvents were stripped in vacuo. The resulting oil was washed with diethyl ether and the precipitate was filtered off. The mother liquor was adsorbed onto silica gel and the product purified by flash column chromatography (20% dichloromethane/hexane), affording 0.12 g of a pink oil (36% yield).

¹H NMR (CDCl₃): δ 7.51 (t, 1H, J=7.5 Hz), 6.71 (d, 1H, J=9 Hz), 6.67 (d, 1H, J=10 Hz), 4.78 (q, 1H, J=7 Hz), 3.77 (s, 3H), 1.64 (d, 3H, J=7 Hz).

Preparation 12

(R)-2-(4-Aminomethyl-3-fluoro-phenoxy)-propionic acid methyl ester of Formula (5.0.13)

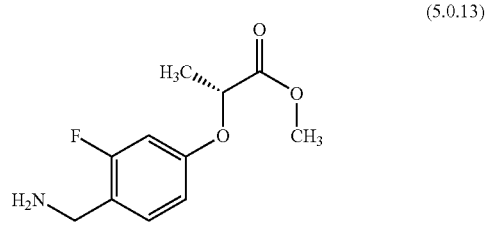

(5.0.13)

The compound of Formula (5.0.13) was prepared in a manner analogous to that described in Preparation 10, substituting (R)-2-(4-cyano-3-fluoro-phenoxy)-propionic acid methyl ester for the corresponding tert-butyl ester material.

¹H NMR (CDCl₃): δ 7.41 (t, 1H, J=8 Hz), 6.90 (br, 2H), 6.58 (m, 2H), 4.69 (q, 1H, J=7 Hz), 4.00 (s, 2H), 3.71 (s, 3H), 1.56 (d, 3H, J=7 Hz).

Preparation 13

(S)-2-(4-Cyano-3-fluoro-phenoxy)-propionic acid methyl ester of Formula (5.0.14)

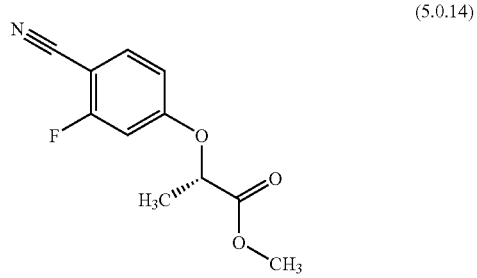

(5.0.14)

The compound of Formula (5.0.14) was prepared in a manner analogous to that described in Preparation 11, substituting methyl (R)-(+)-lactate for the methyl (S)-(−)-lactate.

¹H NMR (CDCl₃): δ 7.51 (t, 1H, J=7.5 Hz), 6.72 (d, 1H, J=9 Hz), 6.67 (d, 1H, J=10 Hz), 4.78 (q, 1H, J=7 Hz), 3.77 (s, 3H), 1.64 (d, 3H, J=7 Hz).

Preparation 14

(S)-2-(4-Aminomethyl-3-fluoro-phenoxy)-propionic acid methyl ester of Formula (5.0.15)

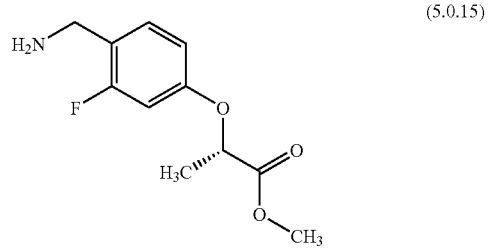

(5.0.15)

The compound of Formula (5.0.15) was prepared in a manner analogous to that described in Preparation 12, based on Preparation 10, substituting (−)-2-(4-cyano-3-fluoro-phenoxy)-propionic acid methyl ester for the corresponding (+) material.

¹H NMR (CDCl₃): δ 7.41 (t, 1H, J=8 Hz), 6.90 (br, 2H), 6.58 (m, 2H), 4.69 (q, 1H, J=7 Hz), 4.00 (s, 2H), 3.71 (s, 3H), 1.56 (d, 3H, J=7 Hz).

Preparation 15

(R)-2-(4-Cyano-3-fluoro-phenoxy)-propionic acid of Formula (5.0.16)

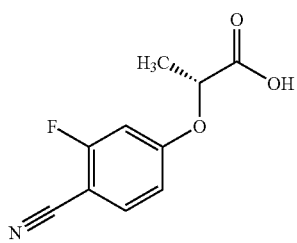

(5.0.16)

To a stirred solution of (R)-2-(4-cyano-3-fluoro-phenoxy)-propionic acid methyl ester (0.40 g, 1.8 mmol) in 50 mL 1:1 tetrahydrofuran/methanol at room temperature was added lithium hydroxide (5.5 mL 1 M aqueous solution, 5.5 mmol) and the solution was stirred over night. The reaction was quenched into dilute aqueous hydrochloric acid and extracted with ethyl acetate. The organic layers were pooled and washed with brine, dried (Na₂SO₄) and concentrated in vacuo to afford a colorless oil (0.37 g, 98%).

¹H NMR (CDCl₃): δ 7.50 (t, 1H, J=7 Hz), 6.69 (m, 2H), 4.81 (q, 1H, J=7 Hz), 1.68 (d, 3H, J=7 Hz).

Preparation 16

(R)-2-(4-Cyano-3-fluoro-phenoxy)-propionic acid tert-butyl ester of Formula (5.0.17)

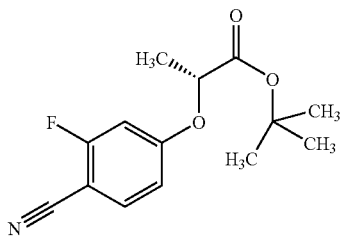

(5.0.17)

A solution of (R)-2-(4-cyano-3-fluoro-phenoxy)-propionic acid (55 mg, 026 mmol) in dry toluene (30 mL) and N,N-dimethylformamide di-tert-butyl acetal (0.25 mL, 1.05 mmol) was stirred at 90° C. 1 hour. The reaction mix was adsorbed onto silica gel and purified by flash column chromatography (30% ethyl acetate/hexane) to afford 51 mg of a white solid (74% yield).

¹H NMR (CDCl₃): δ 7.48 (t, 1H, J=7 Hz), 6.65 (m, 2H), 4.61 (q, 1H, J=7 Hz), 1.58 (d, 3H, J=7 Hz), 1.41 (s, 9H).

Preparation 17

(4-Cyano-3-fluoro-phenoxy)-acetic acid methyl ester of Formula (5.0.18)

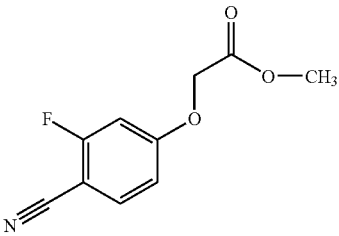

(5.0.18)

The compound of Formula (5.0.18) was prepared in a manner analogous to that described in Preparation 9, substituting bromoacetic acid methyl ester for the bromopropionic acid tert-butyl ester material.

MS (m/z): 209 (M⁺, 100).

Preparation 18

(4-Aminomethyl-3-fluoro-phenoxy)-acetic acid methyl ester of Formula (5.0.19)

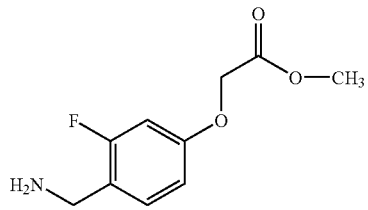

(5.0.19)

The compound of Formula (5.0.19) was prepared in a manner analogous to that described in Preparation 10, substituting (4-cyano-3-fluoro-phenoxy)-acetic acid methyl ester for the corresponding 2-(4-cyano-3-fluoro-phenoxy)-propionic acid tert-butyl ester material.

MS (m/z): 212 (M⁺, 100).

Preparation 19

(R)-2-(4-Aminomethyl-3-fluoro-phenoxy)-propionic acid tert-butyl ester of Formula (5.0.20)

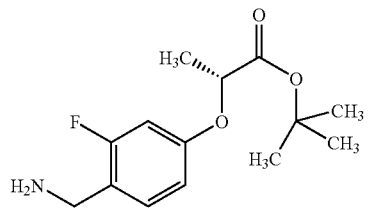

(5.0.20)

The compound of Formula (5.0.20) was prepared in a manner analogous to that described in Preparation 10, substituting (R)-2-(4-Cyano-3-fluoro-phenoxy)-propionic acid tert-butyl ester for the corresponding (+)-2-(4-cyano-3-fluoro-phenoxy)-propionic acid tert-butyl ester material.

¹H NMR (CDCl₃): δ 7.17 (t, 1H, J=9 Hz), 6.55 (t, 2H, J=8 Hz), 4.53 (q, 1H, J=7 Hz), 3.78 (s, 2H), 2.57 (br, 2H), 1.52 (d, 3H, J=7 Hz), 1.39 (s, 9H).

Preparation 20

[4-({[2-(Benzo[1,3]dioxol-5-yloxy)-pyridine-3-carbonyl]-amino}-methyl)-3-fluoro-phenoxy]-acetic acid methyl ester of Formula (5.0.21)

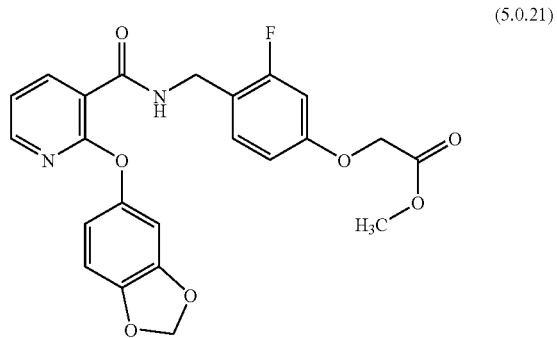

(5.0.21)

2-(Benzo-[1,3]-dioxol-5-yloxy)-nicotinic acid (0.31 g, 1.1 mmol), (4-aminomethyl-3-fluoro-phenoxy)-acid methyl ester (0.46 g, 2.15 mmol), 1-hydroxybenzotriazole hydrate (0.16 g, 1.2 mmol), and 1-[3-(dimethylamino)propyl]-3-ethylcarbodiimide hydrochloride (0.23 g, 1.2 mmol) were dissolved in 1:1 N,N-dimethylformamide/dichloromethane (40 mL) and stirred at room temperature over night. Solvents were removed in vacuo. The residue was taken up in ethyl acetate and washed successively with dilute aqueous hydrochloric acid, dilute aqueous sodium hydroxide, and brine, and dried (Na₂SO₄). The product was purified by flash column chromatography (20% ethyl acetate/hexane) to afford a yellow oil (0.19 g, 38%).

MS (m/z): 455 (M⁺+1, 100).

Preparation 21

(±)-2-[4-({[2-(Benzo[1,3]dioxol-5-yloxy)-pyridine-3-carbonyl]-amino}-methyl)-3-fluoro-phenoxy]-propionic acid tert-butyl ester of Formula (5.0.22)

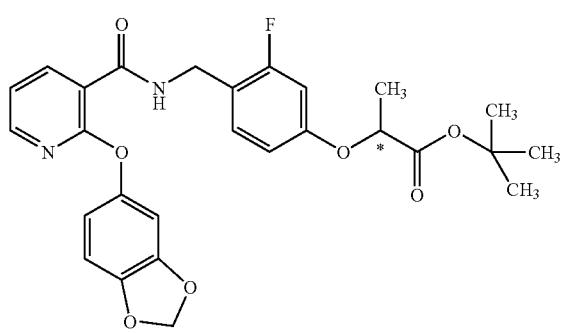

(5.0.22)

The compound of Formula (5.0.22) was prepared in a manner analogous to that described in Preparation 20, substituting (±)-2-(4-aminomethyl-3-fluoro-phenoxy)-propionic acid tert-butyl ester for the (4-aminomethyl-3-fluoro-phenoxy)-acetic acid methyl ester material.

¹H NMR (CDCl₃): δ 8.58 (dd, 1H, J=2 Hz, 8 Hz), 8.19 (dd, 2H, J=2 Hz, 5 Hz), 7.26 (m, 1H), 7.10 (m, 1H), 6.78 (d, 1H, J=8 Hz), 6.63 (d, 1H, J=2 Hz), 6.55 (m, 2H), 5.99 (s, 1H), 4.62 (d, 2H, J=5 Hz), 4.51 (q, 1H, J=7 Hz), 1.53 (d, 3H, J=7 Hz), 1.40 (s, 9H).

Preparation 22

(±)-2-[4-({[2-(Benzo[2,1,3]oxadiazol-5-yloxy)-pyridine-3-carbonyl]-amino}-methyl)-3-fluoro-phenoxy]-propionic acid tert-butyl ester of Formula (5.0.23)

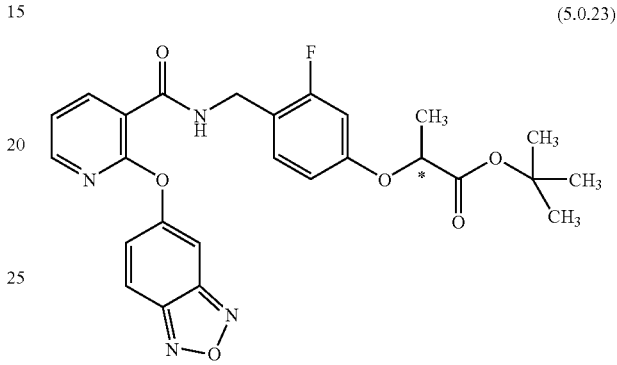

(5.0.23)

The compound of Formula (5.0.23) was prepared in a manner analogous to that described in Preparation 20, substituting 2-(benzo[2,1,3]oxadiazol-5-yloxy)-nicotinic acid and (+)-2-(4-aminomethyl-3-fluoro-phenoxy)-propionic acid tert-butyl ester for the corresponding 2-(benzo-[1,3]-dioxol-5-yloxy)-nicotinic acid and (4-aminomethyl-3-fluoro-phenoxy)-acetic acid methyl ester materials, respectively.

¹H NMR (CDCl₃): δ 8.62 (dd, 1H, J=2 Hz, 5 Hz), 8.18 (dd, 1H, J=2 Hz, 5 Hz), 7.88 (t, 1H, J=5 Hz), 7.85 (dd, 1H, J=1 Hz, 9 Hz), 7.54 (s, 1H), 7.23 (m, 2H), 6.55 (m, 2H), 4.64 (d, 2H, J=6 Hz), 4.52 (q, 1H, J=7 Hz), 1.53 (d, 3H, J=7 Hz), 1.39 (s, 9H).

Preparation 23

(±)-2-[3-Fluoro-4-({[2-(4-fluoro-phenoxy)-pyridine-3-carbonyl]-amino}-methyl)-phenoxy]-propionic acid tert-butyl ester of Formula (5.0.24)

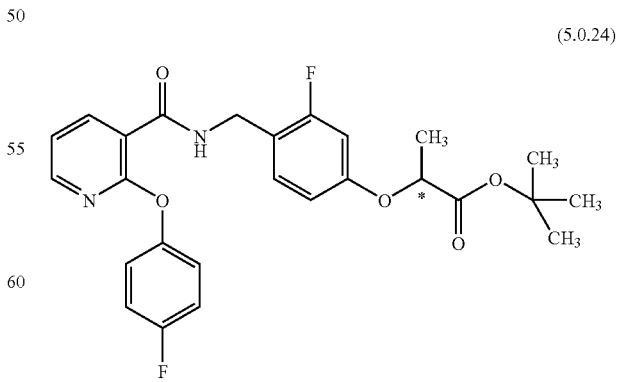

(5.0.24)

The compound of Formula (5.0.24) was prepared in a manner analogous to that described in Preparation 20, substituting 2-(4-fluoro-phenoxy)-nicotinic acid and (±)-2-(4-aminomethyl-3-fluoro-phenoxy)-propionic acid tert-butyl ester for the corresponding 2-(benzo-[1,3]-dioxol-5-yloxy)-nicotinic acid and (4-aminomethyl-3-fluoro-phenoxy)-acetic acid methyl ester materials, respectively.

MS (m/z): 484 (M⁺, 100).

Preparation 24

(±)-2-[3-Fluoro-4-({[2-(3-cyano-phenoxy)-pyridine-3-carbonyl]-amino}-methyl)-phenoxy]-propionic acid tert-butyl ester of Formula (5.0.25)

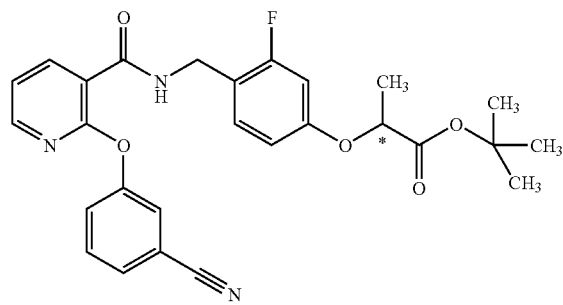
(5.0.25)

The compound of Formula (5.0.25) was prepared in a manner analogous to that described in Preparation 20, substituting 2-(3-cyano-phenoxy)-nicotinic acid and (+)-2-(4-aminomethyl-3-fluoro-phenoxy)-propionic acid tert-butyl ester for the corresponding 2-(benzo-[1,3]-dioxol-5-yloxy)-nicotinic acid and (4-aminomethyl-3-fluoro-phenoxy)-acetic acid methyl ester materials, respectively.

MS (m/z): 491 (M⁺, 100).

Preparation 25

(±)-2-[4-({[2-(Benzo[1,3]dioxol-5-yloxy)-5-fluoro-pyridine-3-carbonyl]-amino}-methyl)-3-fluoro-phenoxy]-propionic acid tert-butyl ester of the Formula (5.0.26)

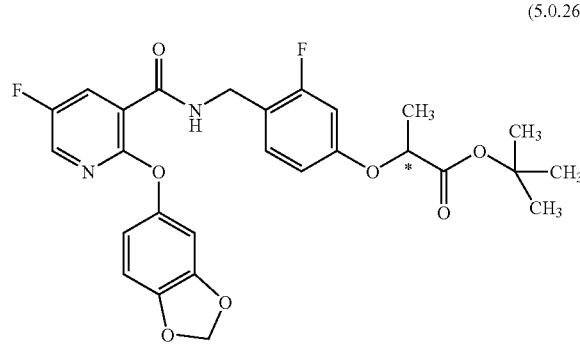
(5.0.26)

The compound of Formula (5.0.26) was prepared in a manner analogous to that described in Preparation 20, substituting 2-(benzo[1,3]dioxol-5-yloxy)-5-fluoro-nicotinic acid and (±)-2-(4-aminomethyl-3-fluoro-phenoxy)-propionic acid tert-butyl ester for the corresponding 2-(benzo-[1, 3]-dioxol-5-yloxy)-nicotinic acid and (4-aminomethyl-3-fluoro-phenoxy)-acetic acid methyl ester materials, respectively.

MS (m/z): 529 (M⁺, 100).

Preparation 26

(±)-2-[4-({[2-(Benzo[2,1,3]thiadiazol-5-yloxy)-pyridine-3-carbonyl]-amino}-methyl)-3-fluoro-phenoxy]-propionic acid tert-butyl ester of the Formula (5.0.27)

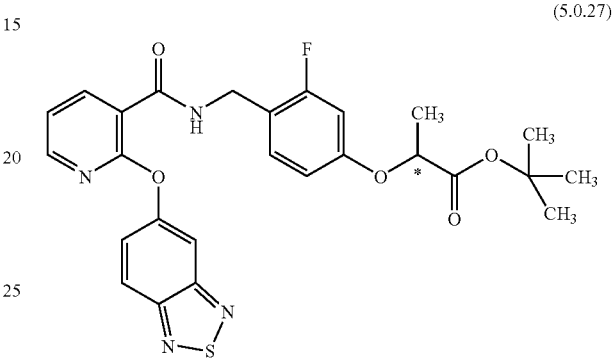
(5.0.27)

The compound of Formula (5.0.27) was prepared in a manner analogous to that described in Preparation 20, substituting 2-(benzo[2,1,3]thiadiazol-5-yloxy)-nicotinic acid and (+)-2-(4-aminomethyl-3-fluoro-phenoxy)-propionic acid tert-butyl ester for the corresponding 2-(benzo-[1,3]-dioxol-5-yloxy)-nicotinic acid and (4-aminomethyl-3-fluoro-phenoxy)-acetic acid methyl ester materials, respectively.

MS (m/z): 524 (M⁺, 100).

Preparation 27

(R)-2-[4-({[2-(Benzo[1,3]dioxol-5-yloxy)-pyridine-3-carbonyl]-amino}-methyl)-3-fluoro-phenoxy]-propionic acid methyl ester of the Formula (5.0.28)

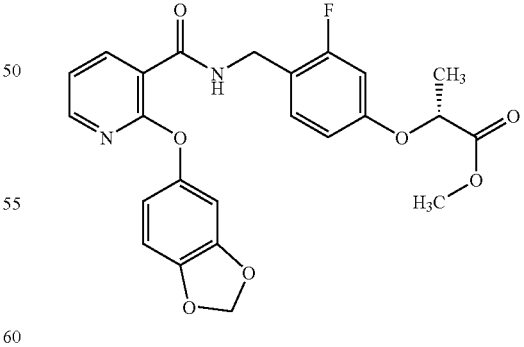
(5.0.28)

The compound of Formula (5.0.28) was prepared in a manner analogous to that described in Preparation 20, substituting (R)-2-(4-aminomethyl-3-fluoro-phenoxy)-propionic acid methyl ester for the corresponding (4-aminomethyl-3-fluoro-phenoxy)-acetic acid methyl ester material.

MS (m/z): 469 (M⁺+1, 20), 455 (M⁺−14, 100).

Preparation 28

(S)-2-[4-({[2-(Benzo[1,3]dioxol-5-yloxy)-pyridine-3-carbonyl]-amino}-methyl)-3-fluoro-phenoxy]-propionic acid methyl ester of the Formula (5.0.29)

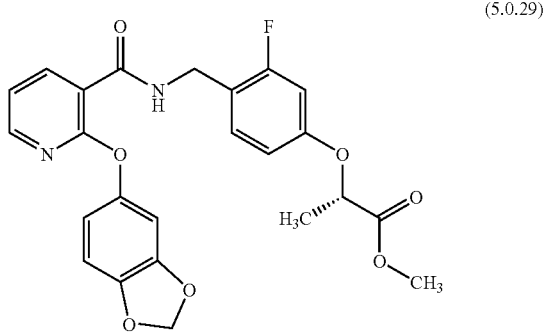

(5.0.29)

The compound of Formula (5.0.29) was prepared in a manner analogous to that described in Preparation 20, substituting (S)-2-(4-aminomethyl-3-fluoro-phenoxy)-propionic acid methyl ester for the corresponding (4-aminomethyl-3-fluoro-phenoxy)-acetic acid methyl ester material.

$^1$H NMR (CDCl$_3$): δ 8.55 (dd, 1H, J=2, 7 Hz), 8.26 (t, 1H, J=5 Hz), 8.19 (dd, 1H, J=2, 5 Hz), 7.27 (t, 1H, J=9 Hz), 7.10 (m, 1H), 6.79 (d, 1H, J=8 Hz), 6.55 (m, 3H), 5.98 (s, 2H), 4.68 (q, 1H, J=6 Hz), 4.61 (d, 2H, J=6 Hz), 3.71 (s, 3H), 1.57 (d, 3H, J=7 Hz).

Preparation 29

(R)-2-[4-({[2-(Benzo[2,1,3]oxadiazol-5-yloxy)-pyridine-3-carbonyl]-amino}-methyl)-3-fluoro-phenoxy]-propionic acid tert-butyl ester of Formula (5.0.30)

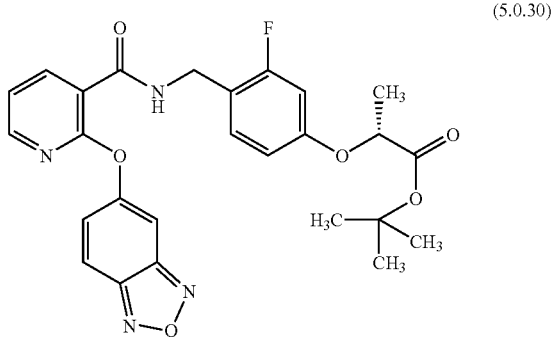

(5.0.30)

The compound of Formula (5.0.30) was prepared in a manner analogous to that described in Preparation 20, substituting 2-(benzo[2,1,3]oxadiazol-5-yloxy)-nicotinic acid and (R)-2-(4-aminomethyl-3-fluoro-phenoxy)-propionic acid tert-butyl ester for the corresponding 2-(benzo-[1,3]-dioxol-5-yloxy)-nicotinic acid and (4-aminomethyl-3-fluoro-phenoxy)-acetic acid methyl ester materials, respectively.

$^1$H NMR (CDCl$_3$): 8.61 (dd, 1H, J=2, 8 Hz), 8.18 (dd, 1H, J=2, 5 Hz), 7.86 (t, 1H, J=9 Hz), 7.84 (d, 1H, J=10 Hz), 7.53 (s, 1H), 7.23 (m, 2H), 6.55 (m, 2H), 4.63 (d, 2H, J=6 Hz), 4.52 (q, 1H, J=7 Hz), 1.52 (d, 3H, J=7 Hz), 1.38 (s, 9H).

Preparation 30

(R)-2-[3-Fluoro-4-({[2-(3-cyano-phenoxy)-pyridine-3-carbonyl]-amino}-methyl)-phenoxy]-propionic acid methyl ester of the Formula (5.0.31)

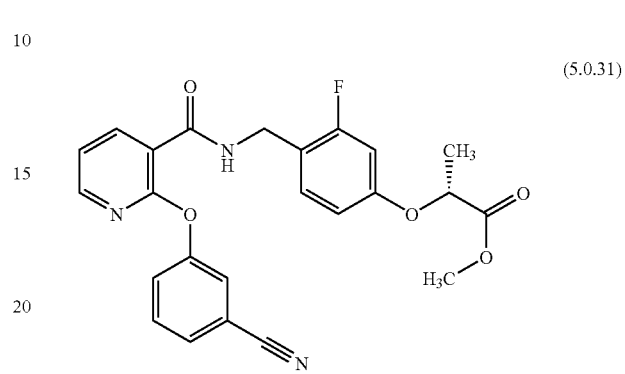

(5.0.31)

The compound of Formula (5.0.31) was prepared in a manner analogous to that described in Preparation 20, substituting 2-(3-cyano-phenoxy)-nicotinic acid and (R)-2-(4-aminomethyl-3-fluoro-phenoxy)-propionic acid methyl ester for the corresponding 2-(benzo-[1,3]-dioxol-5-yloxy)-nicotinic acid and (4-aminomethyl-3-fluoro-phenoxy)-acetic acid methyl ester materials, respectively.

$^1$H NMR (CDCl$_3$): δ 8.59 (dd, 1H, J=2, 8 Hz), 8.15 (dd, 1H, J=2, 5 Hz), 8.00 (t, 1H, J=5 Hz), 7.35 (m, 5H), 6.56 (m, 2H), 4.68 (q, 1H, J=7 Hz), 4.62 (d, 2H, J=6 Hz), 3.71 (s, 3H), 1.57 (d, 3H, J=7 Hz).

Preparation 31

(R)-2-[4-({[2-(Benzo[1,3]dioxol-5-yloxy)-5-fluoro-pyridine-3-carbonyl]-amino}-methyl)-3-fluoro-phenoxy]-propionic acid methyl ester of Formula (5.0.32)

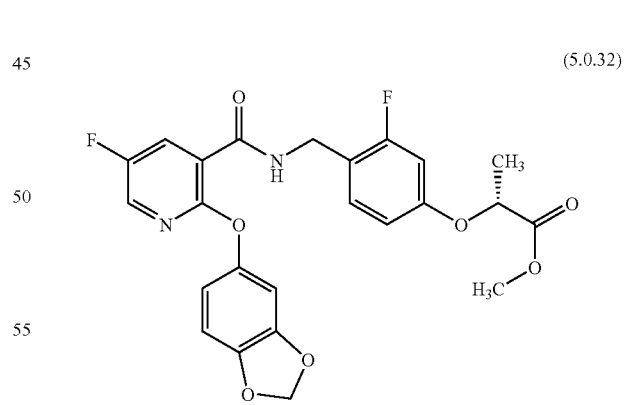

(5.0.32)

The compound of Formula (5.0.32) was prepared in a manner analogous to that described in Preparation 20, substituting 2-(benzo[1,3]dioxol-5-yloxy)-5-fluoro-nicotinic acid and (R)-2-(4-aminomethyl-3-fluoro-phenoxy)-propionic acid methyl ester for the corresponding 2-(benzo-[[1,3]-dioxol-5-yloxy)-nicotinic acid and (4-aminomethyl-3-fluoro-phenoxy)-acetic acid methyl ester materials, respectively.

¹H NMR (CDCl₃): δ 8.32 (dd, 1H, J=3, 8 Hz), 8.26 (s, 1H), 8.02 (d, 1H, J=3 Hz), 7.28 (t, 1H, J=8 Hz), 6.80 (d, 1H, J=8 Hz), 6.56 (m, 3H), 6.00 (s, 2H), 4.68 (q, 1H, J=7 Hz), 4.61 (d, 2H, J=6 Hz), 3.72 (s, 3H), 1.57 (d, 3H, J=7 Hz).

Preparation 32

(R)-2-[4-({[2-(Benzo[2,1,3]thiadiazol-5-yloxy)-pyridine-3-carbonyl]-amino}-methyl)-3-fluoro-phenoxy]-propionic acid methyl ester of Formula (5.0.33)

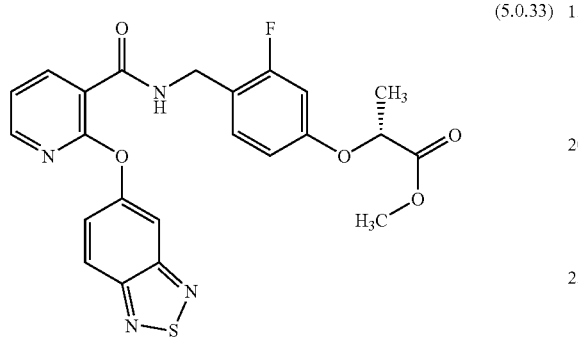

(5.0.33)

The compound of Formula (5.0.33) was prepared in a manner analogous to that described in Preparation 20, substituting 2-(benzo[2,1,3]thia-diazol-5-yloxy)-nicotinic acid and (R)-2-(4-aminomethyl-3-fluoro-phenoxy)-propionic acid methyl ester for the corresponding 2-(benzo-[1,3]-dioxol-5-yloxy)-nicotinic acid and (4-aminomethyl-3-fluoro-phenoxy)-acetic acid methyl ester materials, respectively.

¹H NMR (CDCl₃): δ 8.62 (dd, 1H J=2, 8 Hz), 8.17 (dd, 1H, J=2, 5 Hz), 8.10 (t, 1H, J=5 Hz), 8.00 (dd, 1H, J=1, 10 Hz), 7.74 (d, 1H, J=3 Hz), 7.39 (dd, 1H, J=2, 9 Hz), 7.30 (t, 1H, J=9 Hz), 7.20 (m, 1H), 6.56 (m, 2H), 4.66 (m, 3H), 3.70 (s, 3H), 1.56 (d, 3H, J=7 Hz).

Preparation 33

(R)-2-[4-({[2-(Benzo[1,3]dioxol-5-yloxy)-pyridine-3-carbonyl]-amino}-methyl)-3-fluoro-phenoxy]-propionimidic acid ethyl ester of Formula (5.0.34)

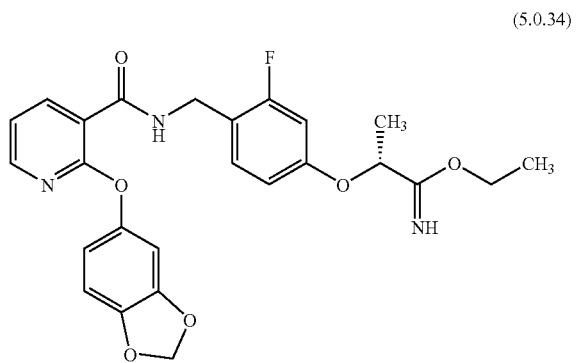

(5.0.34)

To a stirred solution of (R)-2-(benzo[1,3]dioxol-5-yloxy)-N-[4-(1-carbamoyl-ethoxy)-2-fluoro-benzyl]-nicotinamide (0.4 g, 0.88 mmol) in dichloromethane (20 ml)triethyloxonium tetrafluoroborate (0.17 g, 0.88 mmol) was added. The reaction was stirred at room temperature 16 h. The reaction was adsorbed onto a small amount of silica gel and column chromatography (2% methanol/dichloromethane) afforded 160 mg of the desired product as a colorless oil (38% yield).

MS (m/z): 481 (M⁺, 100).

Preparation 34

(R)-2-(Benzo[1,3]dioxol-5-yloxy)-5-fluoro-N-[2-fluoro-4-(1-thiocarbamoyl-ethoxy)-benzyl]-nicotinamide of Formula (5.0.35)

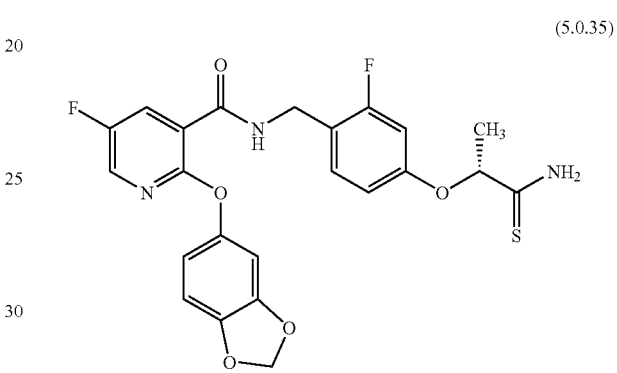

(5.0.35)

A solution of (R)-2-(benzo[1,3]dioxol-5-yloxy)-N-[4-(1-carbamoyl-ethoxy)-2-fluoro-benzyl]-5-fluoro-nicotinamide (1.0 g, 2.12 mmol) and Lawesson's reagent (0.52 g, 1.27 mmol) in dry tetrahydrofuran (10 ml) was stirred at room temperature 2 h. The solvent was removed in vacuo. The residue was adsorbed onto silica gel and purified by column chromatography (20% ethyl acetate/hexane) to afford 1.01 g of a yellow solid (98% yield).

MS (m/z): 486 (M⁺, 100).

Preparation 35

2-(Benzo[1,3]dioxol-5-yloxy)-N-(2-fluoro-4-hydroxy-benzyl)-nicotinamide of Formula (5.0.36)

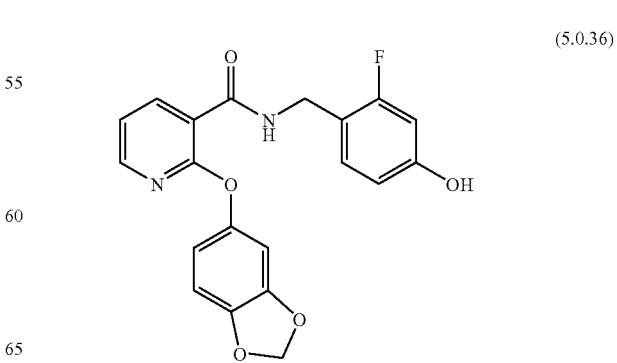

(5.0.36)

A solution of 4-aminomethyl-3-fluoro-phenol hydrochloride (4.75 g, 27 mmol) in N,N-dimethylformamide (20 ml) was added to a stirred solution of 2-(benzo-[1,3]-dioxol-5-yloxy)-nicotinic acid (14 g, 54 mmol), 1-hydroxybenzotriazole hydrate (7.29 g, 54 mmol), 1-[3-(dimethylamino)propyl]-3-ethylcarbodiimide hydrochloride (10.37 g, 54 mmol), and triethylamine (3.76 ml, 27 mmol) in N,N-dimethylformamide (130 ml) at room temperature and stirred over night. The reaction was quenched into dilute aqueous hydrochloric acid and extracted with diethyl ether, then ethyl acetate. The pooled organic layers were washed successively with dilute aqueous sodium hydroxide, water, and brine. The solvents were stripped in vacuo to afford 12.2 g crude. The residue was dissolved in methanol (100 ml) and stirred with lithium hydroxide (10 ml, 1M) for 1 h to hydrolyze the ester of the bis-acylated product. Solvents were stripped in vacuo, the residue was diluted with water (200 ml) and saponified to pH 12 with sodium hydroxide. The precipitate was filtered off, and the filtrate was acidified to pH 1 with concentrated hydrochloric acid and extracted with ethyl acetate (2×200 ml). The pooled organics were washed with 2N sodium carbonate, then brine and dried ($MgSO_4$). The solvents were stripped in vacuo to afford pure product (5.7 g, 14.9 mmol) in 55% yield.

$^1$H NMR ($CDCl_3$): 8.53 (dd, 1H, J=2 Hz, 8 Hz), 8.16 (dd, 1H, J=2 Hz, 5 Hz), 7.11 (m, 2H), 6.78 (d, 1H, J=8 Hz), 6.61 (d, 1H, J=2 Hz), 6.52 (m, 3H), 5.97 (s, 2H), 4.57 (s, 2H).

MS (m/z): 383 ($M^+$+1, 10).

Preparation 36

(±)-2-(Benzo[1,3]dioxol-5-yloxy)-N-[4-(1-cyanoethoxy)-2-fluoro-benzyl]-nicotinamide of Formula (5.0.37)

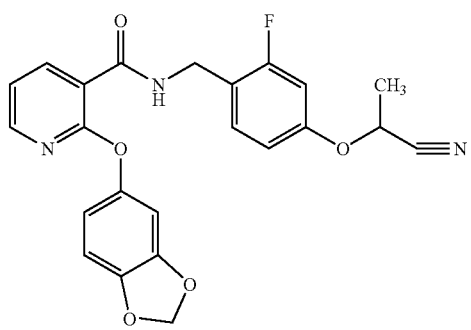

To a stirred solution of 2-(benzo[1,3]dioxol-5-yloxy)-N-(2-fluoro-4-hydroxy-benzyl)-nicotinamide (5 g, 13.1 mmol), (+/−)-lactonitrile (0.93 g, 13.1 mmol) and triphenylphosphine (3.78 g, 14.4 mmol) in tetrahydrofuran (200 mL) at room temperature, diethyl azodicarboxylate (2.3 mL, 14.4 mmol) was added dropwise with stirring. The mixture was stirred at room temperature overnight. Solvents were stripped in vacuo, diluted with ethyl acetate and washed with dilute aqueous sodium hydroxide, brine, and dried ($MgSO_4$). Solvents were stripped in vacuo. The resulting oil was washed with diethyl ether and the precipitate was filtered off. The mother liquor was purified by flash column chromatography (35% ethyl acetate/hexane), affording 1.5 g white solid (26% yield).

$^1$H NMR ($CDCl_3$): 8.59 (d, 1H, J=8 Hz), 8.28 (t, 1H, J=6 Hz), 8.21 (dd, 1H, J=2 Hz, 4 Hz), 7.40 (t, 1H, J=8 Hz), 7.12 (dd, 1H, J=5 Hz, 8 Hz), 6.82 (d, 1H, J=8 Hz), 6.66 (m, 3H), 6.00 (s, 2H), 4.83 (q, 1H, J=7 Hz), 4.66 (d, 2H, J=6 Hz), 1.76 (d, 3H, J=7 Hz).

Preparation 37

(S)-3-(4-Cyano-3-fluoro-phenoxy)-2-methyl-propionic acid methyl ester of Formula (5.0.38)

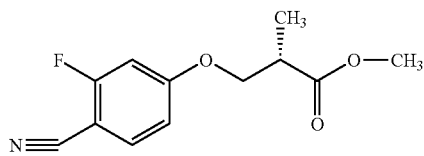

To a stirred solution of 2-fluoro-4-hydroxybenzonitrile (1.0 g, 7.3 mmol), (S)-3-hydroxy-2-methyl-propionic acid methyl ester (0.8 mL, 7.3 mmol) and triphenylphosphine (2.3 g, 8.8 mmol) at room temperature, diethyl azodicarboxylate (1.4 mL, 8.8 mmol) was added dropwise. The mixture was stirred at room temperature overnight, diluted with ethyl acetate and washed successively with dilute aqueous sodium hydroxide, dilute aqueous hydrochloric acid, brine, and dried ($MgSO_4$). Solvents were stripped in vacuo. The resulting oil was washed with diethyl ether and the precipitate was filtered off. The mother liquor was adsorbed onto silica gel and the product purified by flash column chromatography (40% ethyl acetate/hexane), affording 0.14 g of a yellow oil (8% yield).

$^1$H NMR ($CDCl_3$): 7.49 (t, 1H, J=8 Hz), 6.73 (d, 1H, J=9 Hz), 6.70 (d, 1H, J=9 Hz), 4.21 (dd, 1H, J=7, 9 Hz), 4.01 (dd, 1H, J=6, 9 Hz), 3.71 (s, 3H), 2.95 (m, 1H), 1.29 (d, 3H, J=7 Hz).

Preparation 38

(S)-3-(4-Aminomethyl-3-fluoro-phenoxy)-2-methyl-propionic acid methyl ester hydrochloride of Formula (5.0.39)

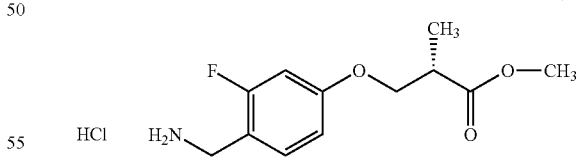

(S)-3-(4-Cyano-3-fluoro-phenoxy)-2-methyl-propionic acid methyl ester (0.14 g) was shaken on a Parr shaker under 50 psi hydrogen for 16 h, using palladium hydroxide on carbon (0.01 g, 30% Pd by wt) in anhydrous methanol (20 mL) and concentrated hydrochloric acid (0.5 mL). The reaction mixture was filtered through sintered glass, and solvents removed in vacuo to afford 0.18 g of a white solid (95% yield).

MS (m/z): 241 ($M^+$, 100).

EXAMPLE 1

[4-({[2-(Benzo[1,3]dioxol-5-yloxy)-pyridine-3-carbonyl]-amino}-methyl)-3-fluoro-phenoxy]-acetic acid of Formula (5.5.1)

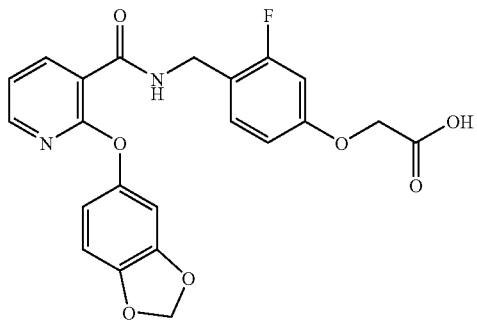

(5.5.1)

To a stirred solution of [4-({[2-(benzo[1,3]dioxol-5-yloxy)-pyridine-3-carbonyl]-amino}-methyl)-3-fluoro-phenoxy]-acetic acid methyl ester (0.40 g, 0.88 mmol) in tetrahydrofuran (10 mL) and methanol (2 mL) was added aqueous lithium hydroxide (2 mL, 1 M, 2 mmol). The reaction was stirred at room temperature 1 hour. The solvents were stripped in vacuo and the residue partitioned between dilute aqueous hydrochloric acid and ethyl acetate. The aqueous was extracted with 2 aliquots ethyl acetate and the pooled organics were washed with brine, dried over sodium sulfate and concentrated in vacuo to afford a yellow solid. The crude product was recrystallized from ethyl acetate to afford 80 mg of a white crystalline solid (0.18 mmol, 21% yield). mp 180° C.

$^1$H NMR (CD$_3$OD): δ 8.52 (dd, 1H, J=2, 8 Hz), 8.24 (br, 1H), 8.16 (dd, 1H, J=2, 5 Hz), 7.29 (t, 1H, J=4 Hz), 7.09 (dd, 1H, J=5, 8 Hz), 6.77 (d, 1H, J=8 Hz), 6.55 (m, 3H), 5.96 (s, 2H), 4.59 (d, 2H, J=6 Hz), 4.52 (s, 2H).

EXAMPLE 2

(±)-2-[4-({[2-(Benzo[1,3]dioxol-5-yloxy)-pyridine-3-carbonyl]-amino}-methyl)-3-fluoro-phenoxy]-propionic acid of Formula (5.5.2)

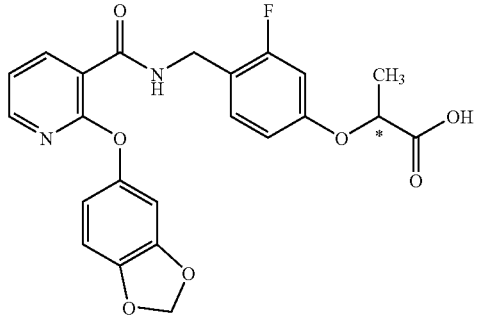

(5.5.2)

The compound of Formula (5.5.2) was prepared in a manner analogous to that described in Example 1, substituting (±)-2-[4-({[2-(benzo[1,3]dioxol-5-yloxy)-pyridine-3-carbonyl]-amino}-methyl)-3-fluoro-phenoxy]-propionic acid tert-butyl ester for the corresponding [4-({[2-(benzo[1,3]dioxol-5-yloxy)-pyridine-3-carbonyl]-amino}-methyl)-3-fluoro-phenoxy]-acetic acid methyl ester material.

mp=136.4–138.0° C.

$^1$H NMR (CDCl$_3$): δ 8.59 (dd, 1H, J=2, 8 Hz), 8.30 (t, 1H, J=6 Hz), 8.21 (dd, 1H, J=2, 5 Hz), 7.30 (t, 1, J=8 Hz), 7.12 (dd, 1H, J=5, 8 Hz), 6.81 (d, 1H, J=8 Hz), 6.60 (s, 2H), 4.74 (q, 1H, J=7 Hz), 4.63 (d, 2H, J=6 Hz), 1.63 (d, 3H, J=7 Hz).

EXAMPLE 3

(±)-2-[4-({[2-(Benzo[2,1,3]oxadiazol-5-yloxy)-pyridine-3-carbonyl]-amino}-methyl)-3-fluoro-phenoxy]-propionic acid of Formula (5.5.3)

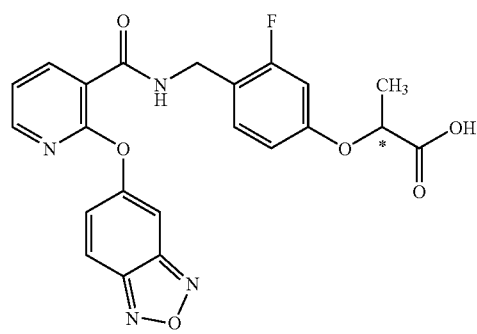

(5.5.3)

(±)-2-[4-({[2-(Benzo[2,1,3]oxadiazol-5-yloxy)-pyridine-3-carbonyl]-amino}-methyl)-3-fluoro- phenoxy]-propionic acid tert-butyl ester (0.17 g, 0.33 mmol) was stirred in formic acid (5 mL) at room temperature 2 hours. Formic acid was removed in vacuo and the product stored over night under high vacuum to afford a white solid (0.12 g, 80% yield).

$^1$H NMR (CDCl$_3$): δ 8.36 (dd, 1H, J=2, 7 Hz), 8.09(dd, 1H, J=2, 5 Hz), 8.03 (br, 1H), 7.75 (d, 1H, J=9 Hz), 7.42 (s, 1H), 7.13 (m, 2H), 6.50 (m, 2H), 4.54 (q, 1H, J=7 Hz), 4.49 (, 1H, J=6 Hz), 1.46 (d, 3H, J=7 Hz).

MS (m/z): 452 (M$^+$, 100).

EXAMPLE 4

(±)-2-[3-Fluoro-4-({[2-(4-fluoro-phenoxy)-pyridine-3-carbonyl]-amino}-methyl)-phenoxy]-propionic acid of Formula (5.5.4)

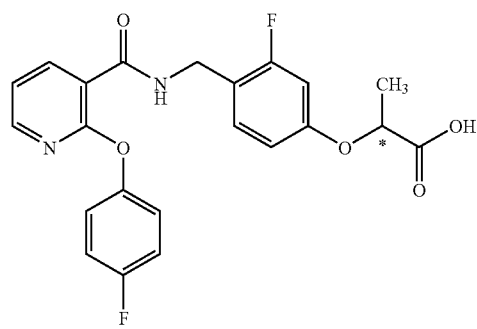

(5.5.4)

The compound of Formula (5.5.4) was prepared in a manner analogous to that described in Example 3, substituting(±)-2-[3-fluoro-4-({[2-(4-fluoro-phenoxy)-pyridine-3-carbonyl]-amino}-methyl) -phenoxy]-propionic acid tert-butyl ester for the corresponding (±)-2-[4-({[2-(benzo[2,1,3]oxadiazol-5-yloxy)-pyridine-3-carbonyl]-amino}-methyl)-3-fluoro-phenoxy]-propionic acid tert-butyl ester material.

¹H NMR (CDCl₃): δ 8.58 (d, 1H, J=7 Hz), 8.26 (s, 1H), 8.16 (d, 1H, J=4 Hz), 7.10 (m, 4H), 6.60 (m, 2H), 4.72 (q, 1H, J=7 Hz), 4.61 (d, 2H, J=6 Hz), 1.62 (d, 3H, J=7 Hz). MS (m/z): 428 (M⁺, 100).

EXAMPLE 5

(±)-2-[3-Fluoro-4-({[2-(3-cyano-phenoxy)-pyridine-3-carbonyl]-amino}-methyl)-phenoxy]-propionic acid of Formula (5.5.5)

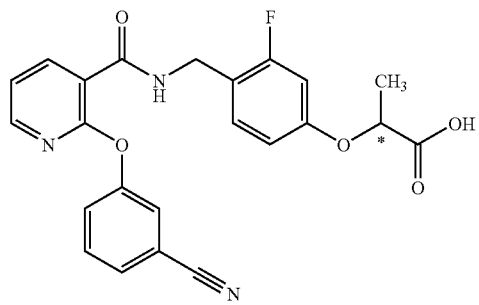

(5.5.5)

The compound of Formula (5.5.5) was prepared in a manner analogous to described in Example 3, substituting (+)-2-[3-fluoro-4-({[2-(3-cyano-phenoxy)-pyridine-3-carbonyl]-amino}-methyl)-phenoxy]-propionic acid tert-butyl ester for the corresponding (±)-2-[4-({[2-(benzo[2,1,3]oxadiazol-5-yloxy)-pyridine-3-carbonyl]-amino}-methyl)-3-fluoro-phenoxy]-propionic acid tert-butyl ester material.

¹H NMR (CDCl₃): δ 8.50(dd, 1H, J=2, 6 Hz), 8.12 (dd, 1H, J=2, 5 Hz), 8.03 (s, 1H), 7.35 (m, 4H), 7.15 (dd, 1H, J=5, 8 Hz), 6.56 (m, 2H), 4.61 (q, 1H, J=7 Hz), 4.57 (d, 2H, J=6 Hz), 1.54 (d, 3H, J=7 Hz).

MS (m/z): 435 (M⁺, 100).

EXAMPLE 6

(±)-2-[4-({[2-(Benzo[1,3]dioxol-5-yloxy)-5-fluoro-pyridine-3-carbonyl]-amino}-methyl)-3-fluoro-phenoxy]-propionic acid of Formula (5.5.6)

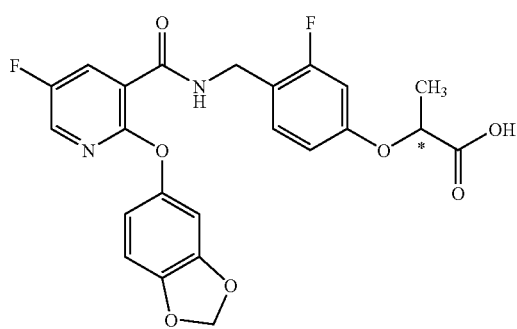

(5.5.6)

The compound of Formula (5.5.6) was prepared in a manner analogous to described in Example 3, substituting (±)-2-[4-({[2-(benzo[1,3]dioxol-5-yloxy)-5-fluoro-pyridine-3-carbonyl]-amino}-methyl)-3-fluoro-phenoxy]-propionic acid for the corresponding (±)-2-[4-({[2-(benzo[2,1,3]oxadiazol-5-yloxy)-pyridine-3-carbonyl]-amino}-methyl)-3-fluoro-phenoxy]-propionic acid tert-butyl ester material.

¹H NMR (CDCl₃): δ 8.31 (dd, 1H, J=3, 8 Hz), 8.02 (d, 1H, J=3 Hz), 7.28 (t, 1H, J=9 Hz), 7.23 (m, 1H), 6.79 (d, 1H, J=8 Hz), 6.55 (m, 3H), 5.99 (s, 2H), 4.73 (q, 1H, J=7 Hz), 4.60 (d, 2H, J=6 Hz), 1.62 (d, 3H, J=7 Hz).

MS (m/z): 472 (M⁺, 100).

EXAMPLE 7

(±)-2-[4-({[2-(Benzo[2,1,3]thiadiazol-5-yloxy)-pyridine-3-carbonyl]-amino}-methyl)-3-fluoro-phenoxy]-propionic acid of Formula (5.5.7)

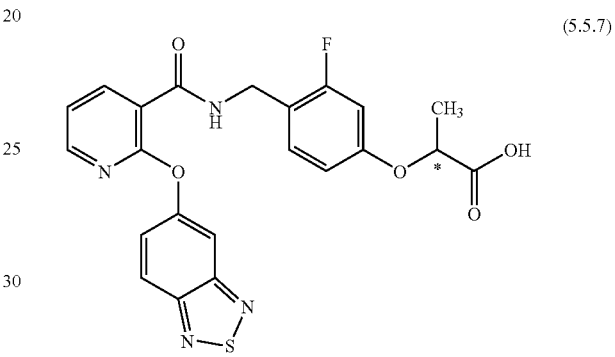

(5.5.7)

The compound of Formula (5.5.7) was prepared in a manner analogous to that described in Example 3, substituting (+)-2-[4-({[2-(benzo[2,1,3]thiadiazol-5-yloxy)-pyridine-3-carbonyl]-amino}-methyl)-3-fluoro-phenoxy]-propionic acid tert-butyl ester for the corresponding (±)-2-[4-({[2-(benzo[2,1,3]oxadiazol-5-yloxy)-pyridine-3-carbonyl]-amino}-methyl)-3-fluoro -phenoxy]-propionic acid tert-butyl ester material.

¹H NMR (CDCl₃): δ 8.61 (d, 1H, J=7 Hz), 8.18 (d, 1H, J=5 Hz), 8.06 (s, 1H), 7.99 (d, 1H, J=10 Hz), 7.64 (s, 1H), 7.43 (d, 1H, J=9 Hz), 7.29 (t, 1H, J=9 Hz), 6.60 (m, 2H), 4.72 (q, 1H, J=7 Hz), 4.63 (d, 2H, J=6 Hz), 1.61 (d, 3H, J=7 Hz).

MS (m/z) 468 (M⁺, 100).

EXAMPLE 8

(R)-2-[4-({[2-(Benzo[1,3]dioxol-5-yloxy)-pyridine-3-carbonyl]-amino}-methyl)-3-fluoro-phenoxy]-propionic acid of Formula (5.5.8)

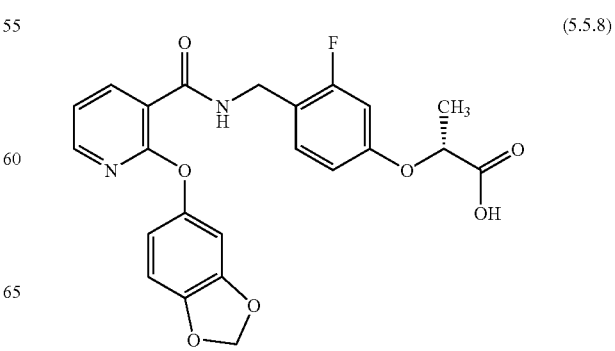

(5.5.8)

The compound of Formula (5.5.8) was prepared in a manner analogous to that described in Example 1, substituting (R)-2-[4-({[2-(benzo[1,3]dioxol-5-yloxy)-pyridine-3-carbonyl]-amino}-methyl)-3-fluoro-phenoxy]-propionic acid methyl ester for the corresponding [4-({[2-(benzo[1,3]dioxol-5-yloxy)-pyridine-3-carbonyl]-amino}-methyl)-3-fluoro-phenoxy]-acetic acid methyl ester material.

$^1$H NMR (CDCl$_3$): δ 8.59 (dd, 1H, J=2, 8 Hz), 8.31 (t, 1H, J=6 Hz), 8.21 (dd, 1H, J=2, 5 Hz), 7.30 (t, 1H, J=8 Hz), 7.12 (dd, 1H, J=5, 8 Hz), 6.81 (d, 1H, J=8 Hz), 6.61 (m, 3H), 6.00 (s, 2H), 4.74 (q, 1H, J=7 Hz), 4.63 (d, 2H, J=6 Hz), 1.64 (d, 3H, J=7 Hz).

EXAMPLE 9

(S)-2-[4-({[2-(Benzo[1,3]dioxol-5-yloxy)-pyridine-3-carbonyl]-amino}-methyl)-3-fluoro-phenoxy]-propionic acid of Formula (5.5.9)

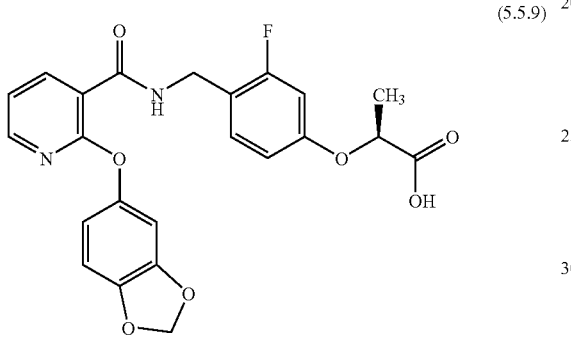

(5.5.9)

The compound of Formula (5.5.9) was prepared in a manner analogous to that described in Example 1, substituting (S)-2-[4-({[2-(benzo[1,3]dioxol-5-yloxy)-pyridine-3-carbonyl]-amino}-methyl)-3-fluoro-phenoxy]-propionic acid methyl ester for the corresponding [4-({[2-(benzo[1,3]dioxol-5-yloxy)-pyridine-3-carbonyl]-amino}-methyl)-3-fluoro-phenoxy]-acetic acid methyl ester material.

$^1$H NMR (CDCl$_3$): δ 8.59 (dd, 1H, J=2, 8 Hz), 8.31 (t, 1H, J=6 Hz), 8.21 (dd, 1H, J=2, 5 Hz), 7.30 (t, 1H, J=8 Hz), 7.12 (dd, 1H, J=5, 8 Hz), 6.81 (d, 1H, J=8 Hz), 6.61 (m, 3H), 6.00 (s, 2H), 4.74 (q, 1H, J=7 Hz), 4.63 (d, 2H, J=6 Hz), 1.64 (d, 3H, J=7 Hz).

EXAMPLE 10

(R)-2-[4-({[2-(Benzo[2,1,3]oxadiazol-5-yloxy)-pyridine-3-carbonyl]-amino}-methyl)-3-fluoro-phenoxy]-propionic acid of Formula (5.5.10)

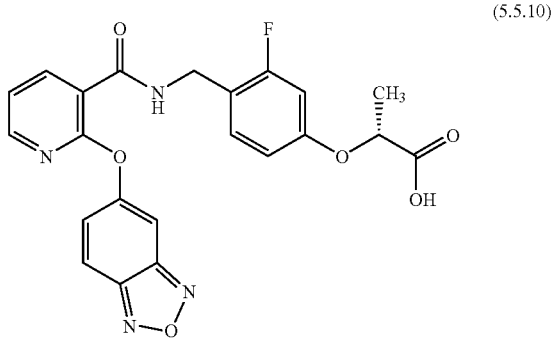

(5.5.10)

The compound of Formula (5.5.10) was prepared in a manner analogous to that described in Example 1, substituting (R)-2-[4-({[2-(benzo[2,1,3]oxadiazol-5-yloxy)-pyridine-3-carbonyl]-amino}-methyl)-3-fluoro-phenoxy]-propionic acid methyl ester for the corresponding [4-({[2-(benzo[1,3]dioxol-5-yloxy)-pyridine-3-carbonyl]-amino}-methyl)-3-fluoro-phenoxy]-acetic acid methyl ester material.

$^1$H NMR (CDCl$_3$): δ 8.36 (dd, 1H, J=2, 7 Hz), 8.09 (dd, 1H, J=2, 5 Hz), 8.03 (br, 1H), 7.75 (d, 1H, J=9 Hz), 7.42 (s, 1H), 7.13 (m, 2H), 6.50 (m, 2H), 4.54 (q, 1H, J=7 Hz), 4.49 (d, 2H, J=6 Hz), 1.46 (d, 3H, J=7 Hz).

MS (m/z): 452 (M$^+$, 100).

EXAMPLE 11

(R)-2-[3-Fluoro-4-({[2-(3-cyano-phenoxy)-pyridine-3-carbonyl]-amino}-methyl)-phenoxy]-propionic acid of Formula (5.5.11)

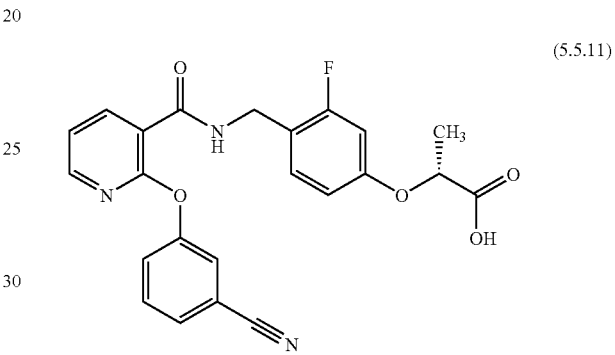

(5.5.11)

The compound of Formula (5.5.11) was prepared in a manner analogous to that described in Example 1, substituting (R)-2-[3-fluoro-4-({[2-(3-cyano-phenoxy)-pyridine-3-carbonyl]-amino}-methyl)-phenoxy]-propionic acid methyl ester for the corresponding [4-({[2-(benzo[1,3]dioxol-5-yloxy)-pyridine-3-carbonyl]-amino}-methyl)-3-fluoro-phenoxy]-acetic acid methyl ester material.

$^1$H NMR (CDCl$_3$): δ 8.50(dd, 1H, J=2, 6 Hz), 8.12 (dd, 1H, J=2, 5 Hz), 8.03 (s, 1H), 7.35 (m, 4H), 7.15 (dd, 1H, J=5, 8 Hz), 6.56 (m, 2H), 4.61 (q, 1H, J=7 Hz), 4.57 (d, 2H, J=6 Hz), 1.54 (d, 3H, J=7 Hz).

MS (m/z): 435 (M$^+$, 100).

EXAMPLE 12

(R)-2-[4-({[2-(Benzo[1,3]dioxol-5-yloxy)-5-fluoro-pyridine-3-carbonyl]-amino}-methyl)-3-flouro-phenoxy]-propionic acid of Formula (5.5.12)

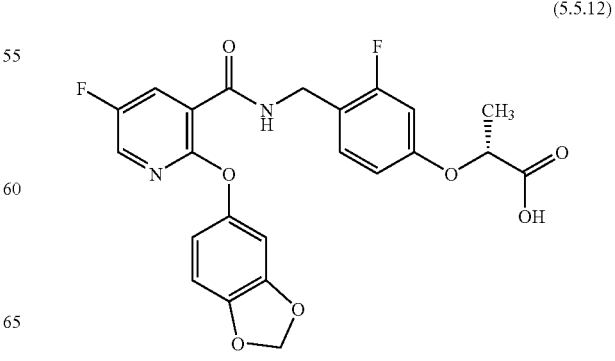

(5.5.12)

The compound of Formula (5.5.12) was prepared in a manner analogous to that described in Example 1, substituting (R)-2-[4-({[2-(benzo[1,3]dioxol-5-yloxy)-5-fluoro-pyridine-3-carbonyl]-amino}-methyl)-3-fluoro-phenoxy]-propionic acid methyl ester for the corresponding [4-({[2-(benzo[1,3]dioxol-5-yloxy)-pyridine-3-carbonyl]-amino}-methyl)-3-fluoro-phenoxy]-acetic acid methyl ester material.

$^1$H NMR (CDCl$_3$): δ 8.33 (dd, 2H, J=3, 8 Hz), 8.04 (d, 1H, J=3 Hz), 7.30 (t, 1H, J=8 Hz), 6.80 (d, 1H, J=8 Hz), 6.62 (m, 3H), 6.56 (dd, 1H, J=2, 8 Hz), 6.01 (s, 2H), 4.74 (q, 1H, J=7 Hz), 4.62 (d, 2H, J=6 Hz), 1.65 (d, 3H, J=7 Hz).

MS (m/z): 472 (M$^+$, 100).

EXAMPLE 13

(R)-2-[4-({[2-(Benzo[2,1,3]thiadiazol-5-yloxy)-pyridine-3-carbonyl]-amino}-methyl)-3-fluoro-phenoxy]-propionic acid of Formula (5.5.13)

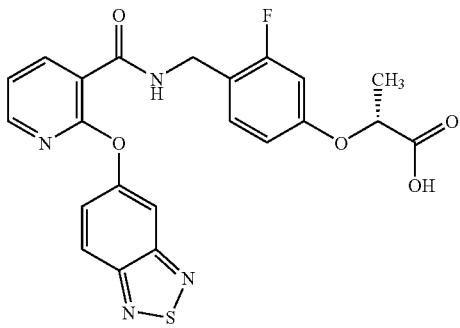

(5.5.13)

The compound of Formula (5.5.13) was prepared in a manner analogous to that described in Example 1, substituting (R)-2-[4-({[2-(benzo[2,1,3]thiadiazol-5-yloxy)-pyridine-3-carbonyl]-amino}-methyl)-3-fluoro-phenoxy]-propionic acid methyl ester for the corresponding [4-({[2-(benzo[1,3]dioxol-5-yloxy)-pyridine-3-carbonyl]-amino}-methyl)-3-fluoro-phenoxy]-acetic acid methyl ester material.

$^1$H NMR (CDCl$_3$): δ 8.60 (d, 1H, J=7 Hz), 8.18 (d, 1H, J=5 Hz), 8.06 (s, 1H), 7.99 (d, 1H, J=10 Hz), 7.64 (s, 1H), 7.43 (d, 1H, J=9 Hz), 7.29 (t, 1H, J=9 Hz), 6.60 (m, 2H), 4,72 (q, 1H, J=7 Hz), 4.63 (d, 2H, J=6 Hz), 1.61 (d, 3H, J=7 Hz).

MS (m/z) 468 (M$^+$, 100).

EXAMPLE 14

(R)-2-(Benzo[1,3]dioxol-5-yloxy)-N-[4-(1-carbamoyl-ethoxy)-2-fluoro-benzyl]-nicotinamide of Formula (5.5.14)

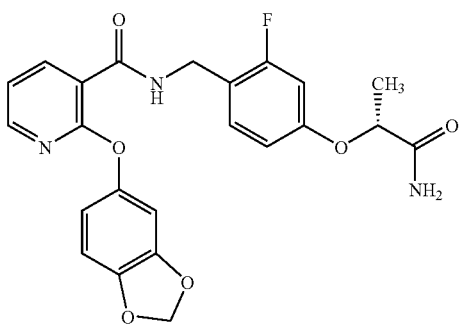

(5.5.14)

To a stirred solution of (R)-2-[4-({[2-(benzo[1,3]dioxol-5-yloxy)-pyridine-3-carbonyl]-amino}-methyl)-3-fluoro-phenoxy]-propionic acid (0.25 g, 0.55 mmol) in ethylene glycol dimethyl ether (20 mL) at −10° C. was added N-methyl morpholine (0.06 mL, 0.55 mmol) followed by dropwise addition of isobutyl chloroformate (0.071 mL, 0.55 mmol). The turbid solution was stirred at −10° C. 10 min. Ammonia gas was bubbled through the reaction mixture 10 min, which was then warmed to room temperature and stirred a further 15 min. The reaction mixture was partitioned between chloroform and water. The organic layer was dried over sodium sulfate and concentrated in vacuo to afford a white solid. Flash column chromatography (1% methanol/dichloromethane) yielded 0.15 g of a white solid (60% yield).

$^1$H NMR (CDCl$_3$): δ 8.57 (d, 1H, J=7 Hz), 8.24 (br, 1H), 8.19 (d, 1H, J=5 Hz), 7.33 (t, 1H, J=9 Hz), 7.10 (m, 1H), 6.80 (d, 1H, J=8 Hz), 6.58 (m, 3H), 6.25 (br, 1H), 5.99 (s, 2H), 5.38 (br, 1H), 4.60 (m, 3H), 1.55 (d, 3H, J=7 Hz).

MS (m/z): 454 (M$^+$+1, 100).

EXAMPLE 15

(R)-2-(Benzo[2,1,3]oxadiazol-5-yloxy)-N-[4-(1-carbamoyl-ethoxy)-2-fluoro-benzyl]-nicotinamide of Formula (5.5.15)

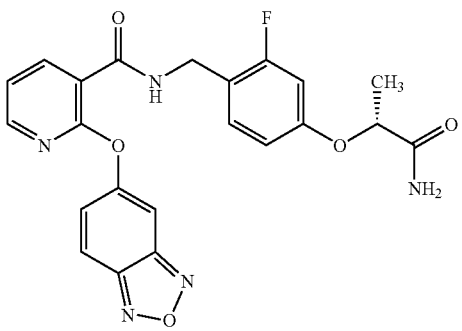

(5.5.15)

The compound of Formula (5.5.15) was prepared in a manner analogous to that described in Example 14, substituting (R)-2-[4-({[2-(benzo[2,1,3]oxadiazol-5-yloxy)-pyridine-3-carbonyl]-amino}-methyl)-3-fluoro-phenoxy]-propionic acid for the corresponding (R)-2-[4-({[2-(benzo[1,3]dioxol-5-yloxy)-pyridine-3-carbonyl]-amino}-methyl)-3-fluoro-phenoxy]-propionic acid material.

$^1$H NMR (CDCl$_3$): δ 8.61 (dd, 1H, J=2, 7 Hz), 8.19 (dd, 1H, J=2, 5 Hz), 7.87 (t, 1H, J=9 Hz), 7.52 (d, 1H, J=2 Hz), 7.33 (s, 1H), 7.25 (t, 1H, J=5 Hz), 6.63 (m, 2H), 6.26 (br, 1H), 5.47 (br, 1H), 4.64 (d, 2H, J=6 Hz), 4.58 (q, 1H, J=7 Hz), 1.54 (d, 3H, J=7 Hz).

MS (m/z): 452 (M$^+$+1, 100).

EXAMPLE 16

(R)-2-(Benzo[2,1,3]thiadiazol-5-yloxy)-N-[4-(1-carbamoyl-ethoxy)-2-fluoro-benzyl]-nicotinamide of Formula (5.5.16)

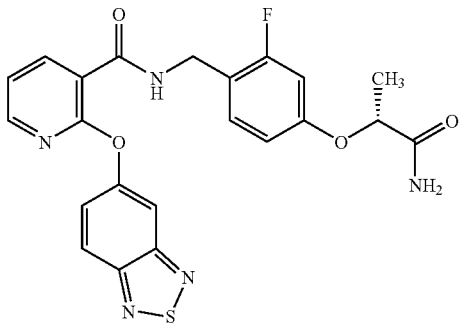

(5.5.16)

The compound of Formula (5.5.16) was prepared in a manner analogous to that described in Example 14, substituting (R)-2-[4-({[2-(benzo[2,1,3]thiadiazol-5-yloxy)-pyridine-3-carbonyl]-amino}-methyl)-3-fluoro-phenoxy]-propionic acid for the corresponding (R)-2-[4-({[2-(benzo[1,3]dioxol-5-yloxy)-pyridine-3-carbonyl]-amino}-methyl)-3-fluoro-phenoxy]-propionic acid material.

$^1$H NMR (CDCl$_3$): δ 8.63 (dd, 1H, J=2, 7 Hz), 8.19 (dd, 1H, J=2, 5 Hz), 7.87 (t, 1H, J=9 Hz), 7.52 (d, 1H, J=2 Hz), 7.33 (s, 1H), 7.25 (t, 1H, J=5 Hz), 6.63 (m, 2H), 6.26 (br, 1H), 5.47 (br, 1H), 4.64 (d, 2H, J=6 Hz), 4.57 (q, 1H, J=7 Hz), 1.54 (d, 3H, J=7 Hz).

MS (m/z): 468 (M$^+$+1, 100).

EXAMPLE 17

(R)-N-[4-(1-Carbamoyl-ethoxy)-2-fluoro-benzyl]-2-(3-cyano-phenoxy)-nicotinamide of Formula (5.5.17)

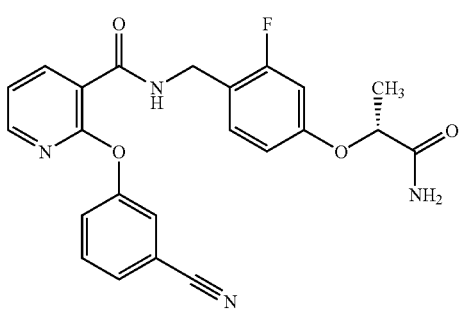

(5.5.17)

The compound of Formula (5.5.17) was prepared in a manner analogous to that described in Example 14, substituting (R)-2-[3-fluoro-4-({[2-(3-cyano-phenoxy)-pyridine-3-carbonyl]-amino}-methyl)-phenoxy]-propionic acid for the corresponding (R)-2-[4-({[2-(benzo[1,3]dioxol-5-yloxy)-pyridine-3-carbonyl]-amino}-methyl)-3-fluoro-phenoxy]-propionic acid material.

$^1$H NMR (CDCl$_3$): ): δ 8.59 (dd, 1H, J=2, 7 Hz), 8.16 (dd, 1H, J=2, 5 Hz), 8.03 (t, 1H, J=9 Hz), 7.38 (m, 4H), 6.63 (m, 2H), 6.27 (br, 1H), 5.48 (br, 1H), 4.59 (m, 3H), 1.55 (d, 3H, J=7 Hz).

MS (m/z): 435 (M$^+$+1, 100).

EXAMPLE 18

(R)-2-(Benzo[1,3]dioxol-5-yloxy)-N-[4-(1-carbamoyl-ethoxy)-2-fluoro-benzyl]-5-fluoro-nicotinamide of Formula (5.5.18)

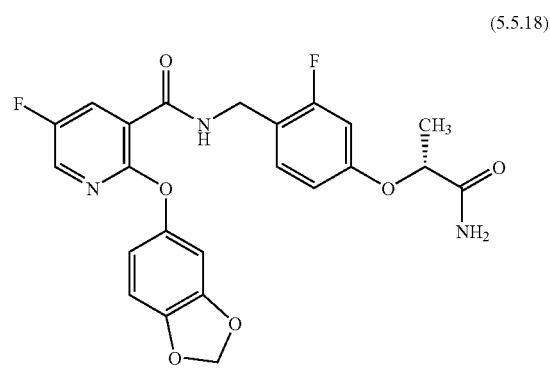

(5.5.18)

The compound of Formula (5.5.18) was prepared in a manner analogous to that described in Example 14, substituting (R)-2-[4-({[2-(benzo[1,3]dioxol-5-yloxy)-5-fluoro-pyridine-3-carbonyl]-amino}-methyl)-3-fluoro-phenoxy]-propionic acid for the corresponding (R)-2-[4-({[2-(benzo[1,3]dioxol-5-yloxy)-pyridine-3-carbonyl]-amino}-methyl)-3-fluoro-phenoxy]-propionic acid material.

$^1$H NMR (CDCl$_3$): δ 8.31 (m, 2H), 8.02 (d, 1H, J=3 Hz), 7.32 (t, 1H, J=8 Hz), 6.80 (d, 1H, J=8 Hz), 6.60 (m, 3H), 6.26 (br, 1H), 6.00 (s, 2H), 5.35 (br, 1H), 4.07 (m, 3H), 1.55 (d, 3H, J=7 Hz).

MS (m/z): 472 (M$^+$+1, 100).

EXAMPLE 19

(±)-2-(Benzo[1,3]dioxol-5-yloxy)-N-{2-fluoro-4-[1-(1H-tetrazol-5-yl)-ethoxy]-benzyl}-nicotinamide of Formula (5.5.19)

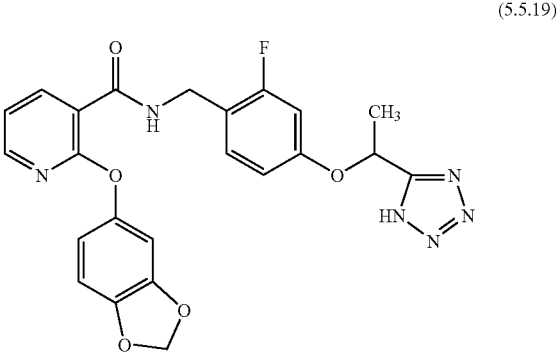

(5.5.19)

A solution of (±)-2-(benzo[1,3]dioxol-5-yloxy)-N-[4-(1-cyano-ethoxy)-2-fluoro-benzyl]-nicotinamide (1.5 g, 3.5 mmol) in anhydrous toluene (5 mL) was transferred to a small pressure flask. Dibutyltin oxide (0.53 g, 2.1 mmol) and trimethylsilyl azide (1.7 mL, 21 mmol) were added. The tube was sealed and placed behind a blast shield. The reaction was stirred 15 min at 55° C., then warmed to 110° C. with stirring over night. The black reaction mix was cooled to 0–5° C., the pressure flask opened, and the residue taken up in methanol. Solvents were removed in vacuo and the residue taken up in ethyl acetate. The organic solution was washed twice with saturated aqueous sodium carbonate. The aqueous phases were pooled and acidified with concentrated hydrochloric acid, and extracted twice with ethyl acetate. The pooled organic phases were dried (MgSO$_4$), concentrated, and loaded onto a silica gel column as a brown oil. Purification by column chromatography (5% methanol/dichloromethane) afforded product as a white solid (0.46 g, 28%).

$^1$H NMR (CDCl$_3$): 8.58 (dd, 1H, J=2 Hz, 8 Hz), 8.43 (t, 1H, J=6 Hz), 8.21 (dd, 1H, J=2 Hz, 5 Hz), 7.13 (m, 2H), 6.79 (d, 1H, J=8 Hz), 6.61 (d, 1H, J=2 Hz), 6.53 (m, 3H), 5.99 (s, 2H), 5.72 (q, 1H, J=7 Hz), 4.57 (d, 2H, J=5 Hz), 1.78 (d, 3H, J=6 Hz).

MS (m/z): 479 (M$^+$+1, 40).

EXAMPLE 20

(R)-2-(Benzo[1,3]dioxol-5-yloxy)-N-{2-fluoro-4-[1-(5-methyl-4H-[1,2,4]triazol-3yl)-ethoxyl]-benzyl}-nicotinamide of Formula (5.5.20)

(5.5.20)

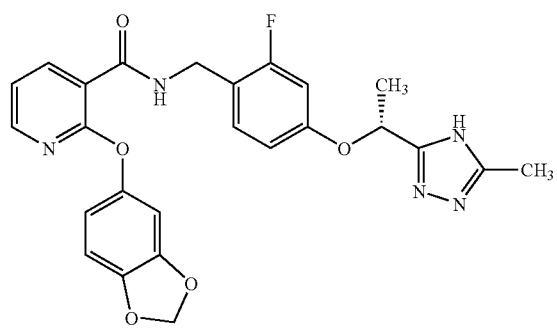

A solution of (R)-2-[4-({[2-(benzo[1,3]dioxol-5-yloxy)-pyridine-3-carbonyl]-amino}-methyl)-3-fluoro-phenoxy]-propionimidic acid ethyl ester (0.16 g, 0.33 mmol) and acetic hydrazide (24 mg, 0.31 mmol) in n-butanol (20 ml) was stirred 20 h at 80° C. The reaction was cooled to room temperature and quenched into saturated aqueous oxalic acid and extracted with ethyl acetate. The organic solution was dried (MgSO$_4$), and concentrated in vacuo. The residue was purified by column chromatography (3% methanol/dichloromethane) to afford a sticky yellow solid (12 mg). The residue was further purified by preparatory thin layer chromatography (10% methanol/dichloromethane) to afford 7 mg of the desired compound (4% yield).

$^1$H NMR (CDCl$_3$): 8.52 (d, 1H, J=7.8 Hz), 8.42 (s, 1H), 8.21 (dd, 1H, J=5.0, 1.9 Hz), 7.19 (t, 1H, J=8.3 Hz), 7.11 (m, 1H), 6.77 (m, 4H), 6.00 (s, 2H), 5.48 (d, 2H, J=6.6 Hz), 460 (s, 2H), 2.45 (s, 3H), 1.75 (d, 3H, J=6.7 Hz).

EXAMPLE 21

(R)-2-(Benzo[1,3]dioxol-5-yloxy)-5-fluoro-N-{2-fluoro-4-[1-(5-methyl-4H-[1,2,4]triazol-3-yl)-ethoxy]-benzyl}-nicotinamide of Formula (5.5.21)

(5.5.21)

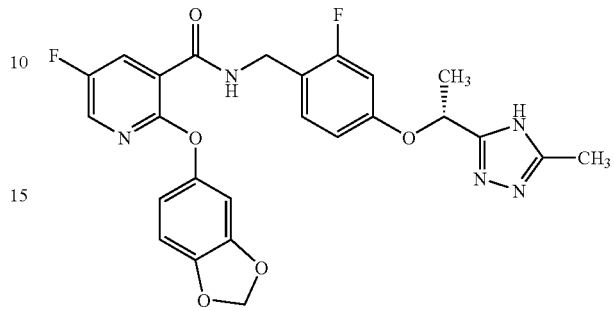

A solution of (R)-2-(benzo[1,3]dioxol-5-yloxy)-5-fluoro-N-[2-fluoro-4-(1-thiocarbamoyl -ethoxy)-benzyl]-nicotinamide (0.1 g, 0.21 mmol) in pyridine (5 ml) was warmed with stirring to 70° C. Anhyd. hydrazine (1.5 ml, 50 mmol) was added with stirring via a syringe. The reaction mixture was stirred at 70° C. 5 min, the cooled to room temperature. The solvent was removed in vacuo, and the residue to stored under house vacuum 1 h. The residue was subsequently taken up in fresh pyridine (5 ml). To this solution was added acetyl chloride (0.057 ml, 0.8 mmol) at room temperature, and the reaction mixture was stirred 2 h. The pyridine was removed in vacuo, and replaced with N,N-dimethylformamide (5 ml) and the resulting wolution was stirred at 130° C. 4 h. The reaction was cooled to room temperature, quenched into water (50 ml) and extracted with diethyl ether. The pooled extracts were dried (MgSO$_4$), filtered and concentrated to near-dryness, then loaded onto a silica gel column and purified by column chromatography (gradient 1% methanol/dicloromethane changing to 5% methanol/dichloromethane) to afford a white solid (7.6 mg, 7% yield).

MS (m/z): 509 (M$^+$, 20).

[α]$_D$=+24° (CHCl$_3$).

EXAMPLE 22

(±)-2-(Benzo[1,3]dioxol-5-yloxy)-N-{2-fluoro-4-[1-(1H-tetrazol-5-yl)-ethoxy]-benzyl}-nicotinamide of Formula (5.5.22)

(5.5.22)

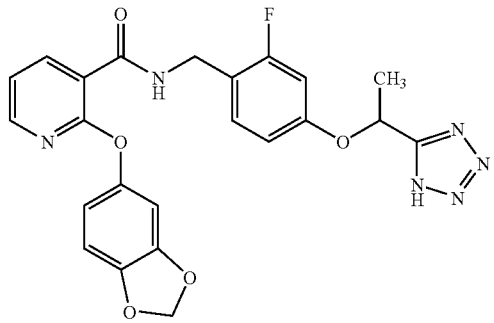

A solution of (±)-2-(benzo[1,3]dioxol-5-yloxy)-N-[4-(1-cyano-ethoxy)-2-fluoro-benzyl]-nicotinamide (1.5 g, 3.5 mmol) in anhydrous toluene (5 mL) was transferred to a small pressure flask. Dibutyltin oxide (0.53 g, 2.1 mmol) and trimethylsilyl azide (1.7 mL, 21 mmol) were added. The tube was sealed and placed behind a blast shield. The reaction was stirred 15 min at 55° C., then warmed to 110° C. with stirring over night. The black reaction mix was cooled to 0–5° C., the pressure flask opened, and the residue taken up in methanol. Solvents were removed in vacuo and the residue taken up in ethyl acetate. The organic solution was washed twice with saturated aqueous sodium carbonate. The aqueous phases were pooled and acidified with concentrated hydrochloric acid, and extracted twice with ethyl acetate. The pooled organic phases were dried (MgSO$_4$), concentrated, and loaded onto a silica gel column as a brown oil. Purification by column chromatography (5% methanol/dichloromethane) afforded product as a white solid (0.46 g, 28%).

$^1$H NMR (CDCl$_3$): 8.58 (dd, 1H, J=2 Hz, 8 Hz), 8.43 (t, 1H, J=6 Hz), 8.21 (dd, 1H, J=2 Hz, 5 Hz), 7.13 (m, 2H), 6.79 (d, 1H, J=8 Hz), 6.61 (d, 1H, J=2 Hz), 6.53 (m, 3H), 5.72 (q, 1H, J=7 Hz), 4.57 (d, 2H, J=5 Hz), 1.78 (d, 3H, J=6 Hz).

MS (m/z): 479 (M$^+$+1, 40).

EXAMPLE 23

(R)-2-(Benzo[1,3]dioxol-5-yloxy)-N-[2-fluoro-4-(2-hydroxy-1,2-dimethyl-propoxy)-benzyl]-nicotinamide of Formula (5.5.23)

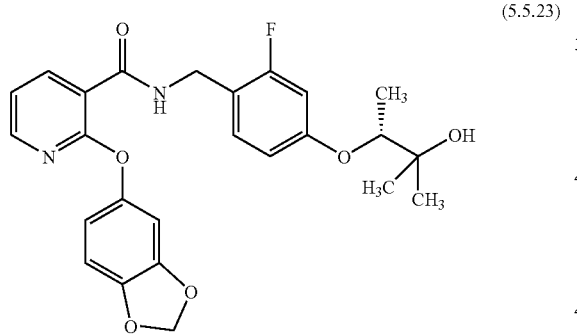

(5.5.23)

To a stirred solution of (R)-2-[4-({[2-(benzo[1,3]dioxol-5-yloxy)-pyridine-3-carbonyl]-amino}-methyl)-3-fluoro-phenoxy]-propionic acid methyl ester (0.10 g, 0.213 mmol) in tetrahydrofuran (5 ml) at −10° C., methyl magnesium chloride (3.0 ml, 1.07 mmol) was added, and stirred at −10° C. 15 min. The solution was allowed to warm to room temperature and stirred a further 16 h. The reaction was quenched into water and extraced with ethyl acetate. The pooled organics were dried (MgSO$_4$), filtered and concentrated to an opaque white oil. The residue was purified by column chromatography (1:1 ethyl acetate/hexane), affording 40 mg white powder (40% yield).

$^1$H NMR (CDCl$_3$): 8.60 (d, 1H, J=7.4 Hz), 8.25 (s, 1H), 8.21 (d, 1H, J=4.6 Hz), 7.31 (t, 1H, J=8.3 Hz), 7.12 (dd, 1H, J=5.0, 7.9 Hz), 6.83 (d, 1H, J=8.3 Hz), 6.67 (m, 4H), 6.00 (s, 2H), 4.64 (d, 2H, J=4.6 Hz), 4.12 (q, 1H, J=6.2 Hz), 1.25 (s, 6H), 1.22 (d, 3H, J=6.2 Hz).

MS (m/z): 467 (M$^-$, 100).

EXAMPLE 24

(R)-2-(Benzo[1,3]dioxol-5-yloxy)-5-fluoro-N-[2-fluoro-4-(2-hydroxy-1,2-dimethyl-propoxy)-benzyl]-nicotinamide of Formula (5.5.24)

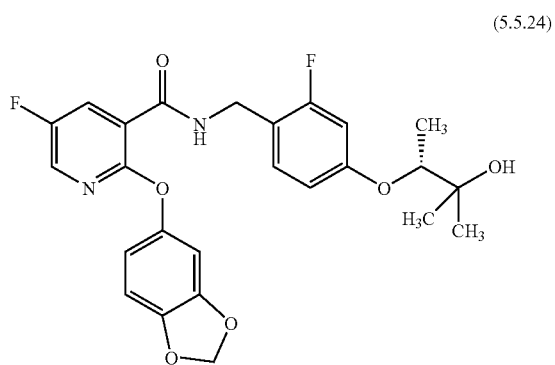

(5.5.24)

Prepared in a manner analogous to Example 23, substituting (R)-2-[4-({[2-(benzo[1,3]dioxol-5-yloxy)-5-fluoro-pyridine-3-carbonyl]-amino}-methyl)-3-fluoro-phenoxy]-propionic acid methyl ester.

$^1$H NMR (CDCl$_3$): 8.33 (dd, 1H, J=8.3, 3.3 Hz), 8.30 (s, 1H), 8.03 (d, 1H, J=2.9 Hz), 7.30 (t, 1H, J=8.7 Hz), 6.81 (d, 1H, J=8.3 Hz), 6.62 (m, 4H), 6.01 (s, 2H), 4.63 (d, 2H, J=5.8 Hz), 4.12 (q, 1H, J=6.2 Hz), 1.25 (s, 6H), 1.22 (d, 3H, J=6.2 Hz).

MS (m/z): 487 (M$^+$ 100).

EXAMPLE 25

(S)-3-[4-({[2-(Benzo[1,3]dioxol-5-yloxy)-pyridine-3-carbonyl]-amino}-methyl)-3-fluoro-phenoxy]-2-methyl-propionic acid of Formula (5.5.25)

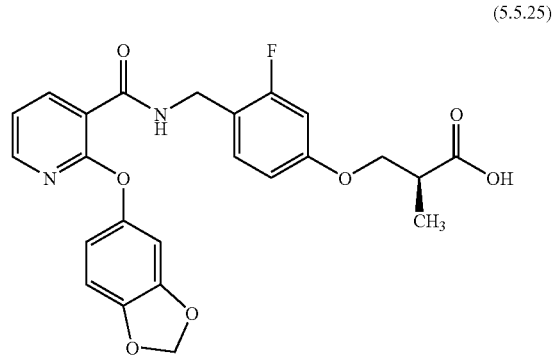

(5.5.25)

2-(Benzo-[1,3]-dioxol-5-yloxy)-nicotinic acid (0.168 g, 0.65 mmol), (S)-3-(4-aminomethyl-3-fluoro-phenoxy)-2-methyl-propionic acid methyl ester hydrochloride (0.18 g, 0.65 mmol), 1-hydroxybenzotriazole hydrate (0.097 g, 0.72 mmol), 1-[3-(dimethylamino)propyl]-3-ethylcarbodiimide hydrochloride (0.138 g, 0.72 mmol) and triethylamine were dissolved in N, N-dimethylformamide (6 mL) and stirred at room temperature over night. The reaction was diluted in ethyl acetate and washed successively with dilute aqueous hydrochloric acid, dilute aqueous sodium hydroxide, and brine, and dried (Na$_2$SO$_4$). The product was purified by flash column chromatography (20% ethyl acetate/hexane). The residue was taken up in tetrahydrofuran (10 mL) and methanol (2 mL) and aqueous lithium hydroxide (2 mL, 1 M, 2 mmol). The reaction was stirred at room temperature 1 h. The solvents were stripped in vacuo and the residue partitioned between dilute aqueous hydrochloric acid and ethyl acetate. The aqueous was extracted with 2 aliquots ethyl acetate and the pooled organics were washed with brine, dried over sodium sulfate and concentrated in vacuo to afford a white solid (0.12 g, 39% yeild).

$^1$H NMR (CDCl$_3$): 8.60 (d, 1H, J=8 Hz), 8.20 (m, 2H), 7.30 (t, 1H, J=8 Hz), 7.11 (m, 1H), 6.81 (d, 1H, J=8 Hz), 6.62 (m, 3H), 6.00 (s, 2H), 4.63 (d, 2H, J=6 Hz), 4.13 (dd, 1H, J=7, 9 Hz), 3.93 (dd, 1H, J=6, 9 Hz), 3.70 (s, 3H), 2.91 (m, 1H), 1.26 (d, 3H, J=7 Hz).

MS (m/z): 469 (MH$^+$, 100).

EXAMPLE 26

2-(Benzo[1,3]dioxol-5-yloxy)-5-fluoro-N-[2-fluoro-4-(pyridin-2-ylmethoxy)-benzyl]-nicotinamide of Formula (5.5.26)

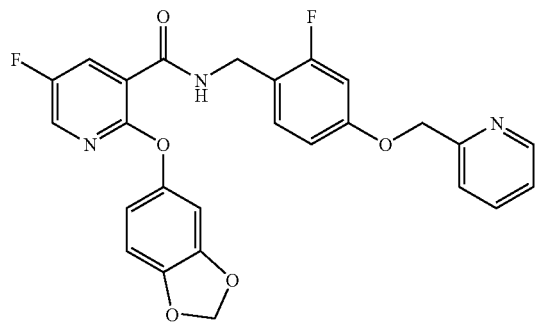

(5.5.26)

To a stirred solution of 100 mg (0.25 mmol.) 2-(benzo[1,3] dioxol-5-yloxy)-5-fluoro-N-(2-fluoro-4-hydroxy-benzyl)-nicotinamide [Prepared analogous to preparation 35 by substituting 2-chloro-5-fluoro-nicotinic acid (EP 0634413 A1)], 10 mL DMF and 175 mg (1.25 mmol.) potassium carbonate was added a solution of DMF (5 mL) containing 82 mg (0.5 mmol.) 2-chloromethyl-pyridine hydrochloride (Aldrich) and 1 equivalent of triethyl amine. The resulting mixture was stirred for 3 days at room temperature. Reaction mixture was poured into ice water (200 mL) and the resulting solid was filtered, washed with cold water and dried in vacuo to afford desired product.

MS (m/z): 492 (M$^+$, 100).

$^1$H-NMR (CDCl$_3$): 8.58 (d, 1H, J=5 Hz), 8.32 (dd, 1H, J=4, 9 Hz), 8.02 (d, 1H, J=3 Hz), 7.71 (dt, 1H, J=2, 10 Hz), 7.47 (d, 1H, J=2 Hz), 7.26 (m, 1H), 6.80 (d, 1H, J=8 Hz), 6.71 (m, 3H), 6.62 (d, 1H, J=3 Hz), 6.56 (dd, 1H, J=2, 8 Hz), 6.00 (s, 2H), 5.2 (s, 2H), 4.63 (d, 2H, J=6Hz).

EXAMPLE 27

2-(Benzo[1,3]dioxol-5-yloxy)-5-fluoro-N-[2-fluoro-4-(pyridin-4-ylmethoxy)-benzyl]-nicotinamide of Formula (5.5.27)

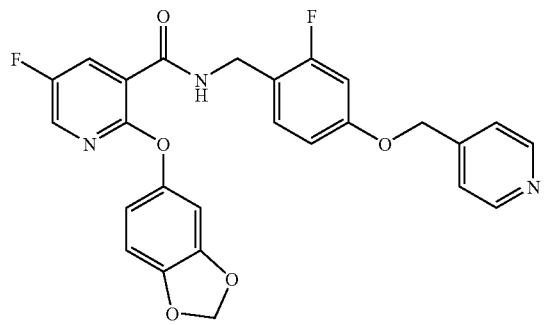

(5.5.27)

Prepared analogous to Example 26 by substituting 4-chloromethyl-pyridine hydrochloride (Aldrich).

MS (m/z): 492 (M$^+$, 100).

$^1$H-NMR (CDCl$_3$): 8.38 (m, 2H), 8.02 (d, 1H, J=3 Hz), 7.74 (m, 1H), 7.26 (m, 1H), 6.80 (d, 1H, J=8 Hz), 6.71 (m, 3H), 6.62 (d, 1H, J=3 Hz), 6.56 (dd, 1H, J=2, 8 Hz), 6.00 (s, 2H), 5.2 (s, 2H), 4.63 (d, 2H, J=6 Hz).

EXAMPLE 28

2-(Benzo[1,3]dioxol-5-yloxy)-5-fluoro-N-[2-fluoro-4-(pyridin-3-ylmethoxy)-benzyl]-nicotinamide of Formula (5.5.28)

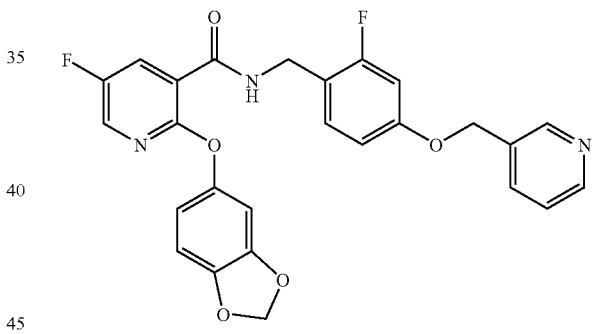

(5.5.28)

Prepared analogous to Example 26 by substituting 4-chloromethyl-pyridine hydrochloride (Aldrich).

MS (m/z): 492 (M$^+$, 100).

$^1$H-NMR (CDCl$_3$): 8.81 (s, 1H), 8.64 (d, 1H, J=5Hz), 8.35 (m, 2H), 8.02 (d, 1H, J=3 Hz), 7.71 (dt, 1H, J=2, 10Hz), 7.47 (d, 1H, J=2 Hz), 7.26 (m, 1H), 6.80 (d, 1H, J=8Hz), 6.71 (m, 3H), 6.62 (d, 1H, J=3Hz), 6.56 (dd, 1H, J=2, 8Hz), 6.00 (s, 2H), 5.2 (s, 2H), 4.63 (d, 2H, J=6Hz). J=6 Hz).

What is claimed is:

1. A compound of the Formula

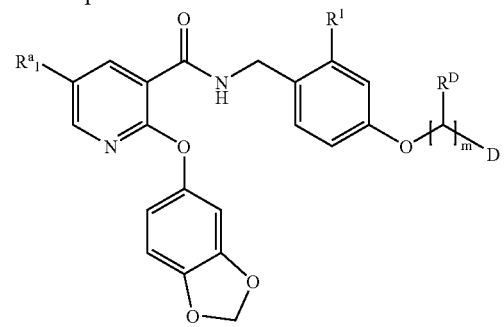

wherein m is 1, 2, or 3;

$R^1_o$ is hydrogen or fluoro;

$R^D$ is hydrogen or methyl;

$R^1$ is hydrogen or fluoro; and

D is carboxy or aminocarbonyl; or a pharmaceutically acceptable salt thereof.

2. A compound of claim 1 wherein $R^1_a$ is F; and $R^1$ is hydrogen.

3. A compound selected from

[4-({[2-(Benzo[1,3]dioxol-5-yloxy)-pyridine-3-carbonyl]-amino}-methyl)-3-fluorophenoxy]-acetic acid;

(±)-2-[4-({[2-(Benzo[1,3]dioxol-5-yloxy)-pyridine-3-carbonyl]-amino}-methyl)-3-fluoro-phenoxy]-propionic acid;

(±)-2-[4-({[2-(Benzo[1,3]dioxol-5-yloxy)-5-fluoro-pyridine-3-carbonyl]-amino) -methyl)-3-fluoro-phenoxy]-propionic acid;

(S)-2-[4-({[2-(Benzo[1,3]dioxol-5-yloxy)-pyridine-3-carbonyl]-amino)-methyl)-3-fluoro-phenoxy]-propionic acid;

(R)-2-[4-({[2-(Benzo[1,3]dioxol-5-yloxy)-5-fluoro-pyridine-3-carbonyl]-amino) -methyl)-3-fluoro-phenoxy]-propionic acid;

(R)-2-(Benzo[1,3]dioxol-5-yloxy)-N-[4-(1-carbamoyl-ethoxy)-2-fluoro-benzyl]-nicotinamide;

(R)-2-(Benzo[1,3]dioxol-5-yloxy)-N-[4-(1-carbamoyl-ethoxy)-2-fluoro-benzyl]-5-fluoro-nicotinamide; and (S)-3-[4-({[2-(Benzo[1,3]dioxol-5-yloxy)-pyridine-3-carbonyl]-amino}-methyl)-3-fluoro-phenoxy]-2-methyl-propionic acid.

* * * * *